US008716344B2

(12) United States Patent
Mazitschek et al.

(10) Patent No.: US 8,716,344 B2
(45) Date of Patent: May 6, 2014

(54) CLASS- AND ISOFORM-SPECIFIC HDAC INHIBITORS AND USES THEREOF
(75) Inventors: Ralph Mazitschek, Belmont, MA (US); James Elliot Bradner, Cambridge, MA (US)
(73) Assignees: President and Fellows of Harvard College, Cambridge, MA (US); Dana-Farber Cancer Institute, Inc., Boston, MA (US)
( * ) Notice: Subject to any disclaimer, the term of this patent is extended or adjusted under 35 U.S.C. 154(b) by 0 days.
(21) Appl. No.: 13/389,814
(22) PCT Filed: Aug. 11, 2010
(86) PCT No.: PCT/US2010/002220
§ 371 (c)(1),
(2), (4) Date: Apr. 24, 2012
(87) PCT Pub. No.: WO2011/019393
PCT Pub. Date: Feb. 17, 2011
(65) Prior Publication Data
US 2012/0208889 A1 Aug. 16, 2012

Related U.S. Application Data
(60) Provisional application No. 61/233,035, filed on Aug. 11, 2009.
(51) Int. Cl.
*A61K 38/05* (2006.01)
*A61K 31/495* (2006.01)
*C12Q 1/48* (2006.01)
*A61K 45/06* (2006.01)
*C07D 239/42* (2006.01)
*C07D 401/04* (2006.01)
(52) U.S. Cl.
CPC ............. *A61K 38/05* (2013.01); *A61K 45/06* (2013.01); *A61K 31/495* (2013.01); *C07D 239/42* (2013.01); *C07D 401/04* (2013.01); *C12Q 1/48* (2013.01)
USPC ............. 514/615; 435/18; 435/184; 549/288; 564/149
(58) Field of Classification Search
CPC .. C07D 239/42; C07D 401/04; C07D 207/14; C07D 211/58; C07D 405/14; C07D 413/04; C12Q 1/48; A61K 45/06; A61K 31/435; A61K 31/495; A61K 31/506; A61K 38/05
USPC ................ 514/615; 435/18, 184; 549/288; 564/149
See application file for complete search history.

(56) References Cited

U.S. PATENT DOCUMENTS 4,160,866 A 7/1979 Brooks et al.
4,608,390 A 8/1986 Summers, Jr.
(Continued)

FOREIGN PATENT DOCUMENTS

DE 32 42 252 1/1987
EP 0 259 149 A2 3/1988
(Continued)

OTHER PUBLICATIONS
JP 2003-221398, translation.*
(Continued)

*Primary Examiner* — Savitha Rao
*Assistant Examiner* — Angela Brown-Pettigrew
(74) *Attorney, Agent, or Firm* — Wolf, Greenfield & Sacks, P.C.; C. Hunter Baker

(57) ABSTRACT

The present invention relates to compounds of the following formula

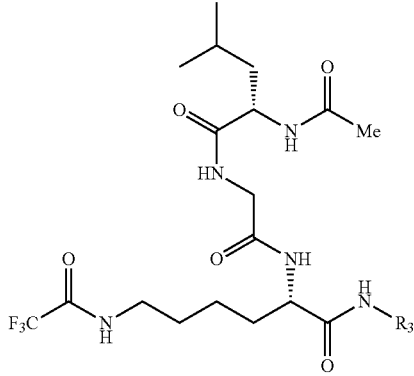

wherein $R_3$ is a fluorescent tag. Another aspect of the invention provides an assay for determining the inhibitory effect of a test compound on an HDAC protein comprising: incubating the HDAC protein with a substrate of the above formula in the presence of a test compound; and determining the activity of the HDAC protein.

21 Claims, 28 Drawing Sheets

(56) References Cited

U.S. PATENT DOCUMENTS

| | | | |
|---|---|---|---|
| 4,631,211 | A | 12/1986 | Houghten |
| 4,639,462 | A | 1/1987 | Kramer et al. |
| 4,683,195 | A | 7/1987 | Mullis et al. |
| 4,683,202 | A | 7/1987 | Mullis |
| 4,820,828 | A | 4/1989 | Demers et al. |
| 4,833,080 | A | 5/1989 | Brent et al. |
| 4,861,798 | A | 8/1989 | Tramposch et al. |
| 5,045,538 | A | 9/1991 | Schneider et al. |
| 5,059,698 | A | 10/1991 | Schulthess et al. |
| 5,096,815 | A | 3/1992 | Ladner et al. |
| 5,143,854 | A | 9/1992 | Pirrung et al. |
| 5,175,191 | A | 12/1992 | Marks et al. |
| 5,176,996 | A | 1/1993 | Hogan et al. |
| 5,198,346 | A | 3/1993 | Ladner et al. |
| 5,223,409 | A | 6/1993 | Ladner et al. |
| 5,225,173 | A | 7/1993 | Wai |
| 5,238,781 | A | 8/1993 | Schadeli |
| 5,256,775 | A | 10/1993 | Froehler |
| 5,264,564 | A | 11/1993 | Matteucci |
| 5,283,317 | A | 2/1994 | Saifer et al. |
| 5,288,514 | A | 2/1994 | Ellman |
| 5,304,121 | A | 4/1994 | Sahatjian |
| 5,328,470 | A | 7/1994 | Nabel et al. |
| 5,359,115 | A | 10/1994 | Campbell et al. |
| 5,362,899 | A | 11/1994 | Campbell |
| 5,393,741 | A | 2/1995 | Pettersen et al. |
| 5,440,016 | A | 8/1995 | Blondelle et al. |
| 5,480,971 | A | 1/1996 | Houghten et al. |
| 5,534,654 | A | 7/1996 | Ohtani et al. |
| 5,659,016 | A | 8/1997 | Nakamura et al. |
| 5,700,811 | A | 12/1997 | Breslow et al. |
| 5,763,182 | A | 6/1998 | Nakamura et al. |
| 5,837,313 | A | 11/1998 | Ding et al. |
| 5,886,026 | A | 3/1999 | Hunter et al. |
| 5,891,507 | A | 4/1999 | Jayaraman |
| 6,030,945 | A | 2/2000 | Ashkenazi |
| 6,037,361 | A | 3/2000 | Roth et al. |
| 6,068,987 | A | 5/2000 | Dulski et al. |
| 6,071,305 | A | 6/2000 | Brown et al. |
| 6,099,562 | A | 8/2000 | Ding et al. |
| 6,153,252 | A | 11/2000 | Hossainy et al. |
| 6,190,619 | B1 | 2/2001 | Kilcoin et al. |
| 6,195,612 | B1 | 2/2001 | Pack-Harris |
| 6,203,551 | B1 | 3/2001 | Wu |
| 6,231,600 | B1 | 5/2001 | Zhong |
| 6,248,127 | B1 | 6/2001 | Shah et al. |
| 6,251,136 | B1 | 6/2001 | Guruwaiya et al. |
| 6,258,121 | B1 | 7/2001 | Yang et al. |
| 6,273,913 | B1 | 8/2001 | Wright et al. |
| 6,428,960 | B1 | 8/2002 | Clark et al. |
| 6,495,719 | B2 | 12/2002 | Lan-Hargest et al. |
| 6,503,708 | B1 | 1/2003 | Lal et al. |
| 6,512,123 | B2 | 1/2003 | Grossmann et al. |
| 6,517,889 | B1 | 2/2003 | Jayaraman |
| 6,541,661 | B1 | 4/2003 | Delorme et al. |
| 6,777,217 | B1 | 8/2004 | Schreiber et al. |
| 6,797,820 | B2 | 9/2004 | Patel et al. |
| 6,897,220 | B2 | 5/2005 | Delorme et al. |
| 6,960,685 | B2 | 11/2005 | Watkins et al. |
| 7,244,853 | B2 | 7/2007 | Schreiber et al. |
| 7,250,504 | B2 | 7/2007 | Grozinger et al. |
| 7,335,753 | B2 | 2/2008 | Wang et al. |
| 7,514,406 | B2 | 4/2009 | Bedalov et al. |
| 7,737,172 | B2 | 6/2010 | Halperin et al. |
| 7,994,362 | B2 | 8/2011 | Schreiber et al. |
| 8,076,116 | B2 | 12/2011 | Grozinger et al. |
| 8,178,579 | B2 | 5/2012 | Schreiber et al. |
| 8,222,423 | B2 | 7/2012 | Bradner et al. |
| 8,304,451 | B2 | 11/2012 | Mazitschek et al. |
| 8,329,945 | B2 | 12/2012 | Schreiber et al. |
| 8,329,946 | B2 | 12/2012 | Schreiber et al. |
| 8,362,084 | B2 | 1/2013 | Schreiber et al. |
| 8,383,855 | B2 | 2/2013 | Bradner et al. |
| 8,399,233 | B2 | 3/2013 | Schreiber et al. |
| 8,426,592 | B2 | 4/2013 | Schreiber et al. |
| 8,435,780 | B2 | 5/2013 | Grozinger et al. |
| 8,440,716 | B2 | 5/2013 | Tang et al. |
| 2001/0027340 | A1 | 10/2001 | Wright et al. |
| 2003/0004209 | A1 | 1/2003 | Hunter et al. |
| 2003/0129724 | A1 | 7/2003 | Grozinger et al. |
| 2003/0187027 | A1 | 10/2003 | Schreiber et al. |
| 2003/0216345 | A1 | 11/2003 | Nakanishi et al. |
| 2004/0072849 | A1 | 4/2004 | Schreiber et al. |
| 2004/0087631 | A1 | 5/2004 | Bacopoulos et al. |
| 2004/0092598 | A1 | 5/2004 | Watkins et al. |
| 2004/0127522 | A1 | 7/2004 | Chiao et al. |
| 2004/0138153 | A1 | 7/2004 | Ramesh et al. |
| 2005/0014839 | A1 | 1/2005 | Kozikowski et al. |
| 2005/0267037 | A1 | 12/2005 | Anderson et al. |
| 2005/0287629 | A1 | 12/2005 | Grozinger et al. |
| 2006/0020131 | A1 | 1/2006 | Raeppel et al. |
| 2006/0079528 | A1 | 4/2006 | Finn et al. |
| 2006/0239909 | A1 | 10/2006 | Anderson et al. |
| 2007/0093413 | A1 | 4/2007 | Schreiber et al. |
| 2008/0207590 | A1 | 8/2008 | Deziel et al. |
| 2008/0269245 | A1 | 10/2008 | Schreiber et al. |
| 2008/0300205 | A1 | 12/2008 | Tsai et al. |
| 2009/0036318 | A1 | 2/2009 | Grozinger et al. |
| 2009/0209590 | A1 | 8/2009 | Mazitschek et al. |
| 2009/0312363 | A1 | 12/2009 | Bradner et al. |
| 2010/0041653 | A1 | 2/2010 | Pellecchia et al. |
| 2010/0056588 | A1 | 3/2010 | Bradner et al. |
| 2010/0137196 | A1 | 6/2010 | Schreiber et al. |
| 2011/0172303 | A1 | 7/2011 | Tang et al. |
| 2011/0218154 | A1 | 9/2011 | Schreiber et al. |
| 2011/0313045 | A1 | 12/2011 | Schreiber et al. |
| 2011/0319493 | A1 | 12/2011 | Schreiber et al. |
| 2012/0094862 | A1 | 4/2012 | Grozinger et al. |
| 2012/0302510 | A1 | 11/2012 | Schreiber et al. |
| 2013/0018103 | A1 | 1/2013 | Bradner et al. |
| 2013/0040998 | A1 | 2/2013 | Bradner et al. |

FOREIGN PATENT DOCUMENTS

| | | | |
|---|---|---|---|
| EP | 0 322 335 | A1 | 6/1989 |
| EP | 0 323 590 | A2 | 7/1989 |
| EP | 0 331 524 | A2 | 9/1989 |
| EP | 0 458 131 | A1 | 11/1991 |
| EP | 0 708 112 | A1 | 4/1996 |
| GB | 1 394 170 | A | 5/1975 |
| GB | 2 169 599 | A | 7/1986 |
| JP | 59-139390 | A | 8/1984 |
| JP | 04-022948 | A | 1/1992 |
| JP | 04-217929 | A | 8/1992 |
| JP | 06-001720 | A | 1/1994 |
| JP | 8-311321 | A | 11/1996 |
| JP | 9-124918 | A | 5/1997 |
| JP | 2003-221398 | A * | 8/2003 |
| JP | 2004-043446 | A | 2/2004 |
| WO | WO 91/00257 | A1 | 1/1991 |
| WO | WO 91/07087 | A1 | 5/1991 |
| WO | WO 92/09690 | A2 | 6/1992 |
| WO | WO 92/10092 | A1 | 6/1992 |
| WO | WO 92/15694 | A1 | 9/1992 |
| WO | WO 93/05807 | A2 | 4/1993 |
| WO | WO 93/07148 | A1 | 4/1993 |
| WO | WO 93/07867 | A1 | 4/1993 |
| WO | WO 93/09668 | A1 | 5/1993 |
| WO | WO 93/19778 | A1 | 10/1993 |
| WO | WO 93/20242 | A1 | 10/1993 |
| WO | WO 94/08051 | A1 | 4/1994 |
| WO | WO 94/10300 | A1 | 5/1994 |
| WO | WO 97/11366 | A1 | 3/1997 |
| WO | WO 97/35990 | A2 | 10/1997 |
| WO | WO 98/16830 | A2 | 4/1998 |
| WO | WO 98/47869 | A1 | 10/1998 |
| WO | WO 98/55449 | A1 | 12/1998 |
| WO | WO 00/20415 | A1 | 4/2000 |
| WO | WO 00/34313 | A1 | 6/2000 |
| WO | WO 00/35911 | A1 | 6/2000 |
| WO | WO 00/36132 | A1 | 6/2000 |
| WO | WO 00/44709 | A2 | 8/2000 |
| WO | WO 02/22577 | A2 | 3/2002 |
| WO | WO 02/089782 | A2 | 11/2002 |

(56) References Cited

FOREIGN PATENT DOCUMENTS

| WO | WO 04/001059 A2 | 12/2003 |
|---|---|---|
| WO | WO 2004/046104 A2 | 6/2004 |
| WO | WO 2004/062601 A2 | 7/2004 |
| WO | WO 2004/103369 A1 | 12/2004 |
| WO | WO 2005/007091 A2 | 1/2005 |
| WO | WO 2005/012247 A1 | 2/2005 |
| WO | WO 2005/018578 A2 | 3/2005 |
| WO | WO 2005/058803 A1 | 6/2005 |
| WO | WO 2005/066151 A2 | 7/2005 |
| WO | WO 2005/080335 A1 | 9/2005 |
| WO | WO 2006/060676 A1 | 6/2006 |
| WO | WO 2006/060809 A2 | 6/2006 |
| WO | WO 2007/111948 A2 | 10/2007 |
| WO | WO 2008/040934 A1 | 4/2008 |
| WO | WO 2009/063054 A1 | 5/2009 |

OTHER PUBLICATIONS

Extended European Search Report for EP 12150229.8, mailed Jul. 31, 2012.
Office Communication, mailed Feb. 13, 2013, for U.S. Appl. No. 13/550,110.
Notice of Allowance, mailed Jan. 22, 2013, for U.S. Appl. No. 13/055,241.
Notice of Allowance, mailed Jul. 2, 2012, for U.S. Appl. No. 12/299,430.
Notice of Allowance, mailed Nov. 30, 2012, for U.S. Appl. No. 10/919,217.
Office Communication, mailed May 6, 2013, for U.S. Appl. No. 12/196,946.
Notice of Allowance, mailed Sep. 21, 2012, for U.S. Appl. No. 13/030,086.
Notice of Allowance, mailed Aug. 13, 2012, for U.S. Appl. No. 13/221,602.
Notice of Allowance, mailed Aug. 13, 2012, for U.S. Appl. No. 13/221,561.
Office Communication, mailed Oct. 16, 2012, for U.S. Appl. No. 13/566,803.
Notice of Allowance, mailed Jan. 30, 2013, for U.S. Appl. No. 13/566,803.
Office Communication, mailed Sep. 27, 2012, for U.S. Appl. No. 13/324,036.
Notice of Allowance, mailed Jan. 9, 2013, for U.S. Appl. No. 13/324,036.
CAS Registry File RN 456-07-05, STN Entry Date: Nov. 16, 1984.
[No Author Listed] TopoTarget. Executive Informational Overview. Jan. 26, 2005. 52 pages.
Dessolin et al., No. 454. Réactivité des acides hydroxamiques vis-à-vis d'esters activés. Étude cinétique. Bull Soc Chim Fr. 1970;7:2573-80.
Hearn et al., Palindromic dihydrazones from N-aminophthalimide. J Chem Eng Data. 1986;31(2):255-256.
Hostein et al., Inhibition of signal transduction by the Hsp90 inhibitor 17-allylamino-17-demethoxygeldanamycin results in cytostasis and apoptosis. Cancer Res. May 15, 2001;61(10):4003-9.
Kelly et al., Phase I clinical trial of histone deacetylase inhibitor: suberoylanilide hydroxamic acid administered intravenously. Clin Cancer Res. Sep. 1, 2003;9(10 Pt 1):3578-88.
Lin et al., Combination of proteasome and HDAC inhibitors for uterine cervical cancer treatment.Clin Cancer Res. Jan. 15, 2009;15(2):570-7.
Saikachi et al., Synthesis of Furan Derivatives. XV. 5-Nitrofuryl Polyene Aldehydes. J Am Chem Soc. 1958;80:3642-45.
Tan et al., Novel histone deacetylase inhibitors in clinical trials as anti-cancer agents. J Hematol Oncol. Feb. 4, 2010;3:5. doi: 10.1186/1756-8722-3-5. 13 pages.
International Search Report and Written Opinion for PCT/US2010/002220 mailed Apr. 27, 2011.
International Preliminary Report on Patentability for PCT/US2010/002220 mailed Feb. 23, 2012.
Extended European Search Report for EP 07872648.6 mailed Apr. 13, 2011.
Invitation to Pay Additional Fees for PCT/US2007/062145 mailed Oct. 29, 2007.
International Search Report and Written Opinion for PCT/US2007/062145 mailed Jun. 24, 2008.
International Preliminary Report on Patentability for PCT/US2007/062145 mailed Aug. 28, 2008.
Extended European Search Report for EP 07757000.0 mailed May 3, 2011.
Invitation to Pay Additional Fees for PCT/US2007/062152 mailed Dec. 7, 2007.
International Search Report and Written Opinion for PCT/US2007/062152 mailed Oct. 7, 2008.
International Search Report and Written Opinion for PCT/US2007/062152 mailed Oct. 14, 2008.
International Preliminary Report on Patentability for PCT/US2007/062152 mailed Mar. 19, 2009.
Extended European Search Report for EP 09800666.1 mailed Aug. 24, 2011.
International Search Report and Written Opinion for PCT/US2009/004235 mailed Mar. 4, 2010.
International Preliminary Report on Patentability for PCT/US2009/004235 mailed Feb. 3, 2011.
Supplementary European Search Report for EP 06748614.2 mailed Oct. 16, 2009.
International Search Report and Written Opinion for PCT/US2006/010676 mailed Jul. 14, 2008.
International Preliminary Report on Patentability for PCT/US2006/010676 mailed Mar. 19, 2009.
Extended European Search Report for EP 07776589.9 mailed Jun. 1, 2012.
International Search Report and Written Opinion for PCT/US2007/010587 mailed Jan. 29, 2008.
International Preliminary Report on Patentability for PCT/US2007/010587 mailed Nov. 13, 2008.
International Search Report for PCT/US2002/014835 mailed Dec. 20, 2002.
Written Opinion for PCT/US2002/014835 mailed Aug. 8, 2003.
International Preliminary Exam Report for PCT/US2002/014835 mailed Jun. 4, 2004.
Invitation to Pay Additional Fees for PCT/US1997/005275 mailed Nov. 21, 1997.
International Search Report for PCT/US1997/005275 mailed Feb. 16, 1998.
Written Opinion for PCT/US1997/005275 mailed Mar. 5, 1998.
International Preliminary Examination Report for PCT/US1997/005275 mailed Jul. 3, 1998.
Office Communication, mailed Jun. 20, 2011, for U.S. Appl. No. 12/279,440.
Office Communication, mailed Sep. 29, 2011, for U.S. Appl. No. 12/279,440.
Notice of Allowance, mailed Mar. 13, 2012, for U.S. Appl. No. 12/279,440.
Office Communication, mailed Dec. 21, 2011, for U.S. Appl. No. 12/279,398.
Office Communication, mailed Oct. 15, 2008, for U.S. Appl. No. 11/386,959.
Office Communication, mailed Jul. 21, 2009, for U.S. Appl. No. 11/386,959.
Advisory Action, mailed Nov. 17, 2009, for U.S. Appl. No. 11/386,959.
Office Communication, mailed Nov. 29, 2011, for U.S. Appl. No. 12/299,430.
Office Communication, mailed Mar. 21, 2012, for U.S. Appl. No. 12/299,430.
Office Communication, mailed Nov. 28, 2005, for U.S. Appl. No. 10/621,276.
Office Communication, mailed Aug. 8, 2006, for U.S. Appl. No. 10/621,276.
Notice of Allowance, mailed Mar. 6, 2007, for U.S. Appl. No. 10/621,276.

(56) References Cited

OTHER PUBLICATIONS

Office Communication, mailed Sep. 16, 2009, for U.S. Appl. No. 11/879,466.
Notice of Allowance, mailed Feb. 4, 2010, for U.S. Appl. No. 11/879,466.
Notice of Allowance, mailed Jan. 17, 2012, for U.S. Appl. No. 11/879,466.
Office Communication, mailed Jan. 21, 1998, for U.S. Appl. No. 08/624,735.
Office Communication, mailed Jan. 17, 2001, for U.S. Appl. No. 08/624,735.
Office Communication, mailed Oct. 10, 2001, for U.S. Appl. No. 08/624,735.
Office Communication, mailed Oct. 16, 2002, for U.S. Appl. No. 08/624,735.
Office Communication, mailed Aug. 12, 2003, for U.S. Appl. No. 08/624,735.
Notice of Allowance, mailed Apr. 13, 2004, for U.S. Appl. No. 08/624,735.
Office Communication, mailed May 6, 2009, for U.S. Appl. No. 10/919,217.
Office Communication, mailed Mar. 4, 2010, for U.S. Appl. No. 10/919,217.
Office Communication, mailed Oct. 14, 2010, for U.S. Appl. No. 10/919,217.
Office Communication, mailed Nov. 23, 2011, for U.S. Appl. No. 10/919,217.
Office Communication, mailed Apr. 8, 2010, for U.S. Appl. No. 12/196,878.
Office Communication, mailed Aug. 10, 2010, for U.S. Appl. No. 12/196,878.
Office Communication, mailed Jan. 18, 2011, for U.S. Appl. No. 12/196,878.
Notice of Allowance, mailed Jun. 8, 2011, for U.S. Appl. No. 12/196,878.
Office Communication, mailed Aug. 5, 2010, for U.S. Appl. No. 12/196,946
Office Communication, mailed Dec. 28, 2010, for U.S. Appl. No. 12/196,946.
Advisory Action, mailed Apr. 14, 2011, for U.S. Appl. No. 12/196,946.
Office Communication, mailed Sep. 23, 2011, for U.S. Appl. No. 13/030,086.
Office Communication, mailed Feb. 24, 2012, for U.S. Appl. No. 13/030,086.
Office Communication, mailed May 1, 2012, for U.S. Appl. No. 13/221,602.
Office Communication, mailed May 1, 2012, for U.S. Appl. No. 13/221,561.
Office Communication, mailed Jun. 30, 2003, for U.S. Appl. No. 09/800,187.
Office Communication, mailed Apr. 13, 2004, for U.S. Appl. No. 09/800,187.
Notice of Allowance, mailed Apr. 13, 2007, for U.S. Appl. No. 10/964,313.
Office Communication, mailed Sep. 17, 2009, for U.S. Appl. No. 11/831,303.
Office Communication, mailed Apr. 2, 2010, for U.S. Appl. No. 12/370,390.
Office Communication, mailed Oct. 8, 2010, for U.S. Appl. No. 12/370,390.
Office Communication, mailed Apr. 28, 2011, for U.S. Appl. No. 12/370,390.
Notice of Allowance, mailed Aug. 17, 2011, for U.S. Appl. No. 12/370,390.
Office Communication, mailed Apr. 24, 2012, for U.S. Appl. No. 13/324,036.
CAS Registry File RN 505-22-6, STN Entry Date: Nov. 16, 1984.
GENBANK Submission: NIH/NCBI, Accession No. AAA68286; GI: 348052, Henkin et al., Jun. 14, 1995.
GENBANK Submission: NIH/NCBI, Accession No. AAD29046, Grozinger et al.; May 6, 1999.
GENBANK Submission: NIH/NCBI, Accession No. AAD29048, Grozinger et al.; May 6, 1999.
GENBANK Submission: NIH/NCBI, Accession No. AAF73428, Buggy et al.; Jun. 1, 2000.
GENBANK Submission: NIH/NCBI, Accession No. AAP63491; Kieliszewski; Jun. 12, 2003.
GENBANK Submission: NIH/NCBI, Accession No. AC_000143, Levy et al.; Jul. 29, 2011.
GENBANK Submission: NIH/NCBI, Accession No. AC_000144, Levy et al.; Jul. 29, 2011.
GENBANK Submission: NIH/NCBI, Accession No. AC_000149, Levy et al.; Jul. 29, 2011.
GENBANK Submission: NIH/NCBI, Accession No. AC_000151, Levy et al.; Jul. 29, 2011.
GENBANK Submission: NIH/NCBI, Accession No. AC000054, Burian et al.; Jul. 29, 2009.
GENBANK Submission; NIH/NCBI, Accession No. AF039241, Swensen.; Mar. 11, 2009.
GENBANK Submission; NIH/NCBI, Accession No. AF132607, Grozinger et al.; May 6, 1999.
GENBANK Submission; NIH/NCBI, Accession No. AF132608, Grozinger et al.; May 6, 1999.
GENBANK Submission; NIH/NCBI, Accession No. AF132609, Grozinger et al.; May 6, 1999.
GENBANK Submission; NIH/NCBI, Accession No. AF230097, Hu et al., May 31, 2000.
GENBANK Submission; NIH/NCBI, Accession No. AF245664, Buggy et al.; Jun. 1, 2000.
GENBANK Submission; NIH/NCBI, Accession No. AJ011972, Strom et al.; Oct. 19, 1998.
GENBANK Submission: NIH/NCBI, Accession No. AK290716, Wakamatsu et al.; Jan. 9, 2008.
GENBANK Submission: NIH/NCBI, Accession No. AM270988, Pel et al.; Jun. 30, 2009.
GENBANK Submission: NIH/NCBI, Accession No. AM270990, Pel et al.; Jun. 30, 2009.
GENBANK Submission; NIH/NCBI, Accession No. AB006626; GI:2564323, Ohara et al.; Mar. 18, 1998.
GENBANK Submission; NIH/NCBI, Accession No. AB006626; GI:6635126, Ohara et al.; Dec. 25, 1999.
GENBANK Submission: NIH/NCBI, Accession No. BAA22957; GI:2564324; Ohara et al., Mar. 18, 1998.
GENBANK Submission: NIH/NCBI, Accession No. BAA22957; GI:6635127; Ohara et al., Dec. 25, 1999.
GENBANK Submission: NIH/NCBI, Accession No. BAA25526; GI: 3043724, Ohara et al., Apr. 10, 1998.
GENBANK Submission: NIH/NCBI, Accession No. BC009676, Strausberg et al.; Jul. 15, 2006.
GENBANK Submission: NIH/NCBI, Accession No. BC012499, Strausberg et al.; Oct. 7, 2003.
GENBANK Submission: NIH/NCBI, Accession No. BC111735, Strausberg et al.; Jan. 17, 2006.
GENBANK Submission; NIH/NCBI, Accession No. CAA09893.1, Strom et al.; Oct. 7, 2008.
GENBANK Submission: NIH/NCBI, Accession No. CM000257, Venter et al.; Jun. 29, 2009.
GENBANK Submission: NIH/NCBI, Accession No. CM000261, Venter et al.; Jun. 29, 2009.
GENBANK Submission: NIH/NCBI, Accession No. CM000262, Venter et al.; Jun. 29, 2009.
GENBANK Submission: NIH/NCBI, Accession No. CM000263, Venter et al.; Jun. 29, 2009.
GENBANK Submission: NIH/NCBI, Accession No. CM000270, Venter et al.; Jun. 29, 2009.
GENBANK Submission: NIH/NCBI, Accession No. CM000663, Lander et al.; Jun. 29, 2009.
GENBANK Submission: NIH/NCBI, Accession No. CU678487, Rual et al.; Feb. 19, 2008.
GENBANK Submission: NIH/NCBI, Accession No. GL000006, Lander et al.; Jun. 29, 2009.

(56) References Cited

OTHER PUBLICATIONS

GENBANK Submission: NIH/NCBI, Accession No. GL000052, Lander et al.; Jun. 29, 2009.
GENBANK Submission: NIH/NCBI, Accession No. GL000099, Lander et al.; Jun. 29, 2009.
GENBANK Submission: NIH/NCBI, Accession No. NC_000011, Taylor et al.; Jul. 29, 2011.
GENBANK Submission: NIH/NCNI, Accession No. NC_000012, Scherer et al.; Jul. 29, 2011.
GENBANK Submission: NIH/NCBI, Accession No. NC_000017, Zody et al.; Jul. 29, 2011.
GENBANK Submission: NIH/NCBI, Accession No. NC_000019, Grimwood et al.; Jul. 29, 2011.
GENBANK Submission: NIH/NCBI, Accession No. NM_001098202, Boulay et al.; Apr. 22, 2012.
GENBANK Submission: NIH/NCBI, Accession No. NM_003173, Syreeni et al.; Apr. 28, 2012.
GENBANK Submission: NIH/NCBI, Accession No. NM_006497, Boulay et al.; Apr. 22, 2012.
GENBANK Submission: NIH/NCBI, Accession No. NM_012237, Krishnan et al.; Apr. 29, 2012.
GENBANK Submission: NIH/NCBI, Accession No. NM_030593, Krishnan et al.; Apr. 29, 2012.
GENBANK Submission: NIH/NCBI, Accession No. NM_033331, Peddibhotla et al.; Apr. 22, 2012.
GENBANK Submission; NIH/NCBI, Accession No. NM_001015053.1, Seo et al.; Mar. 15, 2009.
GENBANK Submission: NIH/NCBI, Accession No. NM_006037.3, Chabane et al.; Mar. 29, 2009.
GENBANK Submission; NIH/NCBI, Accession No. NM_006044.2, Dhakal et al.; Mar. 15, 2009.
GENBANK Submission; NIH/NCBI, Accession No. NM_014707, Muralidhar et al.; Mar. 11, 2011.
GENBANK Submission; NIH/NCBI, Accession No. NM_018486, Bailey et al.; Mar. 11, 2011.
GENBANK Submission; NIH/NCBI, Accession No. NM_032019, Bailey et al.; Mar. 12, 2011.
GENBANK Submission; NIH/NCBI, Accession No. NM_058176, Muralidhar et al.; Feb. 27, 2011.
GENBANK Submission; NIH/NCBI, Accession No. NM_058177, Tam et al.; May 7, 2010.
GENBANK Submission; NIH/NCBI, Accession No. NM_178423, Muralidhar et al.; Mar. 13, 2011.
GENBANK Submission; NIH/NCBI, Accession No. NM_178425, Muralidhar et al.; Feb. 27, 2011.
GENBANK Submission; NIH/NCBI, Accession No. NP_001518, Campos et al.; Mar. 13, 2011.
GENBANK Submission; NIH/NCBI, Accession No. NP_004955, Dong et al; Mar. 27, 2011.
GENBANK Submission; NIH/NCBI, Accession No. NP_005465, Huynh; Mar. 11, 2011.
GENBANK Submission; NIH/NCBI, Accession No. NP_006035; Aldana-Masangkay et al.; Mar. 13, 2011.
GENBANK Submission; NIH/NCBI, Accession No. NT_009775, Scherer et al.; Jul. 29, 2011.
GENBANK Submission; NIH/NCBI, Accession No. NT_010663, Zody et al.; Jul. 29, 2011.
GENBANK Submission: NIH/NCBI, Accession No. NT_166525, Pel; Jun. 1, 2011.
GENBANK Submission: NIH/NCBI, Accession No. NW_001838015, Levy et al.; Jul. 29, 2011.
GENBANK Submission: NIH/NCBI, Accession No. NW_001838459, Levy et al.; Jul. 29, 2011.
GENBANK Submission: NIH/NCBI, Accession No. NW_001838477, Levy et al.; Jul. 29, 2011.
GENBANK Submission; NIH/NCBI, Accession No. O15739, Loomis et al.; Oct. 31, 2006.
GENBANK Submission: NIH/NCBI, Accession No. P56524; GI: 3024889, Ohara et al., Dec. 15, 1998.
GENBANK Submission: NIH/NCBI, Accession No. Q48935; GI.: 3023317, Sakurada et al., Apr. 20, 2010.
GENBANK Submission; NIH/NCBI, Accession No. Q9Z2V5, Verdel et al.; Mar. 2, 2010.
GENBANK Submission; NIH/NCBI, Accession No. Q9Z2V6, Verdel et al.; Mar. 2, 2010.
GENBANK Submission; NIH/NCBI, Accession No. R64669, Wilson; May 26, 1995.
GENBANK Submission; NIH/NCBI, Accession No. U31814, Yang et al.; Nov. 13, 1996.
GENBANK Submission; NIH/NCBI, Accession No. U31814, Yang et al.; Nov. 14, 1996.
NCBI annotation project, GenBank Accession No. XM_002252, Oct. 16, 2001.
NCBI annotation project, GenBank Accession No. XM_004963, Feb. 9, 2001.
NCBI annotation project, GenBank Accession No. XM_004963.2, Oct. 16, 2001.
NCBI annotation project, GenBank Accession No. XM_007047, Nov. 16, 2000.
NCBI annotation project, GenBank Accession No. XM_008359, Oct. 16, 2001.
NCBI annotation project, GenBank Accession No. XP_002252, Oct. 16, 2001.
NCBI annotation project, GenBank Accession No. XP_008359.2, Feb. 10, 2001.
UniProtKB/Swiss-Prot; Accession No. A8K8P3; Jun. 13, 2012.
UniProtKB/Swiss-Prot; Accession No. O15379; Yang et al.; Apr. 18, 2012.
UniProtKB/Swiss-Prot; Accession No. Q13547; Taunton et al.; Apr. 18, 2012.
UniProtKB/Swiss-Prot; Accession No. Q8WU14; Strausberg et al.; Oct. 31, 2006.
UniProtKB/Swiss-Prot; Accession No. Q92769; Yang et al.; Apr. 18, 2012.
UniProtKB/Swiss-Prot; Accession No. Q9BY41; Hu et al.; Apr. 18, 2012.
UniProtKB/Swiss-Prot; Accession No. Q9UBN7; Grozinger et al.; Apr. 18, 2012.
UniProtKB/Swiss-Prot; Accession No. Q9UQL6; Grozinger et al.; Apr. 18, 2012.
[No Author Listed] Inhibitor. Available at http://www.biology-online.org/dictionary/inhibitor. Last accessed Apr. 6, 2011. 1 page.
[No Author Listed] Targeting the aggresome with an HDAC6 inhibitor in combination with velcade for myeloma therapy. Cancer Biology and Therapy. 2005;4(7):i-iv.
Abremski et al., Bacteriophage P1 site-specific recombination. Purification and properties of the Cre recombinase protein. J Biol Chem. Feb. 10, 1984;259(3):1509-14.
Adams et al., Initial assessment of human gene diversity and expression patterns based upon 83 million nucleotides of cDNA sequence. Nature. Sep. 28, 1995;377(6547 Suppl):3-174.
Adams, The proteasome: a suitable antineoplastic target. Nat Rev Cancer. May 2004;4(5):349-60.
Afshar et al., Characterization of a human gene with sequence homology to *Saccharomyces cerevisiae* SIR2. Gene. Jun. 24, 1999;234(1):161-8.
Aggarwal et al., Trifluoromethanesulfonic Acid, an Efficient Catalyst for the Hetero Diels-Alder Reaction and an Improved Synthesis of Mefrosol. Tetrahedron Letters. 1997;38:2569-72.
Ahringer, NuRD and SIN3 histone deacetylase complexes in development. Trends Genet. Aug. 2000;16(8):351-6.
Alonso et al., A novel yeast histone deacetylase: partial characterization and development of an activity assay. Biochim Biophys Acta. Mar. 26, 1986;866(2-3):161-9.
Anderson et al., Analytical Techniques in Combinatorial Chemistry: MAS CH Correlation in Solvent-Swollen Resin. J Org Chem. 1995;60:2650-51.
Andrews et al., Anti-malarial effect of histone deacetylation inhibitors and mammalian tumour cytodifferentiating agents. Int J Parasitol. May 2000;30(6):761-8.

(56) References Cited

OTHER PUBLICATIONS

Anklesaria et al., Engraftment of a clonal bone marrow stromal cell line in vivo stimulates hematopoietic recovery from total body irradiation. Proc Natl Acad Sci U S A. Nov. 1987;84(21):7681-5.

Antón et al., Intracellular localization of proteasomal degradation of a viral antigen, J Cell Biol. Jul. 12, 1999;146(1):113-24.

Antonjuk et al., Asymmetric Induction in the Additions of Anions of Allylic Sulfoxides to Benzaldehyde. Aust J Chem. 1980;33:2635-51.

Aparicio et al., Modifiers of position effect are shared between telomeric and silent mating-type loci in *S. cerevisiae*. Cell. Sep. 20, 1991;66(6):1279-87.

Arkin et al., An algorithm for protein engineering: simulations of recursive ensemble mutagenesis. Proc Natl Acad Sci U S A. Aug. 15, 1992;89(16):7811-5.

Attal et al., Single versus double autologous stem-cell transplantation for multiple myeloma. N Engl J Med. Dec. 25, 2003;349(26):2495-502.

Auffray et al., [IMAGE: molecular integration of the analysis of the human genome and its expression.] C R Acad Sci III. Feb. 1995;318(2):263-72. French.

Baer et al., Eukaryotic RNA polymerase II binds to nucleosome cores from transcribed genes. Nature. Feb. 10, 1983;301(5900):482-8.

Baldwin et al., Total Synthesis of Antitumor Agent At-125-(Aphas, 5S)-Alpha-Amino-3-Chloro-4,5-Isoxazoleacetic Acid. Tetrahedron. 1985;41(22):5241-60.

Ballestar et al., Methyl-CpG-binding proteins. Targeting specific gene repression. Eur J Biochem. Jan. 2001;268(1):1-6.

Barbas et al., Semisynthetic combinatorial antibody libraries: a chemical solution to the diversity problem. Proc Natl Acad Sci U S A. May 15, 1992;89(10):4457-61.

Bartel et al., Elimination of false positives that arise in using the two-hybrid system. Biotechniques. Jun. 1993;14(6):920-4.

Beck-Sickinger et al., Neuropeptide Y: identification of the binding site. Int J Pept Protein Res. Dec. 1990;36(6):522-30.

Beck-Sickinger et al., Semiautomated T-bag peptide synthesis using 9-fluorenyl-methoxycarbonyl strategy and benzotriazol-1-yl-tetramethyl-uronium tetrafluoroborate activation. Pept Res. Mar.-Apr. 1991;4(2):88-94.

Beck-Sickinger et al., Structure/activity relationships of C-terminal neuropeptide Y peptide segments and analogues composed of sequence 1-4 linked to 25-36. Eur J Biochem. Dec. 12, 1990;194(2):449-56.

Ben-Bassat et al., Processing of the initiation methionine from proteins: properties of the *Escherichia coli* methionine aminopeptidase and its gene structure. J Bacteriol. Feb. 1987;169(2):751-7.

Bennett et al., Global impairment of the ubiquitin-proteasome system by nuclear or cytoplasmic protein aggregates precedes inclusion body formation. Mol Cell. Feb. 4, 2005;17(3):351-65.

Berenbaum et al., What is synergy? Pharmacol Rev. Jun. 1989;41(2):93-141.

Berg et al., Long-Chain Polystyrene-Grafted Polyethylene Film Matrix: A New Support for Solid-Phase Peptide Synthesis. J Am Chem Soc. 1989;111:8024-26.

Berge et al., Pharmaceutical salts. J Pharm Sci. Jan. 1977;66(1):1-19.

Bernstein et al., Genomewide studies of histone deacetylase function in yeast. Proc Natl Acad Sci U S A. Dec. 5, 2000;97(25):13708-13.

Blackwell et al., A one-bead, one-stock solution approach to chemical genetics: part 1. Chem Biol. Dec. 2001;8(12):1167-82.

Blankemeyer-Menge et al., Simultaneous Multiple Synthesis of Protected Peptide Fragments on "Allyl"-Functionalized Cellulose Disc Supports. Tetrahedron Lett. 1988;29:5871-74.

Blondelle et al., Soluble combinatorial libraries of organic, peptidomimetic and peptide diversities. Trends Anal Chem. 1995;14:83-92.

Bolden et al., Anticancer activities of histone deacetylase inhibitorsNat Rev Drug Discov. Sep. 2006;5(9):769-84.

Bolger et al., Intracellular trafficking of histone deacetylase 4 regulates neuronal cell death. J Neurosci. Oct. 12, 2005;25(41):9544-53.

Borchardt et al., Synthetic Receptor Binding Elucidated with an Encoded Combinatorial Library. J Am Chem Soc. 1994;116:373-74.

Bottomley et al., Structural and functional analysis of the human HDAC4 catalytic domain reveals a regulatory structural zinc-binding domain. J Biol Chem. Sep. 26, 2008;283(39):26694-704. Epub Jul. 8, 2008.

Bowdish et al., Analysis of RIM11, a yeast protein kinase that phosphorylates the meiotic activator IME1. Mol Cell Biol. Dec. 1994;14(12):7909-19.

Bowdish et al., Bipartite structure of an early meiotic upstream activation sequence from *Saccharomyces cerevisiae*. Mol Cell Biol. Apr. 1993;13(4):2172-81.

Bowers et al., Synthesis and Conformation-Activity Relationships of the Peptide Isosteres of FK228 and Largazole. J Am Chem Soc. 2009;131:2900-05.

Bowers et al., Total synthesis and biological mode of action of largazole: a potent class I histone deacetylase inhibitor. J Am Chem Soc. Aug. 20, 2008;130(33):11219-22. Epub Jul. 19, 2008.

Brachman et al., The SIR2 gene family, conserved from bacteria to humans, functions in silencing, cell cycle progression, and chromosome stability. Genes Dev. Dec. 1, 1995;9(23):2888-902.

Bradley et al., Formation of germ-line chimaeras from embryo-derived teratocarcinoma cell lines. Nature. May 17-23, 1984;309(5965):255-6.

Bradner et al., Chemical phylogenetics of histone deacetylases. Nat Chem Biol. Mar. 2010;6(3):238-243. Epub Feb. 7, 2010.

Branden et al., Chapter 16. Prediction, Engineering, and Design of Protein Structures. In: Introduction to Protein Structure. Garland Publishing Inc., New York. 1991:247.

Braunstein et al., Efficient transcriptional silencing in *Saccharomyces cerevisiae* requires a heterochromatin histone acetylation pattern. Mol Cell Biol. Aug. 1996;16(8):4349-56.

Braunstein et al., Transcriptional silencing in yeast is associated with reduced nucleosome acetylation. Genes Dev. Apr. 1993;7(4):592-604.

Bray et al., Gas Phase Cleavage of Peptides from a Solid Support with Ammonia Vapour. Application in Simultaneous Multiple Peptide Synthesis. Tetrahedron Lett. 1991;32:6163-66.

Bray et al., The Simultaneous Multiple Production of Solution Phase Peptides; Assessment of the Geysen Method of Simultaneous Peptide Synthesis. Tetrahedron Lett. 1990;31:5811-14.

Brenner et al., Encoded combinatorial chemistry. Proc Natl Acad Sci U S A. Jun. 15, 1992;89(12):5381-3.

Breslow et al., Potent cytodifferentiating agents related to hexamethylenebisacetamide. Proc Natl Acad Sci U S A. Jul. 1, 1991;88(13):5542-6.

Brinster et al., Factors affecting the efficiency of introducing foreign DNA into mice by microinjecting eggs. Proc Natl Acad Sci U S A. Jul. 1985;82(13):4438-42.

Brownell et al., Tetrahymena histone acetyltransferase A: a homolog to yeast Gcn5p linking histone acetylation to gene activation. Cell. Mar. 22, 1996;84(6):843-51.

Brummel et al., A mass spectrometric solution to the address problem of combinatorial libraries. Science. Apr. 15, 1994;264(5157):399-402.

Brunet et al., Nuclear translocation of p42/p44 mitogen-activated protein kinase is required for growth factor-induced gene expression and cell cycle entry. EMBO J. Feb. 1, 1999;18(3):664-74.

Buiting et al., Detection of aberrant DNA methylation in unique Prader-Willi syndrome patients and its diagnostic implications. Hum Mol Genet. Jun. 1994;3(6):893-5.

Bundgaard, Chapter 1. Design of prodrugs: Bioreversible derivatives for various functional groups and chemical entities. In: Design of Prodrugs. Elsevier. 1985:1-3.

Burbaum et al., A paradigm for drug discovery employing encoded combinatorial libraries. Proc Natl Acad Sci U S A. Jun. 20, 1995;92(13):6027-31.

Burbelo et al., 14-3-3 proteins. Hot numbers in signal transduction. Curr Biol. Feb. 1, 1995;5(2):95-6.

Byrd et al., Depsipeptide (FR901228): a novel therapeutic agent with selective, in vitro activity against human B-cell chronic lymphocytic leukemia cells. Blood. Aug. 15, 1999;94(4):1401-8.

Calí et al., Nucleotide sequence of a cDNA encoding the human muscle-specific enolase (MSE). Nucleic Acids Res. Apr. 11, 1990;18(7):1893.

(56) References Cited

OTHER PUBLICATIONS

Cameron, Recent advances in transgenic technology. Mol Biotechnol. Jun. 1997;7(3):253-65.
Carmen et al., HDA1 and HDA3 are components of a yeast histone deacetylase (HDA) complex. J Biol Chem. Jun. 28, 1996;271(26):15837-44.
Carter et al., Chemotherapy of Cancer. 2nd ed. John Wiley & Sons, N.Y., N.Y., 1981:362-65.
Catley et al., NVP-LAQ824 is a potent novel histone deacetylase inhibitor with significant activity against multiple myeloma. Blood. Oct. 1, 2003;102(7):2615-22. Epub Jun. 19, 2003.
Cavenee et al., Expression of recessive alleles by chromosomal mechanisms in retinoblastoma. Nature. Oct. 27-Nov. 2, 1983;305(5937):779-84.
Chauhan et al., Blockade of Hsp27 overcomes Bortezomib/proteasome inhibitor PS-341 resistance in lymphoma cells. Cancer Res. Oct. 1, 2003;63(19):6174-7.
Chauhan et al., Hsp27 inhibits release of mitochondrial protein Smac in multiple myeloma cells and confers dexamethasone resistance. Blood. Nov. 1, 2003;102(9):3379-86. Epub Jul. 10, 2003.
Chen et al., "Analogous" Organic Synthesis of Small-Compound Libraries: Validation of Combinatorial Chemistry in Small-Molecule Synthesis. JACS. 1994;116:2661-62.
Chen et al., Gene therapy for brain tumors: regression of experimental gliomas by adenovirus-mediated gene transfer in vivo. Proc Natl Acad Sci U S A. Apr. 12, 1994;91(8):3054-7.
Chu et al., Free Solution Identification of Candidate Peptides from Combinatorial Libraries by Affinity Capillary Electrophoresis/Mass Spectrometry. J Am Chem Soc. 1995;117:5419-20.
Clackson et al., Making antibody fragments using phage display libraries. Nature. Aug. 15, 1991;352(6336):624-8.
Clemons et al., A one-bead, one-stock solution approach to chemical genetics: part 2. Chem Biol. Dec. 2001;8(12):1183-95.
Clipstone et al., Identification of calcineurin as a key signalling enzyme in T-lymphocyte activation. Nature. Jun. 25, 1992;357(6380):695-7.
Cockell et al., Nuclear compartments and gene regulation. Curr Opin Genet Dev. Apr. 1999;9(2):199-205.
Cohen et al., The histone deacetylase HDAC4 connects neural activity to muscle transcriptional reprogramming. J Biol Chem. Nov. 16, 2007;282(46):33752-9. Epub Sep. 16, 2007.
Corcoran et al., A novel action of histone deacetylase inhibitors in a protein aggresome disease model. Curr Biol. Mar. 23, 2004;14(6):488-92.
Cress et al., Histone deacetylases, transcriptional control, and cancer. J Cell Physiol. Jul. 2000;184(1):1-16.
Csordas, On the biological role of histone acetylation. Biochem J. Jan. 1, 1990;265(1):23-38.
Cuperus et al., Locus specificity determinants in the multifunctional yeast silencing protein Sir2. EMBO J. Jun. 1, 2000;19(10:2641-51.
Curtin et al., Succinimide hydroxamic acids as potent inhibitors of histone deacetylase (HDAC). Bioorg Med Chem Lett. Oct. 21, 2002;12(20):2919-23.
Cwirla et al., Peptides on phage: a vast library of peptides for identifying ligands. Proc Natl Acad Sci U S A. Aug. 1990;87(16):6378-82.
Dangond et al., Differential display cloning of a novel human histone deacetylase (HDAC3) cDNA from PHA-activated immune cells. Biochem Biophys Res Commun. Jan. 26, 1998;242(3):648-52.
Dankwardt et al., Solid-phase synthesis of di- and tripeptidic hydroxamic acids as inhibitors of procollagen C-proteinase. Bioorg Med Chem Lett. Nov. 20, 2000;10(22):2513-6.
Dann et al., Human renin: a new class of inhibitors. Biochem Biophys Res Commun. Jan. 14, 1986;134(1):71-7.
David et al., Histone deacetylase associated with mSin3A mediates repression by the acute promyelocytic leukemia-associated PLZF protein. Oncogene. May 14, 1998;16(19):2549-56.
Davie et al., Multiple functions of dynamic histone acetylation. J Cell Biochem. May, 1994;55(1):98-105.

De Ruijter et al., Histone deacetylases (HDACs): characterization of the classical HDAC family. Biochem J. Mar. 15, 2003;370(Pt 3):737-49.
Delgrave et al., Recursive ensemble mutagenesis. Protein Engineer. 1993;6(3):327-31.
Denlinger et al., Proteasome inhibition sensitizes non-small cell lung cancer to histone deacetylase inhibitor-induced apoptosis through the generation of reactive oxygen species. J Thorac Cardiovasc Surg. Nov. 2004;128(5):740-8.
Dev et al., Electrochemotherapy—a novel method of cancer treatment. Cancer Treat Rev. Jan. 1994;20(1):105-15.
Devlin et al., Random peptide libraries: a source of specific protein binding molecules. Science. Jul. 27, 1990;249(4967):404-6.
Dower et al., Chapter 28. The Search for Molecular Diversity (II): Recombinant and Synthetic Randomized Peptide Libraries. Annu Rep Med Chem. 1991;26:271-80.
Dul et al., Hsp70 and antifibrillogenic peptides promote degradation and inhibit intracellular aggregation of amyloidogenic light chains. J Cell Biol. Feb. 19, 2001;152(4):705-15.
Egner et al., Solid Phase Chemistry: Direct Monitoring by Matrix-Assisted Laser Desorption/Ionization Time of Flight Mass Spectrometry. A Tool for Combinatorial Chemistry. J Org Chem. 1995;60:2652-53.
Eichler et al., Application of Cellulose Paper as Support Material in Simultaneous Solid Phase Peptide Synthesis. Collect Czech Chem Commun. 1989;54:1746-52.
Eichler et al., Evaluation of cotton as a carrier for solid-phase peptide synthesis. Pept Res. Sep.-Oct. 1991;4(5):296-307.
Eliel et al., Conformational analysis. XX. Stereochemistry of reaction of Grignard reagents with ortho esters. Synthesis of 1,3-dioxanes with axial substituents at C-2. J Am Chem Soc. 1970;92(3):584-590.
Ellison et al., Epitope-tagged ubiquitin. A new probe for analyzing ubiquitin function. J Biol Chem. Nov. 5, 1991;266(31):21150-7.
Emiliani et al., Characterization of a human RPD3 ortholog, HDAC3. Proc Natl Acad Sci U S A. Mar. 17, 1998;95(6):2795-800.
Evans et al., An engineered poliovirus chimaera elicits broadly reactive HIV-1 neutralizing antibodies. Nature. Jun. 1, 1989;339(6223):385-8.
Evans et al., Establishment in culture of pluripotential cells from mouse embryos. Nature. Jul. 9, 1981;292(5819):154-6.
Ewenson et al., Ketomethylene pseudopeptide analogues of substance P: synthesis and biological activity. J Med Chem. Feb. 1986;29(2):295-9.
Fabian et al., A small molecule-kinase interaction map for clinical kinase inhibitors. Nat Biotechnol. Mar. 2005;23(3):329-36. Epub Feb. 13, 2005.
Fabunmi et al., Activity and regulation of the centrosome-associated proteasome. J Biol Chem. Jan. 7, 2000;275(1):409-13.
Farkas et al., A comparison between the chelating properties of some dihydroxamic acids, desferrrioxamine B and acetohydroxamic acid. Polyhedron. 1999;18(1999):2391-98.
Feling et al., Salinosporamide A: a highly cytotoxic proteasome inhibitor from a novel microbial source, a marine bacterium of the new genus *Salinospora*. Angew Chem Int Ed Engl. Jan. 20, 2003;42(3):355-7.
Felsenfeld, Chromatin as an essential part of the transcriptional mechanism. Nature. Jan. 16, 1992;355(6357):219-24.
Feng et al., Progressive sequence alignment as a prerequisite to correct phylogenetic trees. J Mol Evol. 1987;25(4):351-60.
Finnin et al., Structures of a histone deacetylase homologue bound to the TSA and SAHA inhibitors. Nature. Sep. 9, 1999;401(6749):188-93.
Fischle et al., A new family of human histone deacetylases related to *Saccharomyces cerevisiae* HDA1p. J Biol Chem. Apr. 23, 1999;274(17):11713-20.
Fitch, Distinguishing Homologous from Analogous Proteins. Syst Zool. 1970;19:99-113.
Fitch et al., High-Resolution $^1$H NMR in Solid-Phase Organic Synthesis. J Org Chem. 1994;59:7955-56.
Fleming et al., The total synthesis of ( )-trichostatin A: Some observations on the acylation and alkylation of silyl enol ethers, silyl dienol ethers and a silyl trienol ether. Tetrahedron. 1983;39:841-46.

(56) References Cited

OTHER PUBLICATIONS

Fodor et al., Light-directed, spatially addressable parallel chemical synthesis. Science. Feb. 15, 1991;251(4995):767-73.
Frank et al., Simultaneous Multiple Peptide Synthesis Under Continuous Flow Conditions on Cellulose Paper Discs as Segmental Solid Supports. Tetrahedron. 1988;44:6031-40.
Frank., Spot-Synthesis: An Easy Technique for the Positionally Addressable, Parallel Chemical Synthesis on a Membrane Support. Tetrahedron. 1992;48:9217-32.
Frank., Strategies and Techniques in Simultaneous Solid Phase Synthesis Based on the Segmentation of Membrane Type Supports. Bioorg Med Chem Lett. 1993;3:425-30.
Friend et al., Deletions of a DNA sequence in retinoblastomas and mesenchymal tumors: organization of the sequence and its encoded protein. Proc Natl Acad Sci U S A. Dec. 1987;84(24):9059-63.
Frye et al., Characterization of Five Human cDNAs with Homology to the Yeast SIR2 Gene: Sir2-like Proteins (Sirtuins) Metabolize NAD and May Have Protein ADP-Ribosyltransferase Activity. Biochem Biophys Res Commun. 1999;260:273-79.
Frye, Phylogenetic classification of prokaryotic and eukaryotic Sir2-like proteins. Biochem Biophys Res Commun. Jul. 5, 2000;273(2):793-8.
Furukawa et al., Isolation and mapping of a human gene (RPD3L1) that is homologous to RPD3, a transcription factor in *Saccharomyces cerevisiae*. Cytogenet Cell Genet. 1996;73(1-2):130-3.
Furumai et al., Potent histone deacetylase inhibitors built from trichostatin A and cyclic tetrapeptide antibiotics including trapoxin. Proc Natl Acad Sci U S A. Jan. 2, 2001;98(1):87-92.
Gallop et al., Applications of combinatorial technologies to drug discovery. 1. Background and peptide combinatorial libraries. J Med Chem. Apr. 29, 1994;37(9):1233-51.
Gammon et al., T cell determinant structure: cores and determinant envelopes in three mouse major histocompatibility complex haplotypes. J Exp Med. Mar. 1, 1991;173(3):609-17.
García-Mata et al., Characterization and dynamics of aggresome formation by a cytosolic GFP-chimera. J Cell Biol. Sep. 20, 1999;146(6):1239-54.
Garcia-Mata et al., Hassles with taking out the garbage: aggravating aggresomes. Traffic. Jun. 2002;3(6):388-96.
Garcia-Ramirez et al., Role of the histone "tails" in the folding of oligonucleosomes depleted of histone H1. J Biol Chem. Sep. 25, 1992;267(27):19587-95.
Gardlik et al., Vectors and delivery systems in gene therapy. Med Sci Monit. Apr. 2005;11(4):RA110-21. Epub Mar. 24, 2005.
Gartenberg, The Sir proteins of *Saccharomyces cerevisiae*: mediators of transcriptional silencing and much more. Curr Opin Microbiol. Apr. 2000;3(2):132-7.
Gelmetti et al., Aberrant recruitment of the nuclear receptor corepressor-histone deacetylase complex by the acute myeloid leukemia fusion partner ETO. Mol Cell Biol. Dec. 1998;18(12):7185-91.
Geysen et al., Use of peptide synthesis to probe viral antigens for epitopes to a resolution of a single amino acid. Proc Natl Acad Sci U S A. Jul. 1984;81(13):3998-4002.
Giacomelli et al., Simple one-flask method for the preparation of hydroxamic acids. Org Lett. Jul. 24, 2003;5(15):2715-7.
Gordon et al., Applications of combinatorial technologies to drug discovery. 2. Combinatorial organic synthesis, library screening strategies, and future directions. J Med Chem. May 13, 1994;37(10):1385-401.
Gordon et al., Design of peptide derived amino alcohols as transition-state analog inhibitors of angiotensin converting enzyme. Biochem Biophys Res Commun. Jan. 16, 1985;126(1):419-26.
Görlich, Nuclear protein import. Curr Opin Cell Biol. Jun. 1997;9(3):412-9.
Gossler et al., Transgenesis by means of blastocyst-derived embryonic stem cell lines. Proc Natl Acad Sci U S A. Dec. 1986;83(23):9065-9.
Goy et al., Phase II study of proteasome inhibitor bortezomib in relapsed or refractory B-cell non-Hodgkin's lymphoma. J Clin Oncol. Feb. 1, 2005;23(4):667-75. Epub Dec. 21, 2004.
Gray et al., The human histone deacetylase family. Exp Cell Res. Jan. 15, 2001;262(2):75-83.
Green, When the products of oncogenes and anti-oncogenes meet. Cell. Jan. 13, 1989;56(1):1-3.
Gregoretti et al., Molecular evolution of the histone deacetylase family: functional implications of phylogenetic analysisJ Mol Biol. Apr. 16, 2004;338(1):17-31.
Gregory et al., Combination chemotherapy versus melphalan and prednisolone in the treatment of multiple myeloma: an overview of published trials. J Clin Oncol. Feb. 1992;10(2):334-42.
Griffiths et al., Human anti-self antibodies with high specificity from phage display libraries. EMBO J. Feb. 1993;12(2):725-34.
Grignani et al., Fusion proteins of the retinoic acid receptor-alpha recruit histone deacetylase in promyelocytic leukaemia. Nature. Feb. 19, 1998;391(6669):815-8.
Grozinger et al., Deacetylase enzymes: biological functions and the use of small-molecule inhibitors. Chem Biol. Jan. 2002;9(1):3-16.
Grozinger et al., Regulation of histone deacetylase 4 and 5 and transcriptional activity by 14-3-3-dependent cellular localization. Proc Natl Acad Sci U S A. Jul. 5, 2000;97(14):7835-40.
Grozinger et al., Three proteins define a class of human histone deacetylases related to yeast Had1p. Proc Natl Acad Sci U S A. Apr. 27, 1999;96(9):4868-73.
Grunstein, Histone acetylation in chromatin structure and transcription. Nature. Sep. 25, 1997;3 89(6649):349-52.
Grunstein, Molecular model for telomeric heterochromatin in yeast. Curr Opin Cell Biol. Jun. 1997;9(3):383-7.
Gu et al., Activation of p53 sequence-specific DNA binding by acetylation of the p53 C-terminal domain. Cell. Aug. 22, 1997;90(4):595-606.
Guo et al., Protein tolerance to random amino acid change. Proc Natl Acad Sci U S A. Jun. 22, 2004;101(25):9205-10. Epub Jun. 14, 2004.
Guarente, Sir2 links chromatin silencing, metabolism, and aging. Genes Dev. May 1, 2000;14(9):1021-6.
Habig et al., Glutathione S-transferases. The first enzymatic step in mercapturic acid formation. J Biol Chem. Nov. 25, 1974;249(22):7130-9.
Haggarty et al., Dissecting cellular processes using small molecules: identification of colchicine-like, taxol-like and other small molecules that perturb mitosis. Chem Biol. Apr. 2000;7(4):275-86.
Haggarty et al., Domain-selective small-molecule inhibitor of histone deacetylase 6 (HDAC6)-mediated tubulin deacetylation. Proc Natl Acad Sci U S A. Apr. 15, 2003;100(8):4389-94. Epub Apr. 3, 2003.
Haggarty et al., Mapping chemical space using molecular descriptors and chemical genetics: deacetylase inhibitors. Comb Chem High Throughput Screen. Nov. 2004;7(7):669-76.
Haggarty et al., Multidimensional chemical genetic analysis of diversity-oriented synthesis-derived deacetylase inhibitors using cell-based assays. Chem Biol. May 2003;10(5):383-96.
Hansen et al., Retinoblastoma and the progression of tumor genetics. Trends Genet. May 1988;4(5):125-8.
Hardwick et al., Rapamycin-modulated transcription defines the subset of nutrient-sensitive signaling pathways directly controlled by the Tor proteins. Proc Natl Acad Sci U S A. Dec. 21, 1999;96(26):14866-70.
Hassig et al., A role for histone deacetylase activity in HDAC1-mediated transcriptional repression. Proc Natl Acad Sci U S A. Mar. 31, 1998;95(7):3519-24.
Hassig et al., Histone deacetylase activity is required for full transcriptional repression by mSin3A. Cell. May 2, 1997;89(3):341-7.
Hassig et al., Nuclear histone acetylases and deacetylases and transcriptional regulation: HATs off to HDACs. Curr Opin Chem Biol. Oct. 1997;1(3):300-8.
Hathaway et al., Dissecting cell biology with chemical scalpels. Curr Opin Cell Biol. Feb. 2005;17(1):12-9.
Hay et al., Histone deacetylase. Association with a nuclease resistant, high molecular weight fraction of HeLa cell chromatin. J Biol Chem. Mar. 25, 1983;258(6):3726-34.
Hayes et al., Histones H2A/H2B inhibit the interaction of transcription factor IIIA with the *Xenopus borealis* somatic 5S RNA gene in a nucleosome. Proc Natl Acad Sci U S A. Feb. 15, 1992;89(4):1229-33.

(56) References Cited

OTHER PUBLICATIONS

He et al., Distinct interactions of PML-RARalpha and PLZF-RARalpha with co-repressors determine differential responses to RA in APL. Nat Genet. Feb. 1998;18(2):126-35.
Hecht et al., Histone H3 and H4 N-termini interact with SIR3 and SIR4 proteins: a molecular model for the formation of heterochromatin in yeast. Cell. Feb. 24, 1995;80(4):583-92.
Hicks et al., Protein import into the nucleus: an integrated view. Annu Rev Cell Dev Biol. 1995;11:155-88.
Hideshima et al., Antitumor activity of lysophosphatidic acid acyltransferase-beta inhibitors, a novel class of agents, in multiple myeloma. Cancer Res. Dec. 1, 2003;63(23):8428-36.
Hideshima et al., Molecular mechanisms mediating antimyeloma activity of proteasome inhibitor PS-341. Blood. Feb. 15, 2003;101(4):1530-4. Epub Sep. 26, 2002.
Hideshima et al., Molecular mechanisms of novel therapeutic approaches for multiple myeloma. Nat Rev Cancer. Dec. 2002;2(12):927-37.
Hideshima et al., NF-κB as a therapeutic target in multiple myeloma. J Biol Chem. May 10, 2002;277(19):16639-47. Epub Feb. 28, 2002.
Hideshima et al., Novel therapeutic approaches for multiple myeloma. Immunol Rev. Aug. 2003;194:164-76.
Hideshima et al., p38 MAPK inhibition enhances PS-341 (bortezomib)-induced cytotoxicity against multiple myeloma cells. Oncogene. Nov. 18, 2004;23(54):8766-76.
Hideshima et al., Proteasome inhibitor PS-341 abrogates IL-6 triggered signaling cascades via caspase-dependent downregulation of gp130 in multiple myeloma. Oncogene. Nov. 20, 2003;22(52):8386-93.
Hideshima et al., Small-molecule inhibition of proteasome and aggresome function induces synergistic antitumor activity in multiple myeloma. Proc Natl Acad Sci U S A. Jun. 14, 2005;102(24):8567-72. Epub Jun. 3, 2005.
Hideshima et al., The proteasome inhibitor PS-341 inhibits growth, induces apoptosis, and overcomes drug resistance in human multiple myeloma cells. Cancer Res. Apr. 1, 2001;61(7):3071-6.
Hideshima et al., The role of tumor necrosis factor alpha in the pathophysiology of human multiple myeloma: therapeutic applications. Oncogene. Jul. 27, 2001;20(33):4519-27.
Hochuli et al., New metal chelate adsorbent selective for proteins and peptides containing neighbouring histidine residues. J Chromatogr. Dec. 18, 1987;411:177-84.
Houdebine, The methods to generate transgenic animals and to control transgene expression. J Biotechnol. Sep. 25, 2002;98(2-3):145-60.
Houghten, General method for the rapid solid-phase synthesis of large numbers of peptides: specificity of antigen-antibody interaction at the level of individual amino acids. Proc Natl Acad Sci U S A. Aug. 1985;82(15):5131-5.
Houghten et al., Simplified procedure for carrying out simultaneous multiple hydrogen fluoride cleavages of protected peptide resins. Int J Pept Protein Res. Jun. 1986;27(6):673-8.
Hu et al., Cloning and characterization of a novel human class I histone deacetylase that functions as a transcription repressor. J Biol Chem. May 19, 2000;275(20):15254-64.
Huang et al., Nuclear receptor corepressors partner with class II histone deacetylases in a Sin3-independent repression pathway. Genes Dev. Jan. 1, 2000;14(1):45-54.
Huang et al., Vaccinia virus recombinants expressing an 11-kilodalton beta-galactosidase fusion protein incorporate active beta-galactosidase in virus particles. J Virol. Oct. 1988;62(10):3855-61.
Hubbert et al., HDAC6 is a microtubule-associated deacetylase. Nature. May 23, 2002;417(6887):455-8.
Hunter et al., An Enantioselective Synthesis of Benzylidene-Protected syn-3,5-Dihydroxy Carboxylate Esters via Osmium, Palladium, and Base Catalysis. Org Letter. 2001;3(7):1049-52.
Hynes, Hydroxylamine derivatives as potential antimalarial agents. 1. Hydroxamic acids. J Med Chem. Nov. 1970;13(6):1235-7.

Ike et al., Solid phase synthesis of polynucleotides. VIII. Synthesis of mixed oligodeoxyribonucleotides by the phosphotriester solid phase method. Nucleic Acids Res. Jan. 25, 1983;11(2):477-88.
Imai et al., Transcriptional silencing and longevity protein Sir2 is an NAD-dependent histone deacetylase. Nature. Feb. 17, 2000;403(6771):795-800.
Imamoto et al., Preparation and Synthetic Use of Trimethylsilyl Polyphosphate. A New Stereoselective Aldol-Type Reaction in the Presence of Trimethylsilyl Polyphosphate. J Org Chem. 1984;49:1105-10.
Imamoto et al., The Reaction of Aryl Methyl Ketones with Aromatic Aldehydes in Trimethylsilyl Polyphosphate (PPSE). Formation of MESO-2,4,6-Trisubstituted-5-ACYL-1,3-Dioxl. Tetrahedron Letters. 1982;23(14):1467-70.
Imhof et al., Acetylation of general transcription factors by histone acetyltransferases. Curr Biol. Sep. 1, 1997;7(9):689-92.
Itakura et al., Expression in *Escherichia coli* of a Chemically Synthesized Gene for the Hormone Somatostatin. Science. 1984;198:1056-63.
Itakura et al., Synthesis and use of synthetic oligonucleotides. Annu Rev Biochem. 1984;53:323-56.
Iwabuchi et al., Use of the two-hybrid system to identify the domain of p53 involved in oligomerization. Oncogene. Jun. 1993;8(6):1693-6.
Jacobs et al., Combinatorial chemistry—applications of light-directed chemical synthesis. Trends Biotechnol. Jan. 1994;12(1):19-26.
Jaenisch, Germ line integration and Mendelian transmission of the exogenous Moloney leukemia virus. Proc Natl Acad Sci U S A. Apr. 1976;73(4):1260-4.
Jaenisch, Transgenic animals. Science. Jun. 10, 1988;240(4858):1468-74.
Jähner et al., De novo methylation and expression of retroviral genomes during mouse embryogenesis. Nature. Aug. 12, 1982;298(5875):623-8.
Jähner et al., Insertion of the bacterial gpt gene into the germ line of mice by retroviral infection. Proc Natl Acad Sci U S A. Oct. 1985;82(20):6927-31.
Janknecht et al., Rapid and efficient purification of native histidine-tagged protein expressed by recombinant vaccinia virus. Proc Natl Acad Sci U S A. Oct. 15, 1991;88(20):8972-6.
Jin et al., Transcriptional regulation of the MDR1 gene by histone acetyltransferase and deacetylase is mediated by NF-Y. Mol Cell Biol. Jul. 1998;18(7):4377-84.
Johnson et al., Deacetylase activity associates with topoisomerase II and is necessary for etoposide-induced apoptosis. J Biol Chem. Feb. 16, 2001;276(7):4539-42. Epub Jan. 2, 2001.
Johnson et al., Genetic evidence for an interaction between SIR3 and histone H4 in the repression of the silent mating loci in *Saccharomyces cerevisiae*. Proc Natl Acad Sci U S A. Aug. 1990;87(16):6286-90.
Johnson et al., Molecular cloning of *Drosophila melanogaster* cDNAs that encode a novel histone deacetylase dHDAC3. Gene. Oct. 9, 1998;221(1):127-34.
Johnston et al., Aggresomes: a cellular response to misfolded proteins. J Cell Biol. Dec. 28, 1998;143(7):1883-98.
Johnstone, Histone-deacetylase inhibitors: novel drugs for the treatment of cancer. Nat Rev Drug Discov. Apr. 2002;1(4):287-99.
Jones et al., Probing the elusive catalytic activity of vertebrate class IIa histone deacetylases. Bioorg Med Chem Lett. Mar. 15, 2008;18(6):1814-9. Epub Feb. 14, 2008.
Jung et al., Amide analogues of trichostatin A as inhibitors of histone deacetylase and inducers of terminal cell differentiation. J Med Chem. Nov. 4, 1999;42(22):4669-79.
Junn et al., Parkin accumulation in aggresomes due to proteasome impairment. J Biol Chem. Dec. 6, 2002;277(49):47870-7. Epub Oct. 2, 2002.
Kao et al., Isolation of a novel histone deacetylase reveals that class I and class II deacetylases promote SMRT-mediated repression. Genes Dev. Jan. 1, 2000;14(1):55-66.
Kappel et al., Regulating gene expression in transgenic animals. Curr Opin Biotechnol. Oct. 1992;3(5):548-53.

(56) References Cited

OTHER PUBLICATIONS

Katoh et al., MAFFT: a novel method for rapid multiple sequence alignment based on fast Fourier transform. Nucleic Acids Res. Jul. 15, 2002;30(14):3059-66.

Kawaguchi et al., the deacetylase HDAC6 regulates aggresome formation and cell viability in response to misfolded protein stress. Cell. Dec. 12, 2003;115(6):727-38.

Kennedy et al., Redistribution of silencing proteins from telomeres to the nucleolus is associated with extension of life span in S. cerevisiae. Cell. May 2, 1997;89(3):381-91.

Kerr et al., Encoded Combinatorial Peptide Libraries Containing Non-Natural Amino Acids. J Am Chem, Soc. 1993;115:2529-31.

Khockbin et al., Functional significance of histone deacetylase diversity. Curr Opin Genet Dev. Apr. 2001;11(2):162-6.

Khomutov et al., Directed synthesis of inhibitors of enzymic changes of glutamic acid. Doklady Akademii Nauk SSSR. 1965;161(5):1227-30. Russian.

Kijima et al., Trapoxin, an antitumor cyclic tetrapeptide, is an irreversible inhibitor of mammalian histone deacetylase. J Biol Chem. Oct. 25, 1993;268(30):22429-35.

Kikuchi et al., Multiplicity of histone deacetylase from calf thymus. FEBS Lett. Feb. 1, 1973;29(3):280-282.

Kleff et al., Identification of a gene encoding a yeast histone H4 acetyltransferase. J Biol Chem. Oct. 20, 1995;270(42):24674-7.

Koeller et al., Chemical genetic modifier screens: small molecule trichostatin suppressors as probes of intracellular histone and tubulin acetylation. Chem Biol. May 2003;10(5):397-410.

Kohler et al., Continuous cultures of fused cells secreting antibody of predefined specificity. Nature. Aug. 7, 1975;256(5517):495-7.

Kopito et al., Aggresomes and Russell bodies. Symptoms of cellular indigestion? EMBO Rep. Sep. 2000;l(3):225-31.

Kopito, Aggresomes, inclusion bodies and protein aggregation. Trends Cell Biol. Dec. 2000;10(12):524-30.

Kouzarides, Acetylation: a regulatory modification to rival phosphorylation? EMBO J. Mar. 15, 2000;19(6):1176-9.

Kozbar et al., The production of monoclonal antibodies from human lymphocytes. Immunology Today. 1983;4:72-79.

Krieger et al., Chemical studies of histone acetylation. Substrate specificity of a histone deacetylase from calf thymus nuclei. J Biol Chem. Jan. 10, 1974;249(1):332-4.

Kumar et al., MEGA: a biologist-centric software for evolutionary analysis of DNA and protein sequences. Brief Bioinform. Jul. 2008;9(4):299-306. Epub Apr. 16, 2008.

Kuruvilla et al., Dissecting glucose signaling with diversity-oriented synthesis and small-molecule microarrays. Nature. Apr. 11, 2002;416(6881):653-7.

Kwon et al., Depudecin induces morphological reversion of transformed fibroblasts via the inhibition of histone deacetylase. Proc Natl Acad Sci U S A. Mar. 31, 1998;95(7):3356-61.

Lahm et al., Unraveling the hidden catalytic activity of vertebrate class IIa histone deacetylases. Proc Natl Acad Sci U S A. Oct. 30, 2007;104(44):17335-40. Epub Oct. 23, 2007.

Lam et al., The "One-Bead-One-Compound" Combinatorial Library Method. Chem Rev. Apr. 1, 1997;97(2):411-48.

Landegren et al., A ligase-mediated gene detection technique. Science. Aug. 26, 1998;241(4869):1077-80.

Landry et al., The silencing protein SIR2 and its homologs are NAD-dependent protein deacetylases. Proc Natl Acad Sci U S A. May 23, 2000;97(11):5807-11.

Lasko et al., Targeted oncogene activation by site-specific recombination in transgenic mice. Proc Natl Acad Sci U S A. Jul. 15, 1992;89(14):6232-6.

Lee et al., A positive role for histone acetylation in transcription factor access to nucleosomal DNA. Cell. Jan. 15, 1993;72(1):73-84.

Lee et al., A Strategy for Macrocyclic Ring Closure and Functionalization Aimed toward Split-Pool Syntheses. J Am Chem Soc. 1999;121(45):10648-49.

Lee et al., Histone acetyltransferase complexes: one size doesn't fit all. Nat Rev Mol Cell Biol. Apr. 2007;8(4):284-95.

Lee et al., Proteasome inhibitors disrupt the unfolded protein response in myeloma cells. Proc Natl Acad Sci U S A. Aug. 19, 2003;100(17):9946-51. Epub Aug. 5, 2003.

Lin et al., Generation and Aldol Reaction of Endlate Anion Adjacnet to a $\eta 3$-Allyl-Mo(Co)$^2$Cp Moiety. A New Approach to the Stereoselctive Synthesis of 1,3,5-Triol and 2-Vinyl-3-Hydroxyl-Tetrahydrofuran. Tetrahedron Letters. 1990;31(52):7645-48.

Lin et al., Role of the histone deacetylase complex in acute promyelocytic leukaemia. Nature. Feb. 19, 1998;391(6669):811-4.

Lizcano et al., Cell type-specific roles of histone deacetylase in TR ligand-independent transcriptional repression. Mol Cell Endocrinol. Feb. 14, 2001;172(1-2):13-20.

Look et al., Methods for Combinatorial Organic Synthesis: The Use of Fast $^{13}$C NMR Analysis for Gel Phase Reaction Monitoring. J Org Chem. 1994;59:7588-90.

Lopez-Girona et al., Nuclear localization of Cdc25 is regulated by DNA damage and a 14-3-3 protein. Nature. Jan. 14, 1999;397(6715):. 172-5.

Luger et al., Crystal structure of the nucleosome core particle at 2.8 A resolution. Nature. Sep. 18, 1997;389(6648):251-60.

Lutterbach et al., ETO, a target of t(8;21) in acute leukemia, interacts with the N-CoR and mSin3 corepressors. Mol Cell Biol. Dec. 1998;18(12):7176-84.

MacBeath et al., Printing proteins as microarrays for high-throughput function determination. Science. Sep. 8, 2000;289(5485):1760-3.

Macherla et al., Structure-activity relationship studies of salinosporamide A (NPI-0052), a novel marine derived proteasome inhibitor. J Med Chem. Jun. 2, 2005;48(11):3684-7.

Maddry et al., Inhibition of the Her2 Tyrosine Kinase and Characterization of a Hydrophobic Site Near the Nucleotide Binding Domain. Bioorganic Med Chem Letter. 1997;7(16):2109-14.

Madura et al., N-recognin/Ubc2 interactions in the N-end rule pathway. J Biol Chem. Jun. 5, 1993;268(16):12046-54.

Maeji et al., Multi-pin peptide synthesis strategy for T cell determinant analysis. J Immunol Methods. Nov. 6, 1990;134(1):23-33.

Magnaghi-Jaulin et al., Retinoblastoma protein represses transcription by recruiting a histone deacetylase. Nature. Feb. 5, 1998;391(6667):601-4.

Mahboobi et al., Design of chimeric histone deacetylase- and tyrosine kinase-inhibitors: a series of imatinib hybrides as potent inhibitors of wild-type and mutant BCR-ABL, PDGF-Rbeta, and histone deacetylases. J Med Chem. Apr. 23, 2009;52(8):2265-79.

Mai et al., Class II (IIa)-selective histone deacetylase inhibitors. 1. Synthesis and biological evaluation of novel (aryloxopropenyl)pyrrolyl hydroxyamides. J Med Chem. May 5, 2005;48(9):3344-53.

Manetto et al., Selective presence of ubiquitin in intracellular inclusions. Am J Pathol. Mar. 1989;134(3):505-13.

Marcand et al., Silencing of genes at nontelomeric sites in yeast is controlled by sequestration of silencing factors at telomeres by Rap 1 protein. Genes Dev. Jun. 1, 1996;10(11):1297-309.

Marks et al., Histone deacetylases and cancer: causes and therapies. Nat Rev Cancer. Dec. 2001;1(3):194-202.

Marks et al., Histone deacetylases. Curr Opin Pharmacol. Aug. 2003;3(4):344-51.

Marks et al., Molecular evolution of proteins on filamentous phage. Mimicking the strategy of the immune system. J Biol Chem. Aug. 15, 1992;267(23):16007-10.

Marks et al., Polar/apolar chemical inducers of differentiation of transformed cells: strategies to improve therapeutic potential. Proc Natl Acad Sci U S A. Aug. 1989;86(16):6358-62.

Marmuse et al., "Click chemistry"en route to pseudo-starch. Org Biomol Chem. Jun. 21, 2005;3(12):2225-7. Epub May 11, 2005.

Martinelli et al., Molecular therapy for multiple myeloma. Haematologica. Sep. 2001;86(9):908-17.

Marushige et al., Template properties of liver chromatin. J Mol Biol. Jan. 1966;15(1):160-74.

Marx et al., Bench to bedside: the development of rapamycin and its application to stent restenosis. Circulation. Aug. 21, 2001;104(8):852-5.

Massa et al., Synthesis and antimicrobial and cytotoxic activities of pyrrole-containing analogues of trichostatin A. J Med Chem. Oct. 1990;33(10):2845-9.

(56) References Cited

OTHER PUBLICATIONS

McKenzie et al., the centromere and promoter factor, 1, CPF1, of *Saccharomyces cerevisiae* modulates gene activity through a family of factors including SPT21, RPD1 (SIN3), RPD3 and CCR4. Mol Gen Genet. Sep. 1993;240(3):374-86.

Megee et al., Genetic analysis of histone H4: essential role of lysines subject to reversible acetylation. Science. Feb. 16, 1990;247(4944):841-5.

Meinke et al., Histone deacetylase: a target for antiproliferative and antiprotozoal agents. Curr Med Chem. Feb. 2001;8(2):211-35.

Menger et al., Chemical Reaction between Colliding Vesicles. Chem Int Ed Engl. Oct. 15, 2001;40(20):3905-3907.

Meinke et al., Synthesis of apicidin-derived quinolone derivatives: parasite-selective histone deacetylase inhibitors and antiproliferative agents. J Med Chem. Dec. 14, 2000;43(25):4919-22.

Merrifield, Solid Phase Peptide Syntheses. I. The Synthesis of a Tetrapeptide. J Am Chem Soc. 1963;85:2149-54.

Metzger et al., Ion-Spray Mass Spectrometry and High-Performance Liquid Chromatography-Mass Spectrometry of Synthetic Peptide Libraries. Angew Chem Int Ed Engl. 1993;32:894-96.

Miano et al., HDAC7 supports vascular integrity. Nat Med. Sep. 2006;12(9):997-8.

Miller et al., Histone deacetylase inhibitors. J Med Chem. Nov. 20, 2003;46(24):5097-116.

Miller et al., N-terminal methionine-specific peptidase in *Salmonella typhimurium*. Proc Natl Acad Sci U S A. May, 1987;84(9):2718-22.

Minucci et al., Histone deacetylase inhibitors and the promise of epigenetic (and more) treatments for cancer. Nat Rev Cancer. Jan. 2006;6(1):38-51.

Miska et al., HDAC4 deacetylase associates with and represses the MEF2 transcription factor. EMBO J. Sep. 15, 1999;18(18):5099-107.

Mitchison, Towards a pharmacological genetics. Chem Biol. Sep. 1994;1(1):3-6.

Mitsiades et al., Inhibition of the insulin-like growth factor receptor-1 tyrosine kinase activity as a therapeutic strategy for multiple myeloma, other hematologic malignancies, and solid tumors. Cancer Cell. Mar. 2004;5(3):221-30.

Mitsiades et al., Molecular sequelae of histone deacetylase inhibition in human malignant B cells. Blood. May 15, 2003;101(10):4055-62. Epub Jan. 16, 2003.

Mitsiades et al., Molecular sequelae of proteasome inhibition in human multiple myeloma cells. Proc Natl Acad Sci U S A. Oct. 29, 2002;99(22):14374-9. Epub Oct. 21, 2002.

Mitsiades et al., Novel biologically based therapies for Waldenstrom's macroglobulinemia. Semin Oncol. Apr. 2003;30(2):309-12.

Mitsiades et al., The proteasome inhibitor PS-341 potentiates sensitivity of multiple myeloma cells to conventional chemotherapeutic agents: therapeutic applications. Blood. Mar. 15, 2003;101(6):2377-80. Epub Nov. 7, 2002.

Mitsiades et al., Transcriptional signature of histone deacetylase inhibition in multiple myeloma: biological and clinical implications. Proc Natl Acad Sci U S A. Jan. 13, 2004;101(2):540-5. Epub Dec. 26, 2003.

Moazed, Enzymatic activities of Sir2 and chromatin silencing. Curr Opin Cell Biol. Apr. 2001;13(2):232-8.

Mori et al., Synthesis of trichostatin A, a potent differentiation inducer of friend leukemic cells, and its antipode. Tetrahedron. 1988;44:6013-20.

Mottet et al., Histone deacetylase 7 silencing alters endothelial cell migration, a key step in angiogenesis. Circ Res. Dec. 7, 2007;101(12):1237-46. Epub Oct. 18, 2007.

Mowat et al., Rearrangements of the cellular p53 gene in erythroleukaemic cells transformed by Friend virus. Nature. Apr. 18-24, 1985;314(6012):633-6.

Mullins et al., Transgenesis in nonmurine species. Hypertension. Oct. 1993;22(4):630-3.

Munegumi et al., Amidation of carboxyl group involved in N-protected amino acids using O-benzylhydroxylamine. Peptide Chemistry. 1993;31:49-52.

Munshi et al., Acetylation of HMG I(Y) by CBP turns off IFN beta expression by disrupting the enhanceosome. Mol Cell. Oct. 1998;2(4):457-67.

Mutch et al., Effects of end groups on the stimulatory capacity of minimal length T cell determinant peptides. Pept Res. May-Jun. 1991;4(3):132-7.

Myers et al., Preparation of the Chiral, C-Protected α-Amino Aldehydes of High Optical Purity and Their Use as Condensation Components in a Linear Synthesis Strategy. J Am Chem Soc. 1999;121:8401-02.

Nagai et al., Synthesis of a Bicyclic Dipeptide with the Shape of β-Turn Central Part. Tetrahedron Lett. 1985;26:647-50.

Nagy et al., Nuclear receptor repression mediated by a complex containing SMRT, mSin3A, and histone deacetylase. Cell. May 2, 1997;89(3):373-80.

Nakatsuka et al., Total Synthesis of FK506 and an FKBP Probe Reagent, ($C_8$, $C_9$-$^{13}C_2$)-FK506. J. Am. Chem. Soc. 1990; 112: 5583-5601.

Nakazawa et al., UV and skin cancer: specific p53 gene mutation in normal skin as a biologically relevant exposure measurement. Proc Natl Acad Sci U S A. Jan. 4, 1994;91(1):360-4.

Narang, DNA Synthesis. Tetrahedron. 1983;39:3-22.

Nardelii et al., A chemically defined synthetic vaccine model for HIV-1. J Immunol. Feb. 1, 1992;148(3):914-20.

Nasmyth et al., Both positive and negative regulators of HO transcription are required for mother-cell-specific mating-type switching in yeast. Cell. Feb. 27, 1987;48(4):579-87.

Needleman et al., A general method applicable to the search for similarities in the amino acid sequence of two proteins. J Mol Biol. Mar. 1970;48(3):443-53.

Needles et al., Generation and screening of an oligonucleotide-encoded synthetic peptide library. Proc Natl Acad Sci. 1993;90:10700-04.

Neer et al., The ancient regulatory-protein family of WD-repeat proteins. Nature. Sep. 22, 1994;371(6495):297-300.

Nefzi et al., The Current Status of Heterocyclic Combinatorial Libraries. Chem Rev. Apr. 1, 1997;97(2):449-472.

Nestler et al., A General Method for Molecular Tagging of Encoded Combinatorial Chemistry Libraries. J Org Chem. 1994;59:4723-24.

Newman et al., The influence of natural products upon drug discovery. Nat Prod Rep. Jun. 2000;17(3):215-34.

Ng et al., Histone deacetylases: silencers for hire. Trends Biochem Sci. Mar. 2000;25(3):121-6.

Ngo et al., Computational complexity, protein structure prediction, and the ILeventhal paradox. In: The Protein Folding Problem and Tertiary Structure Prediction. Merz et al., eds, Birhauser, Boston, MA. 1994:433-506.

Nielsen et al., Crystal structure of a bacterial class 2 histone deacetylase homologue. J Mol Biol. Nov. 18, 2005;354(1):107-20. Epub Oct. 7, 2005.

Nielsen et al., Synthetic Methods for the Implementation of Encoded Combinatorial Chemistry. J Am Chem Soc. 1993;115:9812-13.

Nielsen et al., Toward Chemical Implementation of Encoded Combinatorial Libraries. Methods Compan Methods Enzymol. 1994;6:361-71.

Nikolaiev et al., Peptide-encoding for structure determination of nonsequenceable polymers within libraries synthesized and tested on solid-phase supports. Pept Res. May-Jun. 1993;6(3):161-70.

Noll, Characterization of macromolecules by constant velocity sedimentation. Nature. Jul. 22, 1967;215(5099):360-3.

Notterpek et al., PMP22 accumulation in aggresomes: implications for CMT1A pathology. Neurobiol Dis. Oct. 1999;6(5):450-60.

O'Connor, Developing new drugs for the treatment of lymphoma. European Journal of Haematology. 2005;75:150-58.

O'Gorman et al., Recombinase-mediated gene activation and site-specific integration in mammalian cells. Science. Mar. 15, 1991;251(4999):1351-5.

Ohlmeyer et al., Complex synthetic chemical libraries indexed with molecular tags. Proc Natl Acad Sci U S A. Dec. 1, 1993;90(23):10922-6.

(56) References Cited

OTHER PUBLICATIONS

Oliva et al., Histone hyperacetylation can induce unfolding of the nucleosome core particle. Nucleic Acids Res. May 11, 1990;18(9):2739-47.

Orban et al., Tissue- and site-specific DNA recombination in transgenic mice. Proc Natl Acad Sci U S A. Aug. 1, 1992;89(15):6861-5.

Park et al., Point mutations in the yeast histone H4 gene prevent silencing of the silent mating type locus HML. Mol Cell Biol. Sep. 1990;10(9):4932-4.

Parra et al., Protein kinase D1 phosphorylates HDAC7 and induces its nuclear export after T-cell receptor activation J Biol Chem. Apr. 8, 2005;280(14):13762-70. Epub Dec. 28, 2004.

Patani et al., Bioisosterism: A Rational Approach in Drug Design. Chem Rev. Dec. 19, 1996;96(8):3147-3176.

Patek et al., Safety-catch anchoring linkage for synthesis of peptide amides by Boc/Fmoc strategu. Tetrahedron Lett. 1991;32:3891-94.

Patel et al., Identification and characterization of small molecule inhibitors of a class I histone deacetylase from *Plasmodium falciparum*. J Med Chem. Apr. 23, 2009;52(8):2185-7.

Pei et al., Synergistic induction of oxidative injury and apoptosis in human multiple myeloma cells by the proteasome inhibitor bortezomib and histone deacetylase inhibitors. Clin Cancer Res. Jun. 1, 2004;10(11):3839-52.

Perrod et al., A cytosolic NAD-dependent deacetylase, Hst2p, can modulate nucleolar and telomeric silencing in yeast. EMBO J. Jan. 15, 2001;20(1-2):197-209.

Peterson et al., Small molecule developmental screens reveal the logic and timing of vertebrate development. Proc Natl Acad Sci U S A. Nov. 21, 2000;97(24):12965-9.

Phillips, The challenge of gene therapy and DNA delivery. J Pharm Pharmacol. Sep. 2001;53(9):1169-74.

Posnett et al., A novel method for producing anti-peptide antibodies. Production of site-specific antibodies to the T cell antigen receptor beta-chain. J Biol Chem. Feb. 5, 1988;263(4):1719-25.

Powell et al., Anti-1,3-diols by Addition of Dialkylzinc Reagents to 4-Acetoxy-1,3-dioxanes. J Org Chem. Mar. 19, 1999;64(6):2026-2037.

Presbitero et al., Drug-eluting stents do they make the difference? Minerva Cardioangiol. Oct. 2002;50(5):431-42. Italian.

Probst et al., Human liver arylacetamide deacetylase. Molecular cloning of a novel esterase involved in the metabolic activation of arylamine carcinogens with high sequence similarity to hormone-sensitive lipase. J Biol Chem. Aug. 26, 1994;269(34):21650-6.

Pyne et al., Reactions of Lithiated *N*-Tosyl *S*-Phenyl *S*-2-Propenyl Sulfoximine with Aldehydes. Sulfur Letters. 1997;20(6):255-60.

Qian et al., A retinoblastoma-binding protein related to a negative regulator of Ras in yeast. Nature. Aug. 12, 1993;364(6438):648-52.

Raje et al., Combination of the mTOR inhibitor rapamycin and CC-5013 has synergistic activity in multiple myeloma. Blood. Dec. 15, 2004;104(13):4188-93. Epub Aug. 19, 2004.

Remiszewski, The discovery of NVP-LAQ824: from concept to clinic. Curr Med Chem. Nov. 2003;10(22):2393-402.

Renthal et al., Histone deacetylase 5 epigenetically controls behavioral adaptations to chronic emotional stimuli. Neuron. Nov. 8, 2007;56(3):517-29.

Reuben et al., A new group of potent inducers of differentiation in murine erythroleukemia cells. Proc Natl Acad Sci U S A. Mar. 1976;73(3):862-6.

Richardson et al., A phase 2 study of bortezomib in relapsed, refractory myeloma. N Engl J Med. Jun. 26, 2003;348(26):2609-17.

Richon et al., A class of hybrid polar inducers of transformed cell differentiation inhibits histone deacetylases. Proc Natl Acad Sci U S A. Mar. 17, 1998;95(6):3003-7.

Richon et al., Histone deacetylase inhibitor selectively induces p21WAF1 expression and gene-associated histone acetylation. Proc Natl Acad Sci U S A. Aug. 29, 2000;97(18):10014-9.

Richon et al., Second generation hybrid polar compounds are potent inducers of transformed cell differentiation. Proc Natl Acad Sci U S A. Jun. 11, 1996;93(12):5705-8.

Riester et al., Members of the histone deacetylase superfamily differ in substrate specificity towards small synthetic substrates. Biochem Biophys Res Commun. Nov. 19, 2004;324(3):1116-23.

Rine et al., Four genes responsible for a position effect on expression from HML and HMR in *Saccharomyces cerevisiae*. Genetics. May 1987;116(1):9-22.

Rittinger et al., Structural analysis of 14-3-3 phosphopeptide complexes identifies a dual role for the nuclear export signal of 14-3-3 in ligand binding. Mol Cell. Aug. 1999;4(2):153-66.

Roberts et al., Directed evolution of a protein: selection of potent neutrophil elastase inhibitors displayed on M13 fusion phage. Proc Natl Acad Sci U S A. Mar. 15, 1992;89(6):2429-33.

Robertson et al., Germ-line transmission of genes introduced into cultured pluripotential cells by retroviral vector. Nature. Oct. 2-8, 1986;323(6087):445-8.

Rosato et al., Histone deacetylase inhibitors in clinical development. Expert Opin Investig Drugs. Jan. 2004;13(1):21-38.

Rudinger, Characteristics of the amino acids as components of a peptide hormone sequence. In: Peptide Hormones. J.A. Parsons, ed. University Park Press, Baltimore, MD. 1976;1-7.

Rundlett et al., HDA 1 and RPD3 are members of distinct yeast histone deacetylase complexes that regulate silencing and transcription. Proc Natl Acad Sci U S A. Dec. 10, 1996;93(25):14503-8.

Ruygrok et al., Rapamycin in cardiovascular medicine. Intern Med J. Mar. 2003;33(3):103-9.

Saitou et al., The neighbor-joining method: a new method for reconstructing phylogenetic trees. Mol Biol Evol. Jul. 1987;4(4):406-25.

Sanchez Del Pino et al., Properties of the yeast nuclear histone deacetylase. Biochem J. Nov. 1, 1994;303 ( Pt 3):723-9.

Sarraf et al., Rhodium-catalyzed formylation of organomercurials: application to efficient polyol synthesis. Org Lett. Oct. 5, 2000;2(20):3205-8.

Sasaki et al., Ligand-induced recruitment of a histone deacetylase in the negative-feedback regulation of the thyrotropin beta gene. EMBO J. Oct. 1, 1999;18(19):5389-98.

Sato et al., Synthesis and Antibiotic Activity of a Gramicidin S Analogue containing Bicyclic β-Turn Dipeptides. J Chem Soc Perkin Trans. 1986;1:1231-34.

Sawa et al., Histone deacetylase inhibitors such as sodium butyrate and trichostatin A induce apoptosis through an increase of the bcl-2-related protein Bad. Brain Tumor Pathol. 2001;18(2):109-14.

Schena, Quantitative Monitoring of Gene Expression Patterns with a Complementary DNA Microarray. Science. 1995;270:467-70.

Schlienger et al., Human immunodeficiency virus type 1 major neutralizing determinant exposed on hepatitis B surface antigen particles is highly immunogenic in primates. J Virol. Apr. 1992;66(4):2570-6.

Schmidt et al., Rapid determination of methadone in plasma, cerebrospinal fluid, and urine by gas chromatography and its application to routine drug monitoring. Pharm Res. Mar. 1993;10(3):441-4.

Schreiber, Chemical genetics resulting from a passion for synthetic organic chemistry. Bioorg Med Chem. Aug. 1998;6(8):1127-52.

Schreiber, Target-oriented and diversity-oriented organic synthesis in drug discovery. Science. Mar. 17, 2000;287(5460):1964-9.

Schreiber, Using the Principles of Organic Chemistry to Explore Cell Biology. Chem and Eng News. 1992; 70(43): 22-32.

Schuetz et al., Human HDAC7 harbors a class IIa histone deacetylase-specific zinc binding motif and cryptic deacetylase activity. J Biol Chem. Apr. 25, 2008;283(17):11355-63. Epub Feb. 19, 2008.

Scott et al., Searching for peptide ligands with an epitope library. Science. Jul. 27, 1990;249(4967):386-90.

Secrist et al., HDAC inhibitors for the treatment of cancer. Curr Opin Investig Drugs. Dec. 2003;4(12):1422-7.

Seffernick et al., Melamine deaminase and atrazine chlorohydrolase: 98 percent identical but functionally different. J Bacteriol. Apr. 2001;183(8):2405-10.

Serrador et al., HDAC6 deacetylase activity links the tubulin cytoskeleton with immune synapse organization. Immunity. Apr. 2004;20(4):417-28.

Shpaer, GeneAssist. Smith-Waterman and other database similarity searches and identification of motifs. Methods Mol Biol. 1997;70:173-87.

(56) References Cited

OTHER PUBLICATIONS

Sikorski et al., A system of shuttle vectors and yeast host strains designed for efficient manipulation of DNA in *Saccharomyces cerevisiae*. Genetics. May 1989;122(1):19-27.
Singh et al., Chemistry and structure-activity relationship of HIV-1 integrase inhibitor integracide B and related natural products. J Nat Prod. Oct. 2003;66(10):1338-44.
Smith et al., A phylogenetically conserved Nad+-dependent protein deacetylase activity in the Sir2 protein family. Proc Natl Acad Sci U S A. Jun. 6, 2000;97(12):6658-63.
Smith et al., Comparison of biosequences. Adv Appl Math. 1981;2:482-89.
Smith et al., Mechanisms and molecular probes of sirtuins. Chem Biol. Oct. 20, 2008;15(10):1002-13.
Somoza et al., Structural snapshots of human HDAC8 provide insights into the class I histone deacetylases. Structure. Jul. 2004;12(7): 1325-34.
Stamatakis et al., A rapid bootstrap algorithm for the RAxML Web servers. Syst Biol. Oct. 2008;57(5):758-71.
Sternson et al., Split—pool synthesis of 1,3-dioxanes leading to arrayed stock solutions of single compounds sufficient for multiple phenotypic and protein-binding assays. J Am Chem Soc. Feb. 28, 2001;123(8):1740-7.
Sternson et al., Synthesis of 7200 small molecules based on a substructural analysis of the histone deacetylase inhibitors trichostatin and trapoxin. Org Lett. Dec. 27, 2001;3(26):4239-42.
Stevanovic et al., Natural and Synthetic Peptide Pools: Characterization by Sequencing and Electrospray Mass Spectrometry. Bioorg Med Chem Lett. 1993;3(3):431-36.
Stewart et al., Expression of retroviral vectors in transgenic mice obtained by embryo infection. EMBO J. Feb. 1987;6(2):383-8.
Stillman et al., Epistasis analysis of suppressor mutations that allow HO expression in the absence of the yeast SW15 transcriptional activator. Genetics. Mar. 1994;136(3):781-8.
Stowell et al., The synthesis of N-hydroxy-N'-phenyloctanediamide and its inhibitory effect on proliferation of AXC rat prostate cancer cells. J Med Chem. Apr. 14, 1995;38(8):1411-3.
Strebhardt et al., Additional member of the protein-tyrosine kinase family: the src- and lck-related protooncogene c-tkl. Proc Natl Acad Sci U S A. Dec. 1987;84(24):8778-82.
Sullivan et al., Localization of the BiP molecular chaperone with respect to endoplasmic reticulum foci containing the cystic fibrosis transmembrane conductance regulator in yeast. J Histochem Cytochem. Apr. 2003;51(4):545-8.
Suzuki et al., Synthesis and histone deacetylase inhibitory activity of new benzamide derivatives. J Med Chem. Jul. 29, 1999;42(15):3001-3.
Tallarico et al., An alkylsilyl-tethered, high-capacity solid support amenable to diversity-oriented synthesis for one-bead, one-stock solution chemical genetics. J Comb Chem. May-Jun. 2001;3(3):312-8.
Tan et al., Stereoselective Synthesis of over Two Million Compounds Having Structural Features Both Reminiscent of Natural Products and Compatible with Miniaturized Cell-Based Assays. J. Am. Chem. Soc. 1998; 120: 8565-66.
Tanaka et al., Syntheses and anti-inflammatory and analgesic activities of hydroxamic acids and acid hydrazides. Chem Pharm Bull (Tokyo). Aug. 1983;31(8):2810-9.
Tanner et al., Silent information regulator 2 family of NAD-dependent histone/protein deacetylases generates a unique product, 1-O-acetyl-ADP-ribose. Proc Natl Acad Sci U S A. Dec. 19, 2000;97(26):14178-82.
Tanny et al., Coupling of histone deacetylation to NAD breakdown by the yeast silencing protein Sir2: Evidence for acetyl transfer from substrate to an NAD breakdown product. Proc Natl Acad Sci U S A. Jan. 16, 2001;98(2):415-20. Epub Dec. 26, 2000.
Tao et al., Deacetylase inhibition promotes the generation and function of regulatory T cells. Nat Med. Nov. 2007;13(11):1299-307. Epub Oct. 7, 2007.

Taunton et al., A mammalian histone deacetylase related to the yeast transcriptional regulator Rpd3p. Science. Apr. 19, 1996;272(5260):408-11.
Taunton et al., Deacetylation. The Scientist. 1999;13:13.
Taunton et al., Synthesis of Natural and Modified Trapoxins, Useful Reagents for Exploring Histone Deacetylase Function. J Am Chem Soc. 1996;118:10412-22.
Thornton et al., Protein Engineering: Editorial Overview. Curr Opin Biotechnol. 1995;6(4):367-69.
Tissenbaum et al., Increased dosage of a sir-2 gene extends lifespan in *Caenorhabditis elegans*. Nature. Mar. 8, 2001;410(6825):227-30.
Tong et al., Chromatin deacetylation by an ATP-dependent nucleosome remodeling complex. Nature. 1997;395:917-21.
Tsang et al., CobB, a new member of the SIR2 family of eucaryotic regulatory proteins, is required to compensate for the lack of nicotinate mononucleotide:5,6-dimethylbenzimidazole phosphoribosyltransferase activity in cobT mutants during cobalamin biosynthesis in *Salmonella typhimurium* LT2. J Biol Chem. Nov. 27, 1998;273(48):31788-94.
Tsankova et al., Sustained hippocampal chromatin regulation in a mouse model of depression and antidepressant action. Nat Neurosci. Apr. 2006;9(4):519-25. Epub Feb. 26, 2006.
Turner, Decoding the nucleosome. Cell. Oct. 8, 1993;75(1):5-8.
Uchiyama et al., Adhesion of human myeloma-derived cell lines to bone marrow stromal cells stimulates interleukin-6 secretion. Blood. Dec. 15, 1993;82(12):3712-20.
Uong et al., Stereocontrolled Functionalization of Acyclic Molybdenum-$\eta^3$-Allyl Complexes: A New Approach to the Stereoselective Synthesis of 1,3-Diols. J Chem Soc Chem Commun. 1990:1285-87.
Urnov et al., Targeting of N-CoR and histone deacetylase 3 by the oncoprotein v-erbA yields a chromatin infrastructure-dependent transcriptional repression pathway. EMBO J. Aug. 1, 2000;19(15):4074-90.
Valerio et al., Multipin peptide synthesis at the micromole scale using 2-hydroxyethyl methacrylate grafted polyethylene supports. Int J Pept Protein Res. Jul. 1993;42(1):1-9.
Valerio et al., Synthesis of peptide analogues using the multipin peptide synthesis method. Anal Biochem. Aug. 15, 1991;197(1):168-77.
Van Der Krol et al., Modulation of eukaryotic gene expression by complementary RNA or DNA sequences. Biotechniques. Nov.-Dec. 1988;6(10):958-76.
Van Der Putten et al., Efficient insertion of genes into the mouse germ line via retroviral vectors. Proc Natl Acad Sci U S A. Sep. 1985;82(18):6148-52.
Vannini et al., Crystal structure of a eukaryotic zinc-dependent histone deacetylase, human HDAC8, complexed with a hydroxamic acid inhibitor. Proc Natl Acad Sci U S A. Oct. 19, 2004;101(42):15064-9. Epub Oct. 11, 2004.
Varga-Weisz et al., Chromatin-remodeling factors: machines that regulate? Curr Opin Cell Biol. Jun. 1998;10(3):346-53.
Vegas et al., Fluorous-based small-molecule microarrays for the discovery of histone deacetylase inhibitors. Angew Chem Int Ed Engl. 2007;46(42):7960-4.
Venter et al., The sequence of the human genome. Science. Feb. 16, 2001;291(5507):1304-51.
Verdel et al., Identification of a new family of higher eukaryotic histone deacetylases. Coordinate expression of differentiation-dependent chromatin modifiers. J Biol Chem. Jan. 22, 1999;274(4):2440-5.
Vidal et al., RPD3 encodes a second factor required to achieve maximum positive and negative transcriptional states in *Saccharomyces cerevisiae*. Mol Cell Biol. Dec. 1991;11(12):6317-27.
Vong et al., Regio-and Stereocontrolled Functionalization of Acyclic Molybdenum-$\eta^3$-Allyl Complexes. J Am Chem Soc. 1991;113:573-82.
Walker et al., Affinity chromatography of mammalian and yeast nucleosomes. Two modes of binding of transcriptionally active mammalian nucleosomes to organomercurial-agarose columns, and contrasting behavior of the active nucleosomes of yeast. J Biol Chem. Apr. 5, 1990;265(10):5736-46.

(56) References Cited

OTHER PUBLICATIONS

Wallace et al., Understanding cytochrome c function: engineering protein structure by semisynthesis. FASEB J. Apr. 1, 1993;7(6):505-15.
Wang et al., ETO, fusion partner in t(8;21) acute myeloid leukemia, represses transcription by interaction with the human N-CoR/mSin3/HDAC1 complex. Proc Natl Acad Sci U S A. Sep. 1, 1998;95(18):10860-5.
Wang et al., HDAC4, a human histone deacetylase related to yeast HDA1, is a transcriptional corepressor. Mol Cell Biol. Nov. 1999;19(11):7816-27.
Wang et al., Isolation of high-affinity peptide antagonists of 14-3-3 proteins by phage display. Biochemistry. Sep. 21, 1999;38(38):12499-504.
Wang et al., Zinc binding in HDAC inhibitors: a DFT study. J Org Chem. Jul. 6, 2007;72(14):5446-9. Epub Jun. 19, 2007.
Warrell et al., Therapeutic targeting of transcription in acute promyelocytic leukemia by use of an inhibitor of histone deacetylase. J Natl Cancer Inst. Nov. 4, 1998;90(21):1621-5.
Wegener et al., A fluorogenic histone deacetylase assay well suited for high-throughput activity screening. Chem Biol. Jan. 2003;10(1):61-8.
Weinberg, Finding the anti-oncogene. Sci Am. Sep. 1988;259(3):44-51.
Wennemers et al., Cyclooligomeric Receptors Based on Trimesic Acid and 1,2-Diamines. Minimal Structure for Sequence-Selective Peptide Binding. J Org Chem. 1995;60:1108-09.
Whelan et al., A general empirical model of protein evolution derived from multiple protein families using a maximum-likelihood approach. Mol Biol Evol. May 2001;18(5):691-9.
Wilen et al., Strategies in Optical Resolution. Tetrahedron. 1977;33:2725-36.
Witkowski et al., Conversion of a beta-ketoacyl synthase to a malonyl decarboxylase by replacement of the active-site cysteine with glutamine. Biochemistry. Sep. 7, 1999;38(36):11643-50.
Wong et al., Modular synthesis and preliminary biological evaluation of stereochemically diverse 1,3-dioxanes. Chem Biol. Sep. 2004;11(9):1279-91.
Wong et al., Structural biasing elements for in-cell histone deacetylase paralog selectivity. J Am Chem Soc. May 14, 2003;125(19):5586-7.
Workman et al., Alteration of nucleosome structure as a mechanism of transcriptional regulation. Annu Rev Biochem. 1998;67:545-79.
Xie et al., Sum1 and Hst1 repress middle sporulation-specific gene expression during mitosis in *Saccharomyces cerevisiae*. EMBO J. Nov. 15, 1999;18(22):6448-54.
Xu et al., Coactivator and corepressor complexes in nuclear receptor function. Curr Opin Genet Dev. Apr. 1999;9(2):140-7.
Xue et al., NURD, a novel complex with both ATP-dependent chromatin-remodeling and histone deacetylase activities. Mol Cell. Dec. 1998;2(6):851-61.
Yaffe et al., The structural basis for 14-3-3:phosphopeptide binding specificity. Cell. Dec. 26, 1997;91(7):961-71.
Yang et al., Cloning and characterization of two mouse genes with homology to the yeast Sir2 gene. Genomics. Nov. 1, 2000;69(3):355-69.
Yang et al., Isolation and characterization of cDNAs corresponding to an additional member of the human histone deacetylase gene family. J Biol Chem. Oct. 31, 1997;272(44):28001-7.
Yang et al., Maintenance of G2 arrest in the *Xenopus oocyte*: a role for 14-3-3-mediated inhibition of Cdc25 nuclear import. EMBO J. Apr. 15, 1999;18(8):2174-83.
Yang et al., Transcriptional repression by YY1 is mediated by interaction with a mammalian homolog of the yeast global regulator RPD3. Proc Natl Acad Sci U S A. Nov. 12, 1996;93(23):12845-50.
Yoon et al., Cyclooligomeric Receptors for the Sequence Selective Binding of Peptides. A Tetrahedral Receptor from the Trimesic Acid and 1,2-Diamines. Tetrahedron Lett. 1994;35:8557-60.
Yoshida et al., A novel tetracyclic peptide, trapoxin, induces phenotypic change from transformed to normal in sis-oncogene-transformed NIH3T3 cells. Jpn J Cancer Res. Apr. 1992;83(4):324-8.
Yoshida et al., Potent and specific inhibition of mammalian histone deacetylase both in vivo and in vitro by trichostatin A. J Biol Chem. Oct. 5, 1990;265(28):17174-9.
Yoshida et al., Trichostatin A and trapoxin: novel chemical probes for the role of histone acetylation in chromatin structure and function. Bioessays. May 1995;17(5):423-28.
Youngquist et al., Matrix-assisted laser desorption ionization for rapid determination of the sequences of biologically active peptides isolated from support-bound combinatorial peptide libraries. Rapid Commun Mass Spectrom. Jan. 1994;8(1):77-81.
Yu et al., The proteasome inhibitor bortezomib interacts synergistically with histone deacetylase inhibitors to induce apoptosis in Bcr/Abl+ cells sensitive and resistant to ST1571. Blood. Nov. 15, 2003;102(10):3765-74. Epub Jul. 31, 2003.
Zervos et al., Mxi1, a protein that specifically interacts with Max to bind Myc-Max recognition sites. Cell. Jan. 29, 1993;72(2):223-32.
Zhang et al., The dermatomyositis-specific autoantigen Mi2 is a component of a complex containing histone deacetylase and nucleosome remodeling activities. Cell. Oct. 16, 1998;95(2):279-89.
Zhou et al., Cloning and characterization of a histone deacetylase, HDAC9. Proc Natl Acad Sci U S A. Sep. 11, 2001;98(19):10572-7. Epub Sep. 4, 2001.
Zhou et al., Identification of a transcriptional repressor related to the noncatalytic domain of histone deacetylases 4 and 5. Proc Natl Acad Sci U S A. Feb. 1, 2000;97(3):1056-61.
Zhu et al., Phosphine-catalyzed synthesis of 1,3-dioxan-4-ylidenes. Org Lett. Mar. 31, 2005;7(7):1387-90.
Zimmermann et al., Conformational and epitope mapping of herpes-simplex-virus type-1 thymidine kinase using synthetic peptide segments. Eur J Biochem. Sep. 1, 1991;200(2):519-28.
International Search Report and Written Opinion for PCT/US2011/020206, mailed Jul. 9, 2013.
International Preliminary Report on Patentability for PCT/US2011/020206, mailed Aug. 1, 2013.
Office Communication, mailed Jul. 8, 2013, for U.S. Appl. No. 13/550,110.
Office Communication, mailed Dec. 18, 2012, for U.S. Appl. No. 11/386,959.
Office Communication, mailed Aug. 6, 2013, for U.S. Appl. No. 11/386,959.
Office Communication, mailed Aug. 16, 2013, for U.S. Appl. No. 13/520,650.
Dancey et al., Strategies for optimizing combinations of molecularly targeted anticancer agents. Nat Rev Drug Discov. Aug. 2006;5(8):649-59.
Gravemann et al., Hydroxamic acid and fluorinated derivatives of valproic acid: anticonvulsant activity, neurotoxicity and teratogenicity. Neurotoxicol Teratol. Sep.-Oct. 2008;30(5):390-4. doi:10.1016/j.ntt.2008.03.060. Epub Mar. 19, 2008.
PubChemCompound, datasheet [online compound summary] Retrieved from the Internet: <URL:http://pubchem.ncbi.nlm.nih.gov/search/search.cgi> See CID 11593538, CID 4215571, CID 24701534, CID 24694283, CID 19936521, CID 137190 CID 144926, CID 24692493, CID 15952018, CID 11643995, etc.

\* cited by examiner

Figure 10

| Compound | HDAC1 | HDAC2 | HDAC3 | HDAC4 | HDAC5 | HDAC6 | HDAC7 | HDAC8 | HDAC9 |
|---|---|---|---|---|---|---|---|---|---|
| APHA | | | | | | | | | |
| Ki | 0.055 | 0.125 | 0.25 | 17.5 | 11.5 | 0.03 | 7 | 0.6 | 10 |
| StdDev | 0.004 | 0.01 | 0.02 | 1.2 | 0.6 | 0.004 | 0.9 | 0.04 | 1 |
| Apicidin | | | | | | | | | |
| Ki | 0.00004 | 0.00012 | 0.00026 | - | - | - | - | 0.049 | - |
| StdDev | 0.000004 | 0.000003 | 0.000005 | - | - | - | - | 0.02 | - |
| CI-994 | | | | | | | | | |
| Ki | 0.05 | 0.19 | 0.55 | - | - | - | - | - | - |
| StdDev | 0.0045 | 0.015 | 0.035 | - | - | - | - | - | - |
| Depudecin | | | | | | | | | |
| Ki | 5.5 | 12.5 | 14.5 | - | - | - | - | - | - |
| StdDev | 0.4 | 0.65 | 0.95 | - | - | - | - | - | - |
| FK-228 | | | | | | | | | |
| Ki | 0.0000015 | 0.000038 | 0.00015 | 0.0205 | 0.55 | 0.0095 | 1.25 | 0.00015 | 1.1 |
| StdDev | 0.0000001 | 0.000003 | 0.000025 | 0.0035 | 0.06 | 0.004 | 0.2 | 0.00003 | 0.22 |
| HC-Toxin | | | | | | | | | |
| Ki | 0.19 | 0.47 | 1.35 | - | - | - | - | 10.5 | - |
| StdDev | 0.02 | 0.06 | 0.115 | - | - | - | - | 1.4 | - |
| ITF-2357 | | | | | | | | | |
| Ki | 0.002 | 0.003 | 0.003 | 1.05 | 0.6 | 0.0042 | 0.24 | 0.039 | 0.39 |
| StdDev | 0.0001 | 0.0001 | 0.0001 | 0.15 | 0.065 | 0.0002 | 0.025 | 0.001 | 0.05 |
| LAQ-824 | | | | | | | | | |
| Ki | 0.00055 | 0.0014 | 0.0042 | 2.25 | 0.42 | 0.0095 | 9.5 | 0.34 | 9 |
| StdDev | 0.0005 | 0.00003 | 0.0001 | 0.3 | 0.04 | 0.00035 | 4.55 | 0.035 | 7.5 |
| LBH-589 | | | | | | | | | |
| Ki | 0.001 | 0.00065 | 0.00011 | 0.55 | 0.08 | 0.0015 | 4.55 | 0.105 | 3.2 |
| StdDev | 0.0001 | 0.0001 | 0.00015 | 0.05 | 0.01 | 0.0005 | 0.315 | 0.02 | 0.2 |
| MGCD-0103 | | | | | | | | | |
| Ki | 0.009 | 0.034 | 0.265 | - | - | - | - | - | - |
| StdDev | 0.001 | 0.002 | 0.015 | - | - | - | - | - | - |
| MS-275 | | | | | | | | | |
| Ki | 0.022 | 0.065 | 0.36 | - | - | - | - | - | - |
| StdDev | 0.002 | 0.005 | 0.015 | - | - | - | - | - | - |
| Niltubacin | | | | | | | | | |
| Ki | - | - | - | - | - | 2.2 | - | 0.75 | - |
| StdDev | - | - | - | - | - | 0.38 | - | 0.07 | - |
| 4-PBHA | | | | | | | | | |
| Ki | 0.295 | 0.43 | 1.65 | - | 16 | 0.15 | - | 1.85 | - |
| StdDev | 0.04 | 0.03 | 0.1 | - | 1.25 | 0.01 | - | 0.1 | - |
| PXD-101 | | | | | | | | | |
| Ki | 0.00085 | 0.00085 | 0.0015 | 0.38 | 0.175 | 0.0016 | 0.075 | 0.025 | 0.25 |
| StdDev | 0.00005 | 0.00005 | 0.00005 | 0.06 | 0.02 | 0.00015 | 0.01 | 0.002 | 0.05 |
| Pyroxamide | | | | | | | | | |
| Ki | 0.0027 | 0.0036 | 0.008 | - | 4.75 | 0.0048 | - | 1 | - |
| StdDev | 0.00015 | 0.0002 | 0.00015 | - | 1.1 | 0.0003 | - | 0.11 | - |
| SAHA | | | | | | | | | |
| Ki | 0.0013 | 0.0016 | 0.005 | - | 3.6 | 0.0016 | - | 0.48 | - |
| StdDev | 0.00005 | 0.00005 | 0.0002 | - | 0.38 | 0.00005 | - | 0.02 | - |
| Scriptaid | | | | | | | | | |
| Ki | 0.0015 | 0.0022 | 0.0041 | 7.5 | 1 | 0.00025 | 2.25 | 0.105 | 8 |
| StdDev | 0.00005 | 0.00005 | 0.00005 | 0.75 | 0.1 | 0.0001 | 0.35 | 0.01 | 1 |
| SuberoHA | | | | | | | | | |
| Ki | 0.019 | 0.029 | 0.125 | - | 9.5 | 0.0145 | - | 0.95 | - |
| StdDev | 0.0035 | 0.0045 | 0.01 | - | 0.5 | 0.0015 | - | 0.1 | - |
| Trichostatin | | | | | | | | | |
| Ki | 0.0002 | 0.00065 | 0.0005 | 1.4 | 0.26 | 0.001 | 0.195 | 0.045 | 0.8 |
| StdDev | 0.000045 | 0.00005 | 0.0001 | 0.1 | 0.035 | 0.0001 | 0.02 | 0.015 | 0.1 |
| Tubacin | | | | | | | | | |
| Ki | 0.028 | 0.042 | 0.275 | 17 | 1.5 | 0.016 | 8.5 | 0.17 | - |
| StdDev | 0.004 | 0.0035 | 0.02 | 2.5 | 0.25 | 0.002 | 1.5 | 0.01 | - |

Figure 11A

```
         1          11         21         31         41        50
         |          |          |          |          |         |
         M-------- ---------- ---------- ---------- ----------   1 HD1
         M-------- ---------- ---------- ---------- ----------   1 HD2
         M-------- ---------- ---------- ---------- ----------   1 HD3
         M-------- ---------- ---------- ---------- ----------   1 HD8
         MSSQSHPDGL SGRDQPVELL NPARVNHMPS TVDVATALPL QVAPSAV---  47 HD4
         MNSPNESDGM SGREPSLEIL PRTSLHSIPV TVEVKPVLP- RAMPSSMGGG  49 HD5
         M--------- ---------- -----HSMIS SVDVKSEVPV GLEPIS----  22 HD9
         M--------- ---------- ---------- ---------- ----------   1 HD7
         M--------- ---------- ---------- ---------- ----------   1 HD6

---------- ---------- ---------- ---------- ----------   1 HD1
         ---------- ---------- ---------- ---------- ----------   1 HD2
         ---------- ---------- ---------- ---------- ----------   1 HD3
         ---------- ---------- ---------- ---------- ----------   1 HD8
         ------PMDL RLDHQFSLPV AEPALREQQL QQELLALKQK QQIQRQILIA  91 HD4
         GGGSPSPVEL RGALVGSV-- -DPTLREQQL QQELLALKQQ QQLQKQLLFA  96 HD5
         ------PLDL RTDLRMMMPV VDPVVREKQL QQELLLIQQQ QQIQKQLLIA  66 HD9
         --------DL RVGQRPPV-- ------EPPP EPTLLALQRP QRLHHHLFLA  35 HD7
         ---------- ---------- ---------- ---------- ----------   1 HD6

---------- ---------- ---------- ---------- ----------   1 HD1
         ---------- ---------- ---------- ---------- ----------   1 HD2
         ---------- ---------- ---------- ---------- ----------   1 HD3
         ---------- ---------- ---------- ---------- ----------   1 HD8
         EFQRQHEQLS RQHEAQLHEH IKQQQEMLAM KHQQEL---- ----LEHQRK 133 HD4
         EFQKQHDHLT RQHEVQLQKH LKQQQEMLAA KQQQEMLAAK RQQELEQQRQ 146 HD5
         EFQKQHENLT RQHQAQLQEH IK---ELLAI KQQQEL---- ----LEKEQK 105 HD9
         GLQQQRS--- ---------- ---------- ---------- ----VEPMR-  47 HD7
         TSTGQDSTTT RQRRSRQNPQ SPPQDSSVTS KRNIKKGAVP RS--IPNLAE  49 HD6

---------- ---------- ---------- ---------- ----------   1 HD1
         ---------- ---------- ---------- ---------- ----------   1 HD2
         ---------- ---------- ---------- ---------- ----------   1 HD3
         ---------- ---------- ---------- ---------- ----------   1 HD8
         LERHRQEQEL EKQHREQKLQ QLKNKEKGKE S---AVASTE VKMKLQEFVL 180 HD4
         REQQRQE-EL EKQRLEQQLL ILRNKEKSKE S---AIASTE VKLRLQEFLL 192 HD5
         LEQQRQEQEV ERHRREQQLP PLRGKDRGRE R---AVASTE VKQKLQEFLL 152 HD9
         LSMDTPMPEL QVGPQEQELR QLLHKDKSKR S---AVASSV VKQKLAEVTL  94 HD7
         VKKKGKMKKL GQAMEEDLIV GLQGMDLNLE AEALAGTGLV LDEQLNEFKC  99 HD6

```
------------ ------------ ------------ ------------ ----------     1 HD2
------------ ------------ ------------ ------------ ----------     1 HD3
------------ ------------ ------------ ------------ ----------     1 HD8
NKK--KALAH   RNLNHCISSD   PRYWYGKTQH   SSLDQSSPPQ   S---GVSTSY   225 HD4
SKS--KEPTP   GGLNHSLPQH   PKCW--GAHH   ASLDQSSPPQ   SGPPGTPPSY   238 HD5
SKSATKDTPT   NGKNHSVSRH   PKLWYTAAHH   TSLDQSSPPL   S---GTSPSY   199 HD9
KKQ--QAALE   RTVH---PNS   PGIPYRTLEP   LETEGATRSM   L------SSF   133 HD7
LWD-D-----   ----------   ----------   ----------   ----------   103 HD6

------------ ------------ ------------ ------------ ----------     1 HD1
------------ ------------ ------------ ------------ ----------     1 HD2
------------ ------------ ------------ ------------ ----------     1 HD3
------------ ------------ ------------ ------------ ----------     1 HD8
NHPVLG-MYD   AKDDFPLRKT   ASEPNLKLRS   RLKQKVAERR   SSPLLRRKDG   274 HD4
KLPLPG-PYD   SRDDFPLRKT   ASEPNLKVRS   RLKQKVAERR   SSPLLRRKDG   287 HD5
KYTLPG-AQD   AKDDFPLRKT   ASEPNLKVRS   RLKQKVAERR   SSPLLRRKDG   248 HD9
LPPVPSLPSD   PPEHFPLRKT   VSEPNLKLRY   KPK-KSLERR   KNPLLRKESA   182 HD7
------------ ------------ ------------ ------------ ----------   103 HD6

----------   ----------   -------A     QTQ-GTR---   ----------     8 HD1
----------   ----------   -------A     YSQGGGK---   ----------     9 HD2
----------   ----------   -------A     ----------   ----------     2 HD3
----------   ----------   -------E     EPEEPADSGQ   S---------    13 HD8
PVVTALKKRP   LDVT------   DSACSSAPGS   GPSSPNNSSG   SVSAENGIAP   318 HD4
TVISTFKKRA   VEITGAGPGA   SSVCNSAPGS   GPSSPNSSHS   TI-AENGFTG   336 HD5
NVVTSFKKRM   FEVT-----E   SSVSSSSPGS   GPSSPNNGPT   GSVTENE-TS   292 HD9
P--PSLRRRP   AETLGD---S   SPSSSSTPAS   GCSSPNDSEH   G---------   218 HD7
----------   ----------   --------S    FPEGPERLHA   I---------   115 HD6

----------   ----------   ----------   ----------   ----------     8 HD1
----------   ----------   ----------   ----------   ----------     9 HD2
----------   ----------   ----------   ----------   ----------     2 HD3
----------   ----------   ----------   ----------   ----------    13 HD8
AVPSIP--AE   TSLAHRLVAR   EGSAAPLPLY   TSPSLPNITL   GLPAT-----   361 HD4
SVPNIP--TE   MLPQHRALPL   DSSPNQFSLY   TSPSLPNISL   GLQATVTVTN   384 HD5
VLPPTPHABQ   MVSQQRILIH   EDSMNLLSLY   TSPSLPNITL   GLPAV----P   338 HD9
--PNPILGSE   ALLGQRLRLQ   ETSVAPFALP   TVSLLPAITL   GLPA------   260 HD7
---KEQLIQE   GLLDRCVSFQ   ARFAEKEELM   LVHSLEYIDL   ----------   152 HD6

----------   ----------   ----------   ----------   ----------     8 HD1
----------   ----------   ----------   ----------   ----------     9 HD2
----------   ----------   ----------   ----------   ----------     2 HD3
----------   ----------   ----------   ----------   ----------    13 HD8
---GPSAGTA   GQQDTERLTL   PALQQRLSLF   PGTHLTPYLS   TS--------   400 HD4
SHLTASPKLS   TQQEAERQAL   QSLRQ-----   GGTLTGKFMS   TSSIPGCLLG   429 HD5
SQLNASNSLK   EKQKCE---T   QTLRQ-----   GVPLPGQYGG   SIPASSSHPH   380 HD9
---------P   ARADSDRRTH   PTLGPRGPIL   GSPHTPLFLP   H---------   292 HD7
-----METTQ   YMNEGELRVL   ADTYDSVYLH   PNSYSCACLA   S---------   188 HD6
```

Figure 11C

```
----------  ----------  ----------  ----------  ----------    8 HD1
----------  ----------  ----------  ----------  ----------    9 HD2
----------  ----------  ----------  ----------  ----------    2 HD3
----------  ----------  ----------  ----------  ----------   13 HD8
-PLERDGGA-  AHSPLLQHMV  LLEQPPAQAP  LVT--GLGAL  PLHAQS-LVG  445 HD4
VALEGDGSPH  GHASLLQHVL  LLEQARQQST  LI------AV  PLHGQSPLVT  473 HD5
VTLEGKPPNS  SHQALLQHLL  LKEQMRQQKL  LVA----GGV  PLHPQSPLAT  436 HD9
-GLEPEAGG-  TLPSRLQPIL  LLDPSGSHAP  LLTVPGLGPL  PFHFAQSLMT  340 HD7
----------  GSVLRLVDAV  LGAEIRNGMA  IIRPPG----  -HHAQHSLMD  223 HD6

----------  ----------  ----------  ----------  ----------    8 HD1
----------  ----------  ----------  ----------  ----------    9 HD2
----------  ----------  ----------  ----------  ----------    2 HD3
----------  ----------  ----------  ----------  ----------   13 HD8
A----DRVSP  SI---HKLRQ  HRPL------  ---GRTQSAP  LPQNAQALQH  479 HD4
G----ERVAT  SMRTVGKLPR  HRPL------  ---SRTQSSP  LPQSPQALQQ  510 HD5
K----ERISP  GIRGTHKLPR  HRPL------  ---NRTQSAP  LPQS--TLAQ  461 HD9
T----ERLSG  S-------GL  HWPL------  ---SRTRSEP  LPPSATA---  367 HD7
GYCMFNHVAV  AARYAQQKHR  IRRVLIVDWD  VHHGQGTQFT  FDQDPSVLYF  273 HD6

----------  ----------  ----------  ----------  ----------    8 HD1
----------  ----------  ----------  ----------  ----------    9 HD2
----------  ----------  ----------  ----------  ----------    2 HD3
----------  ----------  ----------  ----------  ----------   13 HD8
LVIQQQHQQF  LEKHKQQFQQ  Q---------  ----------  ----------  500 HD4
LVMQQQHQQF  LEKQK----Q  Q---------  ----------  ----------  527 HD5
LVIQQQHQQF  LEKQKQ--YQ  Q---------  ----------  ----------  480 HD9
----------  ----------  ----------  ----------  ----------  367 HD7
SIHRYEQGRF  WPHLKASNWS  TTGFGQGQGY  TINVPWNQVG  MRDADYIAAF  323 HD6

----------  ----------  ----------  ----------  ----------    8 HD1
----------  ----------  ----------  ----------  ----------    9 HD2
----------  ----------  ----------  ----------  ----------    2 HD3
----------  ----------  ----------  ----------  ----------   13 HD8
----------  -QLQMNKIIP  KPSEPARQPE  SHPEETEEEL  REHQALLDE-  538 HD4
----------  -QLQLGKILT  KTGELPRQPT  THPEETEEEL  TEQQEVLLG-  565 HD5
----------  -QIHMNKLLS  KSIEQLKQPG  SHLEEAEEEL  QGDQAMQED-  518 HD9
----------  ----------  -----PPPPG  PMQPRLEQLK  THVQVIKRS-  391 HD7
LHVLLPVALE  FQPQLVLVAA  GFDALQGDPK  GEMAATPAGP  AQLTHLLMGL  373 HD6

----------  ----------  ----------  ----------  ----------    8 HD1
----------  ----------  ----------  ----------  ----------    9 HD2
----------  ----------  ----------  ----------  ----------    2 HD3
----------  ----------  ----------  ----------  ----------   13 HD8
-PYLDRLPGQ  KEAHAQAGVQ  -VKQEPIESD  EEEAEPPREV  EPG------Q  580 HD4
-EGALTMPRE  GSTESESTQE  DLEEEDEKED  GEEEEDCIQV  KDERGESGAE  614 HD5
-----RAPSS  GN----STRS  DSSACVDDTL  G--QVGAVKV  KEEPVDS--D  555 HD9
```

Figure 11D

```
-----AKPSE KP----RLRQ IPSAEDLETD GGGPGQVV-- ----------D  421 HD7
AGGKLILSLE GGYNLRALAE GVSASLHTLL G--------- ----------D  405 HD6

---------- ---------- ---------- ---------- ----------    8 HD1
---------- ---------- ---------- ---------- ----------    9 HD2
---------- ---------- ---------- ---------- ----------    2 HD3
---------- ---------- ---------- ---------- ----------   13 HD8
RQPSEQELLF RQ-------- -----QALLL EQQRIHQ--- --LRNYQASM  612 HD4
EGPDLEEPGA GY-------- -----KKLFS DAQPLQP--- --LQVYQAPL  646 HD5
EDAQIQEMES GE-------- -----QAAFM QQPFLEPTHT RALSVRQAPL  592 HD9
DGLEHRELGH GQPEARGPAP LQQHPQVLLW EQQRLAG--- --RLPRGSTG  466 HD7
PCPMLESPGA PC-------- ---------- --RSAQASVS CALEALEPFW  435 HD6

---------- ---------- ---------- ---------- ----------    8 HD1
---------- ---------- ---------- ---------- ----------    9 HD2
---------- ---------- ---------- ---------- ----------    2 HD3
---------- ---------- ---------- ---------- ----------   13 HD8
EAAGIPVSFG GHRPLSRAQS SPASATFPVS V--------- --QEPPTKPR  651 HD4
SLATVP---- -HQALGRTQS SPAAPGGMKS P--------- --PDQPVKHL  680 HD5
AAVCMD-GLE KHRLVSRTHS SPAASVLPHP A--------- --MDRPLQPG  630 HD9
DTVLLPLAQG GHRPLSRAQS SPAAPASLSA PEPASQARVL SSSETPARTL  516 HD7
EVLVRSTETV ERDNMEEDNV EESKEEGPWE P--------- --PVLPILTW  474 HD6

----RKVCYY YDGDVGNY-- -YYGQG-HPM KPHRIRMTHN LLLNYGLYRK   50 HD1
----KKVCYY YDGDIGNY-- -YYGQG-HPM KPHRIRMTHN LLLNYGLYRK   51 HD2
----KTVAYF YDPDVGNF-- -HYGAG-HPM KPHRLALTHS LVLHYGLYKK   44 HD3
----LVPVYI YSPEYVSM-- -CDSLA--K IPKRASMVHS LIEAYALHKQ    53 HD8
----FTTGLV YDTLMLKHQC TCGSSSSHPE HAGRIQSIWS RLQETGLRGK  697 HD4
----FTTGVV YDTFMLKHQC MCGNTHVHPE HAGRIQSIWS RLQETGLLSK  726 HD5
----SATGIA YDPLMLKHQC VCGNSTTHPE HAGRIQSIWS RLQETGLLNK  676 HD9
P---FTTGLI YDSVMLKHQC SCGDNSRHPE HAGRIQSIWS RLQERGLRSQ  563 HD7
PVLQSRTGLV YDQNMMNH-C NLWDSH-HPE VPQRILRIMC RLEELGLAGR  522 HD6

MEIYRPHKAN AEEMTKYHSD DYIKFLRSIR PDNMSEYSKQ ----------   90 HD1
MEIYRPHKAT AEEMTKYHSD EYIKFLRSIR PDNMSEYSKQ ----------   91 HD2
MIVFKPYQAS QHDMCRFHSE DYIDFLQRVS PTNMQGFTKS ----------   84 HD3
MRIVKPKVAS MEEMATFHTD AYLQHLQKVS QEGEDDHPDS ----------   93 HD8
CECIRGRKAT LEELQTVHSE AHT-LLYGTN PLNRQKLDSK KLLGSLA-SV  745 HD4
CERIRGRKAT LDEIQTVHSE YHT-LLYGTS PLNRQKLDSK KLLGPISQKM  775 HD5
CERIQGRKAS LEEIQLVHSE HHS-LLYGTN PLDGQKLDPR ILLGDDSQKF  725 HD9
CECLRGRKAS LEELQSVHSE RHV-LLYGTN PLSRLKLDNG KLAGLLAQRM  612 HD7
CLTLTPRPAT EAELLTCHSA EYVGHLRATE KMKTRELHRE ----------  562 HD6

---MQRFNVG EDCPVFDGLF ------EFCQ LSTGGSVASA VKLNKQ--QT  129 HD1
---MQRFNVG EDCPVFDGLF ------EFCQ LSTGGSVAGA VKLNRQ--QT  130 HD2
---LNAFNVG DDCPVFPGLF ------EFCS RYTGASLQGA TQLNNK--IC  123 HD3
---IE-YGLG YDCPATEGIF ------DYAA AIGGATITAA QCLIDG--MC  131 HD8
```

Figure 11E

```
PVRLPCGGVG VD---SDTIW NEVHSAGAAR LAVGCVVELV FKVATGELKN    792 HD4
YAVLPCGGIG VD---SDTVW NEMHSSSAVR MAVGCLLELA FKVAAGELKN    822 HD5
FSSLPCGGLG VD---SDTIW NELHSSGAAR MAVGCVIELA SKVASGELKN    772 HD9
FVMLPCGGVG VD---TDTIW NELHSSNAAR WAAGSVTDLA FKVASRELKN    659 HD7
---------S SN---FDSIY ICPSTFACAQ LATGAACRLV EAVLSGEVLN    600 HD6

DIAVNWAGGL HHAKKSEASG PCYVNDIVLA ILELLK---Y HQRVLYIDID    176 HD1
DMAVNWAGGL HHAKKSEASG PCYVNDIVLA ILELLK---Y HQRVLYIDID    177 HD2
DIAINWAGGL HHAKKFEASG PCYVNDIVIG ILELLK---Y HPRVLYIDID    170 HD3
KVAINWSGGW HHAKKDEASG PCYLNDAVLG ILRLRR---K FERILYVDLD    178 HD8
GFAVVRPPG- HHAEESTPMG FCYFNSVAVA AKLLQQ-RLS VSKILIVDWD    840 HD4
GFAIIRPPG- HHAEESTAMG FCFFNSVAIT AKLLQQ-KLN VGKVLIVDWD    870 HD5
GFAVVRPPG- HHAEESTAMG FCFFNSVAIT AKYLRD-QLN ISKILIVDLD    820 HD9
GFAVVRPPG- HHADHSTAMG FCFFNSVAIA CRQLQQ-QSK ASKILIVDWD    707 HD7
GAAVVRPPG- HHAEQDAACG FCFFNSVAVA ARHAQTISGH ALRILIVDWD    649 HD6

IHHGDGVEEA FYTTDRVMTV SFHKYGE--Y FP--GTGDLR DIGAGKGKYY    222 HD1
IHHGDGVEEA FYTTDRVMTV SFHKYGE--Y FP--GTGDLR DIGAGKGKYY    223 HD2
IHHGDGVQEA FYLTDRVMTV SFHKYGNY-F FP--GTGDMY EVGAESGRYY    217 HD3
LHHGDGVEDA FSFTSKVMTV SLHKFSPG-F FP--GTGDVS DVGLGKGRYY    225 HD8
VHHGNGTQQA FYSDPSVLYM SLHRYDDGNF FP--GSGAPD EVGTGPGVGF    888 HD4
IHHGNGTQQA FYNDPSVLYI SLHRYDNGNF FP--GSGAPE EVGGGPGVGY    918 HD5
VHHGNGTQQA FYADPSILYI SLHRYDEGNF FP--GSGAPN EVGTGLGEGY    868 HD9
VHHGNGTQQT FYQDPSVLYI SLHRHDDGNF FP--GSGAVD EVGAGSGEGF    755 HD7
VHHGNGTQHM FEDDPSVLYV SLHRYDHGTP FPMGDEGASS QIGRAAGTGF    699 HD6

AVNYPLRDGI D----DESYE AIFKPVMSKV MEMFQPSAVV LQCGSDSLSG    268 HD1
AVNFPMRDGI D----DESYG QIFKPIISKV MEMYQPSAVV LQCGADSLSG    269 HD2
CLNVPLRDGI D----DQSYK HLFQPVINQV VDFYQPTCIV LQCGADSLGC    263 HD3
SVNVPIQDGI Q----DEKYY QICESVLKEV YQAFNPKAVV LQLGADTIAG    271 HD8
NVNMAFTGGL DPPMGDAEYL AAFRTVVMPI ASEFAPDVVL VSSGFDAVEG    938 HD4
NVNVAWTGGV DPPIGDVEYL TAFRTVVMPI AHEFSPDVVL VSAGFDAVEG    968 HD5
NININLAWTGGL DPPMGDVEYL EAFRTIVKPV AKEFDPDMVL VSAGFDALEG    918 HD9
NVNVAWAGGL DPPMGDPEYL AAFRIVVMPI AREFSPDLVL VSAGFDAAEG    805 HD7
TVNVAWNG-- -PRMGDADYL AAWHRLVLPI AYEPNPELVL VSAGFDAARG    746 HD6

--DRLGCFNL TIKGHAKCVE FVKSPNLPML MLG-GGGYTI RNVARCWTYE    315 HD1
--DRLGCFNL TVKGHAKCVE VVKTFNLPLL MLG-GGGYTI RNVARCWTYE    316 HD2
--DRLGCFNL SIRGHGECVE YVKSFNIPLL VLG-GGGYTV RNVARCWTYE    310 HD3
--DPMCSFNM TPVGIGKCLK YILQWQLATL ILG-GGGYNL ANTARCWTYL    318 HD8
HPTPLGGYNL SARCFGYLTK QLMGLAGGRI VLALEGGHDL TAICDASEAC    988 HD4
HLSPLGGYSV TARCFGHLTR QLMTLAGGRV VLALEGGHDL TAICDASEAC   1018 HD5
HTPPLGGYKV TAKCFGHLTK QLMTLADGRV VLALEGGHDL TAICDASEAC    968 HD9
HPAPLGGYHV SAKCFGYMTQ QLMNLAGGAV VLALEGGHDL TAICDASEAC    855 HD7
--DPLGGCQV SPEGYAHLTH LLMGLASGRI ILILEGGYNL TSISKSMAAC    794 HD6

TAVALDTEIP NELPYNDYFE YFGPDFKLHI SPSN-MTNQN TNEYLEKIKQ    364 HD1
```

Figure 11F

```
TAVALDCEIP NELPYNDYFE YFGPDFKLHI SPSN-MTNQN TPEYMEKIKQ   365 HD2
TSLLVEEAIS EELPYSEYFE YFAPDFTLHP DVSTRIENQN SRQYLDQIRQ   360 HD3
TGVILGKTLS SEIPDHEFFT AYGPDYVLEI TPSC-RPDRN EPHRIQQILN   367 HD8
VSALLGNELD PL-------- ---PEKVLQQ RPN--ANAVE SMEKVMEIHS  1025 HD4
VSALLSVELQ PL-------- ---DEAVLQQ KPN--INAVA TLEKVIEIQS  1055 HD5
VNALLGNELE PL-------- ---AEDILHQ SPN--MNAVI SLQKIIEIQS  1005 HD9
VAALLGNRVD PL-------- ---SEEGWKQ KPN--LNAIR SLEAVIRVHS   892 HD7
TRSLLG---D PP-------- ---PLLTLPR PPL--SGALA SITETIQVHR   828 HD6

RLFENLRML- ------PHAP GVQMQAIPED AIPEESGDE- --DED-----   399 HD1
RLFENLRML- ------PHAP GVQMQAIPED AVHEDSGDE- --DGE-----   400 HD2
TIFENLKML- ------NHAP SVQIHDVPAD LLTYDRTDEA DAEER-----   398 HD3
YIKGNLKHV- ---------- ---------- ---------- ----------   376 HD8
KYWRCLQRT- ------TSTA GRSLIEAQ-- ---------- TCENE-----  1051 HD4
KHWSCVQKF- ------AAGL GRSLRRAQ-- ---------- AGETE-----  1081 HD5
M---SLKFS- ---------- ---------- ---------- ----------  1011 HD9
KYWGCMQRL- ------ASCP DSWVPRVP-- ---------- GADKE-----   918 HD7
RYWRSLRVMK VEDREGPSSS KLVTKKAPQP AKPRLAERMT TREKKVLEAG   878 HD6

---------- ---------- ---------- ---------- ----------   399 HD1
---------- ---------- ---------- ---------- ----------   400 HD2
---------- ---------- ---------- ---------- ----------   398 HD3
---------- ---------- ---------- ---------- ----------   376 HD8
---------- ---------- ---------- ---------- ----------  1051 HD4
---------- ---------- ---------- ---------- ----------  1081 HD5
---------- ---------- ---------- ---------- ----------  1011 HD9
---------- ---------- ---------- ---------- ----------   918 HD7
MGKVTSASFG EESTPGQTNS ETAVVALTQD QPSEAATGGA TLAQTISEAA   928 HD6

---------- --------DP DKRISICSSD KRIACEEEFS DSEEEGEGGR   431 HD1
---------- --------DP DKRISIRASD KRIACDEEFS DSEDEGEGGR   432 HD2
---------- --------GP EENYSRPEAF NEFYDGDHDN DKESDVE---   427 HD3
---------- ---------- ---------- ---------- ----------   376 HD8
---------- --------EA ETVTAMASLS VGVKPAEKR- ----------  1072 HD4
---------- --------EA ETVSAMALLS VGAEQAQAAA A---------  1104 HD5
---------- ---------- ---------- ---------- ----------  1011 HD9
---------- --------EV EAVTALASLS VGILAEDR-- ----------   938 HD7
IGGAMLGQTT SEEAVGGATP DQTTSEETVG GAILDQTTSE DAVGGATLGQ   978 HD6

KNSSNFKK-A KRVKTEDEKE KDPEEKKEVT EEEKTKE--- EKPEAKG---   474 HD1
RNVADHKKGA KKARIEEDKK ETEDKKTDVK EEDKSKDNSG EKTDTKG---   479 HD2
---------- ---------- ---------- ---------- ----------   427 HD3
---------- ---------- ---------- ---------- ----------   376 HD8
---------- ---------- ---------- ---------- ---------P  1073 HD4
--REHSPR-- ---------- ---------- ---------- ---------P  1111 HD5
---------- ---------- ---------- ---------- ----------  1011 HD9
---------- ---------- ---------- ---------- ---------P   939 HD7
TTSEEAVGGA TLAQTTSEAA MEGATLDQTT SEEAPGGTEL IQTPLASSTD  1028 HD6
```

Figure 11G

```
                                                                    474  HD1
                                                                    479  HD2
                                                                    427  HD3
                                                                    376  HD8
DEEP------ ---------- ---------- ---------- ----------             1077  HD4
AEEP------ ---------- ---------- ---------- ----------             1115  HD5
---------- ---------- ---------- ---------- ----------             1011  HD9
SEQL------ ---------- ---------- ---------- ----------              943  HD7
HQTPPTSPVQ GTTPQISPST LIGSLRTLEL GSESQGASES QAPGEENLLG             1078  HD6

474  HD1
                                                                    479  HD2
                                                                    427  HD3
                                                                    376  HD8
---------- ---------- ---------- ---------- ----------             1077  HD4
---------- ---------- ---------- ---------- ----------             1115  HD5
---------- ---------- ---------- ---------- ----------             1011  HD9
---------- ---------- ---------- ---------- ----------              943  HD7
EAAGGQDMAD SMLMQGSRGL TDQAIFYAVT PLPWCPHLVA VCPIPAAGLD             1128  HD6

474  HD1
                                                                    479  HD2
                                                                    427  HD3
                                                                    376  HD8
---------- ---------- ---------- ---------- ----------             1077  HD4
---------- ---------- ---------- ---------- ----------             1115  HD5
---------- ---------- ---------- ---------- ----------             1011  HD9
---------- ---------- ---------- ---------- ----------              943  HD7
VTQPCGDCGT IQENWVCLSC YQVYCGRYIN GHMLQHHGNS GHPLVLSYID             1178  HD6

---------- ---------- --------VK EE-VKLA                            482  HD1
---------- ---------- --------TK SEQLSNP                            488  HD2
---------- ---------- ---------- ------I                            428  HD3
---------- ---------- ---------- ------V                            377  HD8
---------- ---------- --------ME EEPPL--                           1084  HD4
---------- ---------- --------ME QEPAL--                           1122  HD5
---------- ---------- ---------- -------                           1011  HD9
---------- ---------- --------VE EEEPMNL                            952  HD7
LSAWCYYCQA YVHHQALLDV KNIAHQNKFG EDMPHPH                           1215  HD6
```

Figure 12

| Sirtuins | IC50 (μM) |
|---|---|
| Sirtuin1 | 11μM |
| Sirtuin2 | 62% @ 100μM |
| Sirtuin3 | 57% @ 100μM |

NI*=No significant inhibition.

Figure 13

| Mlg1-164 (Log µM) | Sirtuin Activity (Fluorescent counts) | | % Activity | |
|---|---|---|---|---|
| | Repeat1 | Repeat2 | Repeat1 | Repeat2 |
| No CPD | 39360 | 41754 | 96.57 | 103.43 |
| -2.5 | 39283 | 40616 | 96.35 | 100.17 |
| -2.0 | 40334 | 40824 | 99.36 | 100.77 |
| -1.5 | 39364 | 40596 | 96.58 | 100.11 |
| -1.0 | 40463 | 40516 | 99.73 | 99.88 |
| -0.5 | 40124 | 43615 | 98.76 | 108.77 |
| 0.0 | 37172 | 36956 | 90.29 | 89.68 |
| 0.5 | 32809 | 34865 | 77.78 | 83.68 |
| 1.0 | 25113 | 24471 | 55.72 | 53.88 |
| 1.5 | 13789 | 13494 | 23.25 | 22.40 |
| 2.0 | 5151 | 5445 | -1.52 | -0.67 |
| Background | 5596 | 5764 | | |

Figure 15

| Mlg1-164 (Log μM) | Sirtuin Activity (Fluorescent counts) | | % Activity | |
|---|---|---|---|---|
| | Repeat1 | Repeat2 | Repeat1 | Repeat2 |
| No CPD | 32166 | 33691 | 97.20 | 102.80 |
| -2.5 | 33611 | 34391 | 102.50 | 105.36 |
| -2.0 | 33516 | 35798 | 102.15 | 110.52 |
| -1.5 | 33828 | 33735 | 103.30 | 102.96 |
| -1.0 | 32870 | 35789 | 99.79 | 110.49 |
| -0.5 | 35702 | 33689 | 110.17 | 102.79 |
| 0.0 | 33760 | 33579 | 103.05 | 102.39 |
| 0.5 | 34174 | 34760 | 104.57 | 106.72 |
| 1.0 | 34140 | 33300 | 104.44 | 101.36 |
| 1.5 | 27007 | 30460 | 78.29 | 90.95 |
| 2.0 | 16408 | 15678 | 39.43 | 36.75 |
| Background | 5622 | 5686 | | |

Figure 17

| Mlg1-164 (Log µM) | Sirtuin Activity (Fluorescent counts) | | % Activity | |
|---|---|---|---|---|
| | Repeat1 | Repeat2 | Repeat1 | Repeat2 |
| No CPD | 40745 | 39611 | 101.64 | 98.36 |
| -2.5 | 39788 | 40790 | 98.87 | 101.77 |
| -2.0 | 41073 | 40152 | 102.59 | 99.92 |
| -1.5 | 40841 | 41208 | 101.92 | 102.98 |
| -1.0 | 41257 | 40890 | 103.13 | 102.06 |
| -0.5 | 41362 | 40636 | 103.43 | 101.33 |
| 0.0 | 41295 | 40187 | 103.24 | 100.03 |
| 0.5 | 40881 | 39851 | 102.04 | 99.05 |
| 1.0 | 38565 | 38316 | 95.33 | 94.61 |
| 1.5 | 33722 | 32522 | 81.30 | 77.82 |
| 2.0 | 20343 | 20718 | 42.54 | 43.63 |
| Background | 5653 | 5660 | | |

… # CLASS- AND ISOFORM-SPECIFIC HDAC INHIBITORS AND USES THEREOF

RELATED APPLICATIONS

The present application is a national stage filing under 35 U.S.C. §371 of international PCT application, PCT/US2010/002220, filed Aug. 11, 2010, which claims priority under 35 U.S.C. §119(e) to U.S. provisional patent application, U.S. Ser. No. 61/233,035, filed Aug. 11, 2009, each of which is incorporated herein by reference.

GOVERNMENT FUNDING

This invention was made with U.S. Government support under grant NCI P01 CA078048-07 awarded by the National Institutes of Health. The U.S. Government has certain rights in the invention.

BACKGROUND OF THE INVENTION

The identification of small organic molecules that affect specific biological functions has the potential to greatly impact both biology and medicine. Such molecules are useful not only as therapeutic agents and as probes of biological function. In but one example from the emerging field of chemical genetics, in which small molecules are used to alter the function of biological molecules to which they bind, these molecules have been useful at elucidating signal transduction pathways by acting as chemical protein knockouts, thereby causing a loss of protein function (Schreiber et al., *J. Am. Chem. Soc.,* 1990, 112, 5583; Mitchison, *Chem. and Biol.,* 1994, 1, 3). Additionally, due to the interaction of these small molecules with particular biological targets and their ability to affect specific biological function, they may also serve as candidates or leads for the development of new therapeutic agents. For example, natural products, which are small molecules obtained from nature, clearly have played an important role in advances in the fields of biology, chemistry, and medicine, serving as pharmaceutical leads, drugs (Newman et al., *Nat. Prod. Rep.* 2000, 17, 215-234), and powerful tools for studying cell biology (Schreiber, S. L. *Chem. and Eng. News* 1992 (October 26), 22-32).

One biological target of recent interest is histone deacetylase (see, for example, a discussion of the use of inhibitors of historic deacetylases in the treatment of cancer: Marks et al. *Nature Reviews Cancer* 2001, 1, 194; Johnstone et al. *Nature Reviews Drug Discovery* 2002, 1, 287). Post-translational modification of proteins (e.g., histones, transcription factors, tubulin) through the acetylation and deacetylation of lysine residues has a critical role in regulating their biological function. HDACs are zinc hydrolases that modulate gene expression through deacetylation of the N-acetyl-lysine residues of histone proteins and other transcriptional regulators (Hassig et al. *Curr. Opin. Chem. Biol.* 1997, 1, 300-308). The function of other proteins such as tubulin is also thought to be regulated by their acetylation state. HDACs participate in cellular pathways that control cell shape and differentiation, and an HDAC inhibitor has been shown effective in treating an otherwise recalcitrant cancer (Warrell et al. *J. Natl. Cancer Inst.* 1998, 90, 1621-1625). Eleven human HDACs, which use zinc as a cofactor, have been characterized (Taunton et al. *Science* 1996, 272, 408-411; Yang et al. *J. Biol. Chem.* 1997, 272, 28001-28007; Grozinger et al. *Proc. Natl. Acad. Sci. U.S.A.* 1999, 96, 4868-4873; Kao et al. *Genes Dev.* 2000, 14, 55-66; Hu et al. *J. Biol. Chem.* 2000, 275, 15254-15264; Mon et al. *Proc. Natl. Acad. Sci. U.S.A.* 2001, 98, 10572-10577; Venter et al. *Science* 2001, 291, 1304-1351). These members fall into three related classes (Class I, II, and IV) (Gregoretti et al., *J. Mol. Biol.* 2004, 338, 17-31). Class I HDACs include HDAC1, HDAC2, and HDAC3. Class II includes HDAC4, HDAC5, HDAC6, HDAC7, HADC9, and HDAC10. Class II is further subdivided into Class IIa, which includes HDAC4, HDAC5, HDAC7, and HDAC9, and Class IIb, which includes HDAC6 and HDAC10. Class IV includes HDAC11. An additional Class of HDACs has been identified which use NAD as a cofactor. These have been termed Class III deacetylases, also known as the sirtuin deacetylases (SIRT1-7).

Class IIa enzymes (HDAC4, 5, 7, and 9) have been shown to have important regulatory functions in the body. To provide a few examples: HDAC9 has been recently shown to have important regulatory function in regulatory T cells, and that HDAC9 inhibitors seem highly desirable for the treatment of transplant patients as well as the treatment of autoimmune diseases (Tao et al. *Nat. Med.* 2007, 13, 1299-1307). HDAC7 inhibitors have been proposed for the treatment of life-threatening vascular diseases (Miano et al. *Nat. Med.* 2006, 12, 997-998), and HDAC5 inhibitors for the treatment of drug addiction (Nestler et al. *Neuron* 2007, 56, 517-529).

Based on this understanding of known HDACs, efforts are currently focused on developing novel HDAC inhibitors that are isoform- or class-specific inhibitors. Such specificity may allow for the development of pharmaceutical agents for the treatment of HDAC-associated diseases, with greater potency and/or decreased unwanted side effects based on greater on-target activity.

SUMMARY OF THE INVENTION

To date, no small molecules have been reported that selectively target either a class or individual member of the HDAC family (on the other hand, ortholog-selective HDAC inhibitors have been reported: (a) Meinke et al. *J. Med. Chem.* 2000, 14, 4919-4922; (b) Meinke et al *Carr. Med. Chem.* 2001, 8, 211-235). Furthermore, no compound is known which inhibits all HDACs (i.e., no or minimal selectivity).

The present invention provides novel cinnamic hydroxymate deacetylase inhibitors and methods of preparing and using these compounds. A phylogenetic analysis of Class I and II HDACs as targets of a comprehensive, structurally diverse panel of inhibitors revealed unexpected isoform selectivity even among inhibitors widely perceived as non-selective. These data informed the design of a focused library of cinnamic hydroxymates, which allowed the identification of a truly non-selective HDAC inhibitor as well as selective HDAC inhibitors. In particular, cinnamic hydroxymates have been discovered that selectively inhibit Class IIa HDACs (HDAC4, 5, 7, and 9). These novel HDAC inhibitors are useful as research tools as well as for the treatment of various HDAC-associated diseases, including, but not limited to, proliferative diseases, such as cancer; autoimmune diseases; allergic and inflammatory diseases; diseases of the central nervous system (CNS), such as neurodegenerative diseases (e.g., Huntington's disease); vascular diseases, such as restenosis; musculoskeletal diseases; cardiovascular diseases, such stroke and myocardial infarction; pulmonary diseases; and gastric diseases.

In one aspect, the present invention provides novel cinnamic hydroxymate compounds of the general formula (I) and (II):

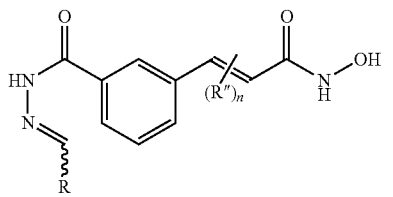
(I)

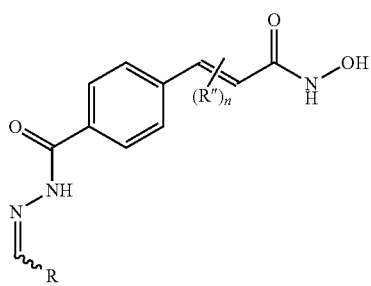
(II)

and pharmaceutically acceptable salts thereof, as described herein. The compounds are useful as inhibitors of histone deacetylases or other deacetylases (e.g., tubulin deacetylase), and thus are useful for the treatment of various diseases and disorders associated with acetylase/deacetylase activity as described herein. The inventive compounds are additionally useful as tools to probe biological function. Exemplary inventive HDAC inhibitors with a 1,4-substitution pattern about the phenyl ring include compounds of the formula:

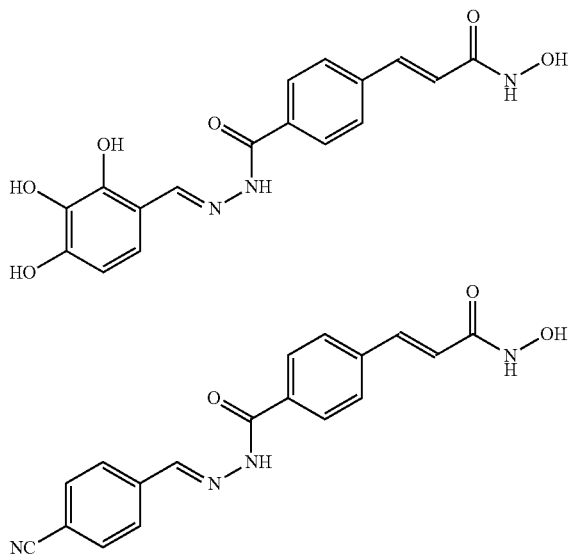

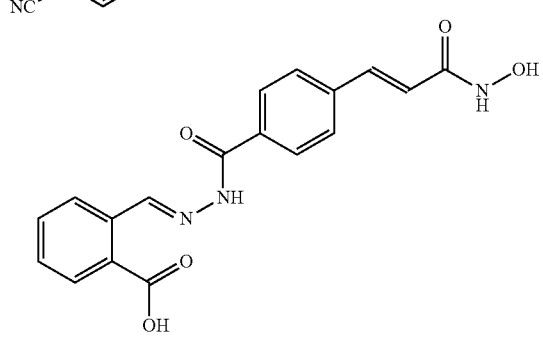

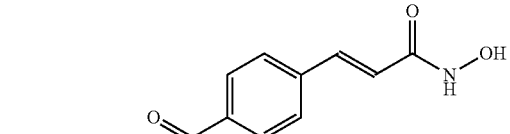

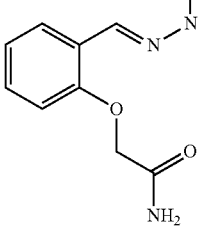

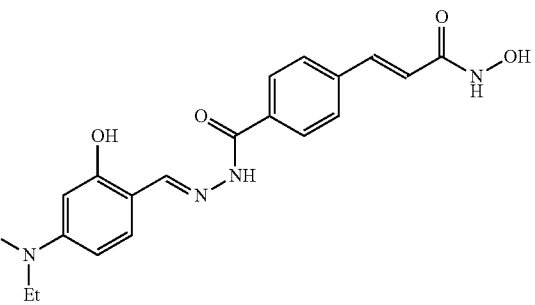

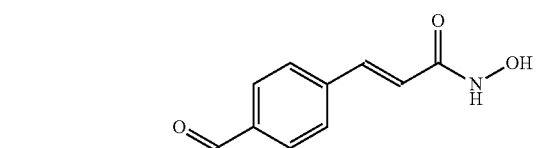

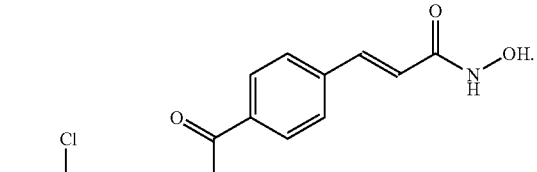

Other exemplary HDAC inhibitors with a 1,3-substitution pattern include compounds of the formula:

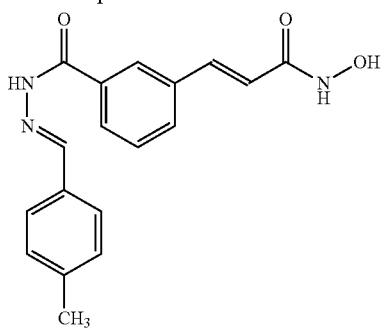

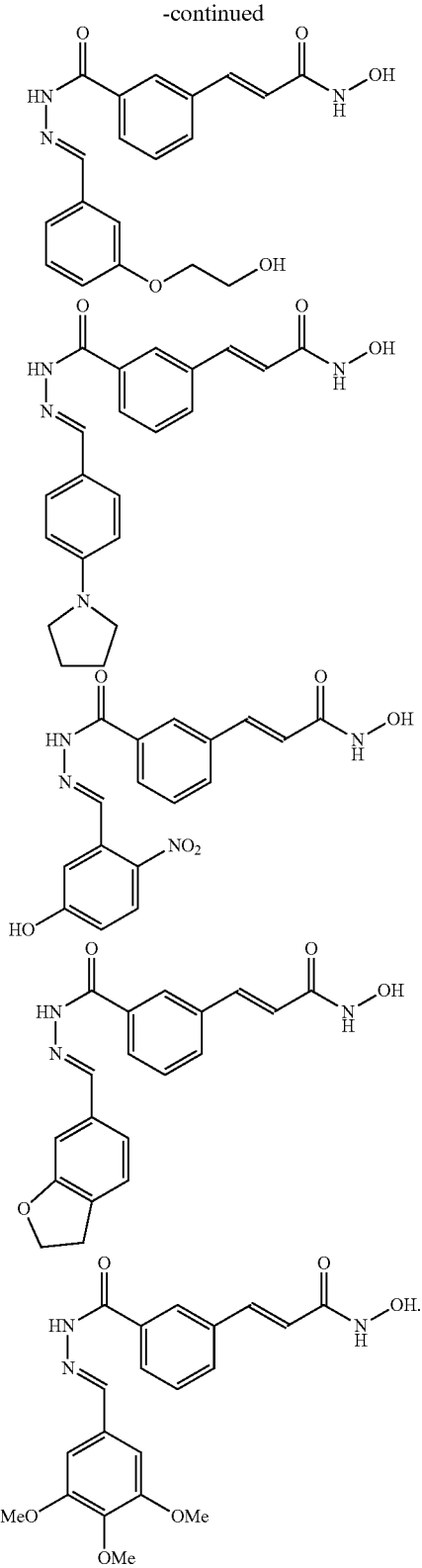

In one aspect, the present invention provides methods for inhibiting histone deacetylase activity or other deacetylase activity in a patient or a biological sample, comprising administering to said patient, or contacting said biological sample, with an effective inhibitory amount of a compound of the invention. In certain embodiments, the compound specifically inhibits a particular HDAC isoform (e.g., HDAC1, HDAC2, HDAC3, HDAC4, HDAC5, HDAC6, HDAC7, HDAC8, HDAC9, HDAC10, HDAC 11) or Class of HDACs (e.g., Class I, II, or IV). In certain embodiments, the compound specifically inhibits Class IIa HDACs. In still another aspect, the present invention provides methods for treating diseases or disorders involving histone deacetylase activity, comprising administering to a subject in need thereof a therapeutically effective amount of a compound of the invention. In certain embodiments, the disease can be proliferative diseases, such as cancer; autoimmune diseases; allergic and inflammatory diseases; diseases of the central nervous system (CNS), such as neurodegenerative diseases (e.g. Huntington's disease); vascular diseases, such as restenosis; musculoskeletal diseases; cardiovascular diseases, such as stroke; pulmonary diseases; and gastric diseases. Diseases associated with Class IIa enzymes include autoimmune diseases, transplant rejection, vascular diseases, and drug addiction; therefore, Class IIa-specific HDAC inhibitors may be particularly useful in treating such diseases.

The compounds may be administered to a subject by any method known in the art. In certain embodiments, the compounds are administered paranterally or orally. The compounds may also be administered topically. The invention also provides pharmaceutical compositions comprising a therapeutically effective amount of an inventive compounds and a pharmaceutically acceptable excipient.

In certain aspect, the present invention provides a kit comprising at least one container having an inventive cinnamic hydroxymate compound or pharmaceutical composition thereof, and instructions for use. In other aspect of the invention the container comprises multiple dosage units of an inventive pharmaceutical composition. For example, the kit may include a whole treatment regimen of the inventive compound.

In another aspect, the present invention provides methods of preparing compounds of the invention. The method comprises reacting a hydrazine of the general formula:

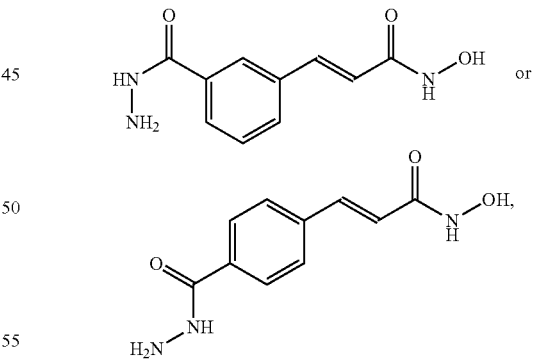

or protected form thereof, with an aldehyde of formula:

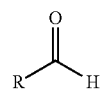

under suitable conditions to yield a compound of the general formulae (I) or (II):

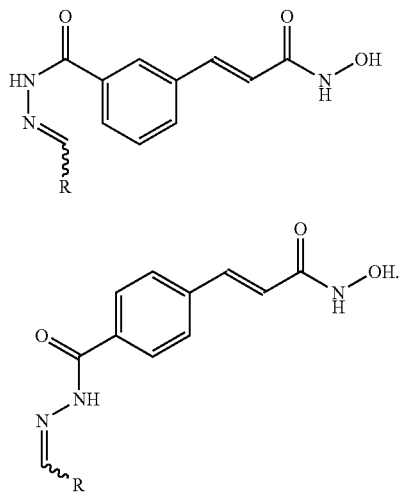

(I)

(II)

Libraries of inventive cinnamic hydroxymates can be prepared by varying either one or both of the starting materials. In certain embodiments, the library is generated by varying the aldehyde. In other embodiments, the library is generated by varying the hydrazine. For example, the double bond of the cinnamic hydroxymate may be substituted.

In certain aspect, the present invention provides an assay to determine the inhibitory effect of a test compound on an HDAC protein. The assay comprises incubating the HDAC protein with a substrate of general formula (III) in the presence of a test compound; and determining the activity of the HDAC protein.

formula (III)

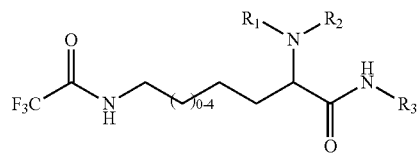

(III)

wherein $R_1$, $R_2$, and $R_3$ are each independently hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR^B$; —C(=O)$R^B$; —CO$_2R^B$; —C(=O)N($R^B$)$_2$; —S$R^B$; —SO$R^B$; —SO$_2R^B$; —N($R^B$)$_2$; —NHC(O)$R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; an amino acid; a peptide; a protecting group; or a tag; or salt thereof; in the presence of a test compound; and determining the activity of the HDAC protein.

In certain embodiments, general formula (III) is

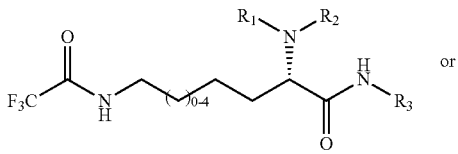

(IIIa)

or

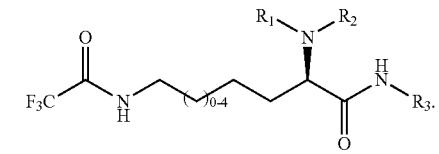

(IIIb)

In another embodiments, formula (IIIa) is formula (IIIc):

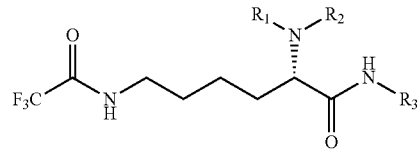

(IIIc)

to be used as a substrate in the assay. With these inventive compounds, Class IIa HDACs exhibit markedly faster kinetics further reducing requisite enzyme concentration and allowing a high-throughput, precise profiling of HDACi against all Class IIa enzymes.

Exemplary inventive compounds of formula (IIIc) include:

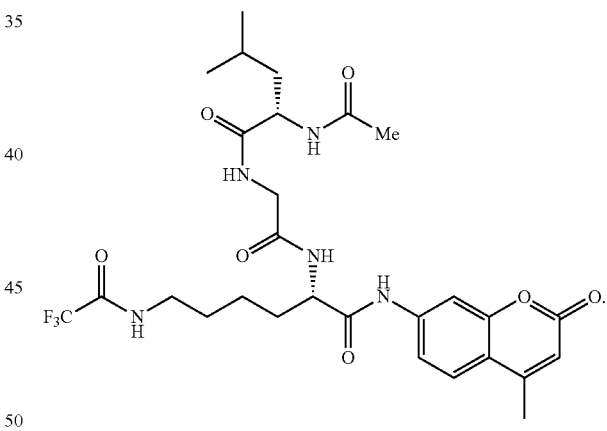

DEFINITIONS

Certain compounds of the present invention, and definitions of specific functional groups are also described in more detail below. For purposes of this invention, the chemical elements are identified in accordance with the Periodic Table of the Elements, CAS version, *Handbook of Chemistry and Physics,* 75th Ed., inside cover, and specific functional groups are generally defined as described therein. Additionally, general principles of organic chemistry, as well as specific functional moieties and reactivity, are described in *Organic Chemistry,* Thomas Sorrell, University Science Books, Sausalito: 1999, the entire contents of which are incorporated herein by reference. Furthermore, it will be appreciated by one of ordinary skill in the art that the synthetic methods, as described herein, utilize a variety of protecting groups. By the term "protecting group," has used herein, it is meant that a particular functional moiety, e.g., C, O, S, or N, is temporarily blocked so that a reaction can be carried out selectively at another reactive site in a multifunctional compound. In certain embodiments, a protecting group reacts selectively in good yield to give a protected substrate that is stable to the projected reactions; the protecting group must be selectively removed in good yield by readily available, preferably nontoxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen, and carbon protecting groups may be utilized. Exemplary protecting groups are detailed herein, however, it will be appreciated that the present invention is not intended to be limited to these protecting groups; rather, a variety of additional equivalent protecting groups can be readily identified using the above criteria and utilized in the method of the present invention. Additionally, a variety of protecting groups are described in *Protective Groups in Organic Synthesis*, Third Ed. Greene, T. W. and Wuts, P. G., Eds., John Wiley & Sons, New York: 1999, the entire contents of which are hereby incorporated by reference. Furthermore, a variety of carbon protecting groups are described in Myers, A.; Kung, D. W.; Zhong, B.; Movassaghi, M.; Kwon, S. *J. Am. Chem. Soc.* 1999, 121, 8401-8402, the entire contents of which are hereby incorporated by reference.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example, of HDAC-associated diseases (e.g., cancer). The term "stable", as used herein, preferably refers to compounds which possess stability sufficient to allow manufacture and which maintain the integrity of the compound for a sufficient period of time to be detected and preferably for a sufficient period of time to be useful for the purposes described herein.

The term "acyl", as used herein, refers to a carbonyl-containing functionality, e.g., —C(=O)R, wherein R is an aliphatic, alycyclic, heteroaliphatic, heterocyclic, aryl, heteroaryl, (aliphatic)aryl, (heteroaliphatic)aryl, heteroaliphatic (aryl), or heteroaliphatic(heteroaryl) moiety, whereby each of the aliphatic, heteroaliphatic, aryl, or heteroaryl moieties is substituted or unsubstituted, or is a substituted (e.g., hydrogen or aliphatic, heteroaliphatic, aryl, or heteroaryl moieties) oxygen or nitrogen containing functionality (e.g., forming a carboxylic acid, ester, or amide functionality).

The term "aliphatic", as used herein, includes both saturated and unsaturated, straight chain (i.e., unbranched) or branched aliphatic hydrocarbons, which are optionally substituted with one or more functional groups. As will be appreciated by one of ordinary skill in the art, "aliphatic" is intended herein to include, but is not limited to, alkyl, alkenyl, and alkynyl moieties. Thus, as used herein, the term "alkyl" includes straight and branched alkyl groups. An analogous convention applies to other generic terms such as "alkenyl", "alkynyl", and the like.

Furthermore, as used herein, the terms "alkyl", "alkenyl", "alkynyl", and the like encompass both substituted and unsubstituted groups. In certain embodiments, as used herein, "lower alkyl" is used to indicate those alkyl groups (substituted, unsubstituted, branched or unbranched) having 1-6 carbon atoms.

In certain embodiments, the alkyl, alkenyl, and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 14 carbon atoms. Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties, and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alicyclic", as used herein, refers to compounds which combine the properties of aliphatic and cyclic compounds and include but are not limited to cyclic, or polycyclic aliphatic hydrocarbons and bridged cycloalkyl compounds, which are optionally substituted with one or more functional groups. As will be appreciated by one of ordinary skill in the art, "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —CH$_2$-cyclopropyl, cyclobutyl, —CH$_2$-cyclopentyl, cyclopentyl, —CH$_2$-cyclopentyl, cyclohexyl, —CH$_2$-cyclohexyl, cyclohexenylethyl, cyclohexanylethyl, norborbyl moieties, and the like, which may bear one or more substituents.

The term "alkoxy" or "alkyloxyl" or "thioalkyl", as used herein, refers to an alkyl group, as previously defined, attached to the parent molecular moiety through an oxygen atom or through a sulfur atom. In certain embodiments, the alkyl group contains 1-20 aliphatic carbon atoms. In certain other embodiments, the alkyl group contains 1-10 aliphatic carbon atoms. In yet other embodiments, the alkyl group contains 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkoxy, include, but are not limited to, methoxy, ethoxy, propoxy, isopropoxy, n-butoxy, tert-butoxy, neopentoxy, and n-hexoxy. Examples of thioalkyl include, but are not limited to, methylthio, ethylthio, propylthio, isopropylthio, n-butylthio, and the like.

The term "alkylamino" refers to a group having the structure —NHR' wherein R' is alkyl, as defined herein. The term "aminoalkyl" refers to a group having the structure $NH_2R'$—, wherein R' is alkyl, as defined herein. In certain embodiments, the alkyl group contains 1-20 aliphatic carbon atoms. In certain other embodiments, the alkyl group contains 1-10 aliphatic carbon atoms. In yet other embodiments, the alkyl contains 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkylamino include, but are not limited to, methylamino, ethylamino, iso-propylamino, n-propylamino, and the like.

Some examples of substituents of the above-described aliphatic (and other) moieties of compounds of the invention include, but are not limited to, aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; —F; —Cl; —Br, —I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$OCO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR_x(CO)R_x$; wherein each occurrence of $R_x$ independently includes, but is not limited to, aliphatic, alycyclic, heteroaliphatic, heterocyclic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments described herein.

In general, the term "aromatic moiety", as used herein, refers to a stable mono- or polycyclic, unsaturated moiety having preferably 3-14 carbon atoms, each of which may be substituted or unsubstituted. In certain embodiments, the term "aromatic moiety" refers to a planar ring having p-orbitals perpendicular to the plane of the ring at each ring atom and satisfying the Huckel rule where the number of pi electrons in the ring is (4n+2), wherein n is an integer. A mono- or polycyclic, unsaturated moiety that does not satisfy one or all of these criteria for aromaticity is defined herein as "non-aromatic," and is encompassed by the term "alicyclic."

In general, the term "heteroaromatic moiety", as used herein, refers to a stable mono- or polycyclic, unsaturated moiety having preferably 3-14 carbon atoms, each of which may be substituted or unsubstituted; and comprising at least one heteroatom selected from O, S, and N within the ring (i.e., in place of a ring carbon atom). In certain embodiments, the term "heteroaromatic moiety" refers to a planar ring comprising at least on heteroatom, having p-orbitals perpendicular to the plane of the ring at each ring atom, and satisfying the Huckel rule where the number of pi electrons in the ring is (4n+2), wherein n is an integer. It will also be appreciated that aromatic and heteroaromatic moieties, as defined herein may be attached via an alkyl or heteroalkyl moiety and thus also include -(alkyl)aromatic, -(heteroalkyl)aromatic, -(heteroalkyl)heteroaromatic, and -(heteroalkyl)heteroaromatic moieties. Thus, as used herein, the phrases "aromatic or heteroaromatic moieties" and "aromatic, heteroaromatic, -(alkyl)aromatic, -(heteroalkyl)aromatic, -(heteroalkyl)heteroaromatic, and -(heteroalkyl)heteroaromatic" are interchangeable. Substituents include, but are not limited to, any of the previously mentioned substituents, i.e., the substituents recited for aliphatic moieties, or for other moieties as disclosed herein, resulting in the formation of a stable compound.

The term "aryl", as used herein, does not differ significantly from the common meaning of the term in the art, and refers to an unsaturated cyclic moiety comprising at least one aromatic ring. In certain embodiments, "aryl" refers to a mono- or bicyclic carbocyclic ring system having one or two aromatic rings including, but not limited to, phenyl, naphthyl, tetrahydronaphthyl, indanyl, indenyl, and the like.

The term "heteroaryl", as used herein, does not differ significantly from the common meaning of the term in the art, and refers to a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups (including bicyclic aryl groups) can be unsubstituted or substituted, wherein substitution includes replacement of one or more of the hydrogen atoms thereon independently with any one or more of the following moieties including, but not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; —F; —Cl; —Br, —I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; and —$NR_x(CO)R_x$; wherein each occurrence of $R_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl, heteroaryl, -(alkyl)aryl or (alkyl)heteroaryl substituents described above and herein may be substituted or unsubstituted. Additionally, it will be appreciated, that any two adjacent groups taken together may represent a 4, 5, 6, or 7-membered substituted or unsubstituted alicyclic or heterocyclic moiety. Additional examples of generally applicable substituents are illustrated by the specific embodiments described herein.

The term "cycloalkyl", as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl, and the like, which, as in the case of aliphatic, alicyclic, heteroaliphatic or heterocyclic moieties, may optionally be substituted with substituents including, but not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; —F; —Cl; —Br, —I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$;

—CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$; wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples of generally applicable substituents are illustrated by the specific embodiments described herein.

The term "heteroaliphatic", as used herein, refers to aliphatic moieties in which one or more carbon atoms in the main chain have been substituted with a heteroatom. Thus, a heteroaliphatic group refers to an aliphatic chain which contains one or more oxygen, sulfur, nitrogen, phosphorus or silicon atoms, e.g., in place of carbon atoms. Heteroaliphatic moieties may be linear or branched, and saturated or unsaturated. In certain embodiments, heteroaliphatic moieties are substituted by independent replacement of one or more of the hydrogen atoms thereon with one or more moieties including, but not limited to, aliphatic; alicyclic; heteroaliphatic; heterocyclic; aromatic; heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; —F; —Cl; —Br, —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; and —NR$_x$(CO)R$_x$; wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described herein may be substituted or unsubstituted. Additional examples of generally applicable substituents are illustrated by the specific embodiments described herein.

The term "heterocycloalkyl", "heterocycle" or "heterocyclic", as used herein, refers to compounds which combine the properties of heteroaliphatic and cyclic compounds and include, but are not limited to, saturated and unsaturated mono- or polycyclic cyclic ring systems having 5-16 atoms wherein at least one ring atom is a heteroatom selected from O, S, and N (wherein the nitrogen and sulfur heteroatoms may be optionally be oxidized), wherein the ring systems are optionally substituted with one or more functional groups, as defined herein. In certain embodiments, the term "heterocycloalkyl", "heterocycle" or "heterocyclic" refers to a non-aromatic 5-, 6-, or 7-membered ring or a polycyclic group wherein at least one ring atom is a heteroatom selected from O, S, and N (wherein the nitrogen and sulfur heteroatoms may be optionally be oxidized), including, but not limited to, a bi- or tri-cyclic group, comprising fused six-membered rings having between one and three heteroatoms independently selected from oxygen, sulfur and nitrogen, wherein (i) each 5-membered ring has 0 to 2 double bonds, each 6-membered ring has 0 to 2 double bonds and each 7-membered ring has 0 to 3 double bonds, (ii) the nitrogen and sulfur heteroatoms may be optionally be oxidized, (iii) the nitrogen heteroatom may optionally be quaternized, and (iv) any of the above heterocyclic rings may be fused to an aryl or heteroaryl ring. Representative heterocycles include, but are not limited to, heterocycles such as furanyl, thiofuranyl, pyranyl, pyrrolyl, thienyl, pyrrolidinyl, pyrazolinyl, pyrazolidinyl, imidazolinyl, imidazolidinyl, piperidinyl, piperazinyl, oxazolyl, oxazolidinyl, isooxazolyl, isoxazolidinyl, dioxazolyl, thiadiazolyl, oxadiazolyl, tetrazolyl, triazolyl, thiatriazolyl, oxatriazolyl, thiadiazolyl, oxadiazolyl, morpholinyl, thiazolyl, thiazolidinyl, isothiazolyl, isothiazolidinyl, dithiazolyl, dithiazolidinyl, tetrahydrofuryl, and benzofused derivatives thereof. In certain embodiments, a "substituted heterocycle, or heterocycloalkyl or heterocyclic" group is utilized and as used herein, refers to a heterocycle, or heterocycloalkyl or heterocyclic group, as defined above, substituted by the independent replacement of one, two or three of the hydrogen atoms thereon with but are not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroaryloxy; heteroaryloxy; alkylthio; arylthio; heteroalkylthio; heteroarylthio; F; Cl; Br, I; —OH; NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$ (R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$; wherein each occurrence of R$_x$ independently includes, but is not limited to, aliphatic, alicyclic; heteroaliphatic, heterocyclic, aromatic, heteroaromatic, aryl, heteroaryl, alkylaryl, alkylheteroaryl, heteroalkylaryl, or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl, or heteroaryl substituents described herein may be substituted or unsubstituted. Additional examples or generally applicable substituents are illustrated by the specific embodiments described herein.

Additionally, it will be appreciated that any of the alicyclic or heterocyclic moieties described herein may comprise an aryl or heteroaryl moiety fused thereto. Additional examples of generally applicable substituents are illustrated by the specific embodiments described herein.

The terms "halo" and "halogen" as used herein refer to an atom selected from fluorine, chlorine, bromine, and iodine.

The term "haloalkyl" denotes an alkyl group, as defined above, having one, two, or three halogen atoms attached thereto and is exemplified by such groups as chloromethyl, bromoethyl, trifluoromethyl, and the like. In certain embodiments, the alkyl group is perhalogenated (e.g., perfluorinated).

The term "amino", as used herein, refers to a primary (—NH$_2$), secondary (—NR$_x$), tertiary (—NR$_x$R$_y$), or quaternary (—N$^+$R$_x$R$_y$R$_z$) amine, where R$_x$, R$_y$, and R$_z$, are independently an aliphatic, alicyclic, heteroaliphatic, heterocyclic, aromatic or heteroaromatic moiety, as defined herein. Examples of amino groups include, but are not limited to, methylamino, dimethylamino, ethylamino, diethylamino, diethylaminocarbonyl, methylethylamino, iso-propylamino, piperidino, trimethylamino, and propylamino.

The term "alkylidene", as used herein, refers to a substituted or unsubstituted, linear or branched saturated divalent radical of carbon and hydrogen atoms, having from one to n carbon atoms and having a free valence at both ends of the radical. The alkylidene moiety may be substituted.

The term "alkenylidene", as used herein, refers to a substituted or unsubstituted, linear or branched unsaturated divalent radical of carbon and hydrogen atoms, having from two to n carbon atoms and having a free valence at both ends of the radical, and wherein the unsaturation is present only as double bonds and wherein a double bond can exist between the first carbon of the chain and the rest of the molecule. The alkenylidene moiety may be substituted.

The term "alkynylidene", as used herein, refers to a substituted or unsubstituted, linear or branched unsaturated divalent radical of carbon and hydrogen atoms, having from two to n carbon atoms, having a free valence "—" at both ends of the radical, and wherein the unsaturation is present only as triple bonds and wherein a triple bond can exist between the first carbon of the chain and the rest of the molecule. The alkynylidene moiety may be substituted.

The term "carbamate", as used herein, refers to any carbamate derivative known to one of ordinary skill in the art. Examples of carbamates include t-Boc, Fmoc, benzyloxycarbonyl, alloc, methyl carbamate, ethyl carbamate, 9-(2-sulfo)fluorenylmethyl carbamate, 9-(2,7-dibromo)fluorenylmethyl carbamate, Tbfmoc, Climoc, Bimoc, DBD-Tmoc, Bsmoc, Troc, Teoc, 2-phenylethyl carbamate, Adpoc, 2-chloroethyl carbamate, 1,1-dimethyl-2-haloethyl carbamate, DB-t-BOC, TCBOC, Bpoc, t-Bumeoc, Pyoc, Bnpeoc, N-(2-pivaloylamino)-1,1-dimethylethyl carbamate, NpSSPeoc. In certain embodiments, carbamates are used as nitrogen protecting groups.

Unless otherwise indicated, as used herein, the terms "alkyl", "alkenyl", "alkynyl", "heteroalkyl", "heteroalkenyl", "heteroalkynyl", "alkylidene", "alkynylidene", -(alkyl)aryl, -(heteroalkyl)aryl, -(heteroalkyl)aryl, -(heteroalkyl)heteroaryl, and the like encompass substituted and unsubstituted, and linear and branched groups. Similarly, the terms "aliphatic", "heteroaliphatic", and the like encompass substituted and unsubstituted, saturated and unsaturated, and linear and branched groups. Similarly, the terms "cycloalkyl", "heterocycle", "heterocyclic", and the like encompass substituted and unsubstituted, and saturated and unsaturated groups. Additionally, the terms "cycloalkenyl", "cycloalkynyl", "heterocycloalkenyl", "heterocycloalkynyl", "aromatic", "heteroaromatic", "aryl", "heteroaryl", and the like encompass both substituted and unsubstituted groups.

The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others pro-drugs. A pro-drug is a derivative of a compound, usually with significantly reduced pharmacological activity, which contains an additional moiety, which is susceptible to removal in vivo yielding the parent molecule as the pharmacologically active species. An example of a pro-drug is an ester, which is cleaved in vivo to yield a compound of interest. Pro-drugs of a variety of compounds, and materials and methods for derivatizing the parent compounds to create the pro-drugs, are known and may be adapted to the present invention. The biological activity of pro-drugs may also be altered by appending a functionality onto the compound, which may be catalyzed by an enzyme. Also, included are oxidation and reduction reactions, including enzyme-catalyzed oxidation and reduction reactions. Certain exemplary pharmaceutical compositions and pharmaceutically acceptable derivatives are discussed in more detail herein.

"Compound": The term "compound" or "chemical compound" as used herein can include organometallic compounds, organic compounds, metals, transitional metal complexes, and small molecules. In certain embodiments, polynucleotides are excluded from the definition of compounds. In other embodiments, polynucleotides and peptides are excluded from the definition of compounds. In certain embodiments, the term compound refers to small molecules (e.g., preferably, non-peptidic and non-oligomeric) and excludes peptides, polynucleotides, transition metal complexes, metals, and organometallic compounds.

"Small Molecule": As used herein, the term "small molecule" refers to a non-peptidic, non-oligomeric organic compound, either synthesized in the laboratory or found in nature. A small molecule is typically characterized in that it contains several carbon-carbon bonds, and has a molecular weight of less than 2000 g/mol, preferably less than 1500 g/mol, although this characterization is not intended to be limiting for the purposes of the present invention. Examples of "small molecules" that occur in nature include, but are not limited to, taxol, dynemicin and rapamycin, Examples of "small molecules" that are synthesized in the laboratory include, but are not limited to, compounds described in Tan et al., ("Stereoselective Synthesis of over Two Million Compounds Having Structural Features Both Reminiscent of Natural Products and Compatible with Miniaturized Cell-Based Assays" *J. Am. Chem. Soc.* 1998, 120, 8565; incorporated herein by reference).

"HDAC": The term "HDAC" or "HDACs" refers to histone deacetylase(s).

"Acetylase activity": The term "acetylase activity" refers to the regulation of a cellular process by modulating protein structure and/or function by the removal of an acetyl group.

"Biological sample": As used herein the term "biological sample" includes, without limitation, cell cultures, or extracts thereof; biopsied material obtained from an animal (e.g., mammal) or extracts thereof; and blood, saliva, urine, feces, semen, tears, or other body fluids or extracts thereof. For example, the term "biological sample" refers to any solid or fluid sample obtained from, excreted by or secreted by any living organism, including single-celled micro-organisms (such as bacteria and yeasts) and multicellular organisms (such as plants and animals, for instance a vertebrate or a mammal, and in particular a healthy or apparently healthy human subject or a human patient affected by a condition or disease to be diagnosed or investigated). The biological sample can be in any form, including a solid material such as a tissue, cells, a cell pellet, a cell extract, cell homogenates, or cell fractions; or a biopsy, or a biological fluid. The biological fluid may be obtained from any site (e.g., blood, saliva (or a mouth wash containing buccal cells), tears, plasma, serum, urine, bile, cerebrospinal fluid, amniotic fluid, peritoneal fluid, and pleural fluid, or cells therefrom, aqueous or vitreous humor, or any bodily secretion), a transudate, an exudate (e.g., fluid obtained from an abscess or any other site of infection or inflammation), or fluid obtained from a joint (e.g., a normal joint or a joint affected by disease such as rheumatoid arthritis, osteoarthritis, gout or septic arthritis). The biological sample can be obtained from any organ or tissue (including a biopsy or autopsy specimen) or may comprise cells (whether primary cells or cultured cells) or medium conditioned by any cell, tissue, or organ. Biological samples may also include sections of tissues such as frozen sections taken for histological purposes. Biological samples also include mixtures of biological molecules including proteins, lipids, carbohydrates, and nucleic acids generated by partial or complete fractionation of cell or tissue homogenates. Although the sample is preferably taken from a human subject, biological samples may be from any animal, plant, bacteria, virus, yeast, etc.

"Animal": The term animal, as used herein, refers to humans as well as non-human animals, at any stage of development, including, for example, mammals, birds, reptiles, amphibians, fish, worms, and single cells. In certain exemplary embodiments, the non-human animal is a mammal (e.g., a rodent, a mouse, a rat, a rabbit, a monkey, a dog, a cat, a sheep, cattle, a primate, or a pig). An animal may be a transgenic animal or a clone.

"Pharmaceutically acceptable salt": As used herein, the term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts of amines, carboxylic acids, and other types of compounds, are well known in the art. For example, Berge et al. describe pharmaceutically acceptable salts in detail in *J. Pharmaceutical Sciences* 1977, 6, 1-19, incorporated herein by reference. The salts can be prepared in situ during the final isolation and purification of a compound of the invention, or separately by reacting a free base or free acid function with a suitable reagent, as described generally below. For example, a free base can be reacted with a suitable acid. Furthermore, where the compound of the invention carries an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid; or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

BRIEF DESCRIPTION OF THE DRAWINGS

FIG. 10 illustrates the biochemical inhibition of HDAC1-9.

FIG. 11 shows the MAFFT alignment of HDAC1-9.

FIG. 12 illustrates the $IC_{50}$ or percentage inhibition of pandacostat (Mlg-1-164) against sirtuins.

FIG. 13 shows the raw data for the effect of pandacostat (Mlg-1-164) on Sirtuin1 activity.

FIG. 15 shows the raw data for the effect of pandacostat (Mlg-1-164) on Sirtuin2 activity.

FIG. 17 represents the raw data for the effect of pandacostat (Mlg-1-164) on Sirtuin3 activity.

DETAILED DESCRIPTION OF THE INVENTION

Figure 1:
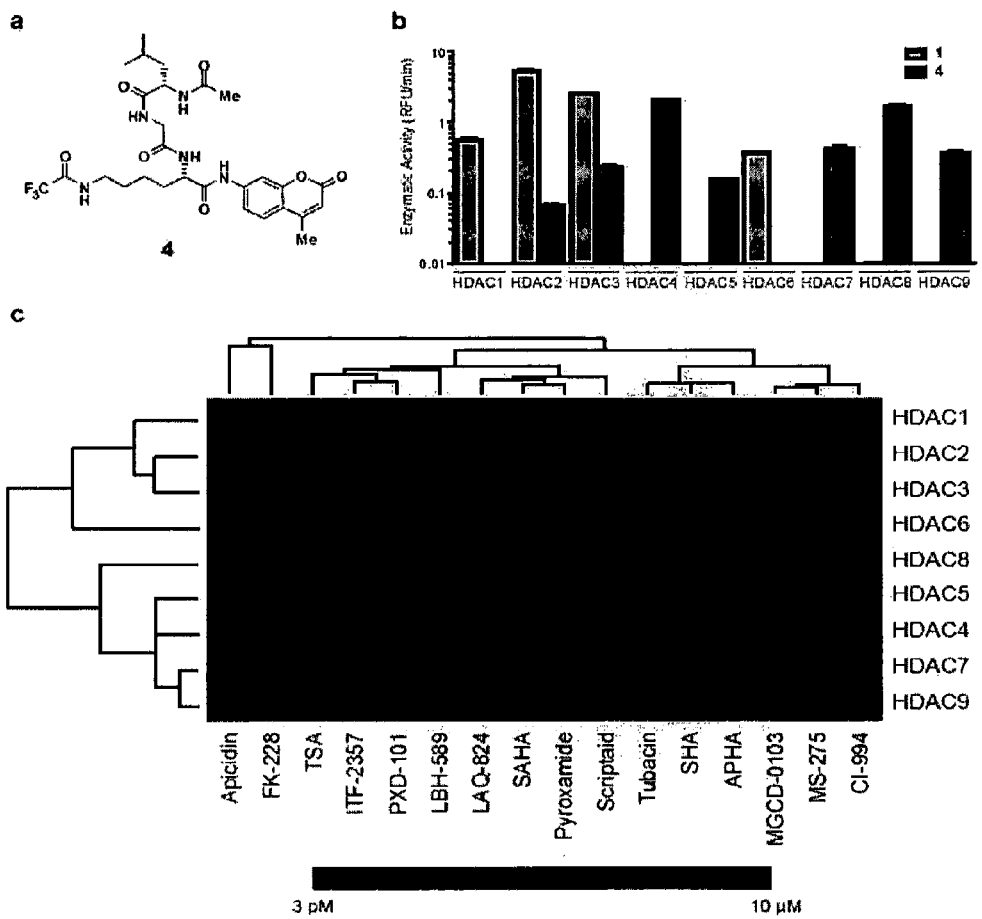
FIG. 1 illustrates chemical phylogenetic analysis of HDACs identifying unexpected selectivity of HDAC inhibitors. (a) Chemical structure of substrate 4. (b) Comparative enzymatic activity of HDAC1-9 with tripeptide substrate 1 and trifluoro acetyl-lysine tripeptide substrate 4, studied at equivalent substrate concentration (10 µM). Substrate 4 allows miniaturized, kinetic study of HDAC4, 5, 7, 8 and 9. (c) Hierarchical clustering of HDACs and a focused library of structurally-diverse HDAC inhibitor tool and investigational compounds weighted by inhibitory potency (KO.

As discussed above, there remains a need for the development of novel histone deacetylase inhibitors, particularly ones that are class- or isoform-specific. The present invention provides novel compounds of general formula (I) and general formula (II), and methods for the synthesis thereof, which compounds are useful as inhibitors of histone deacetylases, and thus are useful for the treatment of diseases or disorders associated with deacetylase activity. In certain embodiments, the inventive compounds are useful in the treatment of proliferative diseases, such as cancer; autoimmune diseases; allergic and inflammatory diseases; diseases of the central nervous system (CNS), such as neurodegenerative diseases (e.g. Huntington's disease); vascular diseases, such as restenosis; musculoskeletal diseases; cardiovascular diseases, such as stroke; pulmonary diseases; and gastric diseases. In particular, the inventive compounds are cinnamic hydroxymates. In certain embodiments, the compounds are class-specific. In certain embodiments, the compounds are isoform-specific. In certain embodiments, the compounds of the invention are Class I HDAC inhibitors. In other embodiments, the compounds are Class IIa HDAC inhibitors. In still other embodiments, the compounds are Class IIb HDAC inhibitors. In certain embodiments, the compounds are Class III HDAC inhibitors. In certain embodiments, the compounds are Class IV HDAC inhibitors.

Compounds of the Invention

Compounds of this invention include those, as set forth above and described herein, and are illustrated in part by the various classes, subgenera, and species disclosed elsewhere herein. In general, the present invention provides cinnamic hydroxymates compounds having the general formula (I) or (II):

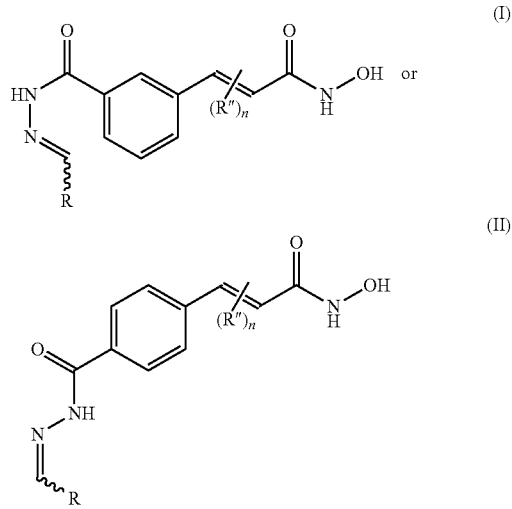

wherein

R is a cyclic or acyclic, substituted or unsubstituted aliphatic moiety; a cyclic or acyclic, substituted or unsubstituted heteroaliphatic moiety; a substituted or unsubstituted aryl-moiety or a substituted or unsubstituted heteroaryl moiety;

each occurrence of R" is independently hydrogen, halogen, or $C_{1-6}$ alkyl;

n is 0, 1, or 2; and pharmaceutically acceptable salts thereof.

In certain embodiments, n is 0. In certain embodiments, n is 1. In certain embodiments, n is 2.

In certain embodiments, R" is halogen. In certain embodiments, R" is fluorine. In certain embodiments, R" is $C_{1-6}$ alkyl. In certain embodiments, R" is methyl. In certain embodiments, R" is ethyl.

In certain embodiments, the compound is of formula:

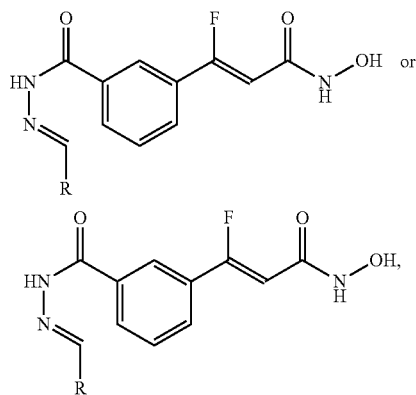

wherein R is as described herein.

In certain embodiments, the compound is of formula:

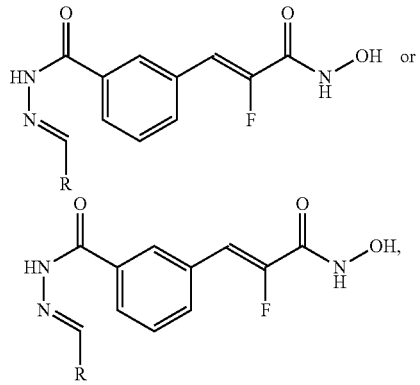

wherein R is as described herein.

In certain embodiments, the compound is of formula:

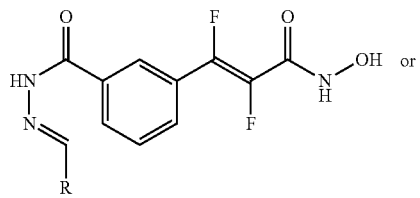

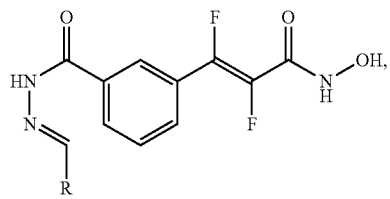

wherein R is as described herein.

In certain embodiments, the compound is of formula (I-1) or (I-2):

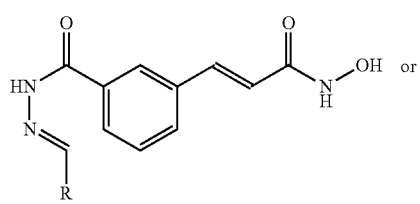

(I-1)

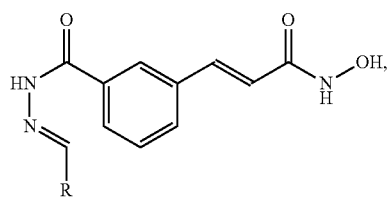

(I-2)

wherein R is as described herein.

In other embodiments, the compound is of formula:

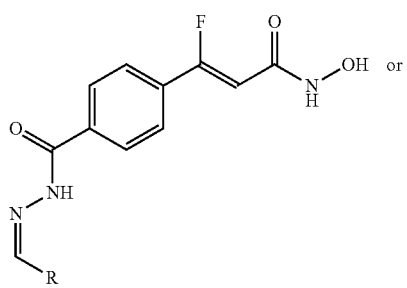

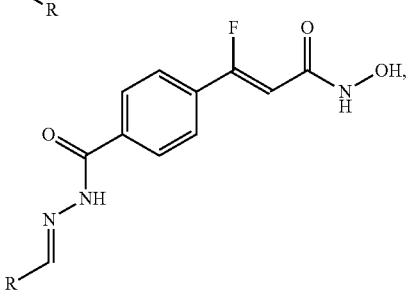

wherein R is as described herein.

In other embodiments, the compound is of formula:

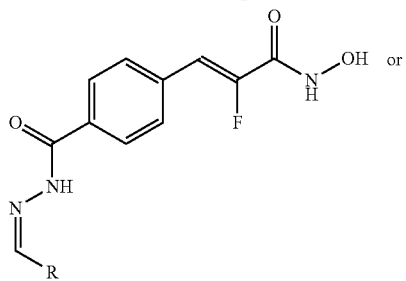

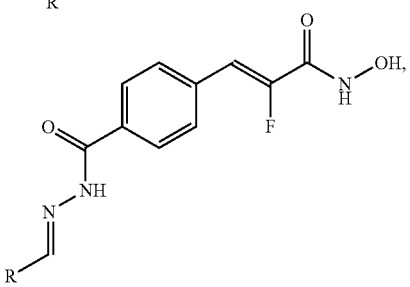

wherein R is as described herein.

In other embodiments, the compound is of formula:

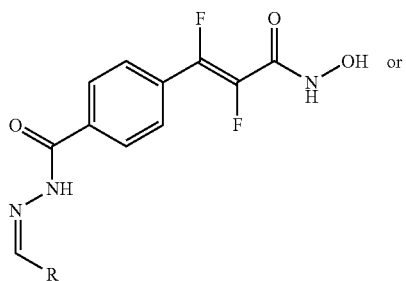

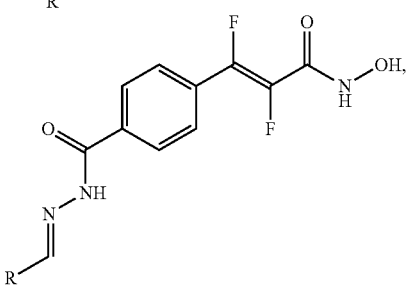

wherein R is as described herein.

In other embodiments, the compound is of formula (II-1) or (II-2):

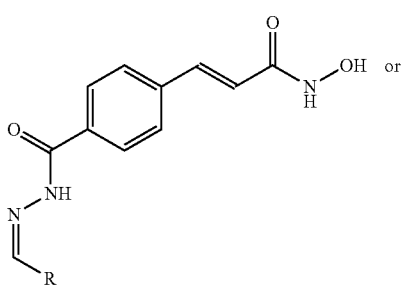

(II-1)

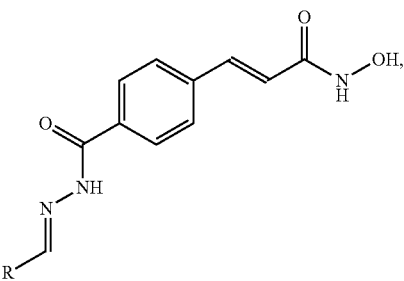

(II-2)

wherein R is as described herein.

In certain embodiments, R is unsubstituted or substituted aryl. In further embodiments, R is unsubstituted or substituted phenyl, bicyclic aryl, tricyclic aryl, or polyclic aryl.

In certain embodiments, R is of the formula:

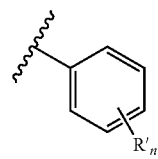

wherein n is an integer 0-5, inclusive;

each occurrence of R' is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $OR^B$; $—C(=O)R^B$; $—CO_2R^B$; $—C(=O)N(R^B)_2$; $—CN$; $—SCN$; $—SR^B$; $—SOR^B$; $—SO_2R^B$; $—NO_2$; $—N(R^B)_2$; $—NHC(O)R^D$; or $—C(R^B)_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; or heteroarylthioxy. In certain embodiments, n is 0. In other embodiments, n is 1, 2, 3, 4 or 5.

In certain embodiments, n is 1. In other embodiments R is selected from the group consisting of:

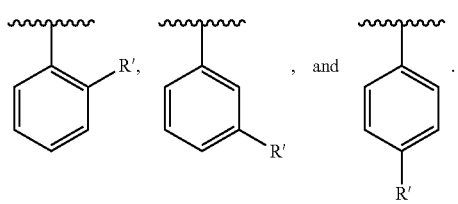

In certain embodiments, R' is halogen. In certain embodiments, R' is fluorine. In other embodiments, R' is cyclic or acyclic, substituted or unsubstituted, branched or unbranched aliphatic. In still other embodiments, R' is cyclic or acyclic, substituted or unsubstituted, branched or unbranched heteroaliphatic. In further embodiments, R' is substituted or unsubstituted, branched or unbranched acyl. In certain embodiments, R' is substituted or unsubstituted, branched or unbranched aryl. In other embodiments, R' is substituted or unsubstituted, branched or unbranched heteroaryl. In still other embodiments, R' is $OR^B$. In further embodiments, R' is $-C(=O)R^B$. In certain embodiments, R' is $-CO_2R^B$. In other embodiments, R' is $-C(=O)N(R^B)_2$. In still other embodiments, R' is $-CN$. In further embodiments, R' is $-SCN$. In certain embodiments, R' is $-SR^B$. In other embodiments, R' is $-SOR^B$. In still other embodiments, R' is $-SO_2R^B$. In further embodiments, R' is $-NO_2$. In certain embodiments, R' is $-N(R^B)_2$. In other embodiments, R' is $-NHC(O)R^B$. In still other embodiments, R' is or $-C(R^B)_3$. In other embodiments, R' is hydroxyl.

In certain embodiments R is selected from the group consisting of:

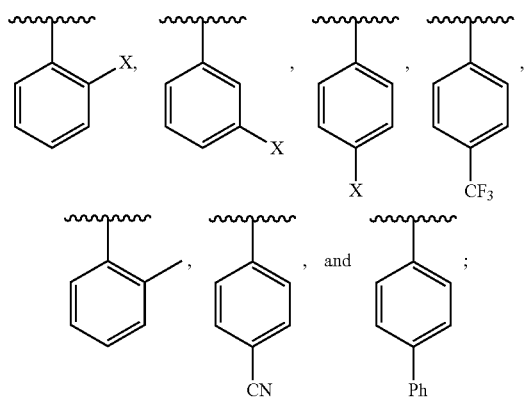

wherein X is halogen. In other embodiments, R is selected from a group consisting of:

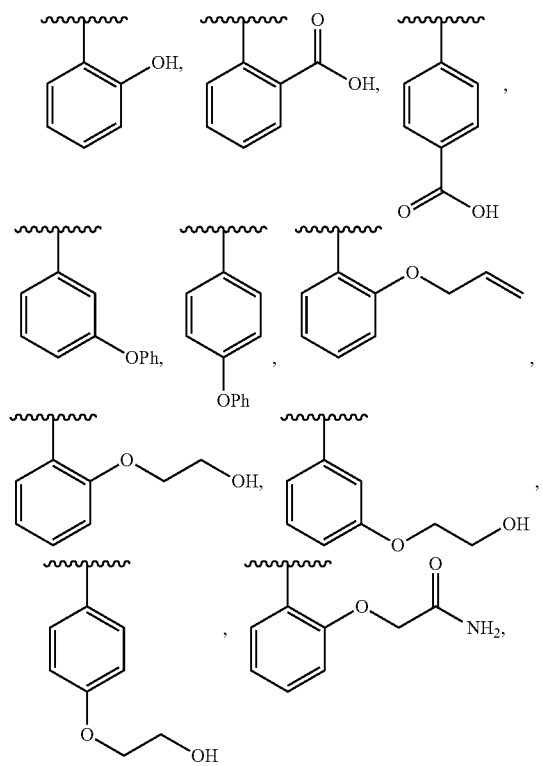

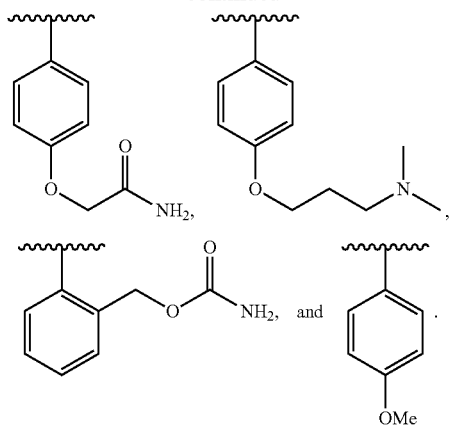

In further embodiments, R is selected from a group consisting of:

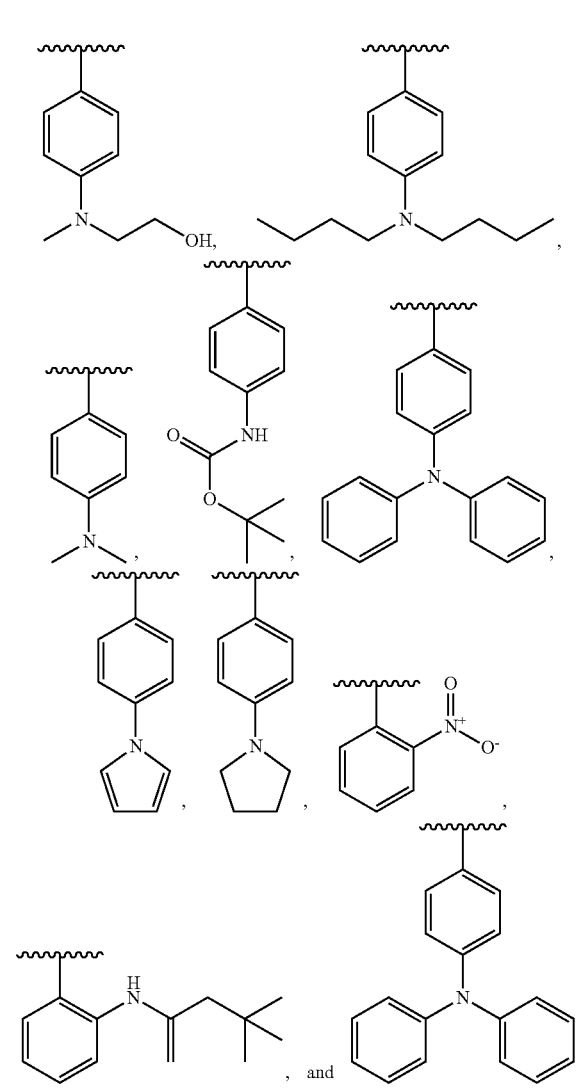

In certain embodiments, R is of the formula:

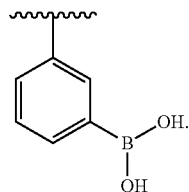 [SMILES: *c1cccc(B(O)O)c1]

In other embodiments, n is 2. In certain embodiments, R is selected from a group consisting of:

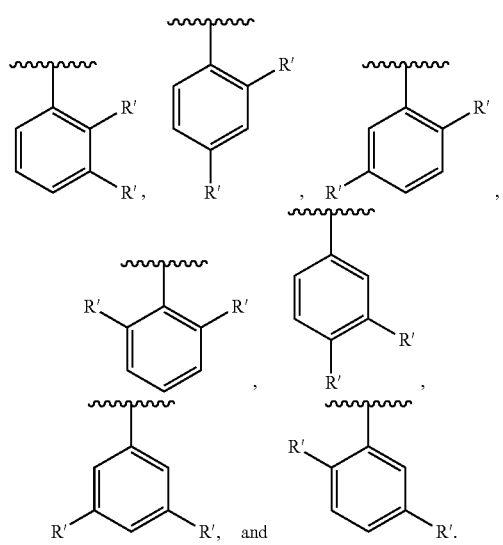

In certain embodiments, the R' groups are the same. In other embodiments, the R' groups are different. In further embodiments, two R' groups are taken together to form a ring. In certain embodiments, two R' groups are taken together to form a carbocyclic ring. In other embodiments, two R' groups are taken together to form a heterocyclic ring. In further embodiments, two R' groups are taken together to form an aromatic ring. In certain embodiments, two R' groups are taken together to form an aryl ring. In other embodiments, two R' groups are taken together to form a heteroaryl ring.

In certain embodiments, R' is halogen. In certain embodiments, R' is fluorine. In other embodiments, R' is cyclic or acyclic, substituted or unsubstituted, branched or unbranched aliphatic. In still other embodiments, R' is cyclic or acyclic, substituted or unsubstituted, branched or unbranched heteroaliphatic. In further embodiments, R' is substituted or unsubstituted, branched or unbranched acyl. In certain embodiments, R' is substituted or unsubstituted, branched or unbranched aryl. In other embodiments, R' is substituted or unsubstituted, branched or unbranched heteroaryl. In still other embodiments, R' is —OR$^B$. In further embodiments, R' is —C(=O)R$^B$. In certain embodiments, R' is —CO$_2$R$^B$. In other embodiments, R' is —C(=O)N(R$^B$)$_2$. In still other embodiments, R' is —CN. In further embodiments, R' is —SCN. In certain embodiments, R' is —SR$^B$. In other embodiments, R' is —SOR$^B$. In still other embodiments, R' is —SO$_2$R$^B$. In further embodiments, R' is —NO$_2$. In certain embodiments, R' is —N(R$^B$)$_2$. In other embodiments, R' is —NHC(O)R$^B$. In still other embodiments, R' is or —C(R$^B$)$_3$. In further embodiments, R' is hydroxyl. In certain embodiments, R is selected from the group consisting of:

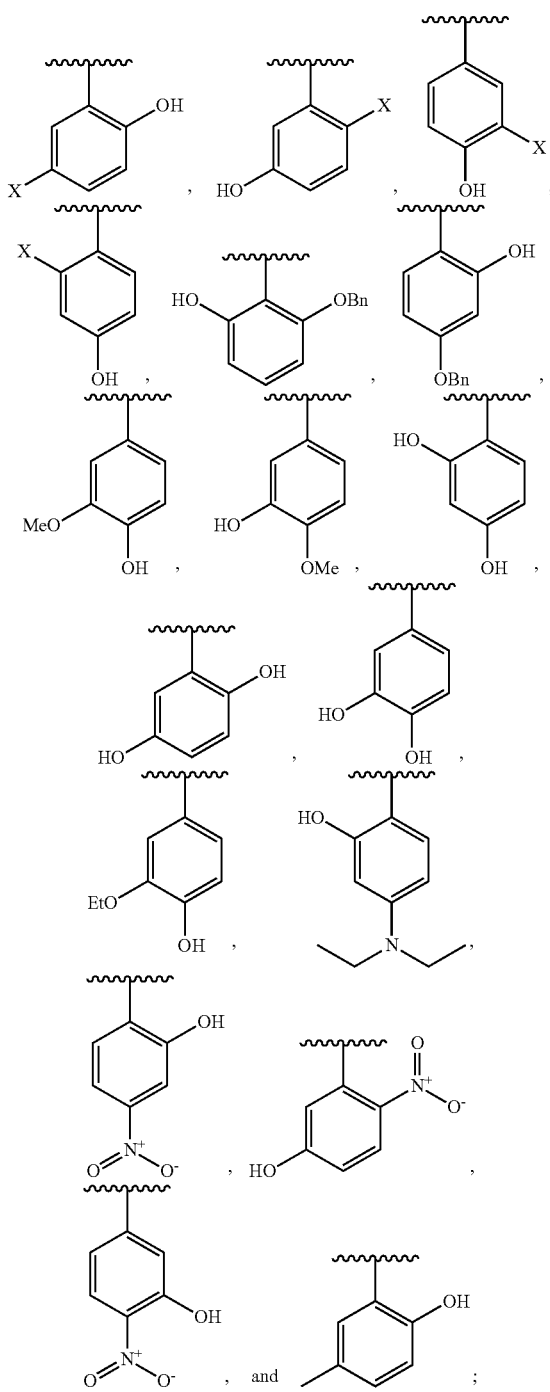

wherein X is halogen. In other embodiments, R is selected from the group consisting of:

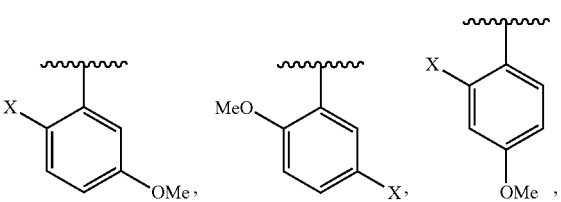

-continued

wherein X is halogen. In still other embodiments, R is selected from the group consisting of:

wherein X is halogen.

In other embodiments, n is 3. In certain embodiments, R is selected from the group consisting of:

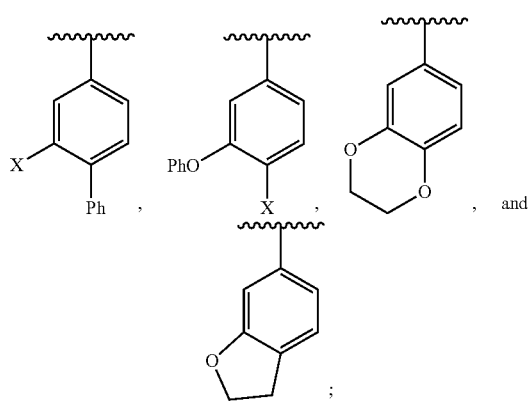

In certain embodiments, the R' groups are the same. In other embodiments, the R' groups are different. In further embodiments, two R' groups are taken together to form a cyclic structure. In certain embodiments, two R' groups are taken together to form a carbocyclic ring. In other embodiments, two R' groups are taken together to form a heterocyclic ring. In further embodiments, two R' groups are taken together to form an aromatic ring. In certain embodiments, two R' groups are taken together to form an aryl ring. In other embodiments, two R' groups are taken together to form a heteroaryl ring.

In certain embodiments, R' is halogen. In certain embodiments, R' is fluorine. In other embodiments, R' is cyclic or acyclic, substituted or unsubstituted, branched or unbranched aliphatic. In still other embodiments, R' is cyclic or acyclic, substituted or unsubstituted, branched or unbranched heteroaliphatic. In further embodiments, R' is substituted or unsubstituted, branched or unbranched acyl. In certain embodiments, R' is substituted or unsubstituted, branched or unbranched aryl. In other embodiments, R' is substituted or unsubstituted, branched or unbranched heteroaryl. In still other embodiments, R' is —OR$^B$. In further embodiments, R' is —C(=O)R$^B$. In certain embodiments, R' is —CO$_2$R$^B$. In other embodiments, R' is —C(=O)N(R$^B$)$_2$. In still other embodiments, R' is —CN. In further embodiments, R' is —SCN. In certain embodiments, R' is —Se. In other embodiments, R' is —SOR$^B$. In still other embodiments, R' is —SO$_2$R$^B$. In further embodiments, R' is —NO$_2$. In certain embodiments, R' is —N(R$^B$)$_2$. In other embodiments, R' is —NHC(O)R$^B$. In still other embodiments, R' is or —C(R$^B$)$_3$. In further embodiments, R' is hydroxyl.

In certain embodiments, R is selected from the group consisting of:

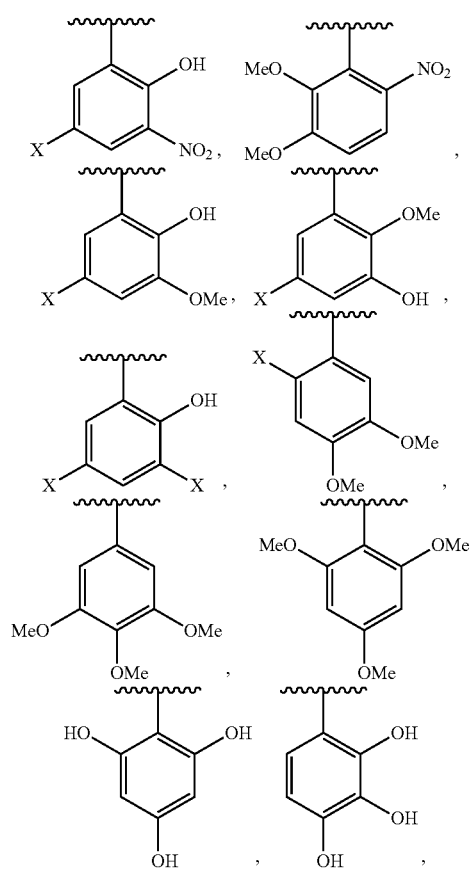

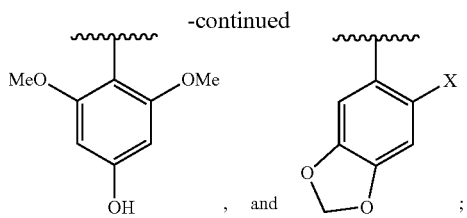, and ;

wherein X is halogen.

In other embodiments n is 4. In certain embodiments, R is selected from the group consisting of:

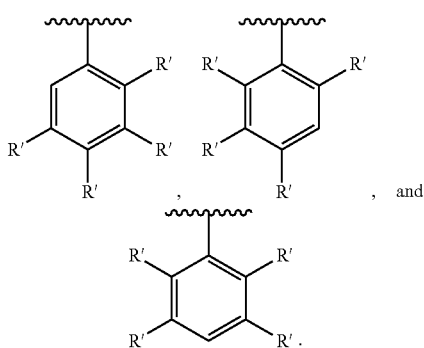

In certain embodiments, the R' groups are the same. In other embodiments, the R' groups are different. In further embodiments, two R' groups are taken together to form a ring. In certain embodiments, two R' groups are taken together to form a carbocyclic ring. In other embodiments, two R' groups are taken together to form a heterocyclic ring. In further embodiments, two R' groups are taken together to form an aromatic ring. In certain embodiments, two R' groups are taken together to form n aryl ring. In other embodiments, two R' groups are taken together to form heteroaryl ring.

In certain embodiments, R' is halogen. In certain embodiments, R' is fluorine. In other embodiments, R' is cyclic or acyclic, substituted or unsubstituted, branched or unbranched aliphatic. In still other embodiments, R' is cyclic or acyclic, substituted or unsubstituted, branched or unbranched heteroaliphatic. In further embodiments, R' is substituted or unsubstituted, branched or unbranched acyl. In certain embodiments, R' is substituted or unsubstituted, branched or unbranched aryl. In other embodiments, R' is substituted or unsubstituted, branched or unbranched heteroaryl. In still other embodiments, R' is —$OR^B$. In further embodiments, R' is —$C(=O)R^B$. In certain embodiments, R' is —$CO_2R^B$. In other embodiments, R' is —$C(=O)N(R^B)_2$. In still other embodiments, R' is —CN. In further embodiments, R' is —SCN. In certain embodiments, R' is —$SR^B$. In other embodiments, R' is —$SOR^B$. In still other embodiments, R' is —$SO_2R^B$. In further embodiments, R' is —$NO_2$. In certain embodiments, R' is —$N(R^B)_2$. In other embodiments, R' is —$NHC(O)R^B$. In still other embodiments, R' is or —$C(R^B)_3$. In further embodiments, R' is hydroxyl.

In certain embodiments, R is of the formula:

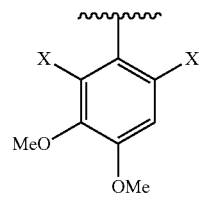

wherein X is halogen.

In other embodiments n is 5. In certain embodiments, R is of the formula:

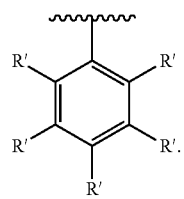

In certain embodiments, the R' groups are the same. In other embodiments, the R' groups are different. In further embodiments, two R' groups are taken together to form a cyclic structure. In certain embodiments, two R' groups are taken together to form a carbocyclic ring. In other embodiments, two R' groups are taken together to form a heterocyclic ring. In further embodiments, two R' groups are taken together to form an aromatic ring. In certain embodiments, two R' groups are taken together to form an aryl ring. In other embodiments, two R' groups are taken together to form a heteroaryl ring.

In certain embodiments, R' is halogen. In certain embodiments, R' is fluorine. In other embodiments, R' is cyclic or acyclic, substituted or unsubstituted, branched or unbranched aliphatic. In still other embodiments, R' is cyclic or acyclic, substituted or unsubstituted, branched or unbranched heteroaliphatic. In further embodiments, R' is substituted or unsubstituted, branched or unbranched acyl. In certain embodiments, R' is substituted or unsubstituted, branched or unbranched aryl. In other embodiments, R' is substituted or unsubstituted, branched or unbranched heteroaryl. In still other embodiments, R' is —$OR^B$. In further embodiments, R' is —$C(=O)R^B$. In certain embodiments, R' is —$CO_2R^B$. In other embodiments, R' is —$C(=O)N(R^B)_2$. In still other embodiments, R' is —CN. In further embodiments, R' is —SCN. In certain embodiments, R' is —$SR^B$. In other embodiments, R' is —$SOR^B$. In still other embodiments, R' is —$SO_2R^B$. In further embodiments, R' is —$NO_2$. In certain embodiments, R' is —$N(R^B)_2$. In other embodiments, R' is —$NHC(O)R^B$. In still other embodiments, R' is or —$C(R^B)_3$. In further embodiments, R' is hydroxyl.

In other embodiments, R is of the formula:

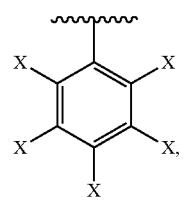

wherein X is halogen.

In certain embodiments, R is a monocyclic substituted or unsubstituted aryl moiety. In other embodiments, R is a bicyclic substituted or unsubstituted aryl moiety. In still other embodiments, R is a polycyclic substituted or unsubstituted aryl moiety. In certain embodiments, R is a polycyclic substituted or unsubstituted aryl moiety. In further embodiments, R is substituted or unsubstituted phenyl, naphthyl, tetrahydronaphthyl, indanyl, or indenyl moiety. In certain embodiments, R is substituted phenyl.

In certain embodiment, R is selected from the group consisting of:

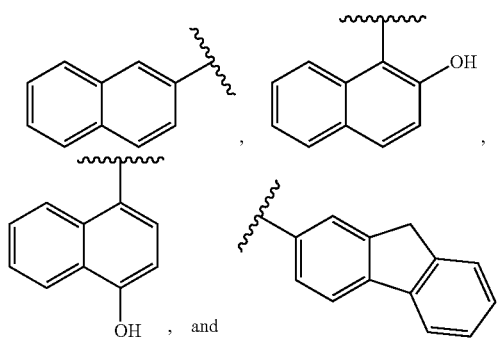

In certain embodiments, R is a monocyclic substituted or unsubstituted heteroaryl moiety. In certain embodiments, R is a substituted or unsubstituted furanyl, thiofuranyl, pyranyl, pyrrolyl, thienyl, pyrrolidinyl, pyrazolinyl, pyrazolidinyl, imidazolinyl, imidazolidinyl, piperidinyl, piperazinyl, oxazolyl, oxazolidinyl, isooxazolyl, isoxazolidinyl, dioxazolyl, thiadiazolyl, oxadiazolyl, tetrazolyl, triazolyl, thiatriazolyl, oxatriazolyl, thiadiazolyl, oxadiazolyl, morpholinyl, thiazolyl, thiazolidinyl, isothiazolyl, isothiazolidinyl, dithiazolyl, dithiazolidinyl, tetrahydrofuryl, and benzofused derivatives thereof. In other embodiments, R is a substituted or unsubstituted heteroaryl moiety. In certain embodiments, R is a substituted or unsubstituted furanyl moiety. In certain embodiments, R is a substituted or unsubstituted thiophenyl moiety. In certain embodiments, R is a substituted or unsubstituted pyridinyl moiety. In yet other embodiments, R is selected from the group consisting of:

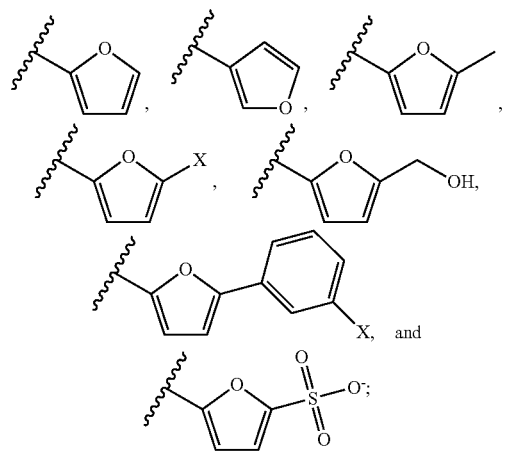

wherein X is halogen. In still other embodiments, R is selected from the group consisting of:

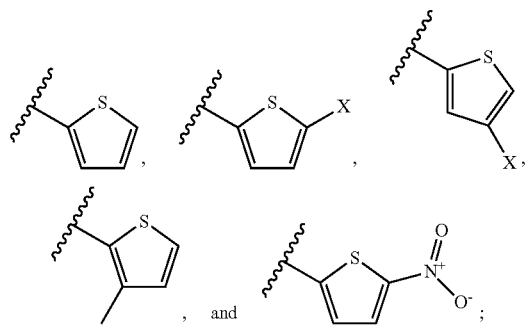

wherein X is halogen. In further embodiments, R is selected from the group consisting of:

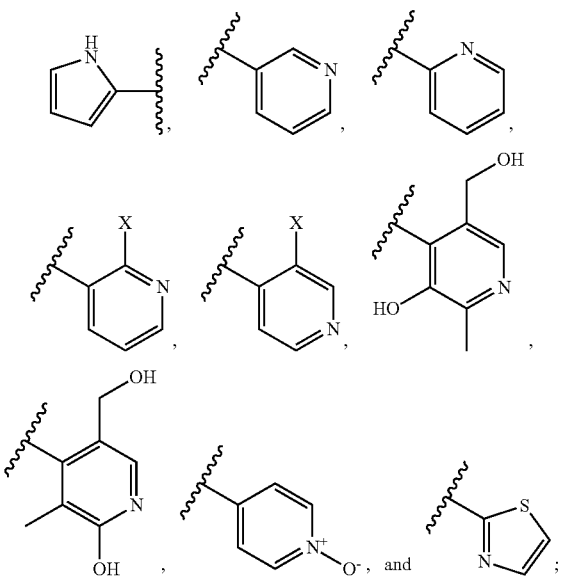

wherein X is halogen.

In other embodiments, R is a bicyclic substituted or unsubstituted heteroaryl moiety. In still other embodiments, R is a polycyclic substituted or unsubstituted heteroaryl moiety. In certain embodiments, R is a polycyclic substituted or unsubstituted heteroaryl moiety. In further embodiments, R is selected from the group consisting of:

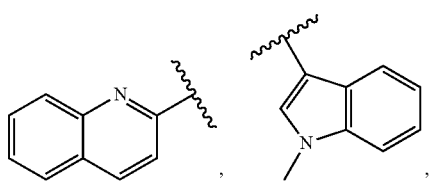

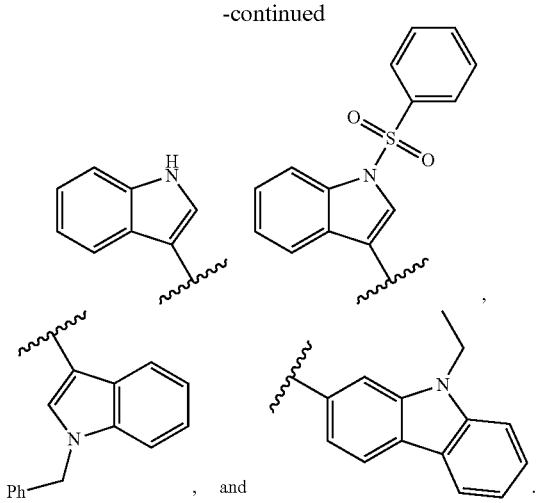

In a specific embodiment, the compound is

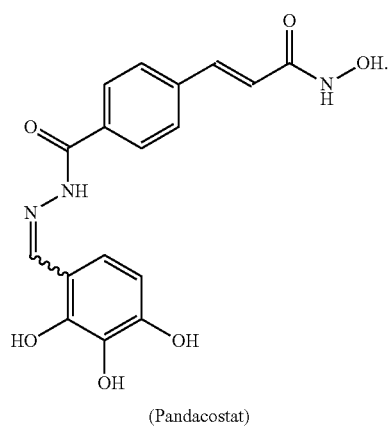 [SMILES: O=C(/C=C/c1ccc(C(=O)NN=Cc2ccc(O)c(O)c2O)cc1)NO]

(Pandacostat)

In certain embodiments, R is a cyclic or acyclic, substituted or unsubstituted aliphatic moiety. In other embodiments, R is a cyclic or acyclic, substituted or unsubstituted $C_{1-12}$ alkyl.

In yet other embodiments, R is a cyclic or acyclic, substituted or unsubstituted $C_{1-6}$ alkyl. In still other embodiments, R is methyl, ethyl, propyl, butyl, pentyl, or hexyl. In certain embodiments R is an aliphatic chain containing at least one stereocenter. In other embodiments, R is a heteroaliphatic chain containing at least one stereocenter.

In certain embodiments, R is a substituted or unsubstituted, branched or unbranched alkenyl. In certain embodiments, R is

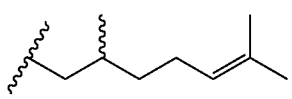

In other embodiments, R is selected from a group consisting of:

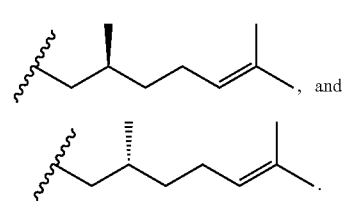

In certain embodiments, R is a hydroxyl substituted alkyl. In other embodiments, R is

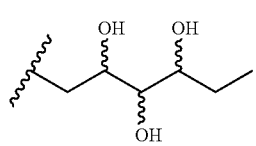

In still other embodiments, R is selected from the group consisting of:

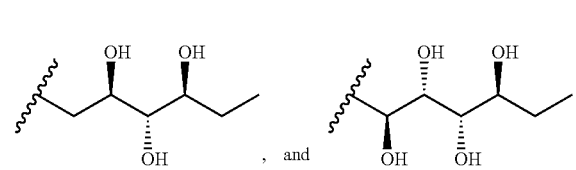

In certain embodiments R is selected from the group consisting of:

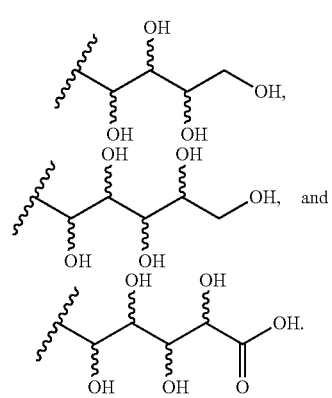

In other embodiments R is selected from the group consisting of:

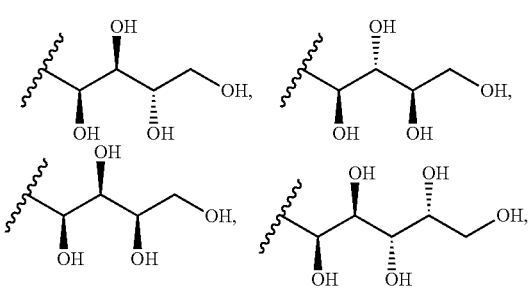

-continued

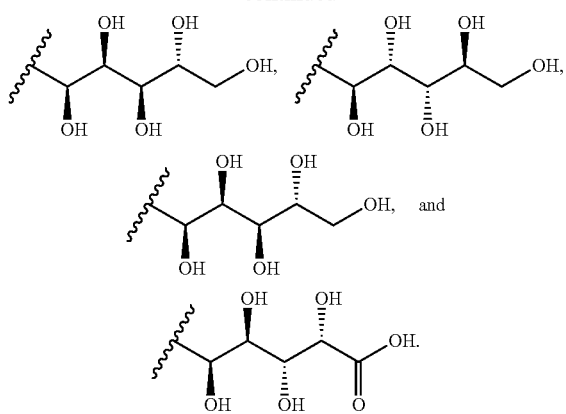

In certain embodiments R comprises glucose. In other embodiments, R is selected from a group consisting of:

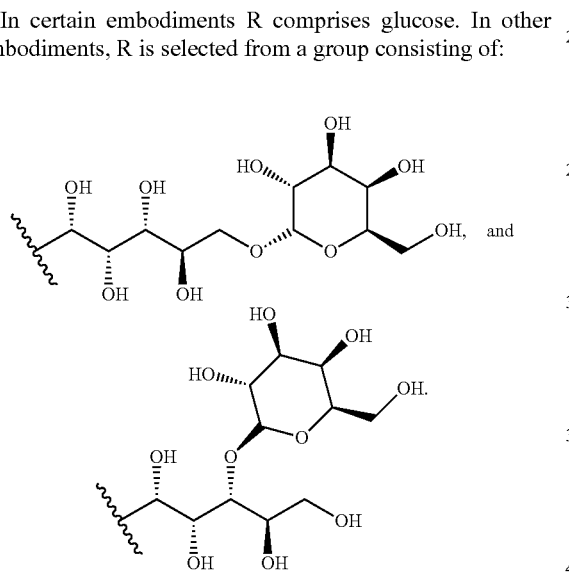

In certain embodiments, R is an aliphatic alkyl. In other embodiments, R is a unsubstituted $C_{1-12}$ alkyl. In still other embodiments, R is a substituted $C_{1-12}$ alkyl. In other embodiments, R is a unsubstituted $C_{1-6}$ alkyl. In still other embodiments, R is a substituted $C_{1-6}$ alkyl. In other embodiments, R is a branched $C_{1-12}$ alkyl. In still other embodiments, R is a unbranched $C_{1-12}$ alkyl. In other embodiments, R is a branched $C_{1-6}$ alkyl. In still other embodiments, R is a unbranched $C_{1-6}$ alkyl. In certain embodiments, R is methyl. In certain embodiments, R is ethyl. In certain embodiments, R is n-propyl. In certain embodiments, R is iso-propyl. In certain embodiments, R is iso-butyl. In certain embodiments, R is n-butyl. In certain embodiments, R is tert-butyl. In certain embodiments, R is pentyl. In certain embodiments, R is hexyl. In certain embodiments, R is heptyl. In certain embodiments, R is octyl. In certain embodiments, R is nonyl. In certain embodiments, R is decyl. In certain embodiments, R is undecyl. In certain embodiments, R is dodecyl.

In certain embodiments, R is selected from the group consisting of:

$C_7H_{15}$, and

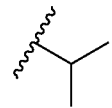

In certain embodiments, R is a substituted or unsubstituted cyclic alkyl. In other embodiments, R is a substituted or unsubstituted carbocyclic alkyl. In other embodiments, R is a substituted or unsubstituted $C_{3-20}$ carbocyclic alkyl. In still other embodiments, R is a substituted or unsubstituted $C_{3-20}$ carbocyclic alkyl. In certain embodiments, R is selected from the group consisting of:

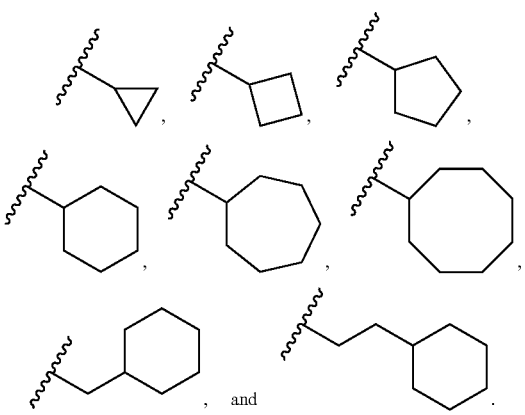

In certain embodiments, R is a substituted or unsubstituted, branched or unbranched alkylenyl. In other embodiments, R is selected from the group consisting of:

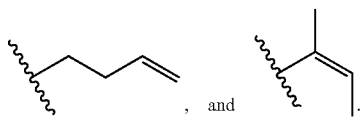

In yet other embodiments, R is selected from the group consisting of:

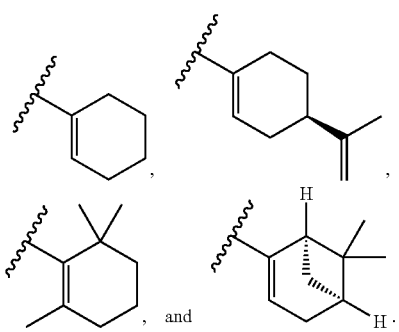

In still other embodiments, R is selected from the group consisting of:

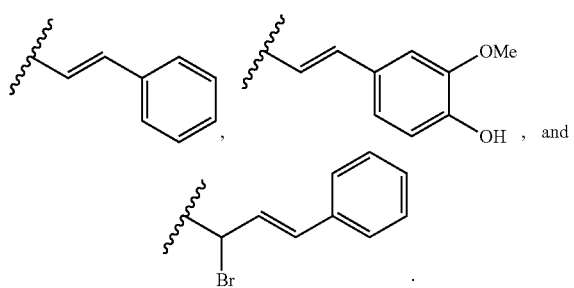
In certain embodiments, R is selected from the group consisting of:
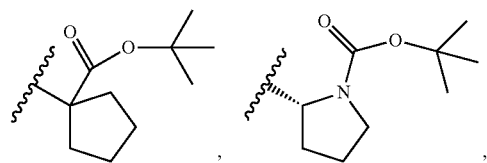
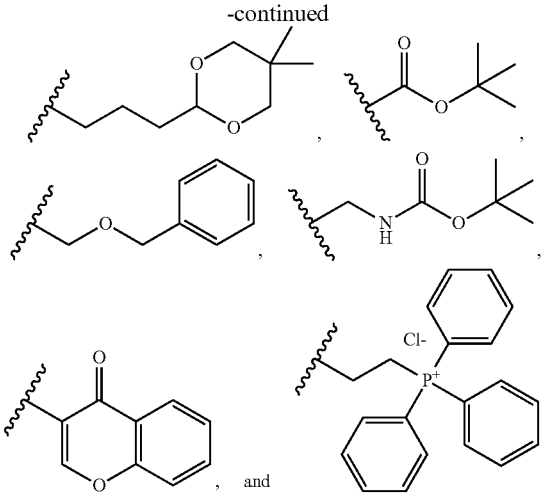
In specific embodiments, the compound is of one of forumulae:
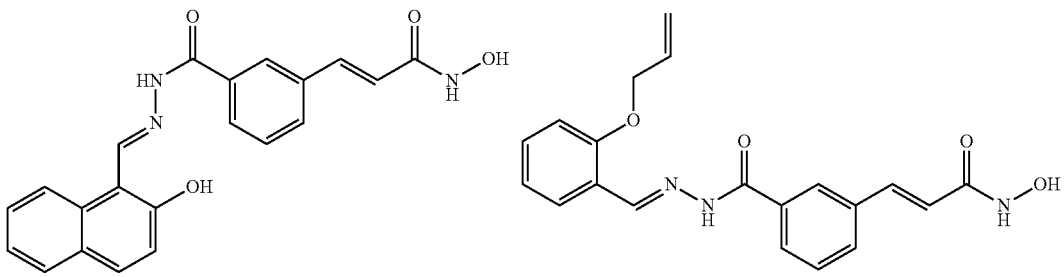
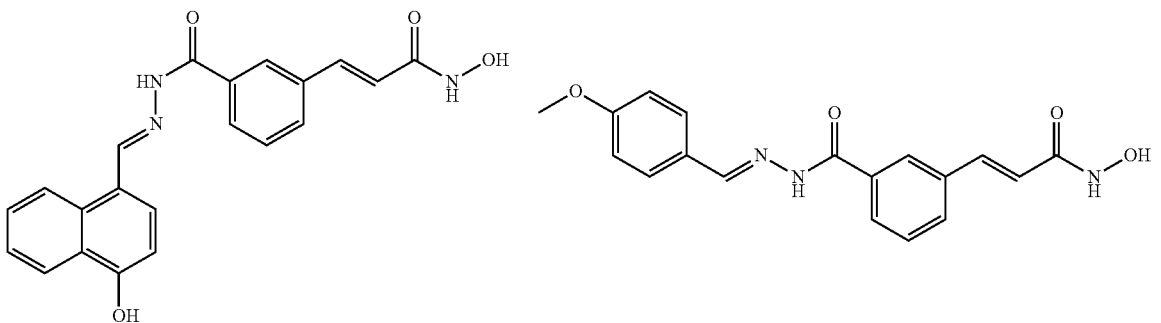
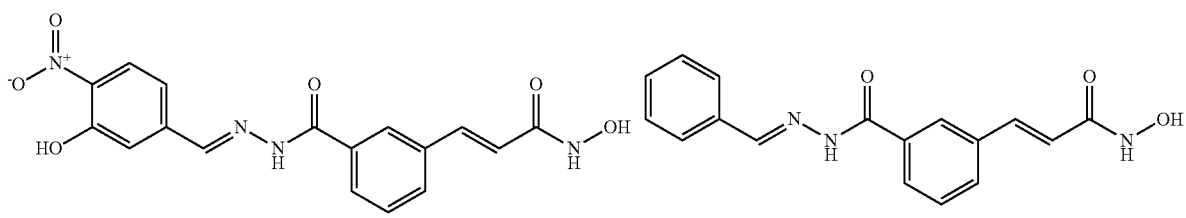
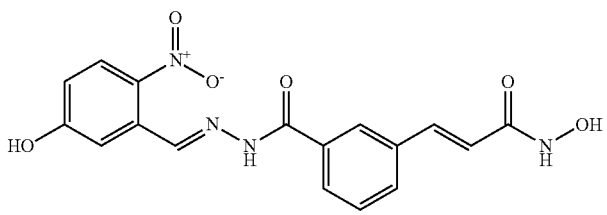

-continued
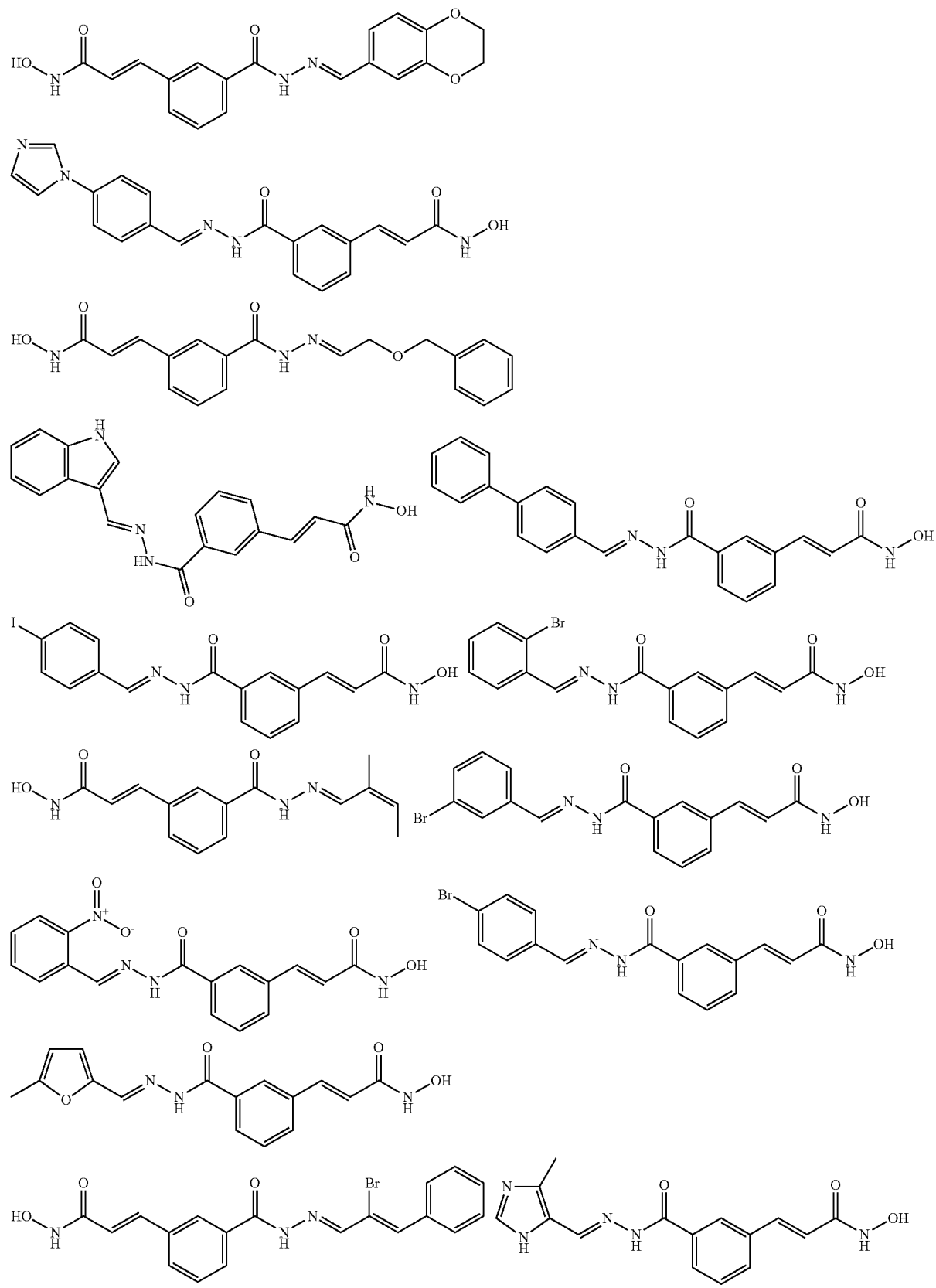

43
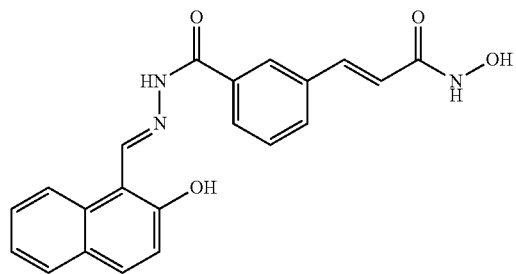
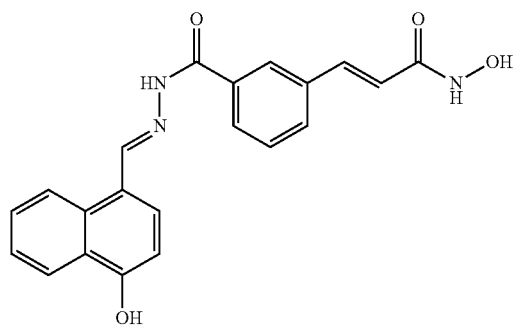
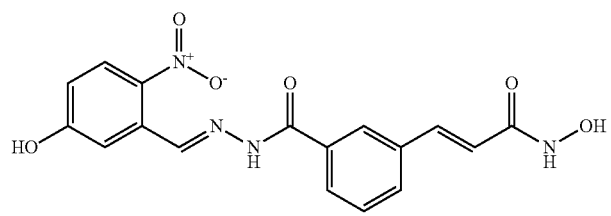
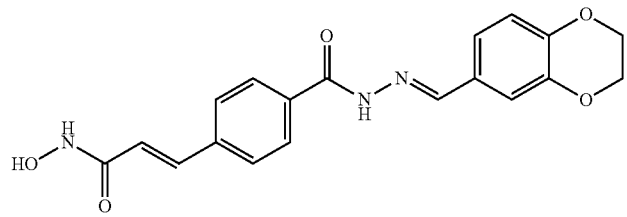
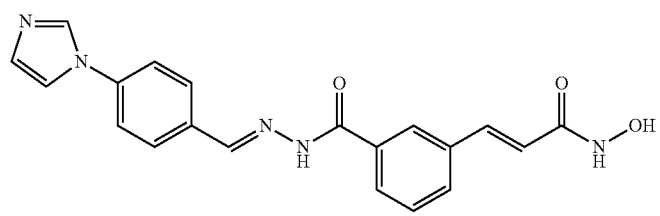
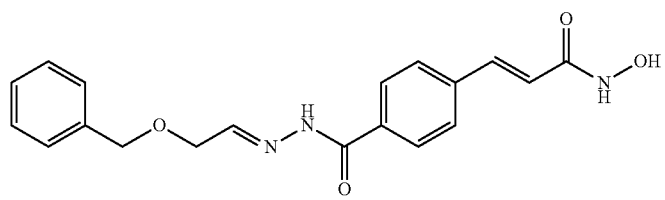
44
-continued
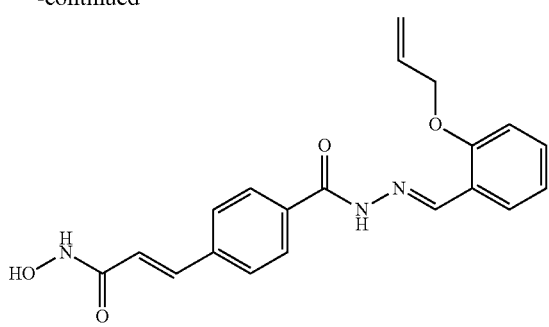
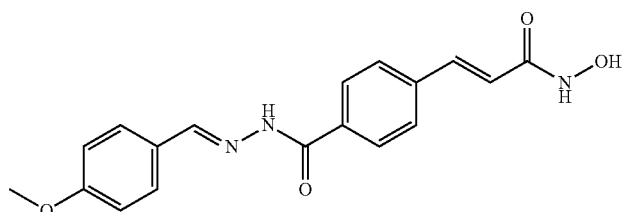
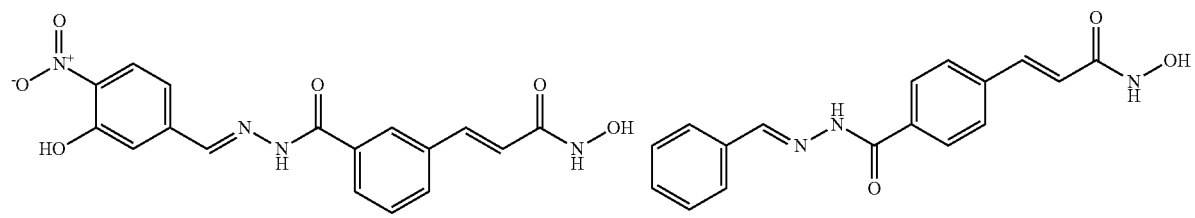

-continued
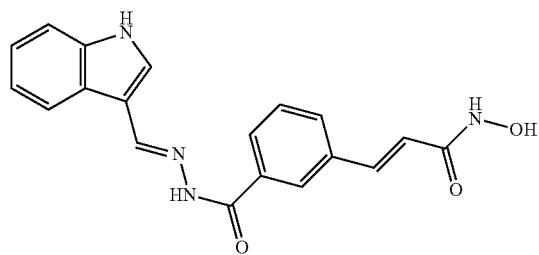
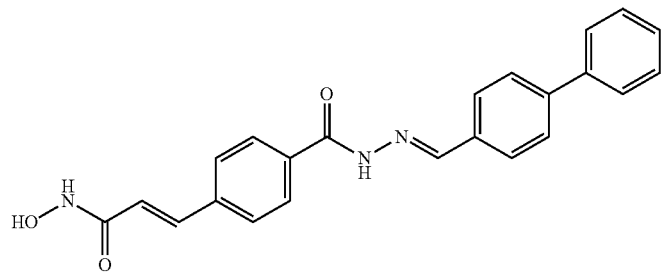
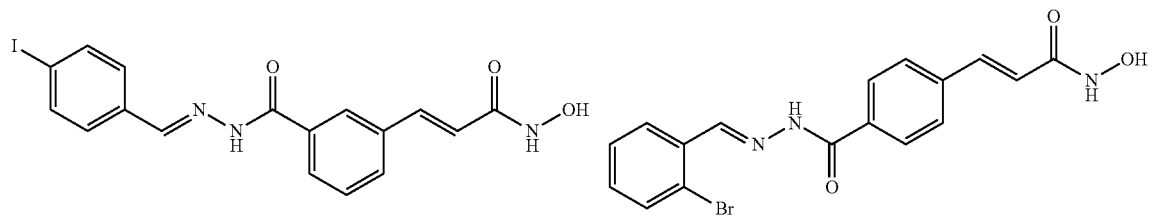
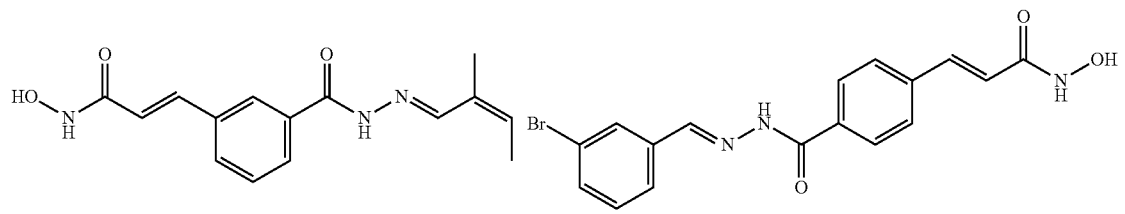
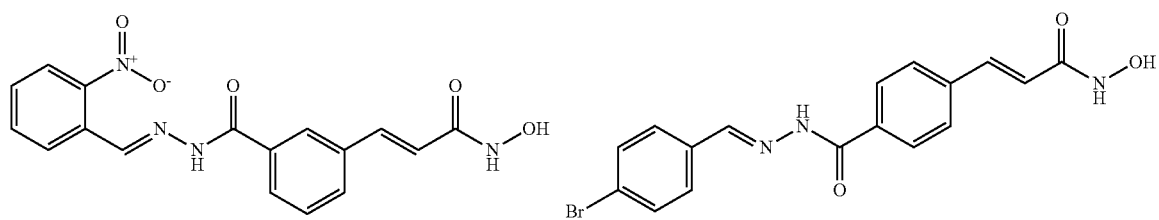
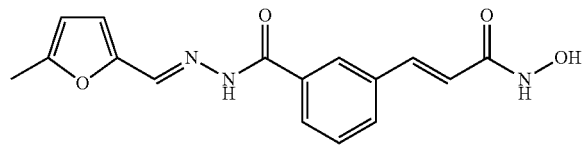
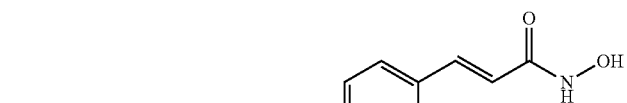
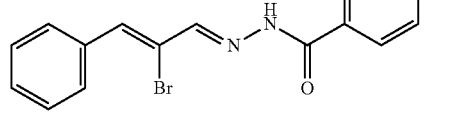
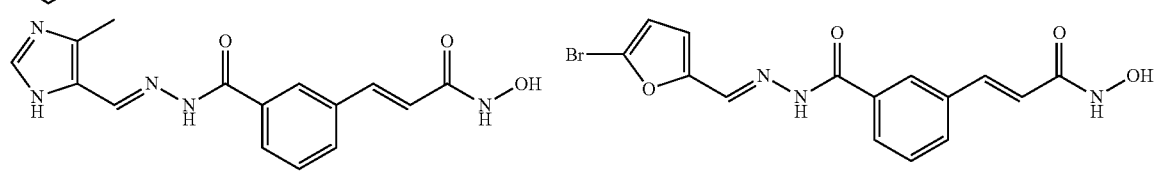

47
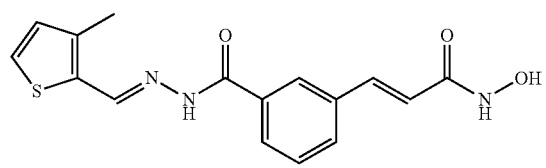
48
-continued
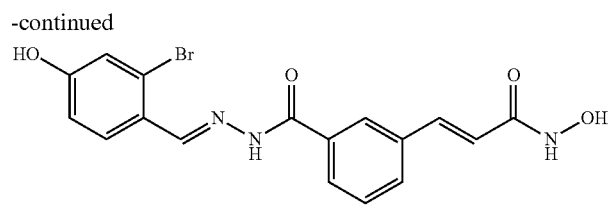
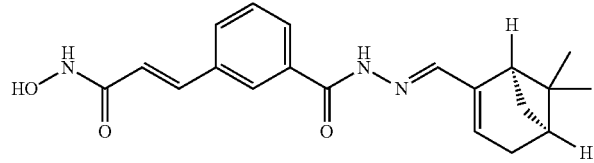
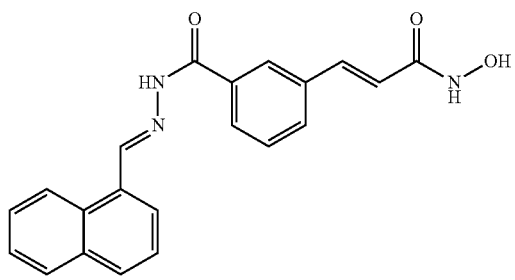
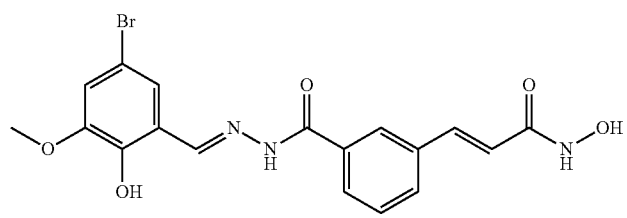
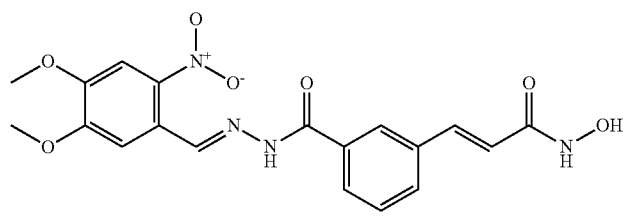
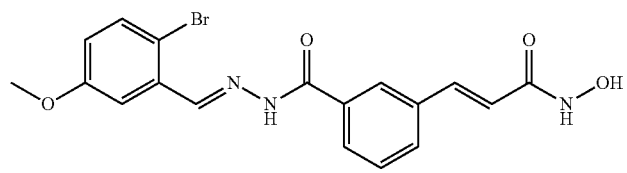
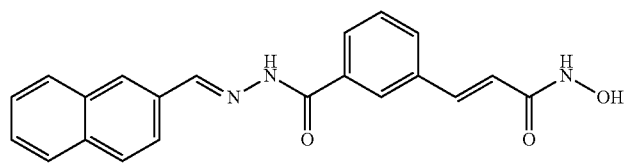
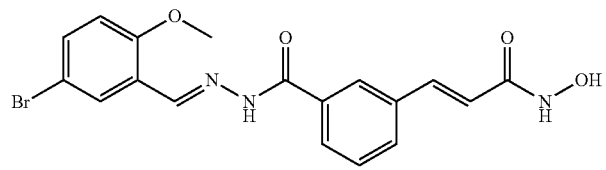
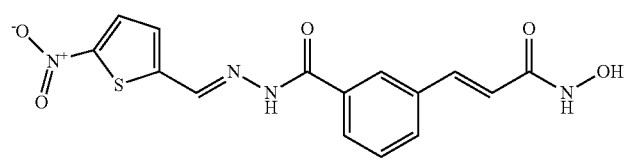

-continued
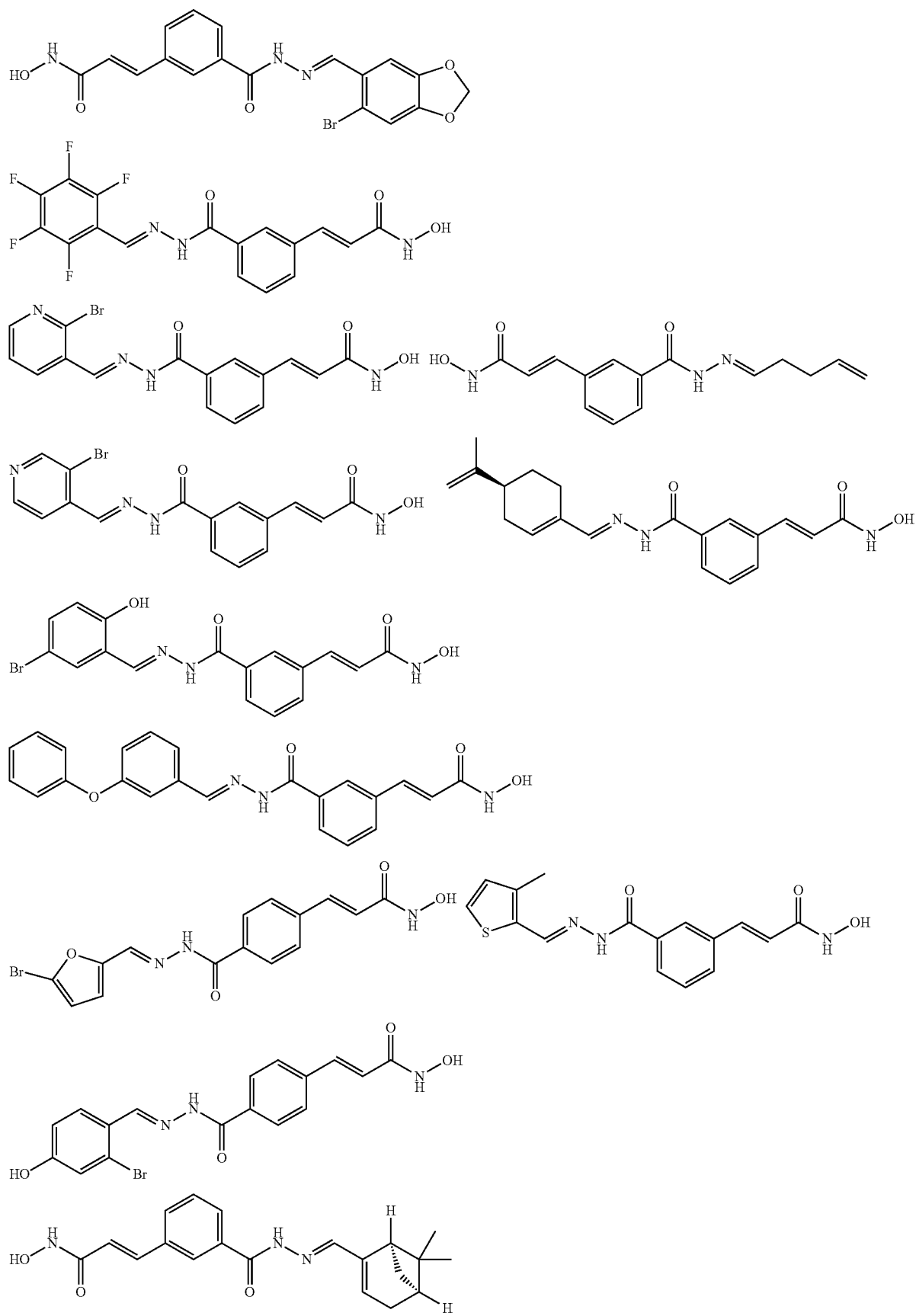

51 52
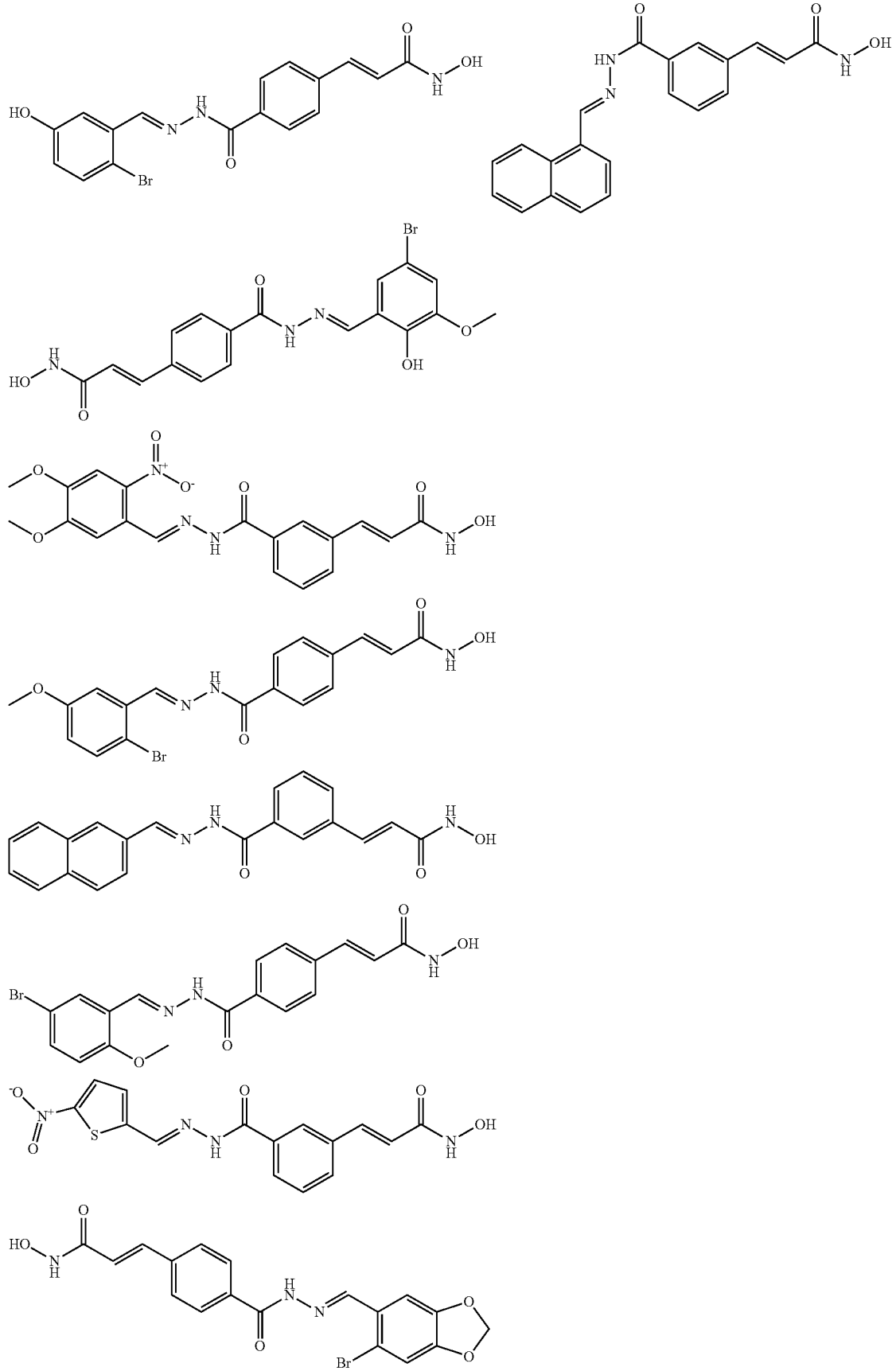

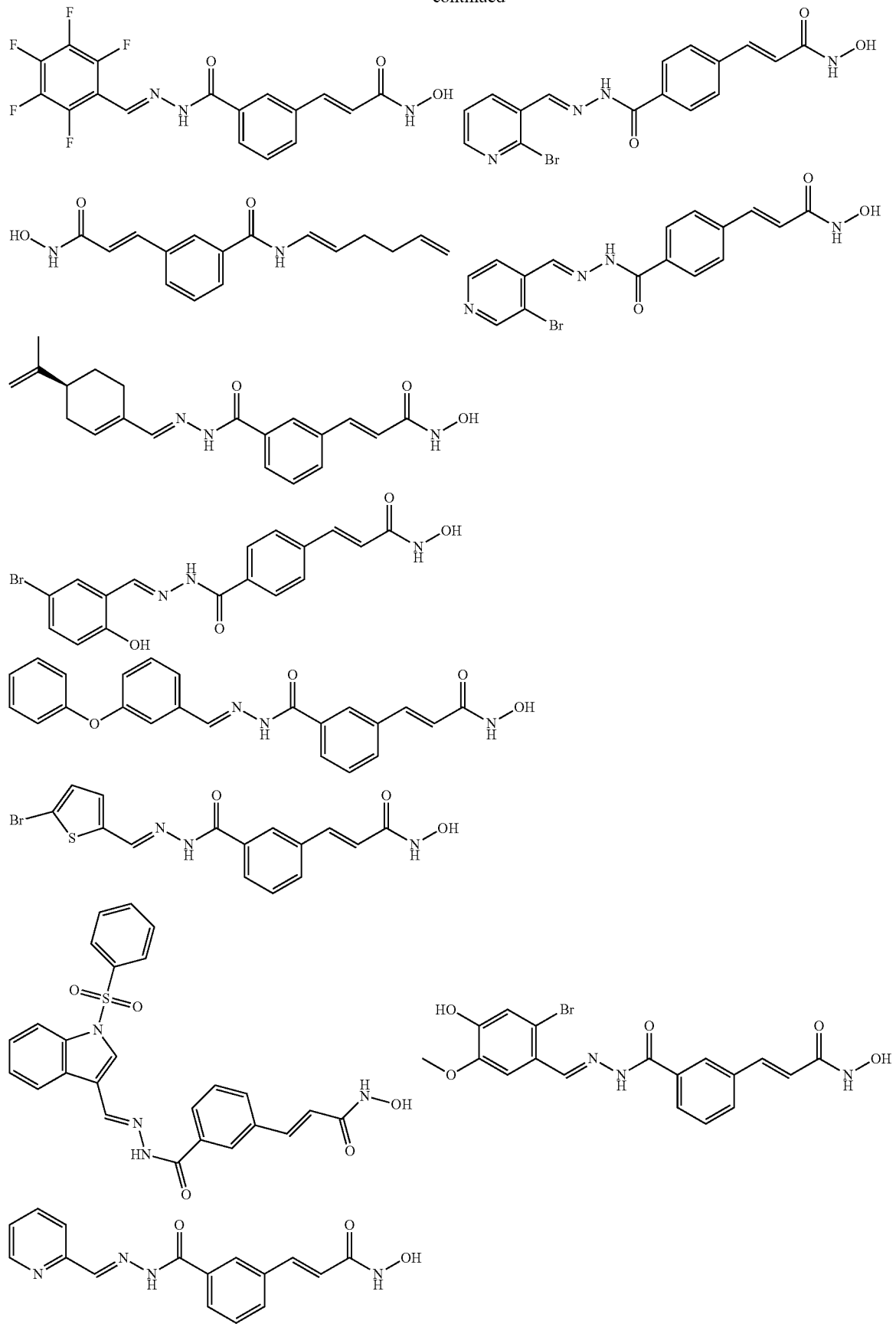

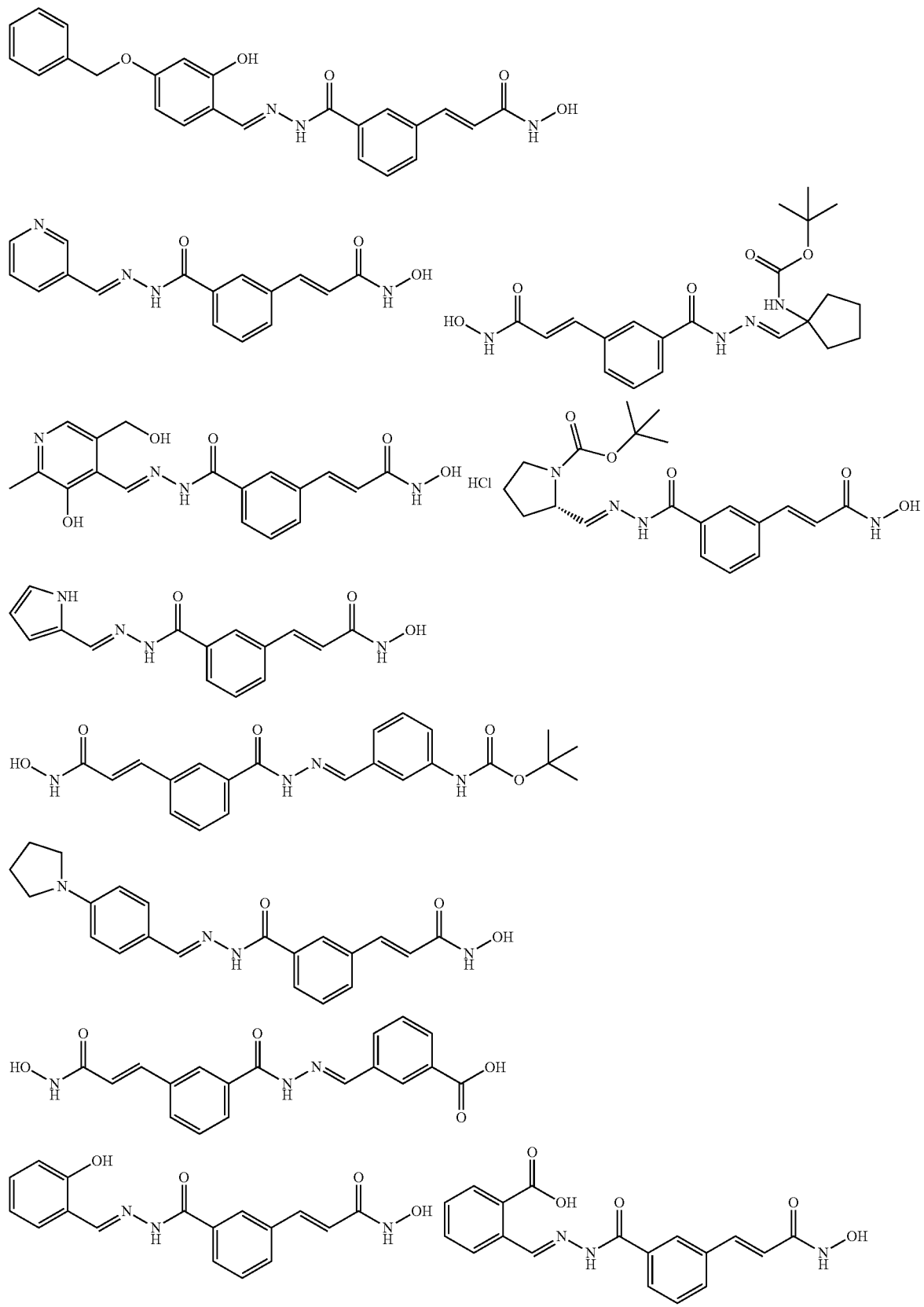

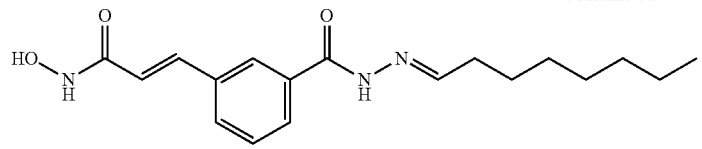
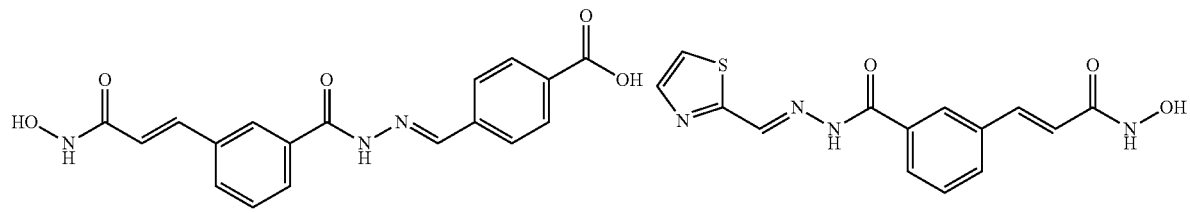
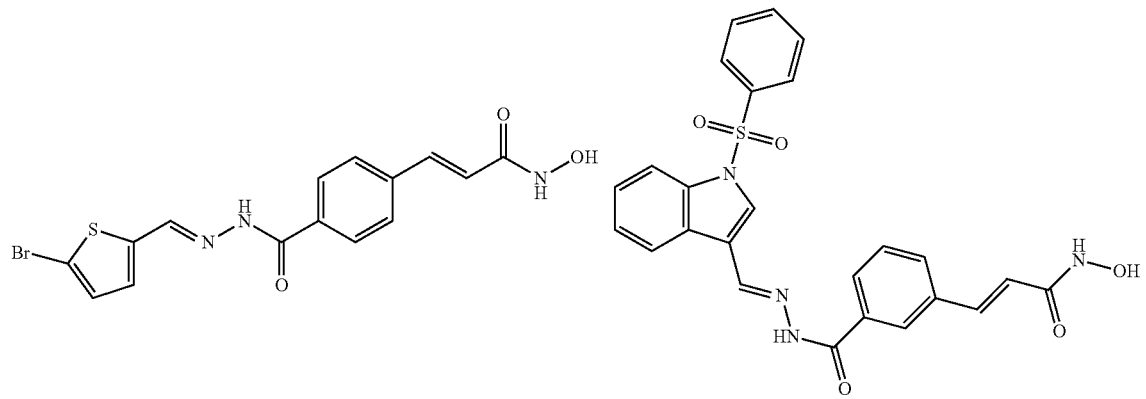
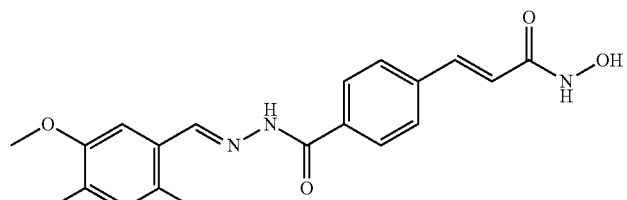
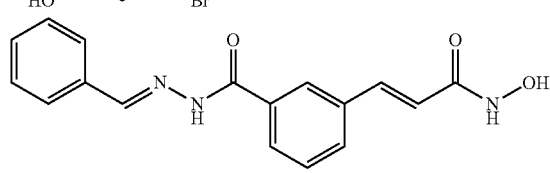
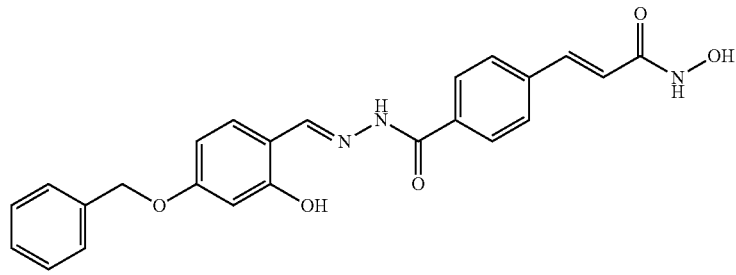
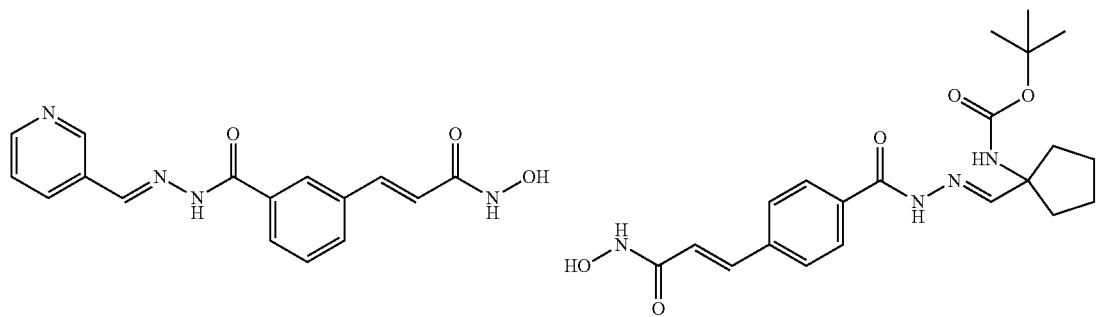

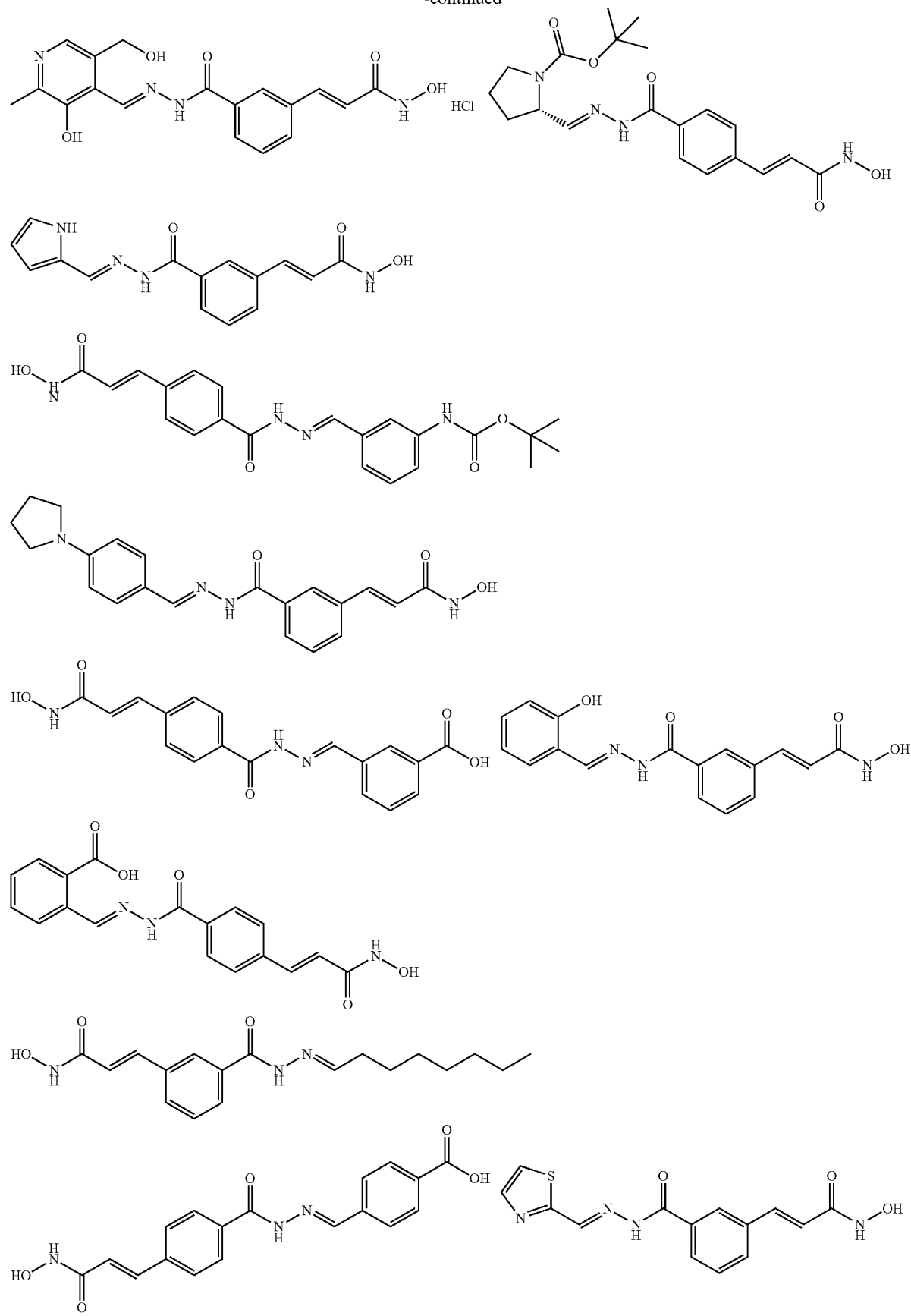

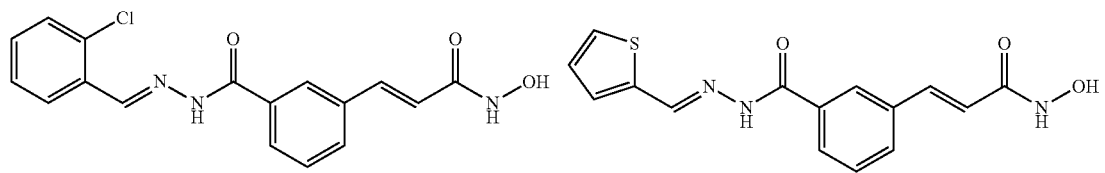
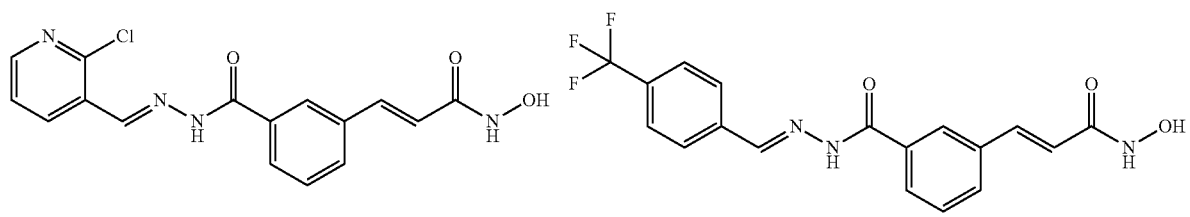
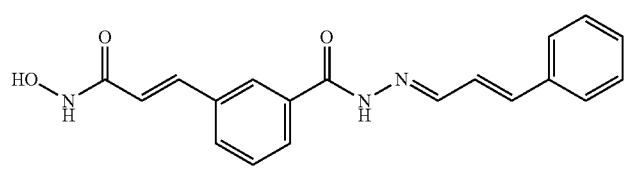
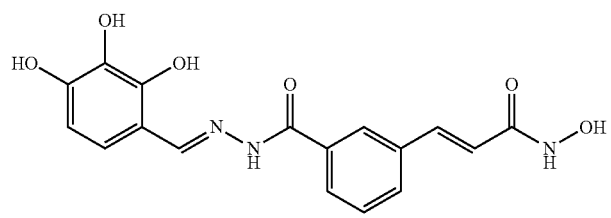
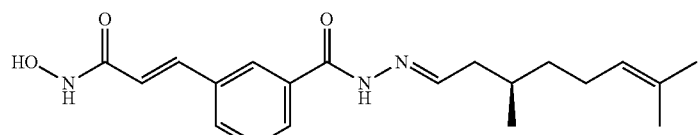
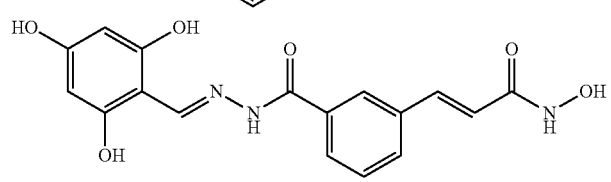
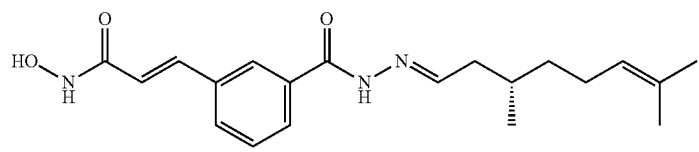
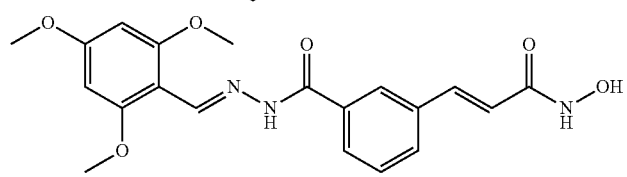
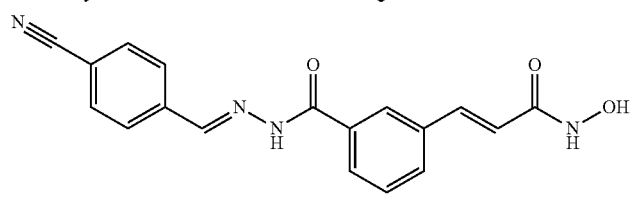

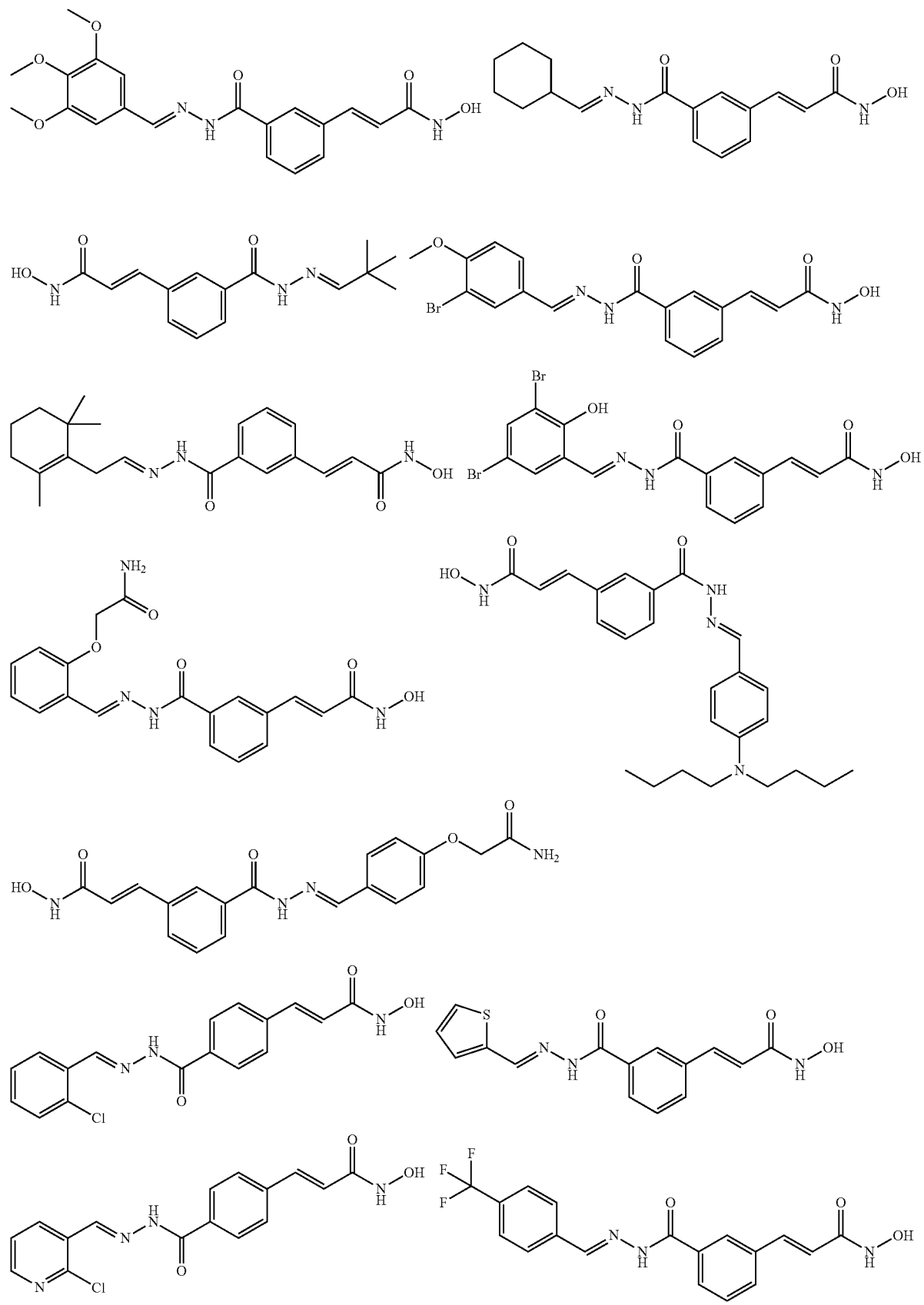

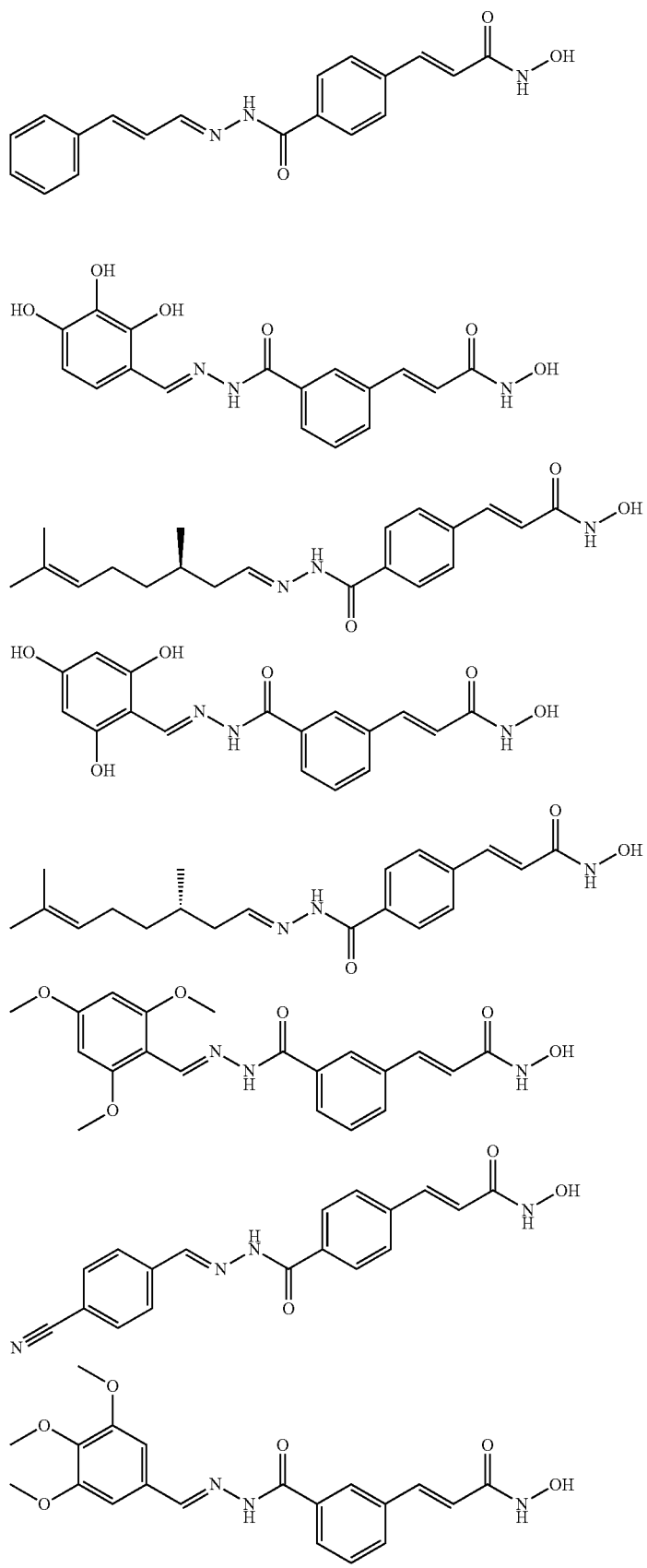

-continued
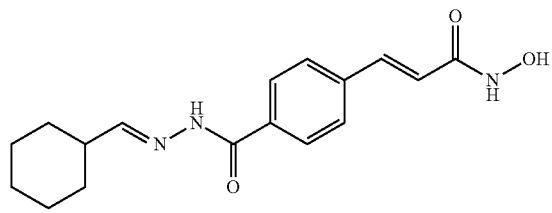
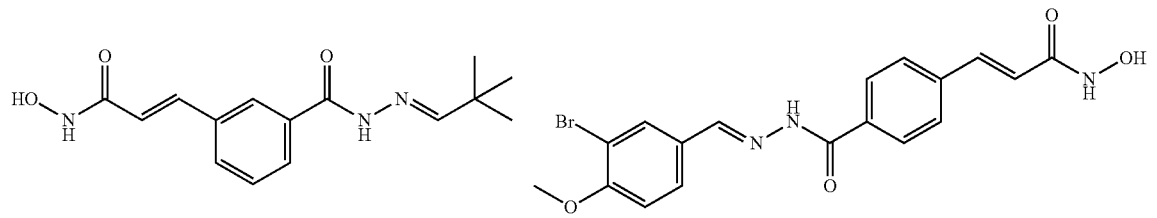
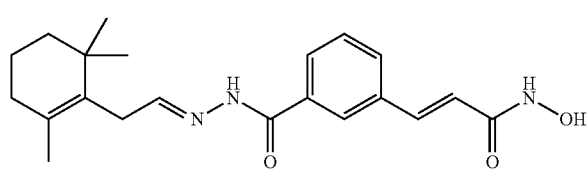
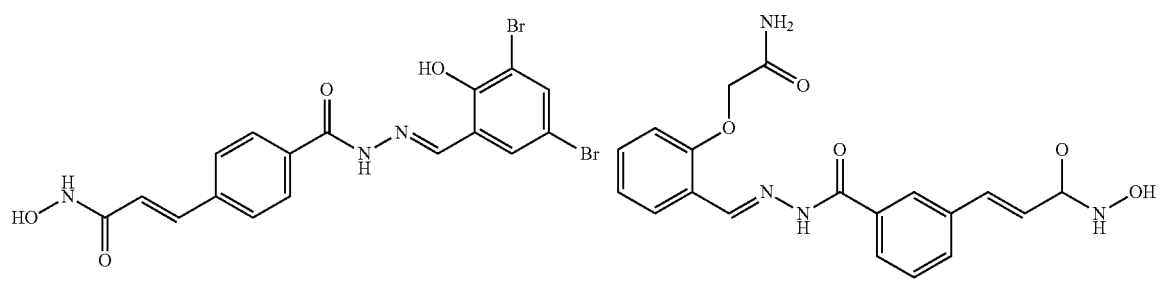
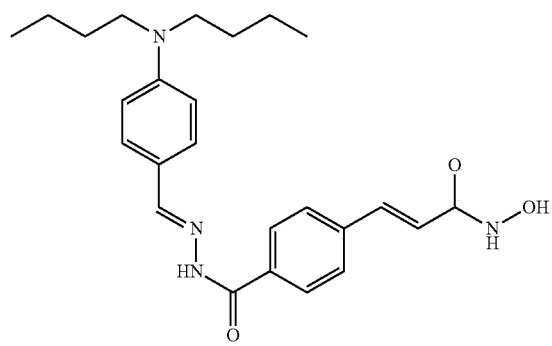
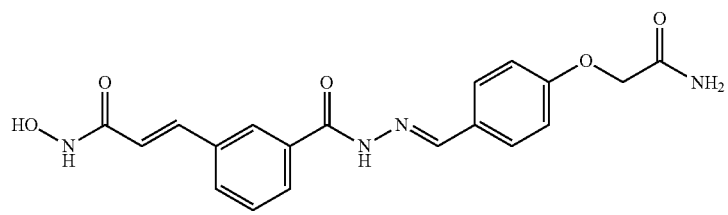
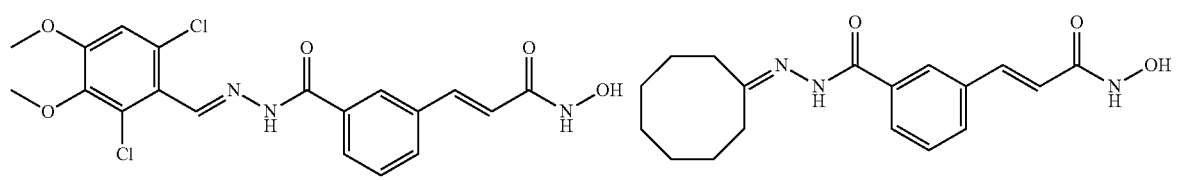

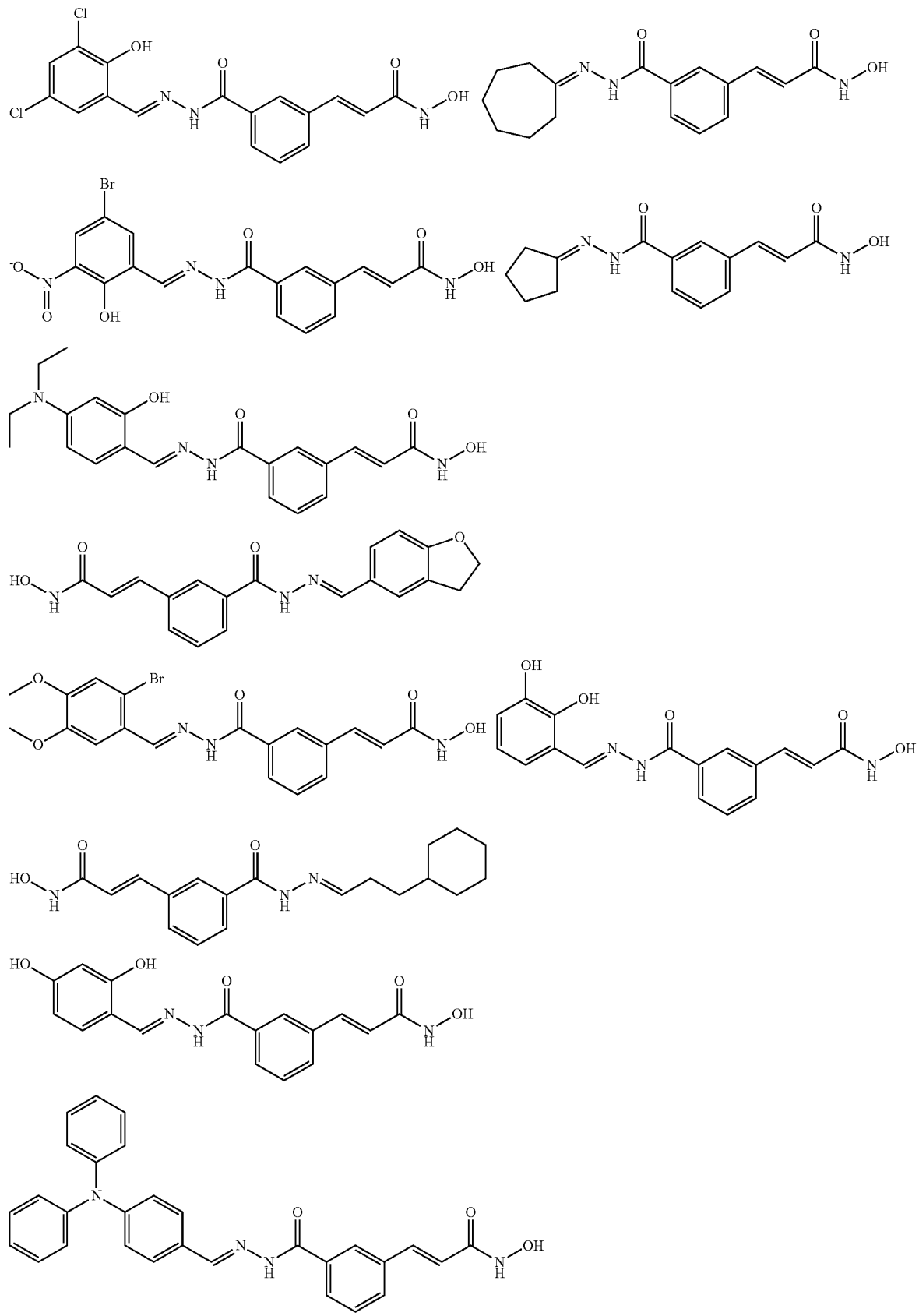

-continued
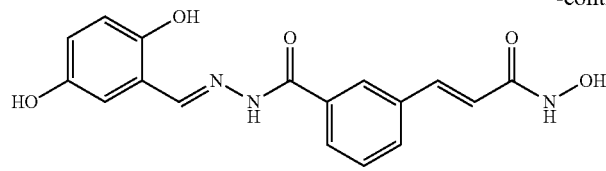
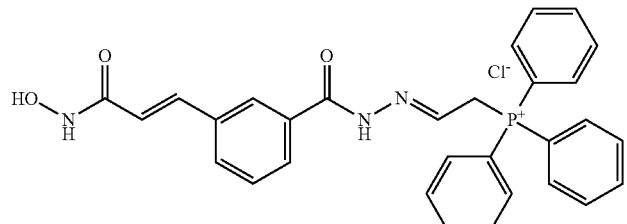
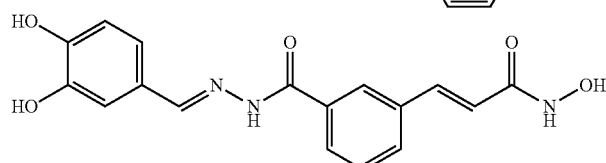
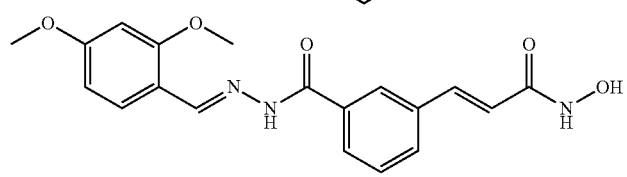
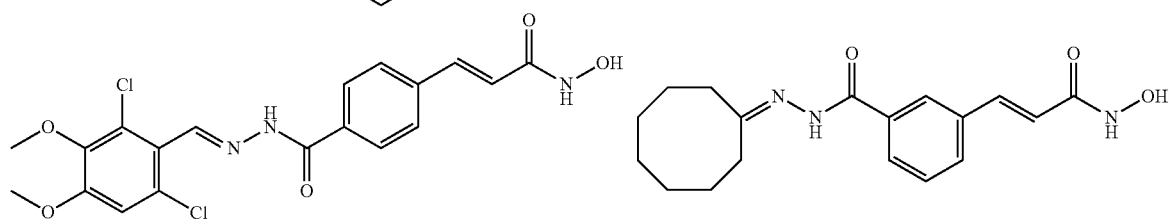
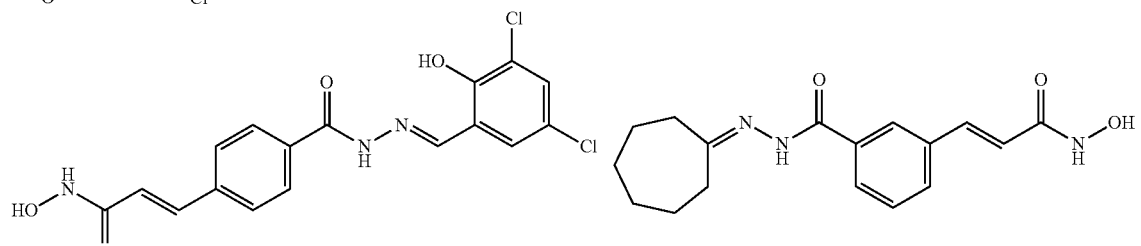
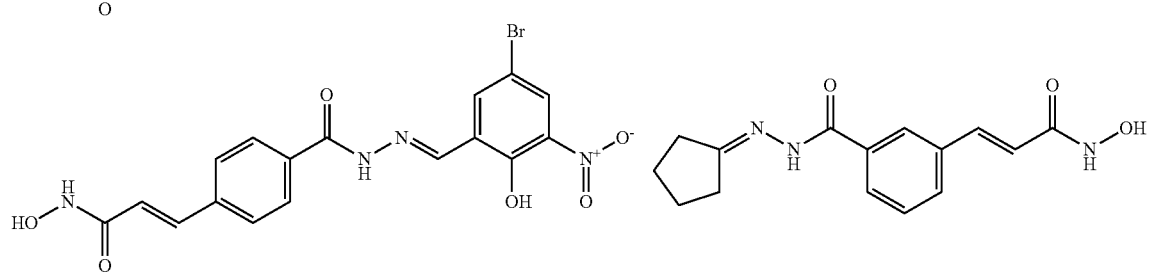
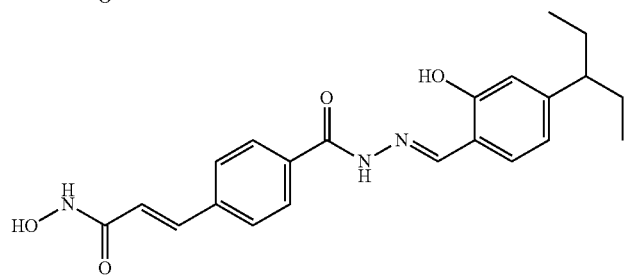

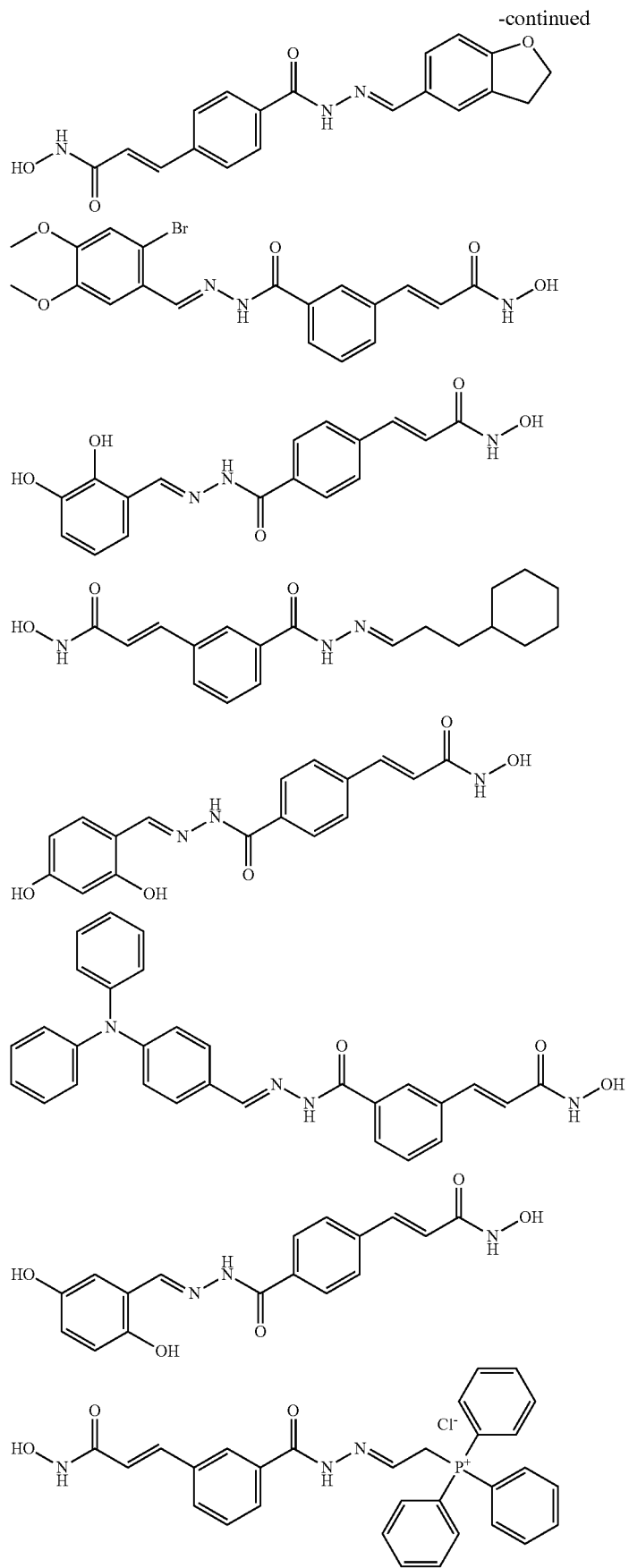

-continued
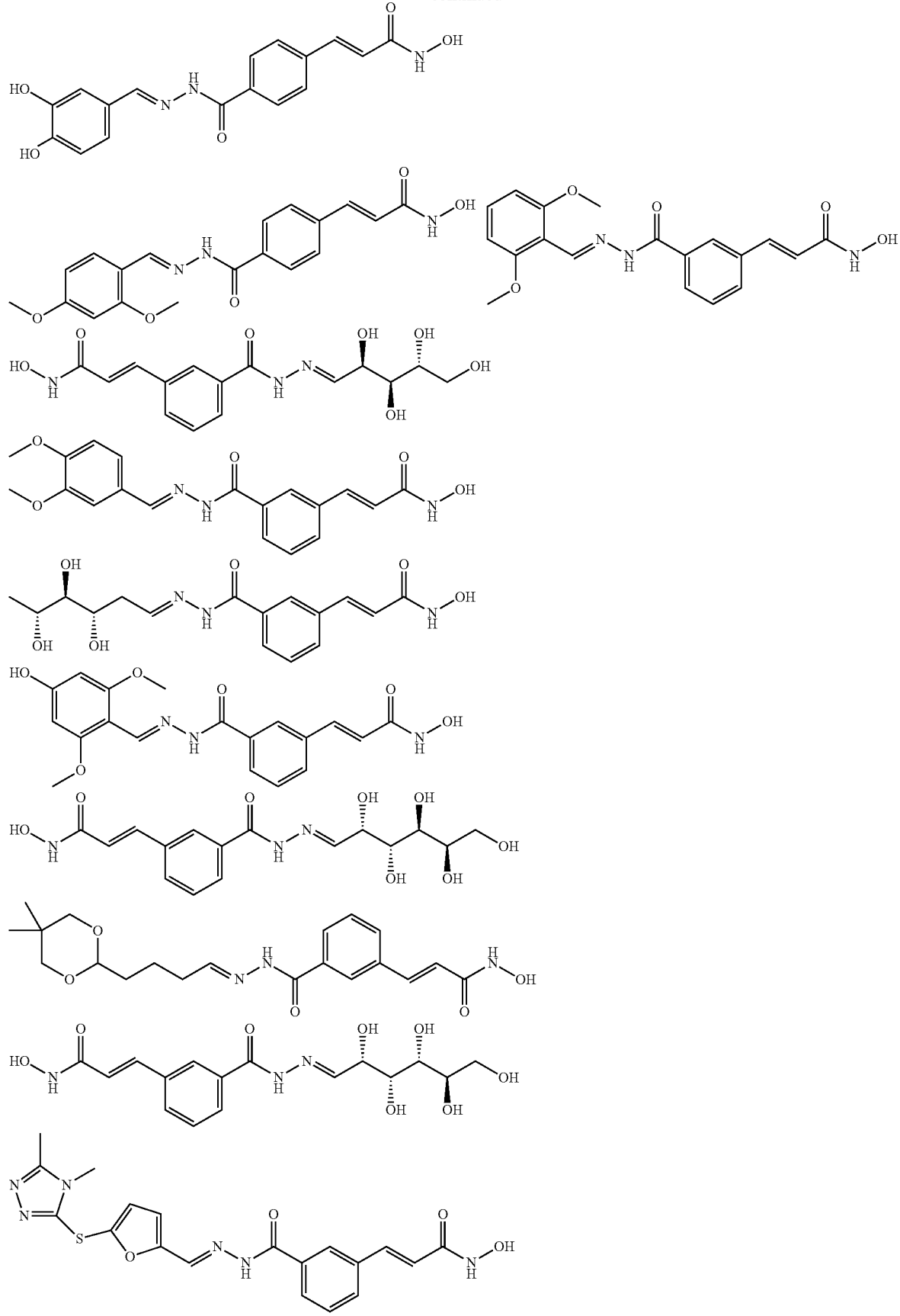

-continued
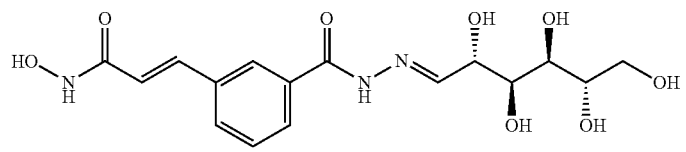
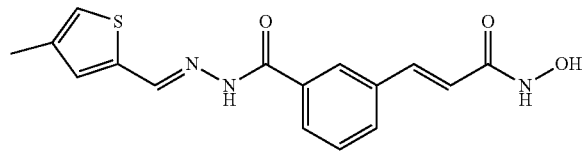
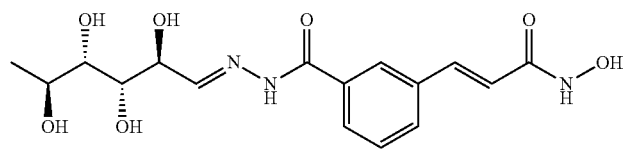
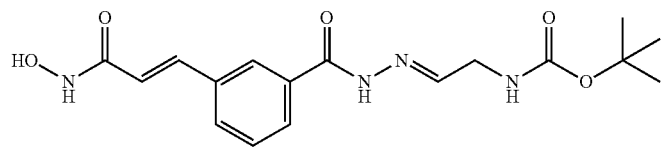
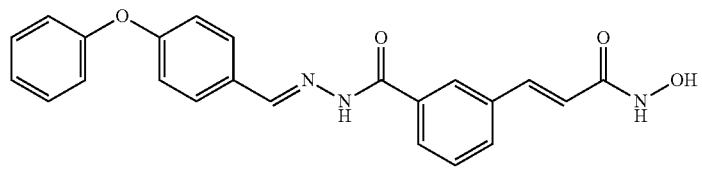
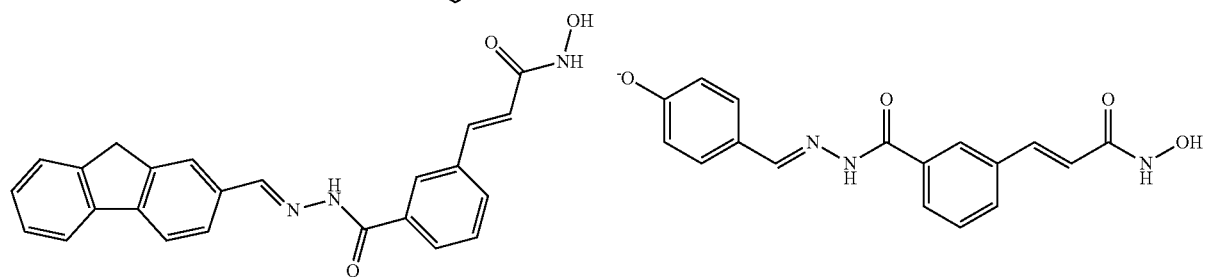
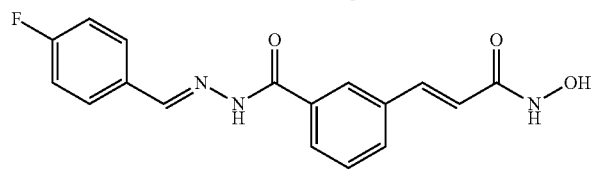
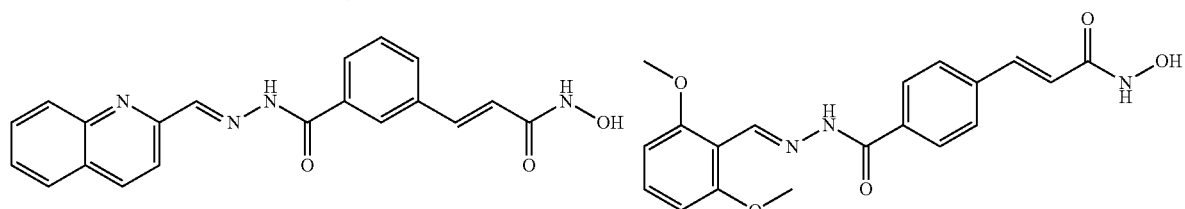
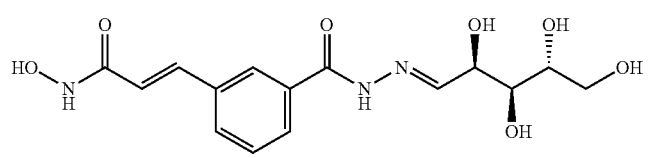

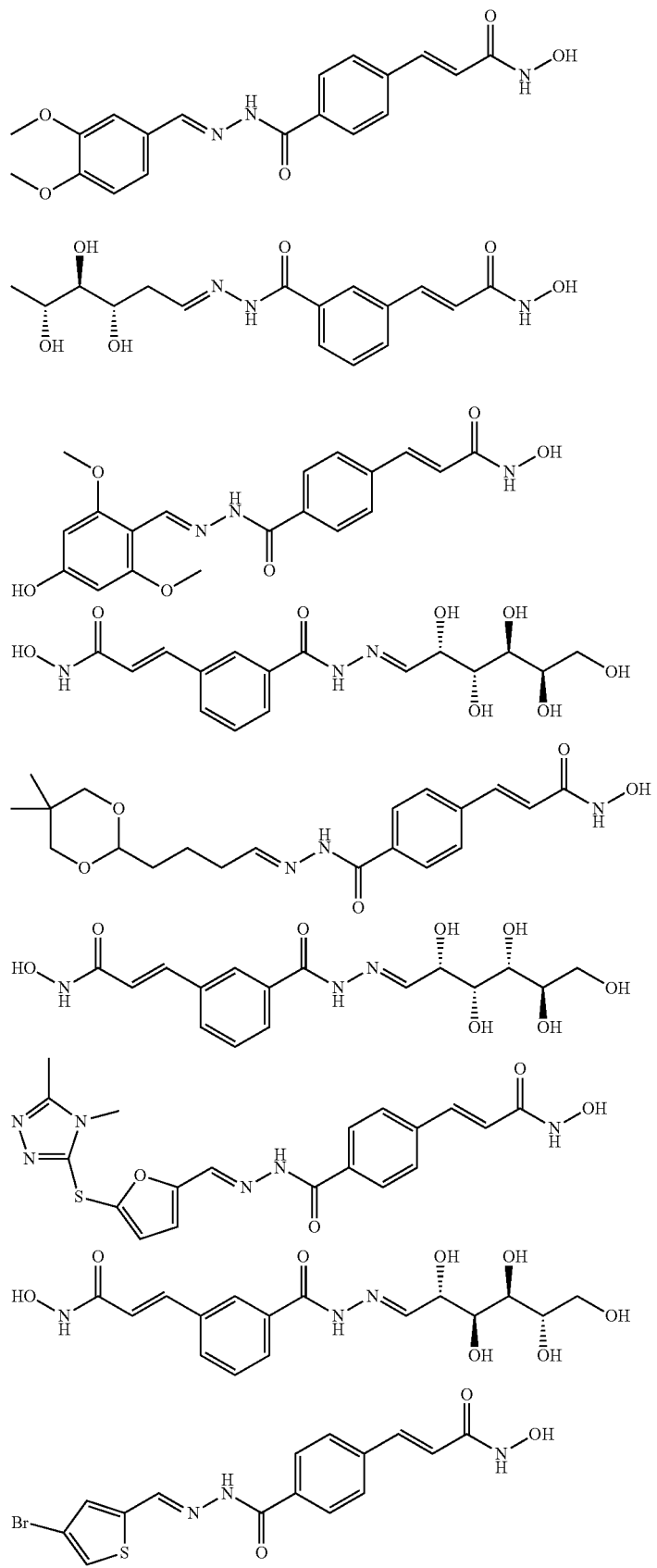

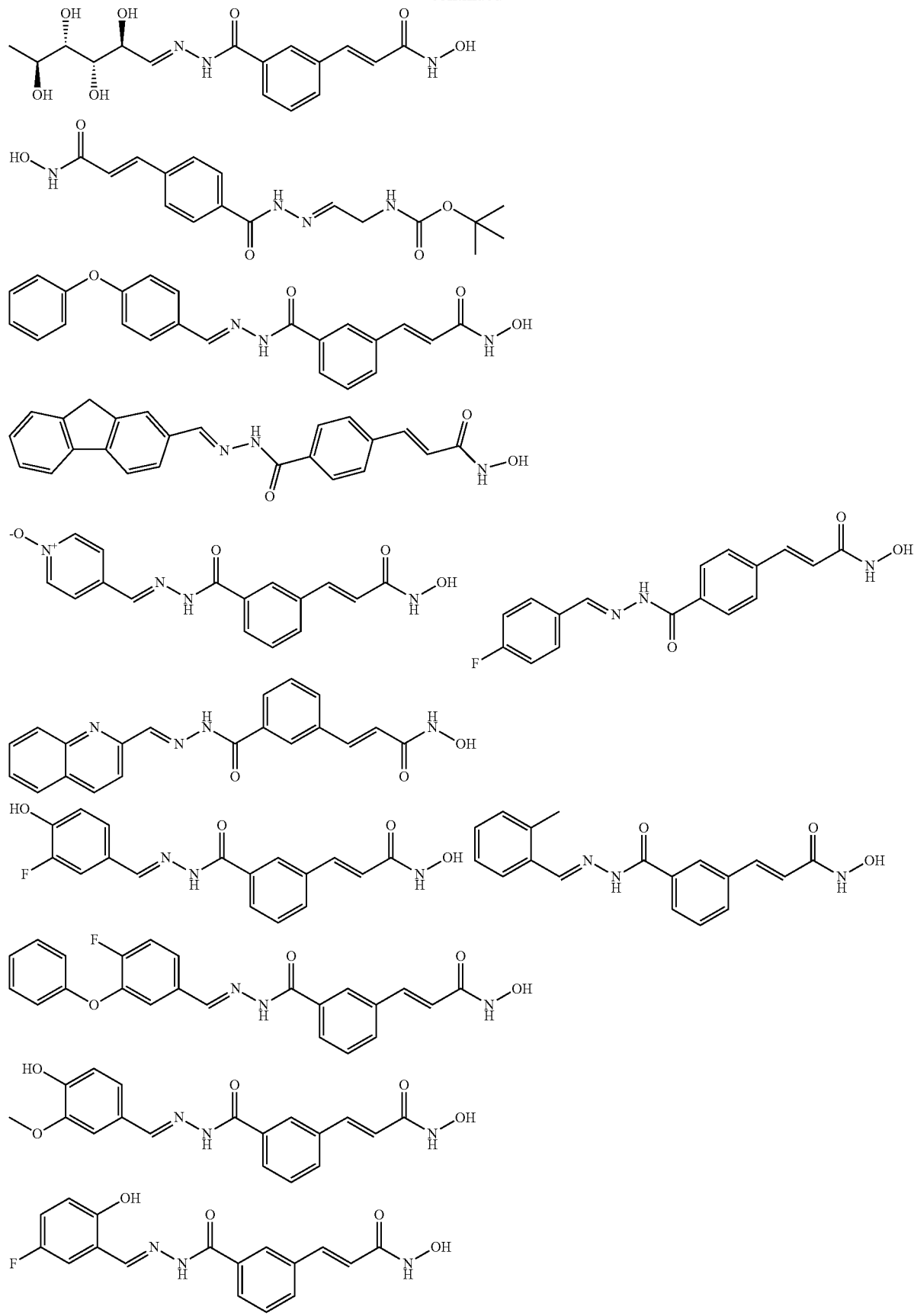

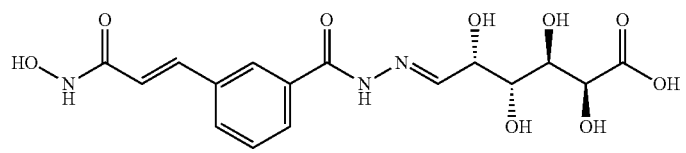
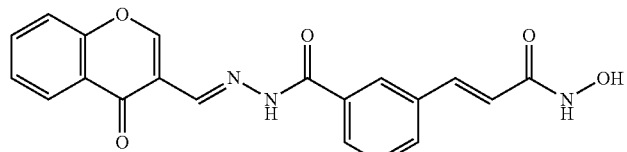
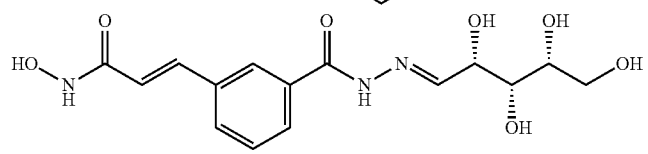
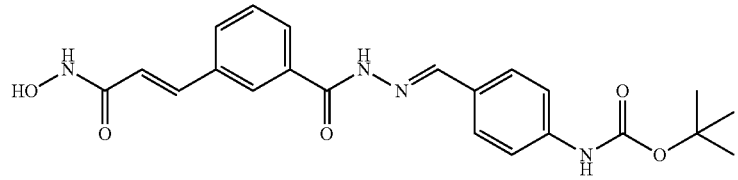
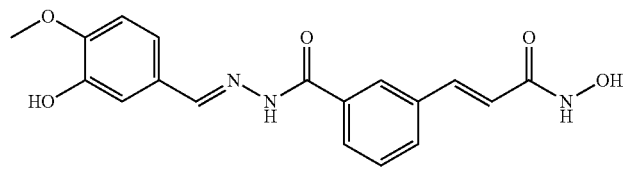
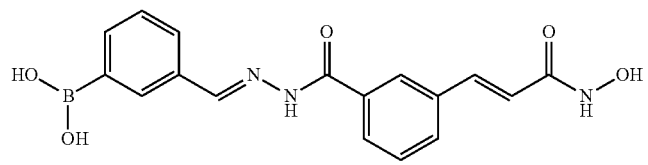
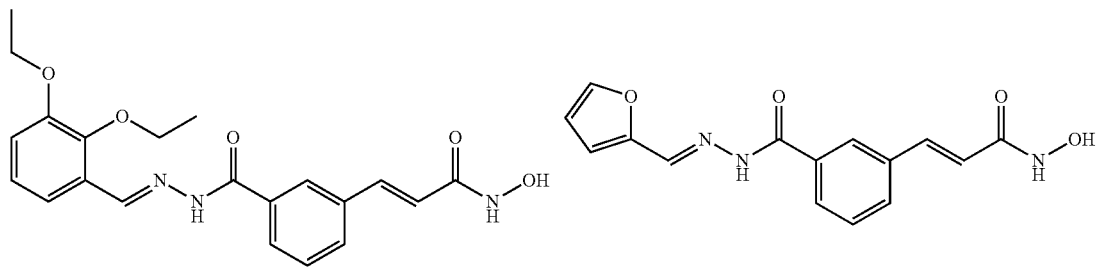
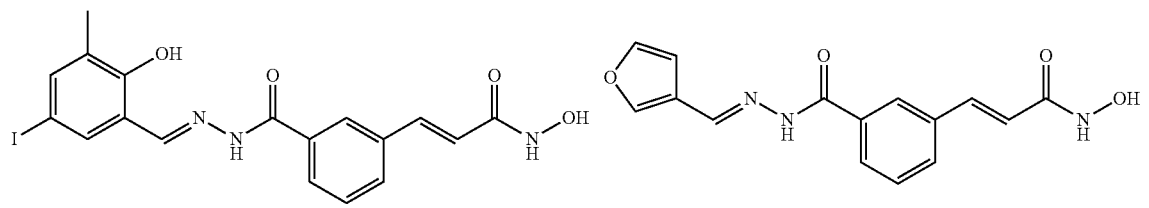
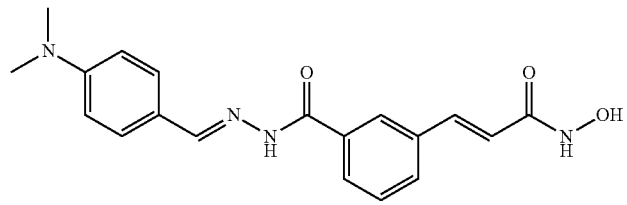

-continued
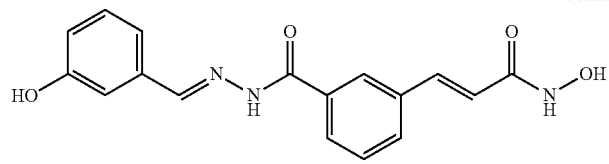
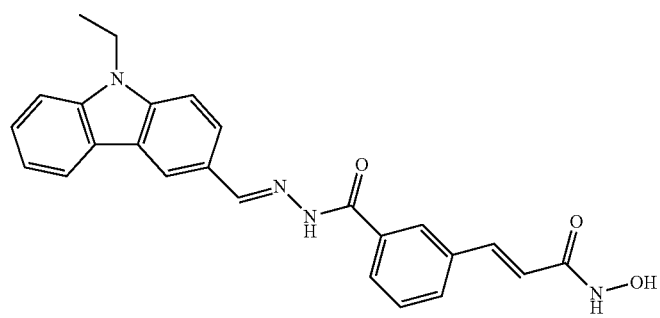
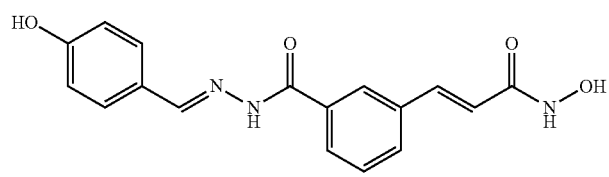
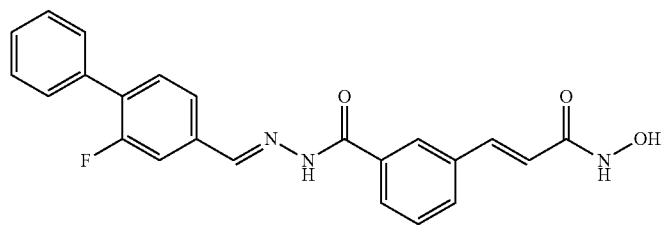
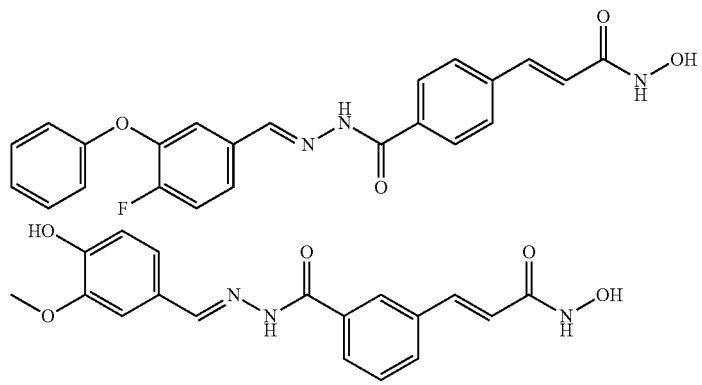
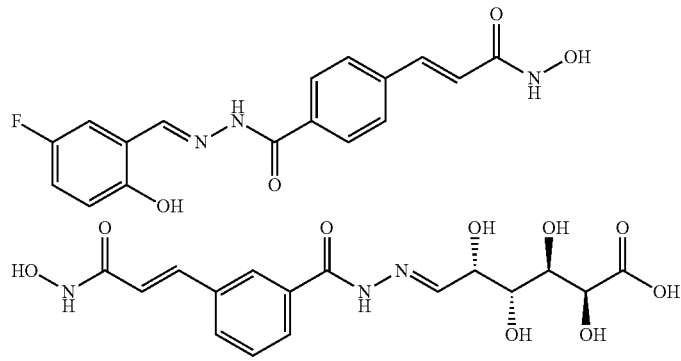

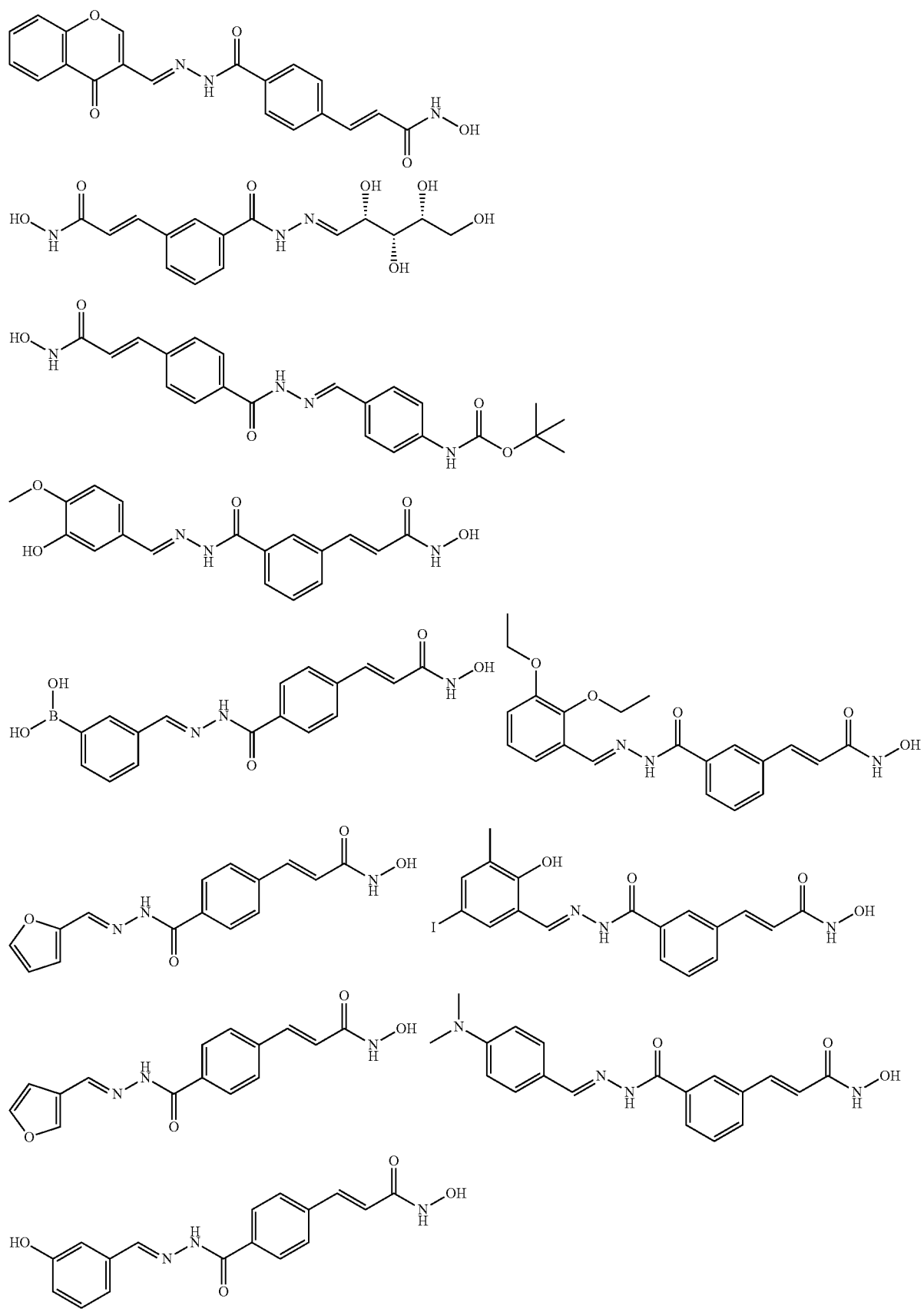

-continued
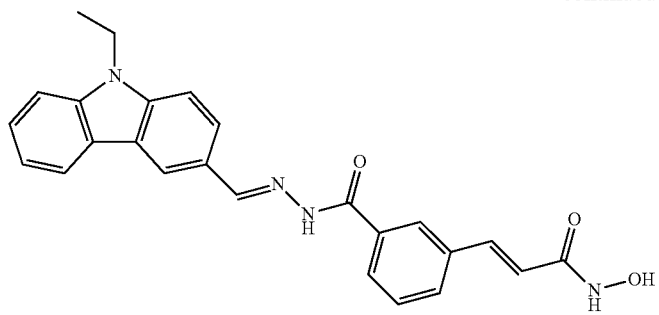
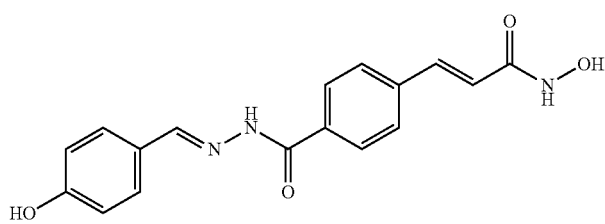
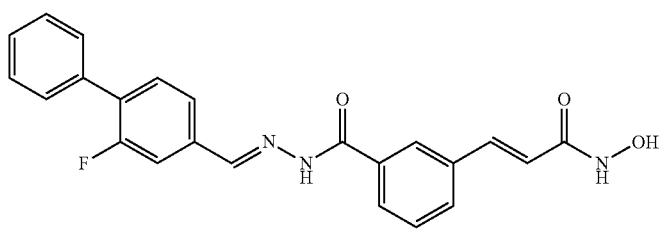
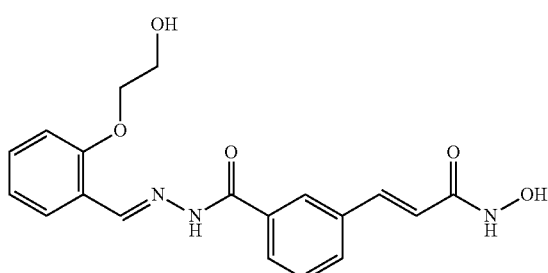
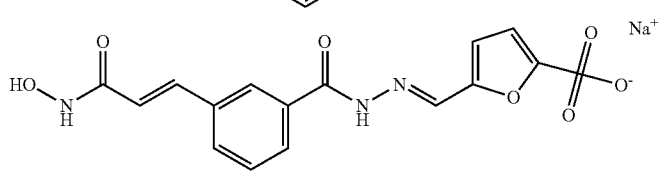
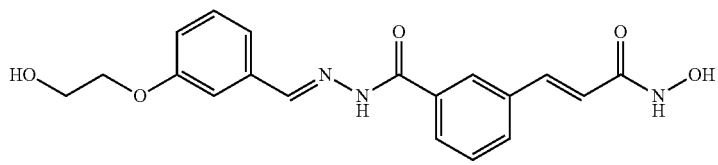
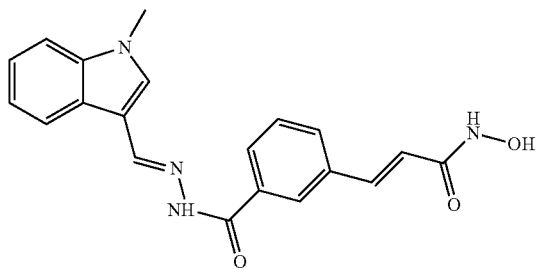

-continued
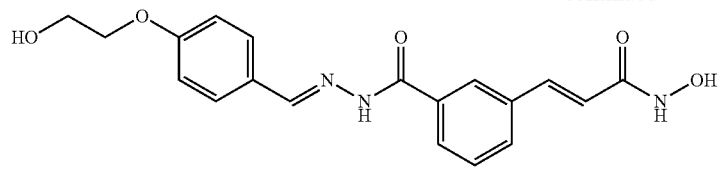
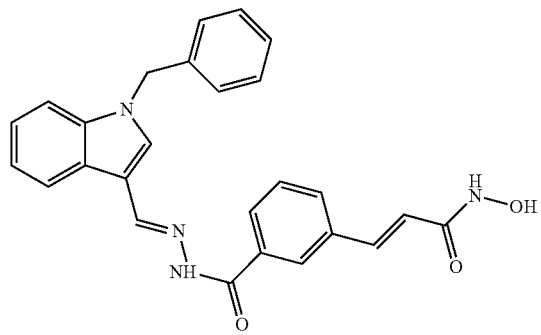
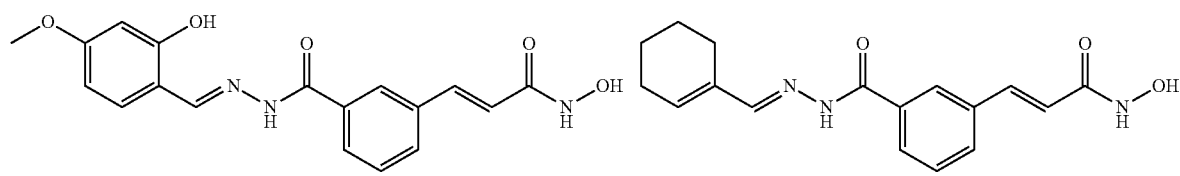
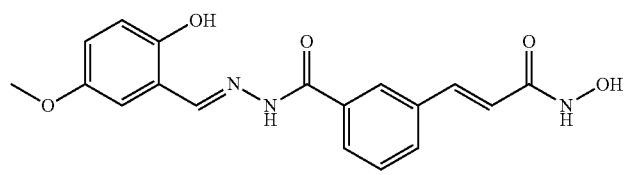
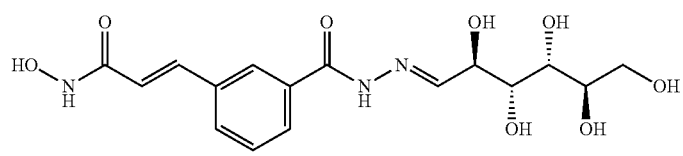
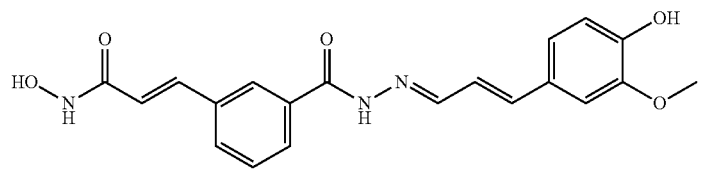
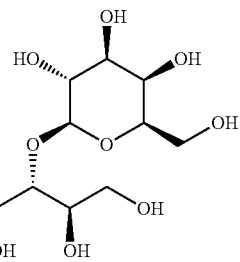
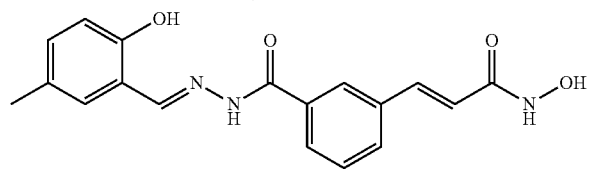

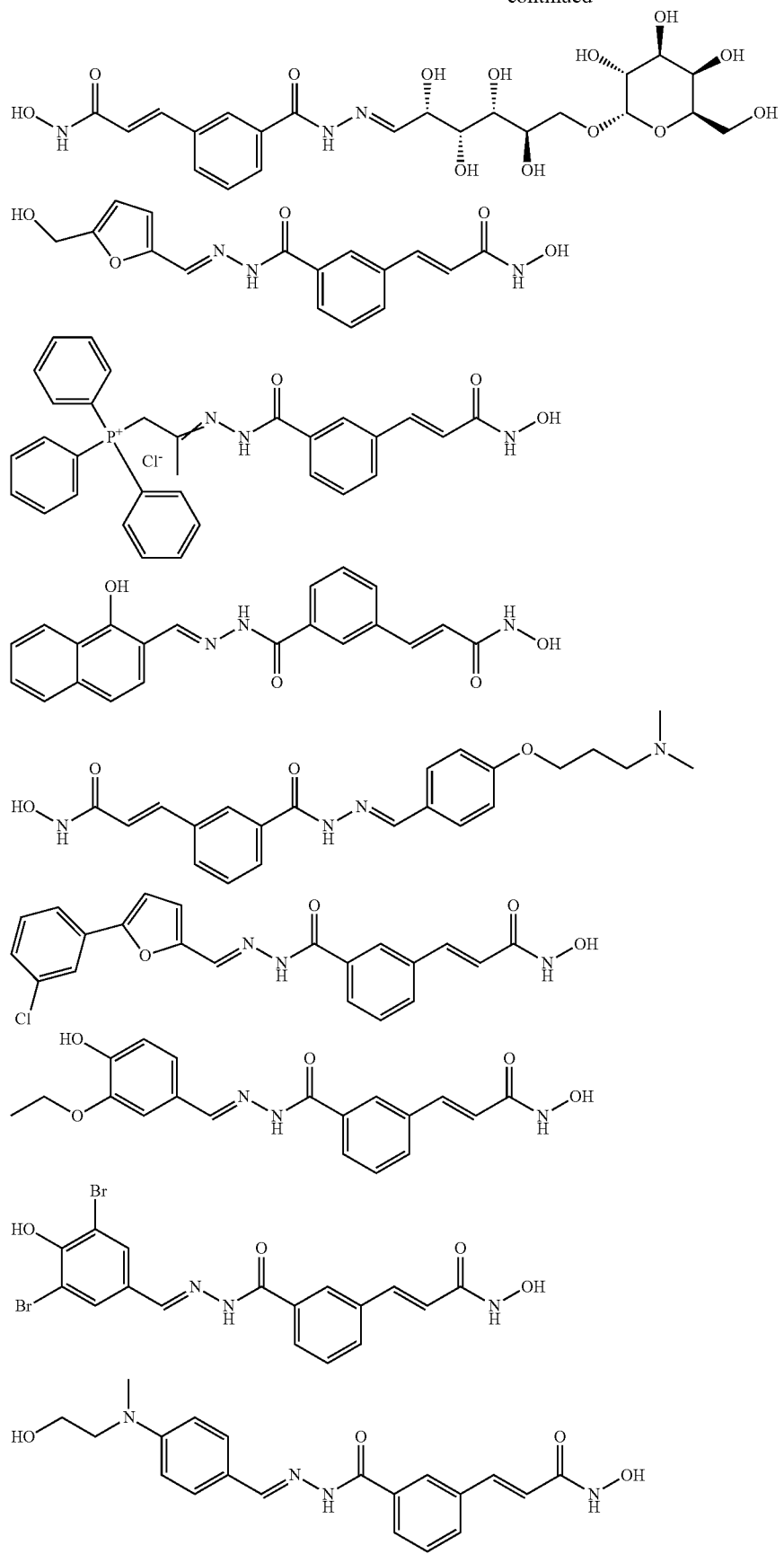

-continued
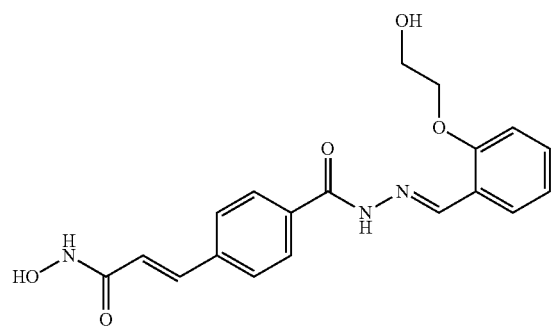
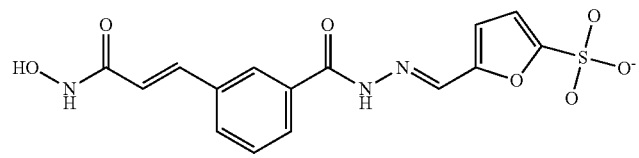
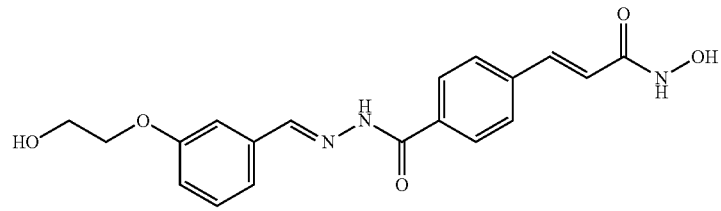
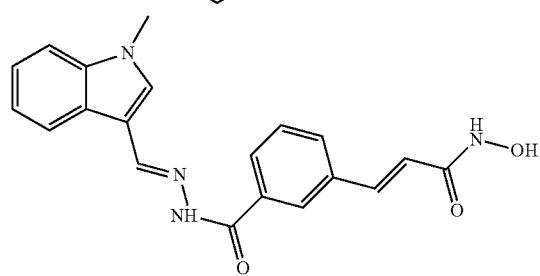
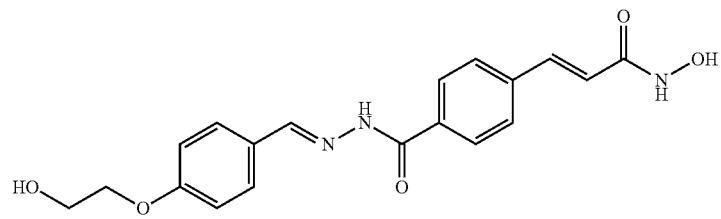
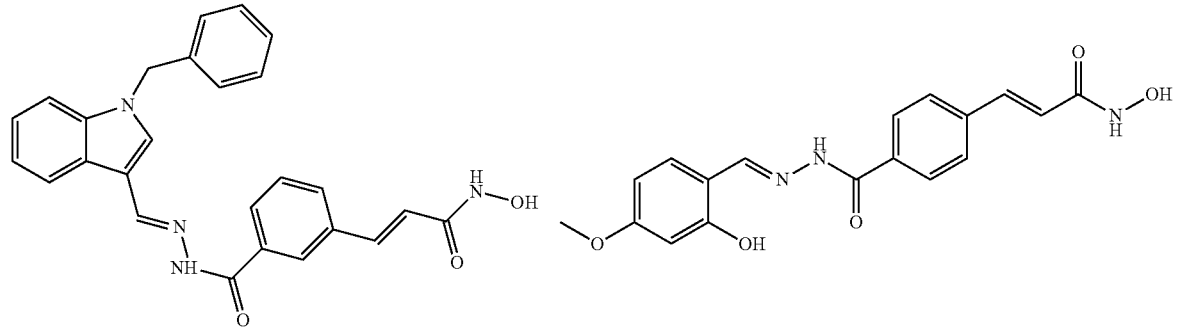
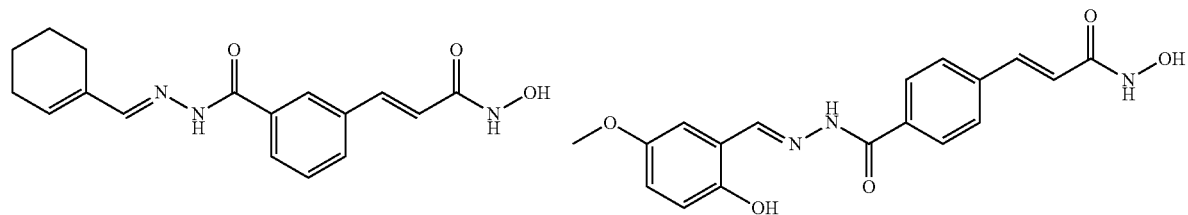

-continued
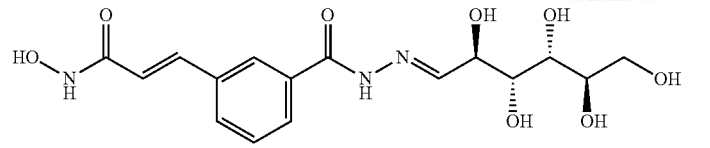
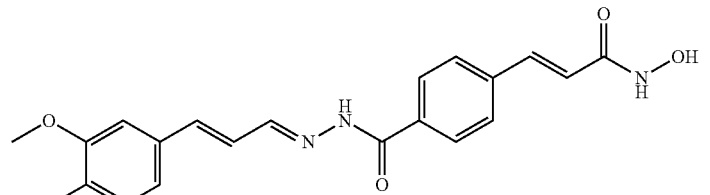
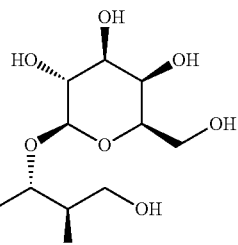
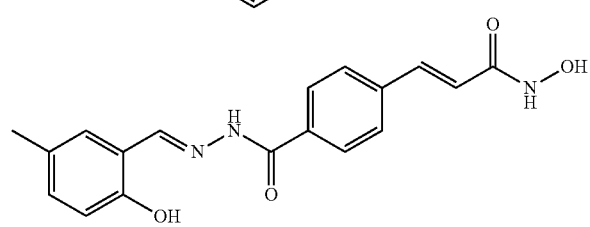
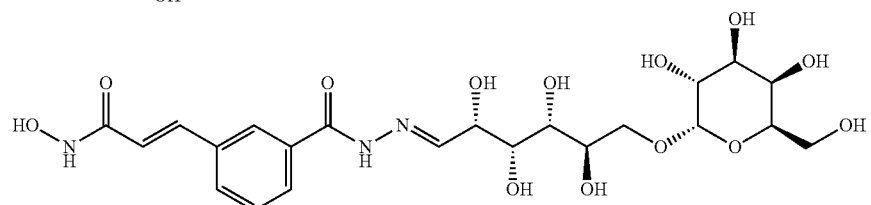
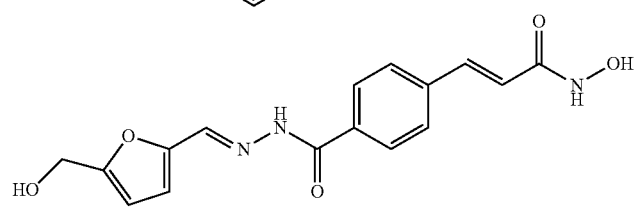
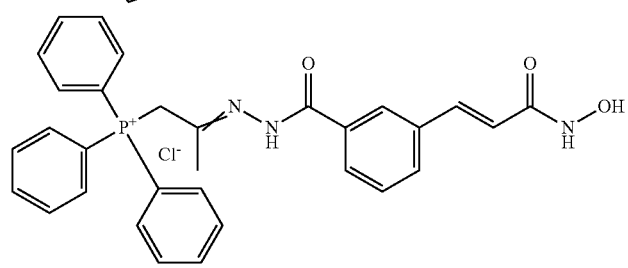
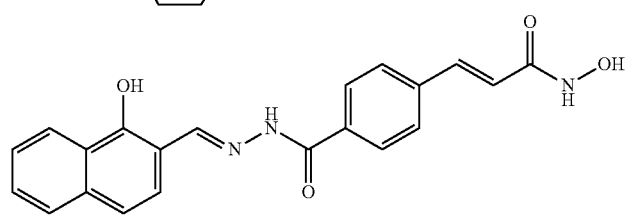

-continued

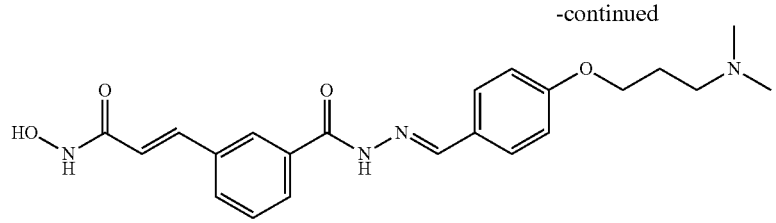

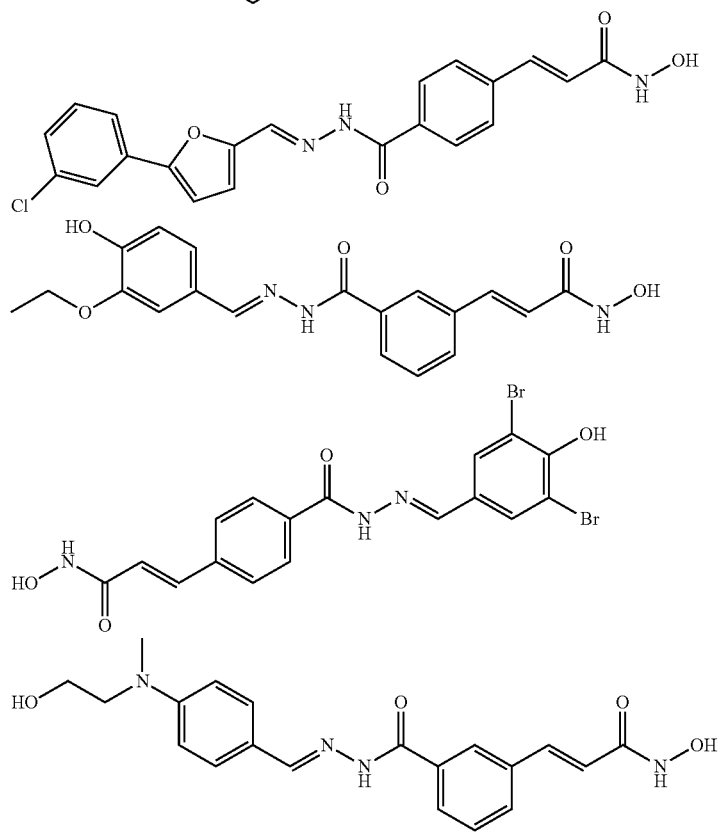

Pharmaceutical Compositions

The present invention provides novel compounds useful in the treatment of diseases or disorders associated with HDAC activity. The compounds are useful in the treatment of diseases or condition that benefit from inhibition of deacetylation activity (e.g., HDAC inhibition). In certain embodiments, the inventive cinnamic hydroxymates are useful in the treatment of proliferative diseases, such as cancer (e.g., cutaneous T-cell lymphoma, peripheral T-cell lymphoma) or benign proliferative diseases; autoimmune diseases; allergic and inflammatory diseases; diseases of the central nervous system (CNS), such as neurodegenerative diseases (e.g. Huntington's disease); vascular diseases, such as restenosis; musculoskeletal diseases; cardiovascular diseases, such as stroke; pulmonary diseases; gastric diseases; and infectious diseases. Class- or isoform-specific HDAC inhibitors may be particularly useful in the treatment of disease or disorders associated with aberrant HDAC activity from a particular Class or isoform. For example, Class IIa HDAC inhibitors may be useful in the treatment of autoimmune or allergic diseases, cardiovascular diseases, or neurodegenerative diseases since Class IIa HDACs have been suggested to play a role in immune tolerance, cardiac remodeling, and neuronal death.

Accordingly, in another aspect of the present invention, pharmaceutical compositions are provided, which comprise any one of the compounds described herein (or a prodrug, pharmaceutically acceptable salt or other pharmaceutically acceptable derivative thereof) and optionally a pharmaceutically acceptable excipient. In certain embodiments, these compositions optionally further comprise one or more additional therapeutic agents. Alternatively, a compound of this invention may be administered to a patient in need thereof in combination with the administration of one or more other therapeutic agents. For example, in the treatment of cancer, an additional therapeutic agents for conjoint administration or inclusion in a pharmaceutical composition with a compound of this invention may be an approved chemotherapeutic agent.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or a pro-drug or other adduct or derivative of a compound of this invention which upon administration to a patient in need is capable of providing, directly or indirectly, a compound as otherwise described herein, or a metabolite or residue thereof.

As described above, the pharmaceutical compositions of the present invention optionally comprise a pharmaceutically acceptable excipient, which, as used herein, includes any and all solvents, diluents, or other liquid vehicle, dispersion or suspension aids, surface active agents, isotonic agents, thickening or emulsifying agents, preservatives, antioxidants, solid binders, lubricants, and the like, as suited to the particular dosage form desired. *Remington's Pharmaceutical Sciences*, Sixteenth Edition, E. W. Martin (Mack Publishing Co., Easton, Pa., 1980) discloses various excipients used in formulating pharmaceutical compositions and known techniques for the preparation thereof. Except insofar as any conventional excipient medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable excipients include, but are not limited to, sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar, buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives, and antioxidants can also be present in the composition, according to the judgment of the formulator.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, com, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable media prior to use.

In order to prolong the effect of a drug, it is often desirable to slow the absorption of the drug from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include (poly (orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol, or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcelhdose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monosteamte, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols, and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols, and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose and starch. Such dosage forms may also comprise, as in normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The present invention encompasses pharmaceutically acceptable topical formulations of inventive compounds. The term "pharmaceutically acceptable topical formulation", as used herein, means any formulation which is pharmaceutically acceptable for intradermal administration of a compound of the invention by application of the formulation to the epidermis. In certain embodiments of the invention, the topical formulation comprises a excipient system. Pharmaceutically effective excipients include, but are not limited to, solvents (e.g., alcohols, poly alcohols, water), creams, lotions, ointments, oils, plasters, liposomes, powders, emulsions, microemulsions, and buffered solutions (e.g., hypotonic or buffered saline) or any other excipient known in the art for topically administering pharmaceuticals. A more complete listing of art-known carvers is provided by reference texts that are standard in the art, for example, *Remington's Pharmaceutical Sciences,* 16th Edition, 1980 and 17th Edition, 1985, both published by Mack Publishing Company, Easton, Pa., the disclosures of which are incorporated herein by reference in their entireties. In certain other embodiments, the topical formulations of the invention may comprise excipients. Any pharmaceutically acceptable excipient known in the art may be used to prepare the inventive pharmaceutically acceptable topical formulations. Examples of excipients that can be included in the topical formulations of the invention include, but are not limited to, preservatives, antioxidants, moisturizers, emollients, buffering agents, solubilizing agents, other penetration agents, skin protectants, surfactants, and propellants, and/or additional therapeutic agents used in combination to the inventive compound. Suitable preservatives include, but are not limited to, alcohols, quaternary amines, organic acids, parabens, and phenols. Suitable antioxidants include, but are not limited to, ascorbic acid and its esters, sodium bisulfite, butylated hydroxytoluene, butylated hydroxyarrisole, tocopherols, and chelating agents like EDTA and citric acid. Suitable moisturizers include, but are not limited to, glycerine, sorbitol, polyethylene glycols, urea, and propylene glycol. Suitable buffering agents for use with the invention include, but are not limited to, citric, hydrochloric, and lactic acid buffers. Suitable solubilizing agents include, but are not limited to, quaternary ammonium chlorides, cyclodextrins, benzyl benzoate, lecithin, and polysorbates. Suitable skin protectants that can be used in the topical formulations of the invention include, but are not limited to, vitamin E oil, allatoin, dimethicone, glycerin, petrolatum, and zinc oxide.

In certain embodiments, the pharmaceutically acceptable topical formulations of the invention comprise at least a compound of the invention and a penetration enhancing agent. The choice of topical formulation will depend or several factors, including the condition to be treated, the physicochemical characteristics of the inventive compound and other excipients present, their stability in the formulation, available manufacturing equipment, and costs constraints. As used herein the term "penetration enhancing agent" means an agent capable of transporting a pharmacologically active compound through the stratum coreum and into the epidermis or dermis, preferably, with little or no systemic absorption. A wide variety of compounds have been evaluated as to their effectiveness in enhancing the rate of penetration of drugs through the skin. See, for example, *Percutaneous Penetration Enhancers*, Maibach H. I. and Smith H. E. (eds.), CRC Press, Inc., Boca Raton, Fla. (1995), which surveys the use and testing of various skin penetration enhancers, and Buyuktimkin et al., *Chemical Means of Transdermal Drug Permeation Enhancement in Transdermal and Topical Drug Delivery Systems*, Gosh T. K., Pfister W. R., Yum S. I. (Eds.), Interpharm Press Inc., Buffalo Grove, Ill. (1997). In certain exemplary embodiments, penetration agents for use with the invention include, but are not limited to, triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate), and N-methylpyrrolidone.

In certain embodiments, the compositions may be in the form of ointments, pastes, creams, lotions, gels, powders, solutions, sprays, inhalants or patches. In certain exemplary embodiments, formulations of the compositions according to the invention are creams, which may further contain saturated or unsaturated fatty acids such as stearic acid, palmitic acid, oleic acid, palmito-oleic acid, cetyl or oleyl alcohols, stearic acid being particularly preferred. Creams of the invention may also contain a non-ionic surfactant, for example, polyoxy-40-stearate. In certain embodiments, the active component is admixed under sterile conditions with a pharmaceutically acceptable excipient and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are made by dissolving or dispensing the compound in the proper medium. As discussed above, penetration enhancing agents can also be used to increase the flux of the compound across the skin. The rate can be controlled by either providing a rate controlling membrane or by dispersing the compound in a polymer matrix (e.g., PLGA) or gel.

It will also be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another immunomodulatory agent or anticancer agent), or they may achieve different effects (e.g., control of any adverse effects).

For example, other therapies or anticancer agents that may be used in combination with the inventive compounds of the present invention for cancer therapy include surgery, radiotherapy (in but a few examples, γ-radiation, neutron beam radiotherapy, electron beam radiotherapy, proton therapy, brachytherapy, and systemic radioactive isotopes, to name a few), endocrine therapy, biologic response modifiers (interferon, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ion (Cisplatin, Carboplatin), enzymes (Asparaginase), and hormones (Tamoxifen, Leuprelide, Flutamide, and Megestrol), to name a few. For a more comprehensive discussion of updated cancer therapies see, *The Merck Manual*, Seventeenth Ed. 1999, the entire contents of which are hereby incorporated by reference. See also the National Cancer Institute (CNI) website (www.nci.nih.gov) and the Food and Drug Administration (FDA) website for a list of the FDA approved oncology drugs (www.fda.gov/cder/cancer/draglis&ame).

In certain embodiments, the pharmaceutical compositions of the present invention further comprise one or more additional therapeutically active ingredients (e.g., chemotherapeutic and/or palliative). For purposes of the invention, the term "palliative" refer, to treatment that is focused on the relief of symptoms of a disease and/or side effects of a therapeutic regimen, but is not curative. For example, palliative treatment encompasses painkillers, antinausea medication and anti-sickness drugs. In addition, chemotherapy, radiotherapy and surgery can all be used palliatively (that is, to reduce symptoms without going for cure; e.g., for shrinking tumors and reducing pressure, bleeding, pain and other symptoms of cancer).

Additionally, the present invention provides pharmaceutically acceptable derivatives of the inventive compounds, and methods of treating a subject using these compounds, pharmaceutical compositions thereof, or either of these in combination with one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or a prodrug or other adduct or derivative of a compound of this invention which upon administration to a patient in need is capable of providing, directly or indirectly, a compound as otherwise described herein, or a metabolite or residue thereof.

Another aspect of the invention relates to a kit for conveniently and effectively carrying out the methods in accordance with the present invention. In general, the pharmaceutical pack or kit comprises one or more containers filled with one or more of the ingredients of the pharmaceutical compositions of the invention. Such kits are especially suited for the topical delivery of the inventive compounds. Optionally associated with such container(s) can be a notice in the form prescribed by a governmental agency regulating the manufacture, use or sale of pharmaceutical products, which notice reflects approval by the agency of manufacture, use or sale for human administration.

Pharmaceutical Uses and Methods of Treatment

In general, methods of using the compounds of the present invention comprise administering to a subject in need thereof a therapeutically effective amount of a compound of the present invention. The compounds of the invention are generally inhibitors of deacetyalse activity. As discussed above, the compounds of the invention are typically inhibitors of histone deacetylases and, as such, are useful in the treatment of disorders modulated by histone deacetylases. Diseases associated with a particular HDAC Class or isoform may be treated by an inventive compound that specifically inhibits that particular Class or isoform. Other deacetylases such as tubulin deacetylases may also be inhibited by the inventive compounds.

In certain embodiments, compounds of the invention are useful in the treatment of proliferative diseases (e.g., cancer, benign neoplasms, inflammatory disease, autoimmune diseases). In other embodiments, the inventive compounds are useful in the treatment of autoimmune diseases; allergic and inflammatory diseases; diseases of the central nervous system (CNS), such as neurodegenerative diseases (e.g. Huntington's disease); vascular diseases, such as restenosis; musculoskeletal diseases; cardiovascular diseases, such as stroke; pulmonary diseases; gastric diseases; and infectious diseases.

In another aspect of the invention, methods for the treatment of cancer are provided comprising administering a therapeutically effective amount of an inventive compound, as described herein, to a subject in need thereof. In certain embodiments, a method for the treatment of cancer is provided comprising administering a therapeutically effective amount of an inventive compound, or a pharmaceutical composition comprising an inventive compound to a subject in need thereof, in such amounts and for such time as is necessary to achieve the desired result. In certain embodiments, the inventive compound is administered parenterally. In certain embodiments, the inventive compound is administered intravenously. In certain embodiments, the inventive compound is administered topically. In certain embodiments of the present invention, a "therapeutically effective amount" of the inventive compound or pharmaceutical composition is that amount effective for killing or inhibiting the growth of tumor cells. The compounds and compositions, according to the method of the present invention, may be administered using any amount and any route of administration effective for killing or inhibiting the growth of tumor cells. Thus, the expression "amount effective to kill or inhibit the growth of tumor cells," as used herein, refers to a sufficient amount of agent to kill or inhibit the growth of tumor cells. The exact amount required will vary from subject to subject, depending on the species, age, and general condition of the subject, the severity of the infection, the particular anticancer agent, its mode of administration, and the like.

In certain embodiments, the method involves the administration of a therapeutically effective amount of the compound or a pharmaceutically acceptable derivative thereof to a subject (including, but not limited to a human or animal) in need of it. In certain embodiments, the inventive compounds as useful for the treatment of cancer (including, but not limited to, glioblastoma, retinoblastoma, breast cancer, cervical cancer, colon and rectal cancer, leukemia, lymphoma, lung cancer (including, but not limited to small cell lung cancer), melanoma and/or skin cancer, multiple myeloma, non-Hodgkin's lymphoma, ovarian cancer, pancreatic cancer, prostate cancer and gastric cancer, bladder cancer, uterine cancer, kidney cancer, testicular cancer, stomach cancer, brain cancer, liver cancer, or esophageal cancer).

In certain embodiments, the inventive anticancer agents are useful in the treatment of cancers and other proliferative disorders, including, but not limited to breast cancer, cervical cancer, colon and rectal cancer, leukemia, lung cancer, melanoma, multiple myeloma, non-Hodgkin's lymphoma, ovarian cancer, pancreatic cancer, prostate cancer, and gastric cancer, to name a few. In certain embodiments, the inventive anticancer agents are active against leukemia cells and melanoma cells, and thus are useful for the treatment of leukemias (e.g., myeloid, lymphocytic, myelocytic and lymphoblastic leukemias) and malignant melanomas. In still other embodiments, the inventive anticancer agents are active against solid tumors. In certain embodiments, the inventive compounds also find use in the prevention of restenosis of blood vessels subject to traumas such as angioplasty and stenting. For example, it is contemplated that the compounds of the invention will be useful as a coating for implanted medical devices, such as tubings, shunts, catheters, artificial implants, pins, electrical implants such as pacemakers, and especially for arterial or venous stents, including balloon-expandable stents. In certain embodiments inventive compounds may be bound to an implantable medical device, or alternatively, may be passively adsorbed to the surface of the implantable device. In certain other embodiments, the inventive compounds may be formulated to be contained within, or, adapted to release by a surgical or medical device or implant, such as, for example, stents, sutures, indwelling catheters, prosthesis, and the like. For example, drugs having antiproliferative and anti-inflammatory activities have been evaluated as stent coatings, and have shown promise in preventing retenosis (See, for example, Presbitero et al., "Drug eluting stents do they make the difference?", *Minerva Cardioangiol.,* 2002, 50(5):431-442; Ruygrok et al., "Rapamycin in cardiovascular medicine", *Intern. Med. J.,* 2003, 33(3):103-109; and Marx et al., "Bench to bedside: the development of rapamycin and its application to stent restenosis", *Circulation,* 2001, 104(8): 852-855, each of these references is incorporated herein by reference in its entirety). Accordingly, without wishing to be bound to any particular theory, Applicant proposes that inventive compounds having antiproliferative effects can be used as stent coatings and/or in stent drug delivery devices, inter alia for the prevention of restenosis or reduction of restenosis rate. Suitable coatings and the general preparation of coated implantable devices are described in U.S. Pat. Nos. 6,099, 562; 5,886,026; and 5,304,121; each of which is incorporated herein by reference. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. A variety of compositions and methods related to stem coating and/or local stent drug delivery for preventing restenosis are known in the art (see, for example, U.S. Pat. Nos. 6,517,889; 6,273, 913; 6,258,121; 6,251,136; 6,248,127; 6,231,600; 6,203,551; 6,153,252; 6,071,305; 5,891,507; 5,837,313 and published U.S. patent application No.: US200110027340, each of which is incorporated herein by reference in its entirety). For example, stents may be coated with polymer-drug conjugates by dipping the stent in polymer-drug solution or spraying the stent with such a solution. In certain embodiment, suitable materials for the implantable device include biocompatible and nontoxic materials, and maybe chosen from the metals such as nickel-titanium alloys, steel, or biocompatible polymers, hydrogels, polyurethanes, polyethylenes, ethylenevinyl acetate copolymers, etc. In certain embodiments, the inventive compound is coated onto a stent for insertion into an artery or vein following balloon angioplasty.

The compounds of this invention or pharmaceutically acceptable compositions thereof may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and in classes and subclasses herein, and a excipient suitable for coating said implantable device. In still another aspect, the present invention includes an implantable device coated with a composition comprising a compound of the present invention as described generally above, and in classes and subclasses herein, and a excipient suitable for coating said implantable device.

Within other aspects of the present invention, methods are provided for expanding the lumen of a body passageway, comprising inserting a stent into the passageway, the stent having a generally tubular structure, the surface of the structure being coated with (or otherwise adapted to release) an inventive compound or composition, such that the passageway is expanded. In certain embodiments, the lumen of a body passageway is expanded in order to eliminate a biliary, gastrointestinal, esophageal, tracheal/bronchial, urethral, and/or vascular obstruction.

Methods for eliminating biliary, gastrointestinal, esophageal, tracheal/bronchial, urethral and/or vascular obstructions using stents are known in the art. The skilled practitioner will know how to adapt these methods in practicing the present invention. For example, guidance can be found in US. Patent Application Publication No.: 2003/0004209 in paragraphs [0146]-[0155], which paragraphs are hereby incorporated herein by reference.

Another aspect of the invention relates to a method for inhibiting the growth of multidrug resistant cells in a biological sample or a patient, which method comprises administering to the patient, or contacting said biological sample with a compound of formula I or II, or a composition comprising said compound.

Additionally, the present invention provides pharmaceutically acceptable derivatives of the inventive compounds, and methods of treating a subject using such compounds, pharmaceutical compositions thereof, or either of these in combination with one or more additional therapeutic agents.

Another aspect of the invention relates to a method of treating or lessening the severity of a disease or condition associated with a proliferation disorder in a patient, said method comprising a step of administering to said patient, a compound of formula I or II, or a composition comprising said compound.

The compounds of the invention are preferably formulated in dosage unit form for ease of administration and uniformity of dosage. The expression "dosage unit form" as used herein refers to a physically discrete unit of therapeutic agent appropriate for the patient to be treated. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, mute of administration, and rate of excretion of the specific compound employed; the duration of the treatment;

drugs used in combination or coincidental with the specific compound employed; and like factors well known in the medical arts (see, for example, *Goodman and Gilman's The Pharmacological Basis of Therapeutics*, Tenth Edition, A. Gilman, J. Hardman and L. Limbird, eds., McGraw-Bill Press, 155-173, 2001, which is incorporated herein by reference in its entirety).

Another aspect of the invention relates to a method for inhibiting histone deacetylase activity in a biological sample or a patient, which method comprises administering to the patient, or contacting said biological sample with an inventive compound or a composition comprising said compound.

Furthermore, after formulation with an appropriate pharmaceutically acceptable excipient in a desired dosage, the pharmaceutical compositions of this invention can be administered to humans and other animals orally, rectally, parenterally, intracisternally, intravaginally, intraperitoneally, topically (as by powders, ointments, creams or drops), bucally, as an oral or nasal spray, or the like, depending on the severity of the infection being treated. In certain embodiments, the compounds of the invention may be administered at dosage levels of about 0.001 mg/kg to about 50 mg/kg, from about 0.01 mg/kg to about 25 mg/kg, or from about 0.1 mg/kg to about 10 mg/kg of subject body weight per day, one or more times a day, to obtain the desired therapeutic effect. It will also be appreciated that dosages smaller than 0.001 mg/kg or greater than 50 mg/kg (for example 50-100 mg/kg) can be administered to a subject. In certain embodiments, compounds are administered orally or parenterally.

Uses

The present invention provides novel compounds useful in the treatment of diseases or disorders associated with HDAC activity. The compounds are useful in the treatment of diseases or condition that benefit from inhibition of deacetylation activity (e.g., HDAC inhibition). In particular, the compounds are useful in treating diseases that benefit from inhibiting a particular HDAC isoform or class of HADCs. In certain embodiments, the compounds are useful in treating a disease that benefits from inhibiting Class IIa HDACs. In certain embodiments, the inventive cinnamic hydroxymates are useful in the treatment of cellular proliferative diseases, such as cancer (e.g., cutaneous T-cell lymphoma) or benign proliferative diseases; autoimmune diseases; allergic and inflammatory diseases; diseases of the central nervous system (CNS), such as neurodegenerative diseases (e.g. Hunington's disease); vascular diseases, such as restenosis; musculoskeletal diseases; cardiovascular diseases; stroke; pulmonary diseases; gastric diseases; and infectious diseases.

In certain embodiments, the compounds of the present invention are useful as inhibitors of histone deacetylases and thus are useful as antiproliferative agents, and thus may be useful in the treatment of cancer, by effecting tumor cell death or inhibiting the growth of tumor cells. In certain exemplary embodiments, the inventive compounds are useful in the treatment of cancers and other proliferative disorders, including, but not limited to breast cancer, cervical cancer, colon and rectal cancer, leukemia, lung cancer, melanoma, multiple myeloma, non-Hodgkin's lymphoma, ovarian cancer, pancreatic cancer, prostate cancer, and gastric cancer, to name a few. In certain embodiments, the inventive anticancer agents are active against leukemia cells and melanoma cells, and thus are useful for the treatment of leukemias (e.g., myeloid, lymphocytic, myelocytic and lymphoblastic leukemias) and malignant melanomas. In certain embodiments, the inventive compounds are active against cutaneous T-cell lymphoma. Additionally, as described hereein, the inventive compounds may also be useful in the treatment of protozoal infections.

Additionally, as described herein, the inventive compounds may also be useful in the treatment of autoimmune or inflammatory diseases. Furthermore, as described herein, the inventive compounds may also be useful in the treatment of neurodegenerative diseases. As described herein, the inventive compounds may also be useful in the treatment of cardiovascular diseases. In certain exemplary embodiments, the compounds of the invention are useful for disorders resulting from protein deacetylation activity or reduced protein acetylation. In certain exemplary embodiments, the compounds of the invention are useful for disorders resulting from histone deacetylation activity or reduced histone acetylation.

Uses according to the present invention, the inventive compounds may be assayed in any of the available assays known in the art for identifying compounds having antiprotozoal, HDAC inhibitory, hair growth, androgen signaling inhibitory, estrogen signaling inhibitory, and/or antiproliferative activity. For example, the assay may be cellular or non-cellular, in vivo or in vitro, high- or low-throughput format, etc.

Thus, in one aspect, compounds of this invention which are of particular interest include those which:

exhibit HDAC inhibitory activity;

exhibit HDAC Class I inhibitory activity (e.g., HDAC1, HDAC2, HDAC3, HDAC8);

exhibit HDAC Class II inhibitory activity (e.g., HDAC4, HDAC5, HDAC6, HDAC7, HDAC9a, HDAC9b, HDRP/HDAC9c, HDAC 10);

exhibit HDAC Class IIa inhibitory activity (e.g., HDAC4, HDAC5, HDAC7, HDAC9a, HDAC9b, HDRP/HDAC9c);

exhibit HDAC Class IIb inhibitory activity (e.g., HDAC6, HDAC10);

exhibit HDAC Class III inhibitory activity;

exhibit HDAC Class IV inhibitory activity (e.g., HDAC11);

exhibit Sirtuin inhibitory activity (e.g., SIRT1, SIRT2, SIRT3, SIRT4, SIRT5, SIRT6, SIRT7)

exhibit the ability to inhibit HDAC1 (Genbank Accession No. NP_004955, incorporated herein by reference);

exhibit the ability to inhibit HDAC2 (Genbank Accession No. NP_001518, incorporated herein by reference);

exhibit the ability to inhibit HDAC3 (Genbank Accession No. 015739, incorporated herein by reference);

exhibit the ability to inhibit HDAC4 (Genbank Accession No. AAD29046, incorporated herein by reference);

exhibit the ability to inhibit HDAC5 (Genbank Accession No. NP_005465, incorporated herein by reference);

exhibit the ability to inhibit HDAC6 (Genbank Accession No. NP_006035, incorporated herein by reference);

md exhibit the ability to inhibit HDAC7 (Genbank Accession No. AAP63491, incorporated herein by reference);

exhibit the ability to inhibit HDAC8 (Genbank Accession No. AAF73428, NM_018486, AF245664, AF230097, each of which is incorporated herein by reference);

exhibit the ability to inhibit HDAC9 (Genbank Accession No. NM_178425, NM_178423, NM_058176, NM_014707, BC111735, NM_058177, each of which is incorporated herein by reference)

exhibit the ability to inhibit HDAC10 (Genbank Accession No. NM 032019, incorporated herein by reference)

exhibit the ability to inhibit HDAC11 (Geabank Accession No. B0009676, incorporated herein by reference);

exhibit the ability to inhibit SIRT1 (Genbank Accession No. NM 003173, NM 001098202, NM 006497, BC 012499, GL 000099, CM000261, each of which is incorporated herein by reference);

exhibit the ability to inhibit SIRT2 (Genbank Accession No. NM 030593, NM 012237, CM000270, AC 000151, NM 033331, CU678487, AK290716, each of which is incorporated herein by reference);

exhibit the ability to inhibit SIRT3 (Genbank Accession No. CM000262, NC 000011, AC 000143, NW 001838015, AC 000054, each of which incorporated herein by reference);

exhibit the ability to inhibit SIRT4 (Genbank Accession No. AM270988, CM000263, NT 166525, NC 000012, NT 009775, AC 000144, each of which is incorporated herein by reference);

exhibit the ability to inhibit SIRT5 (Genbank Accession No. AM270990, AM270988, CM000257, CM000663, GL000052, GL000006, each of which is incorporated herein by reference);

exhibit the ability to inhibit SIRT6 (Genbank Accession No. CM000270, NC 000019, NW 001838477, AC 000151, incorporated herein by reference);

exhibit the ability to inhibit SIRT7 (Genbank Accession No. NC 000017, NT 010663, AC 000149, NW 001838459, each of which is incorporated herein by reference);

exhibit the ability to inhibit tubulin deacetylation (TDAC);

exhibit the ability to inhibit the deacetylation of other acetylated proteins;

exhibit cytotoxic or growth inhibitory effect on cancer cell lines maintained in vitro or in animal studies using a scientifically acceptable cancer cell xenograft model; and/or exhibit a therapeutic profile (e.g., optimum safety and curative effect) that is superior to existing chemotherapeutic agents.

In certain embodiments, the compound's specificity against Class IIa HDACs relative to Class I's inhibition is 1:10. In other embodiments, said specificity is 1:50. In yet other embodiments, said specificity is 1:100. In certain embodiments, said specificity is 1:500. In other embodiments, said specificity is 1:1000.

In certain embodiments, the compound's specificity against Class IIa HDACs relative to Class IIb's inhibition is 1:10. In other embodiments, said specificity is 1:50. In yet other embodiments, said specificity is 1:100. In certain embodiments, said specificity is 1:500. In other embodiments, said specificity is 1:1000.

In certain embodiments, the compound's specificity against Class IIa HDACs relative to Class IV's inhibition is 1:10. In other embodiments, said specificity is 1:50. In yet other embodiments, said specificity is 1:100. In certain embodiments, said specificity is 1:500. In other embodiments, said specificity is 1:1000.

In certain embodiments, the compound's specificity against either HDAC4, 5, 7, 9 relative to either HDAC1, 2, 3, 6, or 8 is 1:10. In certain embodiments, the compound's specificity against either HDAC4, 5, 7, 9 relative to either HDAC1, 2, 3, 6, or 8 is 1:50. In certain embodiments, the compound's specificity against either HDAC4, 5, 7, 9 relative to either HDAC1, 2, 3, 6, or 8 is 1:100. In other embodiments, said specificity is 1:500. In yet other embodiments, said specificity is 1:1000.

As detailed in the exemplification herein, in assays to determine the ability of compounds to inhibit HDAC activity certain inventive compounds may exhibit $IC_{50}$ values ≤100 µM. In certain other embodiments, inventive compounds exhibit $IC_{50}$ values ≤50 µM. In certain other embodiments, inventive compounds exhibit $IC_{50}$ values ≤40 µM. In certain other embodiments, inventive compounds exhibit $IC_{50}$ values ≤30 µM. In certain other embodiments, inventive compounds exhibit $IC_{50}$ values ≤20 µM. In certain other embodiments, inventive compounds exhibit $IC_{50}$ values ≤10. In certain other embodiments, inventive compounds exhibit $IC_{50}$ values ≤7.5 µM. In certain embodiments, inventive compounds exhibit $IC_{50}$ values ≤5. In certain other embodiments, inventive compounds exhibit $IC_{50}$ values ≤2.5. In certain embodiments, inventive compounds exhibit $IC_{50}$ values ≤1 µM. In certain embodiments, inventive compounds exhibit $IC_{50}$ values ≤0.75 µM. In certain embodiments, inventive compounds exhibit $IC_{50}$ values ≤0.5 µM. In certain embodiments, inventive compounds exhibit $IC_{50}$ values ≤0.25 µM. In certain embodiments, inventive compounds exhibit $IC_{50}$ values ≤0.1 µM. In certain other embodiments, inventive compounds exhibit $IC_{50}$ values ≤75 nM. In certain other embodiments, inventive compounds exhibit $IC_{50}$ values ≤50 nM. In certain other embodiments, inventive compounds exhibit $IC_{50}$ values ≤25 nM. In certain other embodiments, inventive compounds exhibit $IC_{50}$ values ≤10 nM. In other embodiments, exemplary compounds exhibited $IC_{50}$ values ≤7.5 nM. In other embodiments, exemplary compounds exhibited $IC_{50}$ values ≤5 nM.

In assays to determine the ability of compounds to inhibit cancer cell growth certain inventive compounds may exhibit $IC_{50}$ values ≤100 µM. In certain other embodiments, inventive compounds exhibit $IC_{50}$ values ≤50 µM. In certain other embodiments, inventive compounds exhibit $IC_{50}$ values ≤40 µM. In certain other embodiments, inventive compounds exhibit $IC_{50}$ values ≤30 µM. In certain other embodiments, inventive compounds exhibit $IC_{50}$ values ≤20 µM. In certain other embodiments, inventive compounds exhibit $IC_{50}$ values ≤10 µM. In certain embodiments, inventive compounds exhibit $IC_{50}$ values ≤7.5 µM. In certain embodiments, inventive compounds exhibit $IC_{50}$ values ≤5 µM. In certain other embodiments, inventive compounds exhibit $IC_{50}$ values ≤2.5 µM. In certain embodiments, inventive compounds exhibit $IC_{50}$ values ≤1 µM. In certain embodiments, inventive compounds exhibit $IC_{50}$ values ≤0.75 µM. In certain embodiments, inventive compounds exhibit $IC_{50}$ values ≤0.5 µM. In certain embodiments, inventive compounds exhibit $IC_{50}$ values ≤0.25 µM. In certain embodiments, inventive compounds exhibit $IC_{50}$ values ≤0.1 µM. In certain other embodiments, inventive compounds exhibit $IC_{50}$ values ≤75 nM. In certain other embodiments, inventive compounds exhibit $IC_{50}$ values ≤50 nM. In certain other embodiments, inventive compounds exhibit $IC_{50}$ values ≤25 nM. In certain other embodiments, inventive compounds exhibit $IC_{50}$ values ≤10 nM. In other embodiments, exemplary compounds exhibited $IC_{50}$ values ≤7.5 nM. In other embodiments, exemplary compounds exhibited $IC_{50}$ values ≤5 nM.

Methods of Synthesis

The invention also provides methods for preparing the inventive compounds. In one aspect of the invention, a method for synthesizing a compound of formula (I) is provided

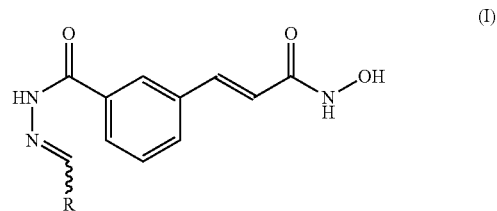

wherein R is a cyclic or acyclic, substituted or unsubstituted aliphatic moiety; a cyclic or acyclic, substituted or unsubstituted heteroaliphatic moiety; a substituted or unsubstituted aryl-moiety or a substituted or unsubstituted heteroaryl moiety; the method comprising:

reacting hydrazine of formula:

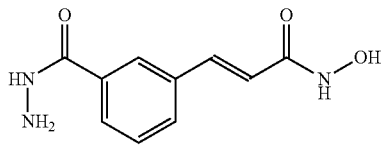 [SMILES: NNC(=O)c1cccc(/C=C/C(=O)NO)c1]

or a protected form thereof with an aldehyde of formula:

under suitable conditions to yield a compound of formula (I):

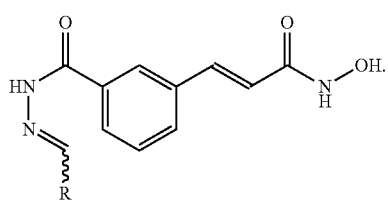

(I)

In another aspect of the invention, a method for synthesizing a compound of formula (II) is provided:

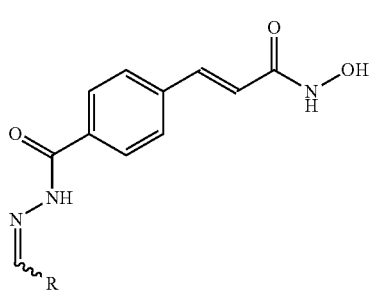

(II)

wherein R is a cyclic or acyclic, substituted or unsubstituted aliphatic moiety; a cyclic or acyclic, substituted or unsubstituted heteroaliphatic moiety; a substituted or unsubstituted aryl-moiety or a substituted or unsubstituted heteroaryl moiety; the method comprising:

reacting hydrazine of formula:

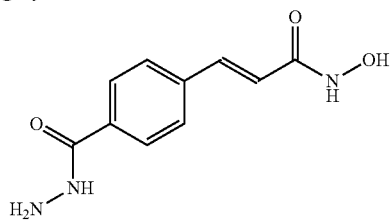

or protected form thereof with an aldehyde of formula:

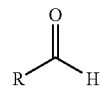

under suitable conditions to yield a compound of formula (II):

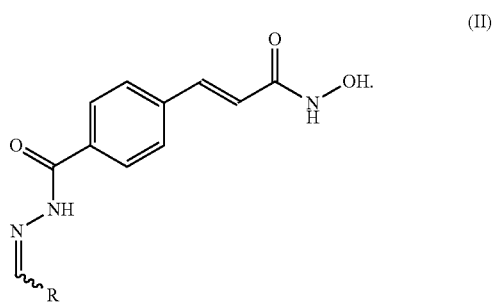

(II)

In certain embodiments, the methods described above are carried out in solution phase. In certain other embodiments, the methods described above are carried out on a solid phase. In certain embodiments, the synthetic method is amenable to high-throughput techniques or to techniques commonly used in combinatorial chemistry.

As would be appreciated by one of skill in the art, the suitable reaction conditions include, temperature, solvent, reaction time, concentration, etc. In certain embodiments, the solvent is a polar solvent. In other embodiments, the solvent is a non-nucleophilic solvent. In still other embodiments, the solvent is a polar aprotic solvent. In further embodiments, the solvent is DMF, dioxane, HMPT (hexamethylphosphorotriamide), THF, or $Et_2O$. In a specific embodiment, the solvent is DMSO.

In certain embodiments, the aldehyde is in a solution of 0.01-0.5 M. In other embodiments, the aldehyde is in solution of 0.1-0.25 M. In other embodiments, the aldehyde is in a solution of 0.2 M. In a specific embodiment, the aldehyde is in DMSO at a concentration of 0.2 M.

In certain embodiments, the hydrazine of general formula:

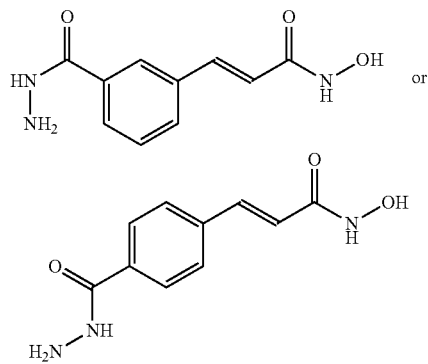

or is in a solution of 0.01-1 M. In other embodiments, the hydrazine is in solution of 0.1-1 M. In other embodiments, the hydrazine is in a solution of 0.1-0.5 M. In yet other embodiments, the hydrazine is in a solution of 0.01-0.1 M. In a specific embodiment, the hydrazine is in DMSO at a concentration of 0.01 M.

In certain embodiments, the starting material are synthesized. In other embodiments, the starting materials are purchased from a commercial source. The starting materials may be protected before reacting them. In certain embodiments, the hydrazine is synthesized as illustrated in Scheme 1.

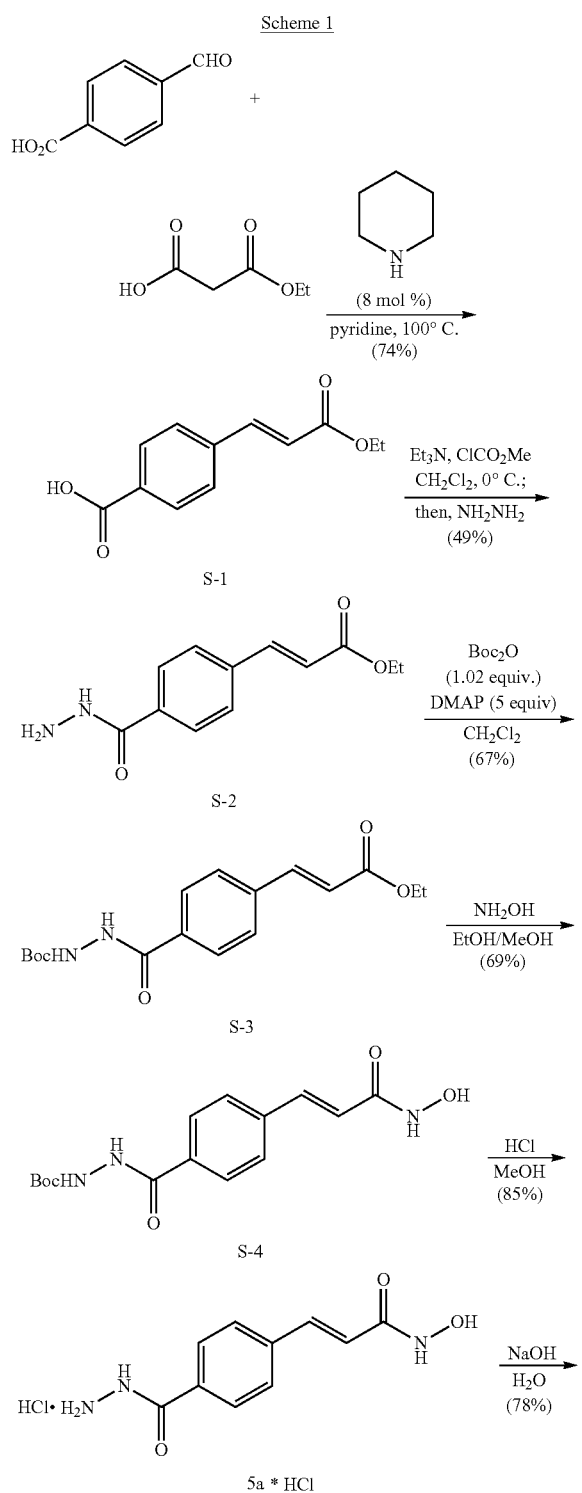

Scheme 1

In certain embodiments, the hydrazine is synthesized as illustrated in Scheme 2.

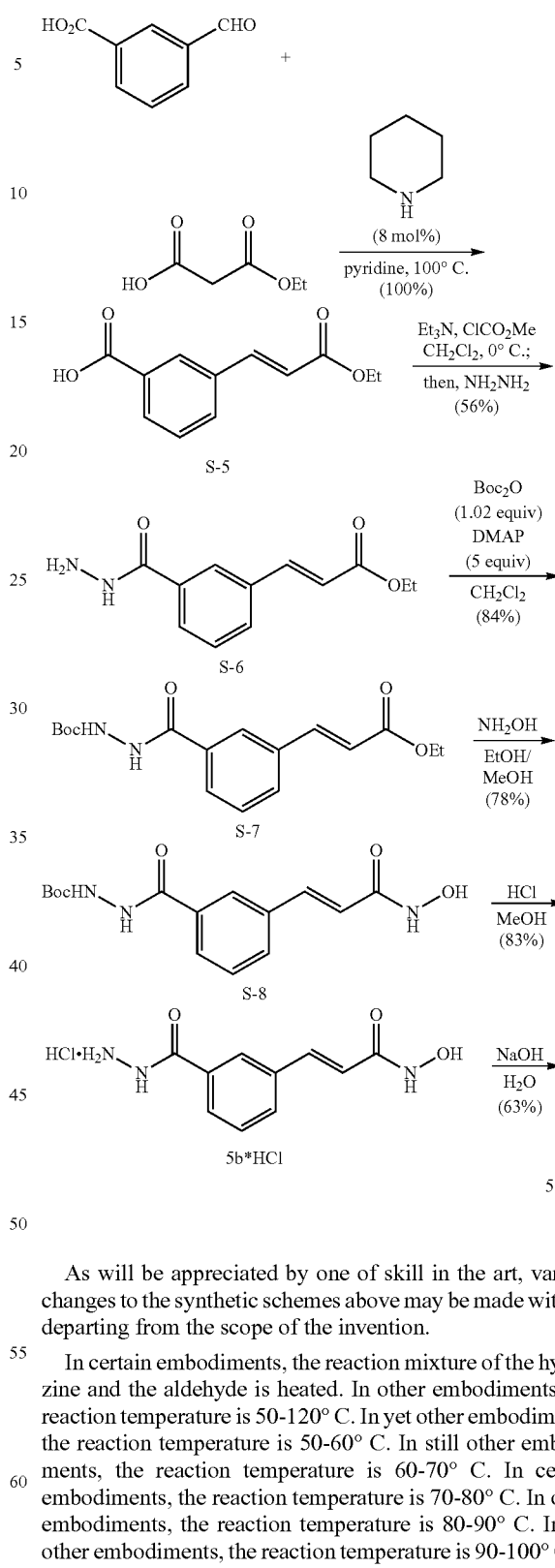

Scheme 2

As will be appreciated by one of skill in the art, various changes to the synthetic schemes above may be made without departing from the scope of the invention.

In certain embodiments, the reaction mixture of the hydrazine and the aldehyde is heated. In other embodiments, the reaction temperature is 50-120° C. In yet other embodiments, the reaction temperature is 50-60° C. In still other embodiments, the reaction temperature is 60-70° C. In certain embodiments, the reaction temperature is 70-80° C. In other embodiments, the reaction temperature is 80-90° C. In yet other embodiments, the reaction temperature is 90-100° C. In still other embodiments, the reaction temperature is 100-110° C. In certain embodiments, the reaction temperature is 110-120° C. In a specific embodiment, the reaction temperature is 70° C.

HDAC Assay

Figure 2:
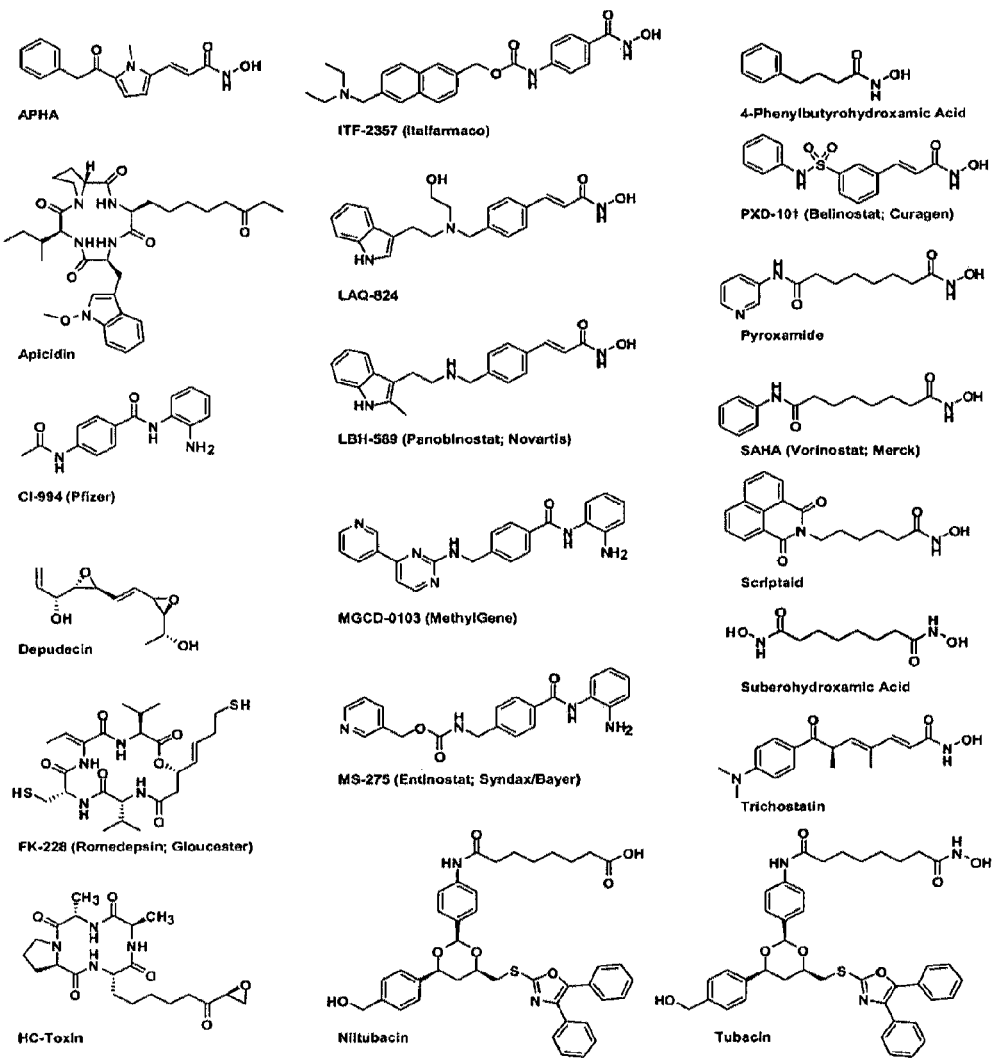
FIG. 2 shows chemical structures of various HDAC inhibitors msed for biochemical profiling.

The invention also provides an assay to determine the inhibitory effect of a test compound on an HDAC protein. To overcome low catalytic turnover of assays for Class IIa HDAC, a new tripeptide substrate 4 (as shown in FIG. 1), which features a relatively labile and sterically demanding trifluoroacetyl group that is readily hydrolyzed by the catalytically less avid Class IIa HDACs (FIG. 1 a,b) was prepared. With substrate 4, Class IIa HDACs exhibit markedly faster kinetics further reducing requisite enzyme concentration (0.002-0.03 ng/μL; Supplementary FIG. 2,3) and allowing a high-throughput, precise profiling of HDACi against all Class IIa enzymes (FIG. 2).

The assay comprises the steps of incubating an HDAC protein with a substrate of general formula (III)

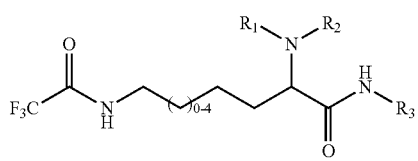

(III)

wherein $R_1$, $R_2$, and $R_3$ are each independently hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR^B$; —C(=O)$R^B$; —$CO_2R^B$; —C(=O)N($R^B$)$_2$; —$SR^B$; —$SOR^B$; —$SO_2R^B$; —N($R^B$)$_2$; —NHC(O)$R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; an amino acid; a peptide; a protecting group; or a tag; or salt thereof; in the presence of a test compound; and determining the activity of the HDAC protein.

In certain embodiments, general formula (III) is

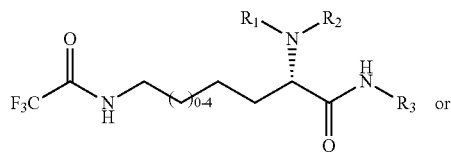

(IIIa)

or

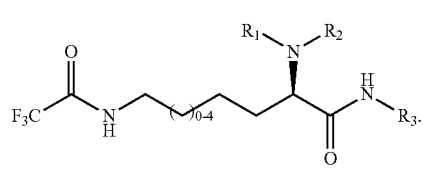

(IIIb)

In other embodiments, general formula (IIIa) is

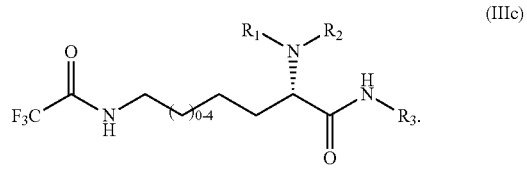

(IIIc)

In certain embodiments, the step of determining the activity of the HDAC protein comprises monitoring the release of a tag from the substrate. In other embodiments, the step of determining the activity of the HDAC protein comprises monitoring the release of the tag from the substrate by an esterase or a protease. Preferably the tag released from the substrated is detectable by a chemical, cpectrophotometric, or physical means. In further embodiments, the protease is a serine protease. In still further embodiments, the serine protease is trypsin.

In certain embodiments, the tag is selected from the group consisting of a fluorescent tag, a bioluminescent tag, a chemoluminescent tag, a photoluminescent tag, a radioluminescent tag, and a thermoluminescent tag. In other embodiments, the tag is selected from the group consisting og: an epitope tag, an isotope tag, a radioactive tag, and a radiolabeled tag. In further embodiments, the tag is a spin label. In other embodiments, the tag comprises coumarin. In still other embodiments, the tag comprises a coumarin derivateive. In further embodiments, the tag is selected from the group consisting of: brodifacoum, bromadiolone, coumafuryl, difenacoum, auraptene, ensaculin, phenprocoumon, warfarin, or derivatives thereof. In specific embodiments, the tag comprises 7-amino-4-methylcoumarin.

In certain embodiments, the tag is removed by a chemical process. In other embodiments, the tag is removed by an enzymatic process. In still other embodiments, the tag is removed by a mechanical process.

In certain embodiments, the HDAC protein is a recombinant, full length HDAC protein. In other embodiments, the HDAC protein is a purified HDAC protein. In still other embodiments, the HDAC protein is a crude HDAC protein. In further embodiments, the HDAC protein is purified from natural sources. In other embodiments, the HDAC protein is a modified form of an HDAC protein. In other embodiments, the HDAC protein is a mutant form of an HDAC protein. In other embodiments, the HDAC protein is a truncated form of an HDAC protein. In still other embodiments, the HDAC protein is a truncated form of an HDAC protein which includes at least an active site.

In certain embodiments, the assay is carried out at a concentration of the substrate greater than the substrate $K_m$. In other embodiments, the assay is carried out at a concentration of the substrate approximately equivalent to the substrate $K_m$.

In certain embodiments, the HDAC protein is a Class I HDAC. In other embodiments, the HDAC protein is a Class II HDAC. In certain embodiments, the HDAC protein is a Class IIa HDAC. In certain embodiments, the HDAC protein is a Class IIb HDAC protein. In still other embodiments, the HDAC protein is a Class III HDAC. In further embodiments, the HDAC protein is a Class IV HDAC. In certain embodiments, the HDAC protein is a sirtuin. In other embodiments, the HDAC protein is a protein with deacetylase activity.

In certain embodiments, the HDAC protein is HDAC1. In other embodiments, the HDAC protein is HDAC2. In specific embodiments, the HDAC protein is a sirtuin. In still other embodiments, the HDAC protein is HDAC3. In further embodiments, the HDAC protein is HDAC4. In certain embodiments, the HDAC protein is HDAC5. In other embodiments, the HDAC protein is HDAC6. In still other embodiments, the HDAC protein is HDAC7. In further embodiments, the HDAC protein is HDAC8. In further embodiments, the HDAC protein is HDAC9. In certain embodiments, the HDAC protein is HDAC10. In other embodiments, the HDAC protein is HDAC11.

The inventive assay is suitable for high-throughput screening, and multiple assy may be run in parallel. This aspect of the assay allows for the screening of many test compounds at multiple concentrations at once using more than one HDAC protein. In certain embodiments, multiple assays are run in parallel. In other embodiments, at least 10 assays are run in parallel. In still other embodiments, at least 50 assays are run in parallel. In further embodiments, at least 100 assays are run in parallel. In certain embodiments, at least 500 assays are run in parallel. In other embodiments, at least 1000 assays are run in parallel.

In certain embodiments, the assay is performed at approximately room temperature. In other embodiments, the assay is performed at approximately 25° C. In still other embodiments, the assay is performed at approximately 37° C. In further embodiments, the assay is performed at approximately 20-40° C. In certain embodiments, the assay is performed below 25° C. In other embodiments, the assay is performed above 25° C. In still other embodiments, the assay is performed at approximately 10-15° C. In further other embodiments, the assay is performed at approximately 15-20° C. In certain embodiments, the assay is performed at approximately 20-25° C. In other embodiments, the assay is performed at approximately 25-30° C. In still other embodiments, the assay is performed at approximately 30-35° C. In further embodiments, the assay is performed at approximately 35-40° C. In certain embodiments, the assay is performed at approximately 40-45° C. In other embodiments, the assay is performed at approximately 45-50° C. In still other embodiments, the assay is performed at approximately 50-60° C. In further embodiments, the assay is performed above 60° C. In certain embodiments, the assay is performed at any temperature at which an HDAC enzyme functions. In other embodiments, the assay is performed at a temperature optimum for an HDAC enzyme to function.

In certain embodiments, the assay is performed for approximately 30 seconds to 12 hours. In other embodiments, the assay is performed for approximately 30 seconds to 5 minutes hours. In still other embodiments, the assay is performed for approximately 5 minutes to 15 minutes. In further embodiments, the assay is performed for approximately 15 minutes to 30 minutes. In certain embodiments, the assay is performed for approximately 30 minutes to 1 hour. In other embodiments, the assay is performed for approximately 1 hour to 3 hours. In still other embodiments, the assay is performed for approximately 3 hours to 6 hours. In further embodiments, the assay is performed for approximately 6 hours to 9 hours. In certain embodiments, the assay is performed for approximately 9 hours to 12 hours. In certain embodiments, the assay is performed for less than 3 hours. In certain embodiments, the assay is performed for approximately 3 hours. In certain embodiments, the assay is performed for less than 12 hours. In other embodiments, the assay is performed for greater than 12 hours.

In certain embodiments, the assay is performed in water. In other embodiments, the assay is performed in an organic solvent. In still other embodiments, the assay in performed in a buffer. In certain embodiments, the buffer is an assay buffer. In other embodiments, the assay buffer comprises HEPES, KCl, Tween-20, BSA, and TCEP. In further embodiments, the assay buffer is 50 nM HEPES, 100 mM KCl, 0.001% Tween-20, 0.05% BSA, 200 µM TCEP, pH 7.4. In certain embodiments, the assay is performed at approximately pH 5.0-6.0. In certain embodiments, the assay is performed at approximately pH 5.0-6.0. In other embodiments, the assay is performed at approximately pH 6.0-6.5. In still other embodiments, the assay is performed at approximately pH 6.5-7.0. In further embodiments, the assay is performed at approximately pH 7.0-7.5. In certain embodiments, the assay is performed at approximately pH 7.4. In other embodiments, the assay is performed at approximately pH 7.5-8.0. In still other embodiments, the assay is performed at approximately pH 8.0-9.0. In certain embodiments, the assay is performed at a pH optimum for an HDAC enzyme to function.

In certain embodiments, the concentration of the substrate is 1-100 µM. In further embodiments, the concentration of the substrate is 1-20 µM. In other embodiments, the concentration of the substrate is 1-5 µM. In still other embodiments, the concentration of the substrate is 5-10 µM. In yet other embodiments, the concentration of the substrate is 10-15 µM. In further embodiments, the concentration of the substrate is 15-20 µM. In other embodiments, the concentration of the substrate is 10-20 µM. In further embodiments, the concentration of the substrate is 20-30 µM. In certain embodiments, the concentration of the substrate is 30-40 µM. In other embodiments, the concentration of the substrate is 40-50 µM. In still other embodiments, the concentration of the substrate is 50-60 µM. In further embodiments, the concentration of the substrate is 60-70 µM. In certain embodiments, the concentration of the substrate is 70-80 µM. In other embodiments, the concentration of the substrate is 80-90 µM. In still other embodiments, the concentration of the substrate is 90-100 µM. In certain embodiments, the concentration of the substrate is less than 20 µM. In other embodiments, the concentration of the substrate is greater than 20 µM.

In certain embodiments, the concentration of the HDAC protein is less than 1 ng/µL. In other embodiments, the concentration of the HDAC protein is greater than 1 ng/µL. In certain embodiments, the concentration of the HDAC protein is less than 5 ng/µL. In other embodiments, the concentration of the HDAC protein is greater than 5 ng/µL. In certain embodiments, the concentration of the HDAC protein is 0.01-5 ng/µL. In other embodiments, the concentration of the HDAC protein is 0.01-0.05 ng/µL. In still other embodiments, the concentration of the HDAC protein is 0.05-0.1 ng/µL. In further embodiments, the concentration of the HDAC protein is 0.1-0.5 ng/µL. In certain embodiments, the concentration of the HDAC protein is 0.5-5 ng/µL.

In certain embodiments, the concentration of HDAC 1 is approximately 1 ng/µL. In other embodiments, the concentration of HDAC1 is approximately 2 ng/µL. In still other embodiments, the concentration of HDAC1 is approximately 3 ng/µL. In further embodiments, the concentration of HDAC1 is approximately 4 ng/µL.

In certain embodiments, the concentration of HDAC2 is approximately 0.5 ng/µL. In other embodiments, the concentration of HDAC2 is approximately 0.75 ng/µL. In still other embodiments, the concentration of HDAC2 is approximately 1 ng/µL. In further embodiments, the concentration of HDAC2 is approximately 1.25 ng/µL. In other embodiments, the concentration HDAC2 is approximately 1.5 ng/µL.

In certain embodiments, the concentration of HDAC3 is approximately 0.1 ng/µL. In other embodiments, the concentration of HDAC3 is approximately 0.15 ng/µL. In still other embodiments, the concentration of HDAC3 is approximately 0.2 ng/µL. In further embodiments, the concentration of HDAC3 is approximately 0.25 ng/µL.

In certain embodiments, the concentration of HDAC4 is approximately 0.001 ng/μL. In other embodiments, the concentration of HDAC4 is approximately 0.0015 ng/μL. In still other embodiments, the concentration of HDAC4 is approximately 0.002 ng/μL. In further embodiments, the concentration of HDAC4 is approximately 0.0025 ng/μL.

In certain embodiments, the concentration of HDAC5 is approximately 0.02 ng/μL. In other embodiments, the concentration of HDAC5 is approximately 0.025 ng/μL. In still other embodiments, the concentration of HDAC5 is approximately 0.03 ng/μL. In further embodiments, the concentration of HDAC5 is approximately 0.033 ng/μL. In certain embodiments, the concentration of HDAC5 is approximately 0.04 ng/μL.

In certain embodiments, the concentration of HDAC6 is approximately 0.75 ng/μL. In other embodiments, the concentration of HDAC6 is approximately 1.0 ng/μL. In still other embodiments, the concentration of HDAC6 is approximately 1.3 ng/μL. In further embodiments, the concentration of HDAC6 is approximately 1.75 ng/μL. In certain embodiments, the concentration of HDAC6 is approximately 2 ng/μL.

In certain embodiments, the concentration of HDAC7 is approximately 0.001 ng/μL. In other embodiments, the concentration of HDAC7 is approximately 0.002 ng/μL. In still other embodiments, the concentration of HDAC7 is approximately 0.003 ng/μL. In further embodiments, the concentration of HDAC7 is approximately 0.004 ng/μL. In certain embodiments, the concentration of HDAC7 is approximately 0.005 ng/μL.

In certain embodiments, the concentration of HDAC8 is approximately 0.02 ng/μL. In other embodiments, the concentration of HDAC8 is approximately 0.025 ng/μL. In still other embodiments, the concentration of HDAC8 is approximately 0.03 ng/μL. In further embodiments, the concentration of HDAC8 is approximately 0.035 ng/μL. In certain embodiments, the concentration of HDAC8 is approximately 0.04 ng/μL.

In certain embodiments, the concentration of HDAC9 is approximately 0.02 ng/μL. In other embodiments, the concentration of HDAC9 is approximately 0.025 ng/μL. In still other embodiments, the concentration of HDAC9 is approximately 0.03 ng/μL. In further embodiments, the concentration of HDAC9 is approximately 0.035 ng/μL. In certain embodiments, the concentration of HDAC9 is approximately 0.04 ng/μL.

In certain embodiments, the concentration of the Sirtuin is approximately 100 to 1500 ng/μL. In other embodiments, the concentration of the Sirtuin is approximately 100-250 ng/μL. In still other embodiments, the concentration of the Sirtuin is approximately 250-500 ng/μL. In further embodiments, the concentration of the Sirtuin is approximately 500-750 ng/μL. In certain embodiments, the concentration of the Sirtuin is approximately 750-1000 ng/μL. In other embodiments, the concentration of the Sirtuin is approximately 1000-1250 ng/μ. In still other embodiments, the concentration of the Sirtuin is approximately 1250-1500 ng/μL. In further embodiments, the concentration of the Sirtuin is approximately 150 ng/μL.

In certain embodiments, the assay is performed at the same concentration per test compound. In other embodiments, the assay is performed at multiple concentrations per test compound.

In another aspect, the invention provides an assay for determining the inhibitory effect of a test compound on an HDAC protein comprising: incubating the HDAC protein with a substrate of formula:

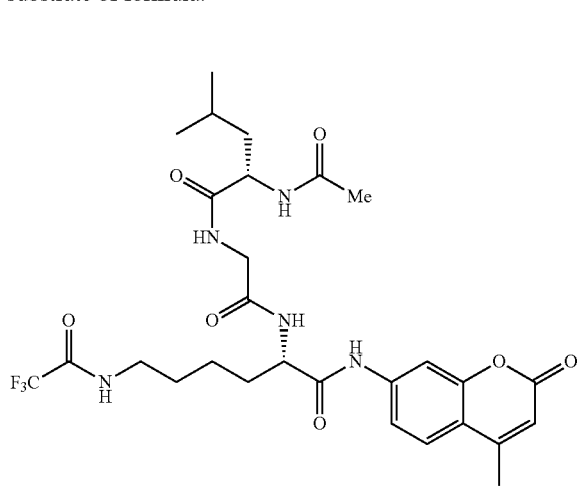

in the presence of a test compound; and determining the activity of the HDAC protein by monitoring the release of 7-amino-4-methylcoumarin after cleavage by trypsin. The assay is represented the scheme below.

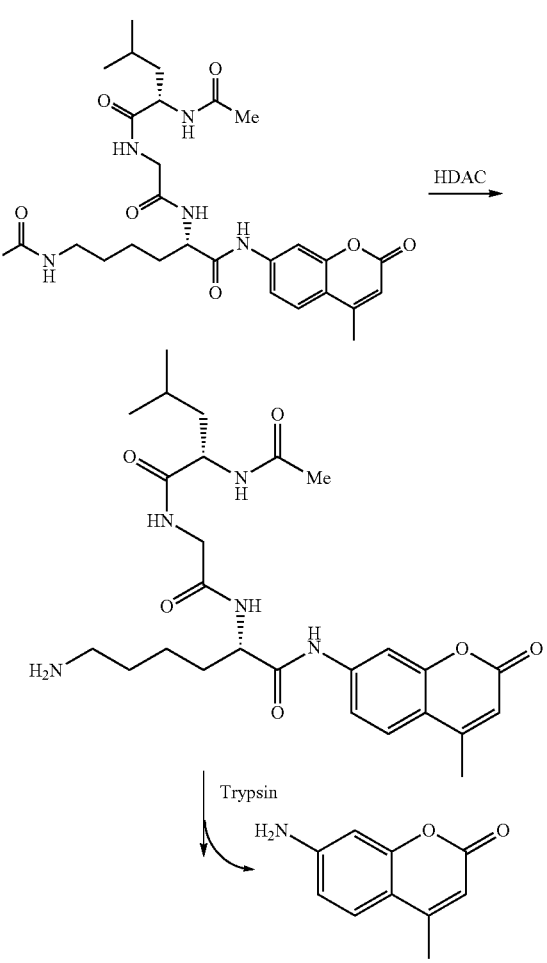

-continued

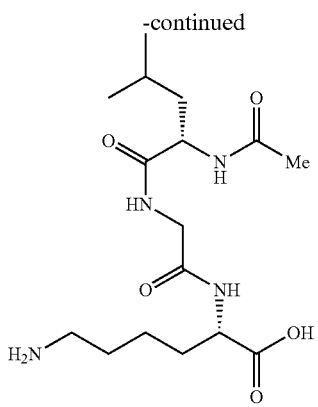

In yet another aspect, the invention provides an assay for determining the binding affinity of a test compound for an HDAC protein comprising incubating HDAC protein with a compound of general formula (IIIc)

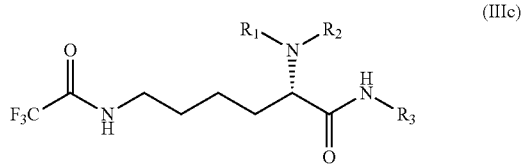

wherein $R_1$, $R_2$ and $R_3$ are as described herein, and determining binding of the test compound to the HDAC protein.

In another aspect of the invention, compounds of general formula (III) are used in the assay

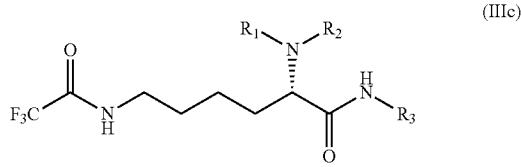

wherein $R_1$, $R_2$ and $R_3$ are as described herein.

In certain embodiments, $R_1$, $R_2$ and $R_3$ are each independently hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $OR^B$; $-C(=O)R^B$; $-CO_2R^B$; $-C(=O)N(R^B)_2$; $-SR^B$; $-SOR^B$; $-SO_2R^B$; $-N(R^B)_2$; $-NHC(O)R^B$; or $-C(R^B)_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; an amino acid; a peptide; a protecting group; or a tag; or pharmaceutically acceptable salt thereof. In further embodiments, neither $R_1$ nor $R_2$ is Boc. In certain embodiments, at least one of $R_1$, $R_2$, or $R_3$ is a tag. In other embodiments, $R_1$ or $R_2$ is a tag. In still other embodiments, $R_1$ and $R_2$ are tags. In certain embodiments, $R_3$ is a tag.

In certain embodiments, at least one of $R_1$, $R_2$, and $R_3$ is an amino acid. In other embodiments, $R_1$ is an amino acid. In still other embodiments, $R_2$ is an amino acid. In further embodiments, $R_1$ is an amino acid. In certain embodiments, $R_2$ is an amino acid. In other embodiments, $R_3$ is an amino acid.

In certain embodiments, at least one of $R_1$, $R_2$, and $R_3$ is a natural amino acid. In other embodiments, $R_1$ is a natural amino acid. In still other embodiments, $R_2$ is a natural amino acid. In further embodiments, $R_1$ is a natural amino acid. In certain embodiments, $R_2$ is a natural amino acid. In other embodiments, $R_3$ is a natural amino acid.

In certain embodiments, at least one of $R_1$, $R_2$, and $R_3$ is an unnatural amino acid. In other embodiments, $R_1$ is an unnatural amino acid. In still other embodiments, $R_2$ is an unnatural amino acid. In further embodiments, $R_1$ is an unnatural amino acid. In certain embodiments, $R_2$ is an unnatural amino acid. In other embodiments, $R_3$ is an unnatural amino acid.

In certain embodiments, at least $R_1$ or $R_2$ is hydrogen. In other embodiments, $R_1$ and $R_2$ are hydrogens. In further embodiments, $R_1$, $R_2$, and $R_3$ are hydrogens.

In certain embodiments, at least $R_1$ or $R_2$ is cyclic or acyclic, substituted or unsubstituted, branched or unbranched aliphatic. In other embodiments, at least $R_1$ or $R_2$ is a $C_{1-6}$ alkyl group. In still other embodiments, at least $R_1$ or $R_2$ is a $C_{1-4}$ alkyl group. In certain embodiments, $R_3$ is cyclic or acyclic, substituted or unsubstituted, branched or unbranched aliphatic. In other embodiments, $R_3$ is a $C_{1-6}$ alkyl group. In still other embodiments, $R_3$ is a $C_{1-4}$ alkyl group.

In certain embodiments, at least one of $R_1$, $R_2$, and $R_3$ is a peptide. In other embodiments, $R_1$ is a peptide. In still other embodiments, $R_2$ is a peptide. In further embodiments, $R_1$ is a peptide. In certain embodiments, $R_2$ is a peptide. In other embodiments, $R_3$ is a peptide. In other embodiments, $R_1$, $R_2$, and $R_3$ are peptides.

In certain embodiments, at least one of $R_1$, $R_2$, and $R_3$ is a two-mer peptide. In other embodiments, $R_1$ is a two-mer peptide. In still other embodiments, $R_2$ is a two-mer peptide. In further embodiments, $R_1$ is a two-mer peptide. In certain embodiments, $R_2$ is a two-mer peptide. In other embodiments, $R_3$ is a two-mer peptide. In other embodiments, $R_1$, $R_2$, and $R_3$ are two-mer peptides.

In certain embodiments, at least one of $R_1$, $R_2$, and $R_3$ is a three-mer peptide. In other embodiments, $R_1$ is a three-mer peptide. In still other embodiments, $R_2$ is a three-mer peptide. In further embodiments, $R_1$ is a three-mer peptide. In certain embodiments, $R_2$ is a three-mer peptide. In other embodiments, $R_3$ is a three-mer peptide. In other embodiments, $R_1$, $R_2$, and $R_3$ are three-mer peptides.

In certain embodiments, at least one of $R_1$, $R_2$, and $R_3$ is a four-mer peptide. In other embodiments, $R_1$ is a four-mer peptide. In still other embodiments, $R_2$ is a four-mer peptide. In further embodiments, $R_1$ is a four-mer peptide. In certain embodiments, $R_2$ is a four-mer peptide. In other embodiments, $R_3$ is a four-mer peptide. In other embodiments, $R_1$, $R_2$, and $R_3$ are four-mer peptides.

In certain embodiments, one of $R_1$ or $R_2$ is a two-mer peptide; and the other of $R_1$ and $R_2$ is hydrogen or cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; an amino acid; a peptide; a protecting group; or a tag. In other embodiments, one of $R_1$ or $R_2$ is a two-mer peptide; and the other of $R_1$ and $R_2$ is hydrogen.

In certain embodiments, one of $R_1$ or $R_2$ is a three-mer peptide; and the other of $R_1$ and $R_2$ is hydrogen or cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; an amino acid; a peptide; a protecting group; or a tag. In other embodiments, one of $R_1$ or $R_2$ is a three-mer peptide; and the other of $R_1$ and $R_2$ is hydrogen.

In certain embodiments, one of $R_1$ or $R_2$ is a four-mer peptide; and the other of $R_1$ and $R_2$ is hydrogen or cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; an amino acid; a peptide; a protecting group; or a tag. In other embodiments, one of $R_1$ or $R_2$ is a four-mer peptide; and the other of $R_1$ and $R_2$ is hydrogen.

In certain embodiments, one of $R_1$ or $R_2$ is a nitrogen protecting group. In other embodiments, $R_1$ and $R_2$ are nitrogen protecting groups. In certain embodiments, $R_1$ is selected from the group consisting of t-Boc, Fmoc, benzyloxy-carbonyl, and alloc. In further embodiments, $R_1$ and $R_2$ are selected from the group consisting of t-Boc, Fmoc, benzyloxy-carbonyl, and alloc. In still further embodiments, $R_1$ and/or $R_2$ lithographic protecting group. In certain embodiments, at least $R_1$, $R_2$, or $R_3$ is a tag. In other embodiments, $R_1$ is a tag. In further embodiments, $R_3$ is a tag. In certain embodiments, neither $R_1$, $R_2$, nor $R_3$ is a tag.

In certain embodiments, the tag is selected from the group consisting of a fluorescent tag, a bioluminescent tag, a chemoluminescent tag, a photoluminescent tag, a radioluminescent tag, and a thermoluminescent tag. In other embodiments, the tag is selected from the group consisting og: an epitope tag, an isotope tag, a radioactive tag, and a radiolabeled tag. In further embodiments, the tag is a spin label.

In certain embodiments, at least $R_1$, $R_2$, or $R_3$ comprises a chromophore. In other embodiments, $R_1$ comprises a chromophore. In still other embodiments, $R_3$ comprises a chromophore. In certain embodiments, at least $R_1$, $R_2$, or $R_3$ comprises a fluorochrome. In other embodiments, $R_1$ comprises a fluorochrome. In still other embodiments, $R_3$ comprises a fluorochrome. In certain embodiments, at least $R_1$, $R_2$, or $R_3$ comprises a ferromagnetic substance. In other embodiments, $R_1$ comprises a ferromagnetic substance. In still other embodiments, $R_3$ comprises a ferromagnetic substance.

In certain embodiments, at least $R_1$, $R_2$, or $R_3$ comprises coumarin. In other embodiments, $R_1$ comprises coumarin. In still other embodiments, $R_3$ comprises coumarin. In further embodiments, $R_1$, and $R_3$ comprises coumarin. In other embodiments, $R_1$, $R_2$, and $R_3$ comprises coumarin.

In certain embodiments, at least $R_1$, $R_2$, or $R_3$ is selected from a group consisting of brodifacoum, bromadiolone, coumafuryl, difenacoum, auraptene, ensaculin, phenprocoumon, warfarin, and derivatives thereof. In other embodiments, $R_1$ is selected from a group consisting of brodifacoum, bromadiolone, coumafuryl, difenacoum, auraptene, ensaculin, phenprocoumon, warfarin, and derivatives thereof. In still other embodiments, $R_3$ is selected from a group consisting of brodifacoum, bromadiolone, coumafuryl, difenacoum, auraptene, ensaculin, phenprocoumon, warfarin, and derivatives thereof. In further embodiments, $R_1$, and $R_3$ are selected from a group consisting of brodifacoum, bromadiolone, coumafuryl, difenacoum, auraptene, ensaculin, phenprocoumon, warfarin, and derivatives thereof. In other embodiments, $R_1$, $R_2$, and $R_3$ are selected from a group consisting of brodifacoum, bromadiolone, coumafuryl, difenacoum, auraptene, ensaculin, phenprocoumon, warfarin, and derivatives thereof.

In certain embodiments, at least $R_1$, $R_2$, or $R_3$ is 7-amino-4-methylcoumarin. In other embodiments, $R_1$ is 7-amino-4-methylcoumarin. In still other embodiments, $R_3$ is 7-amino-4-methylcoumarin. In further embodiments, $R_1$, and $R_3$ are 7-amino-4-methylcoumarin.

In certain embodiments, at least $R_1$, $R_2$, or $R_3$ is ethidium bromide. In other embodiments, $R_1$ is ethidium bromide. In still other embodiments, $R_3$ is ethidium bromide. In further embodiments, $R_1$, and $R_3$ are ethidium bromide. In certain embodiments, at least $R_1$, $R_2$, or $R_3$ is fluorescein. In other embodiments, $R_1$ is fluorescein. In still other embodiments, $R_3$ is fluorescein. In further embodiments, $R_1$, and $R_3$ are fluorescein.

In certain embodiments, at least $R_1$, $R_2$, or $R_3$ can be cleaved by an enzyme. In other embodiments, $R_1$ can be cleaved by an enzyme. In still other embodiments, $R_3$ can be cleaved by an enzyme. In further embodiments, $R_1$, and $R_3$ can be cleaved by an enzyme. In other embodiments, $R_1$, $R_2$, and $R_3$ can be cleaved by an enzyme. In certain embodiments, the enzyme is an esterase. In other embodiments, the enzyme is a protease. In further embodiments, the enzyme is trypsin.

In certain embodiments, the tag is toxic to the cell once cleaved. In other embodiments, the tag is not toxic to the cell once cleaved.

In certain embodiments, at least $R_1$, $R_2$, or $R_3$ can be cleaved by an enzyme. In other embodiments, $R_1$ can be cleaved by an enzyme. In still other embodiments, $R_3$ can be cleaved by an enzyme. In further embodiments, $R_1$, and $R_3$ can be cleaved by an enzyme. In other embodiments, $R_1$, $R_2$, and $R_3$ can be cleaved by an enzyme. In certain embodiments, the enzyme is an esterase. In other embodiments, the enzyme is a protease. In further embodiments, the enzyme is trypsin.

In certain embodiments, at least $R_1$, $R_2$, or $R_3$ comprises the peptide sequence Leu-Gly. In other embodiments $R_1$, comprises the peptide sequence Leu-Gly. In still other embodiments, $R_3$ comprises the peptide sequence Leu-Gly.

In certain embodiments, the compound is

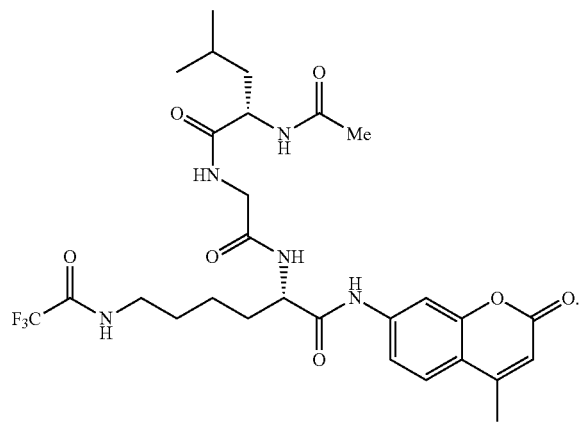 [SMILES: CC(=O)N[C@@H](CC(C)C)C(=O)NCC(=O)N[C@@H](CCCCNC(=O)C(F)(F)F)C(=O)Nc1ccc2c(C)cc(=O)oc2c1]

EQUIVALENTS

The representative examples which follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that, unless otherwise indicated, the entire contents of each of the references cited herein are incorporated herein by reference to help illustrate the state of the art. The following examples contain important additional information, exemplification and guidance which can be adapted to the practice of this invention in its various embodiments and the equivalents thereof.

These and other aspects of the present invention will be further appreciated upon consideration of the following Examples, which are intended to illustrate certain particular embodiments of the invention but are not intended to limit its scope, as defined by the claims.

EXAMPLES

Example 1

(S)-2-amino-N-(4-methyl-2-oxo-2H-chromen-7-yl)-6-(2,2,2-trifluoroacetamido)hexanamide (ε-trifluoroacetyl-L-lysine-AMC hydrochloride)

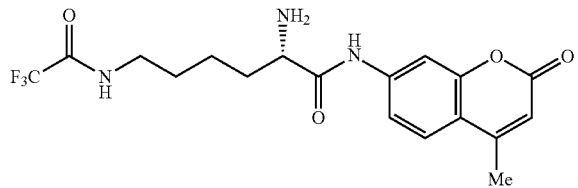 [SMILES: Cc1cc(=O)oc2cc(NC(=O)[C@@H](N)CCCCNC(=O)C(F)(F)F)ccc12]

To a solution of Boc-ε-trifluoroacetyl-L-lysine-AMC (4.6 g, 9.2 mmol) in thy dichloromethane at 0° C. was added 5 mL of a 4 M solution of HCl/dioxane (Lahm, A. et. al. *Proc. Natl. Acad. Sci. U.S.A.* 2007, 104, 17335-17340). The reaction mixture was warmed to room temperature and stirred over night. The solvent was evaporated under reduced pressure to afford the desired product in quantitative yield (4.0 g) and excellent purity as white powder, which was used without further purification. $^1$H NMR (400 MHz, DMSO) δ 11.53 (s, 1H), 9.47 (s, 1H), 8.47 (s, 3H), 7.95-7.80 (m, 1H), 7.76 (d, J=8.8, 1H), 7.58 (d, J=8.1, 1H), 6.30 (s, 1H), 4.12 (s, 1H), 3.17 (d, J=5.5, 2H), 2.41 (d, J=6.7, 3H), 1.88 (s, 2H), 1.61-1.46 (m, 2H), 1.38 (d, J=6.4, 2H); $^{13}$C NMR (101 MHz, DMSO) δ 168.33, 159.93, 156.15 (q, J=35.8), 153.54, 153.09, 141.46, 126.11, 115.64, 115.59 (q, J=289 Hz), 115.47, 112.69, 106.07, 52.93, 38.79, 30.60, 27.75, 21.45, 18.04.

Example 2

(S)-2-(2-((S)-2-acetamido-4-methylpentanamido)acetamido)-N-(4-methyl-2-oxo-2H-chromen-7-yl)-6-(2,2,2-trifluoroacetamido)hexanamide (4)

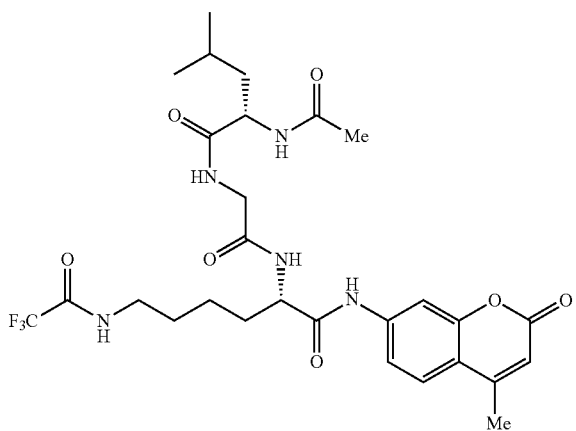

ε-trifluoroacetyl-L-lysine-AMC hydrochloride (1.35 g, 3.10 mmol) was added to a solution of N,N-diisopropylethylamine (2.5 mL) and Ac-Leu-Gly-OH (805 mg, 3.50 mmol) in 100 mL anhydrous dichloromethane followed by PyBop (1.8 g, 3.5 mmol) in dichloromethane (5 mL). After stirring over night at room temperature the reaction mixture was diluted with dichloromethane (200 mL) and washed with dilute HCl and then saturated aqueous sodium bicarbonate solution. The organic layer was dried over sodium sulfate and the solvent was removed under reduced pressure. The crude product was purified on silica gel (dichloromethane, MeOH 10:1) to yield the desired product as off-white solid (1.57 g, 83%). $^1$H NMR (400 MHz, DMSO) δ 10.39 (s, 1H), 9.42 (t, J=5.6, 1H), 8.35 (t, J=5.8, 1H), 8.11 (d, J=7.3, 1H), 8.05 (dd, J=7.9, 4.0, 1H), 7.79 (d, J=2.0, 1H), 7.71 (d, J=8.7, 1H), 7.51 (dd, J=8.7, 2.0, 1H), 6.26 (d, J=1.2, 1H), 4.46-4.28 (m, 1H), 4.22 (dd, J=15.0, 7.3, 1H), 3.85-3.63 (m, 2H), 3.16 (dd, J=13.1, 6.8, 2H), 2.39 (d, J=1.1, 3H), 1.86 (s, 3H), 1.81-1.19 (m, 9H), 0.85 (dd, J=17.5, 6.5, 6H); $^{13}$C NMR (101 MHz, DMSO) (mix of conformers) δ 172.93, 172.31, 171.38, 169.75, 169.13, 169.07, 166.34, 160.04, 156.10 (q, J=36 Hz), 153.65, 153.10, 142.13, 125.95, 115.98 (q, J=288 Hz), 115.30, 115.16, 105.76, 53.53, 51.49, 50.88, 45.57, 44.89, 42.03, 41.24, 40.96, 40.52, 31.30, 27.98, 25.63, 24.18, 23.74, 23.09, 22.95, 22.72, 22.52, 22.49, 21.64, 21.55, 18.02.

Example 3

Synthesis of hydrazine 5a

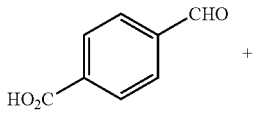

-continued

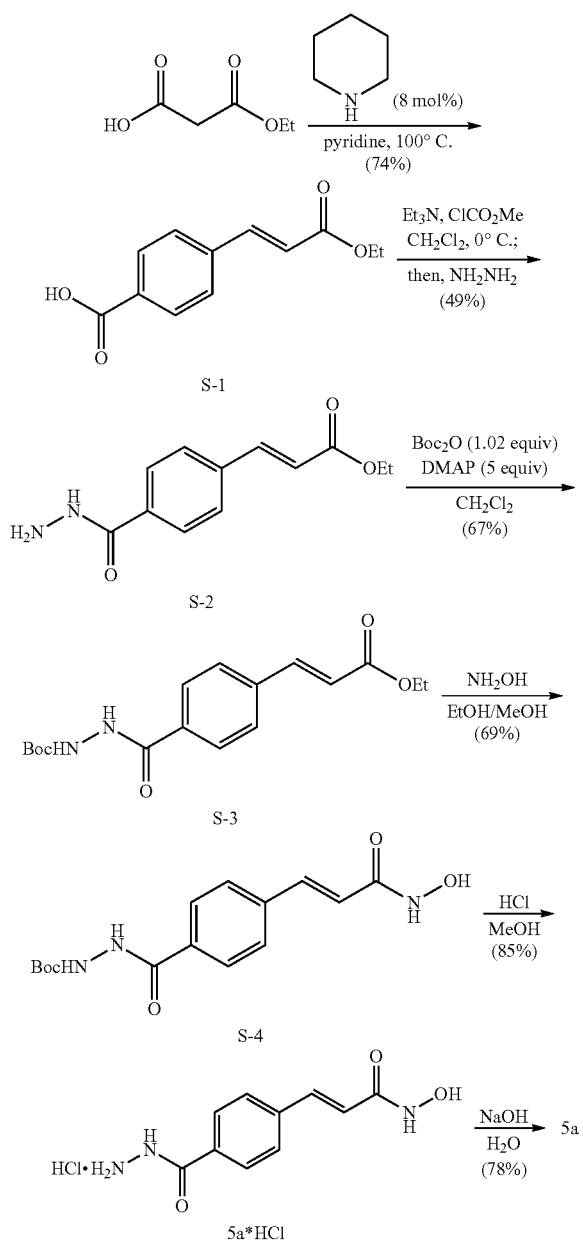

Example 4

(E)-4-(3-ethoxy-3-oxoprop-1-enyl)benzoic acid (S-1)

To a flask was added 4-formylbenzoic acid (1.5 g, 10 mmol), 3-ethoxy-3-oxopropanoic acid (2.0 g, 15 mmol), piperidine (0.08 mL, 0.81 mmol), and pyridine (4 mL) at room temperature. The reaction mixture was heated to 100° C. for 18 h under a steady flow of nitrogen gas, cooled to room temperature, and poured into 2 M aqueous HCl (100 mL). The resulting mixture was cooled to 0° C. and filtered. The filter cake was washed with acetonitrile (2×10 mL) and dried in vacuo. Cinnamyl ester S-1 (1.63 g, 74%) was isolated as a white solid and carried on to hydrazine formation without further purification.

Example 5

(E)-ethyl 3-(4-(hydrazinecarbonyl)phenyl)acrylate (S-2)

To a solution of S-1 (0.44 g, 2.0 mmol) in dichloromethane (10 mL) was added triethylamine (0.36 mL, 2.0 mmol) and methyl chloroformate (0.19 mL, 2.0 mmol) at 0° C. The reaction mixture was stirred for 1 h at 0° C. before hydrazine (0.30 mL, 6.0 mmol) was added. The resulting solution was stirred for an additional 2 h at 0° C. Saturated aqueous $NaHCO_3$ (10 mL) was added to the reaction mixtures and the resulting biphasic solution was stirred for 30 min at room temperature. The organic layer was separated, dried, and the solvent removed via rotary evaporation. The resulting residue was purified by flash chromatography on silica (eluting with EtOAc) to yield compound S-2 (0.23 g, 49%) as a white solid.

Example 6

(E)-tert-butyl 2-(4-(3-ethoxy-3-oxoprop-1-enyl)benzoyl)hydrazinecarboxylate (S-3)

To a solution of hydrazine S-2 (6.00 g, 25.6 mmol) in dichloromethane (300 mL) was added Boc anhdyride (5.40 g, 26.2 mmol) and DMAP (12.5 g, 103 mmol). The mixture was stirred at room temperature for 3 h, concentrated, and loaded directly on to silica. Flash chromatography, eluting with 1:1 EtOAc/petroleum ether, yielded S-3 (5.76 g, 67.3%).

Example 7

(E)-tert-butyl 2-(4-(3-(hydroxyamino)-3-oxoprop-1-enyl)benzoyl)hydrazinecarboxylate (S-4)

To a solution of S-3 (5.76 g, 17.2 mmol) in methanol (300 mL) was added a solution of hydroxylamine hydrochloride (11.9 g, 171 mmol) in 1 M NaOH/ethanol (341 mL). The reaction mixture was stirred for 18 h and concentrated. The residue was dissolved in water to yield a colorless homogenous solution, which was neutralized to pH 7 by the addition of aqueous 1 M HCl. The resulting suspension was extracted with ethyl acetate. The combined organic extracts were dried and concentrated via rotary evaporation. Crude S-4 was loaded on to silica and purified via flash chromatography, eluting with ethyl acetate, to yield S-4 (3.80 g, 68.8%).

Example 8

(E)-3-(4-(hydrazinecarbonyl)phenyl)-N-hydroxyacrylamide hydrochloride (5a.HCl)

Boc protected hydrazine S-4 (3.50 g, 10.9 mmol) was dissolved in 6 M HCl/methanol (20 mL) and stirred at ambient temperature for 1 h, while a white precipitate formed. The reaction mixture was filtered to yield the title compound as a white solid (2.38 g, 84.9%).

Example 9

(E)-3-(4-(hydrazinecarbonyl)phenyl)-N-hydroxy-acrylamide (5a)

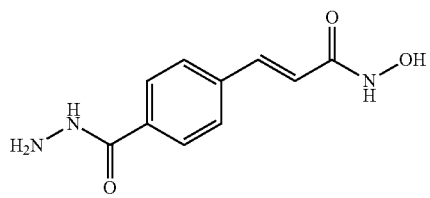

A solution of 1 M aqueous NaOH was added dropwise to a suspension of 5a.HCl (1.8 g, 7.0 mmol) in water (200 mL) until the pH reached 11. The colorless, homogeneous solution was neutralized with dilute aqueous HCl. The resulting precipitate was isolated via filtration and dried in vacuo to yield 5a (1.2 g, 78%) as a gray solid. $^1$H NMR (500 MHz, DMSO) δ 10.85 (s, 1H), 9.84 (s, 1H), 9.12 (s, 1H), 7.85 (d, J=7.8, 2H), 7.63 (d, J=7.8, 2H), 7.49 (d, J=15.8, 1H), 6.55 (d, J=15.8, 1H), 4.72 (s, 2H); $^{13}$C NMR (126 MHz, DMSO) δ 165.92, 163.13, 138.08, 138.03, 134.44, 128.22, 128.07, 121.36.

Example 10

Synthesis of hydrazine 5b

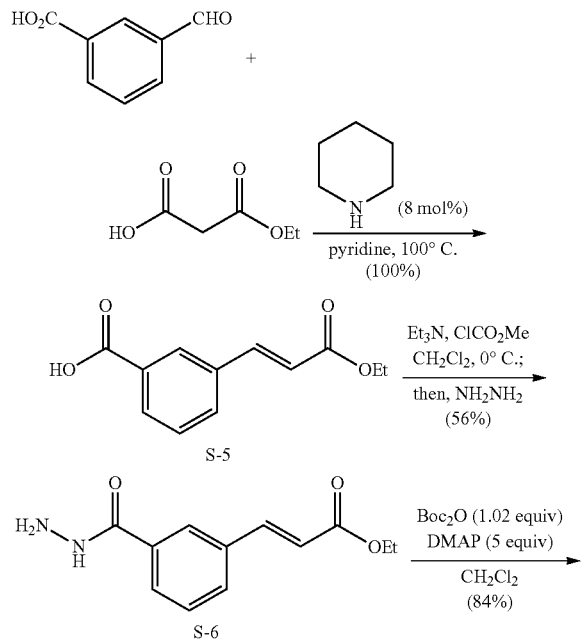

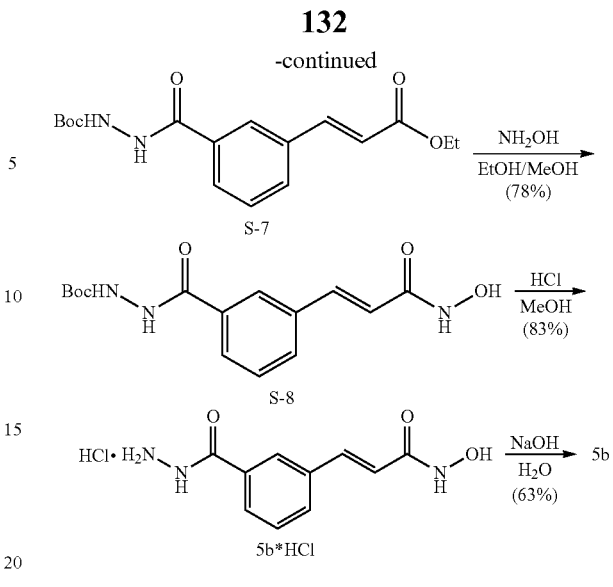

Example 11

(E)-3-(3-ethoxy-3-oxoprop-1-enyl)benzoic acid (S-5)

To a flask was added 3-formylbenzoic acid (1.5 g, 10 mmol), 3-ethoxy-3-oxopropanoic acid (2.0 g, 15 mmol), piperidine (0.08 mL, 0.81 mmol), and pyridine (4 mL) at room temperature. The reaction mixture was heated to 100° C. for 18 h under a steady flow of nitrogen gas, cooled to room temperature, and poured into 2 M aqueous HCl (100 mL). The resulting mixture was cooled to 0° C. and filtered. The filter cake washed with acetonitrile (2×10 mL), and dried in vacuo. Cinnamyl ester S-5 (2.20 g, 100%) was isolated as a white solid and carried on to hydrazine formation without further purification.

Example 12

(E)-ethyl 3-(4-(hydrazinecarbonyl)phenyl)acrylate (S-6)

To a solution of S-5 (0.44 g, 2.0 mmol) in dichloromethane (10 mL) was added triethylamine (0.36 mL, 2.0 mmol) and methyl chloroformate (0.19 mL, 2.0 mmol) at 0° C. The reaction mixture was stirred for 1 h at 0° C. before hydrazine (0.30 mL, 6.0 mmol) was added. The resulting solution was stirred for an additional 2 h at 0° C. Saturated aqueous NaHCO$_3$ (10 mL) was added to the reaction mixture and the resulting biphasic solution was stirred for 30 min at room temperature. The organic layer was separated, dried, and the solvent removed via rotary evaporation. The resulting residue was purified by flash chromatography on silica (eluting with EtOAc) to yield compound S-6 (0.26 g, 56%) as a white solid.

Example 13

(E)-tert-butyl 2-(4-(3-ethoxy-3-oxoprop-1-enyl)benzoyl)hydrazinecarboxylate (S-7)

To a solution of hydrazine S-6 (6.00 g, 25.6 mmol) in dichloromethane (200 mL) was added Boc anhdyride (5.40 g, 26.2 mmol) and DMAP (12.5 g, 103 mmol). The mixture was stirred at room temperature for 3 h. The mixture was concentrated and loaded directly on to silica to yield S-7 (7.2 g, 84%) following flash chromatography (eluting with 1:1 EtOAc/petroleum ether).

Example 14

(E)-tert-butyl 2-(4-(3-(hydroxyamino)-3-oxoprop-1-enyl)benzoyl)hydrazinecarboxylate (S-8)

To a solution of S-7 (7.0 g, 20.8 mmol) in methanol (300 mL) was added a solution of hydroxylamine hydrochloride (14.5 g, 208 mmol) in 1 M NaOH in ethanol 420 mL). The reaction mixture was stirred for 18 h and then concentrated. The residue was dissolved in water to yield a colorless homogenous solution, which was neutralized to pH 7 by the addition of aqueous 1 M HCl. The resulting suspension was extracted with ethyl acetate. The combined organic extracts were dried and concentrated via rotary evaporation. Crude S-8 was loaded on to silica and purified via flash chromatography, eluting with ethyl acetate, to yield S-8 (5.2 g, 78%).

Example 15

(E)-3-(4-(hydrazinecarbonyl)phenyl)-N-hydroxyacrylamide hydrochloride (5b.HCl)

Boc protected hydrazine S-8 (4.50 g, 14.0 mmol) was dissolved in 6 M HCl/methanol (30 mL) and stirred at ambient temperature for 1 h, while a white precipitate formed. The reaction mixture was filtered to yield the title compound as a white solid (3.0 g, 83%).

Example 16

(E)-3-(3-(hydrazinecarbonyl)phenyl)-N-hydroxyacrylamide (5b)

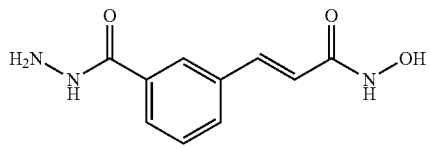

A solution of 1 N aqueous NaOH was added dropwise to a suspension of 5b.HCl (2.0 g, 7.8 mmol) in water (100 mL) until the pH reached 7. A precipitate formed and was isolated via filtration and dried in vacuo to yield 5b (1.1 g, 63%) as a gray solid. $^1$H NMR (500 MHz, DMSO) δ 10.81 (s, 1H), 9.85 (s, 1H), 9.08 (s, 1H), 8.02 (s, 1H), 7.80 (d, J=7.5, 1H), 7.69 (d, J=7.4, 1H), 7.63-7.36 (m, 2H), 6.55 (d, J=15.8, 1H), 4.58 (s, 2H); $^{13}$C NMR (126 MHz, DMSO) δ 166.12, 163.22, 138.37, 135.63, 134.60, 131.04, 129.72, 128.45, 126.28, 120.75.

Example 17

Library synthesis

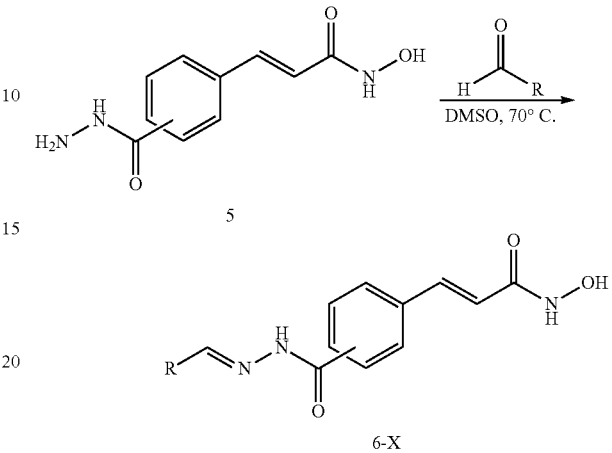

Each well of a 96-well microtiter plate was charged with 10 μL of a distinct, commercially-available aldehyde (0.2 M in DMSO) and 190 μL of a stock solution of the appropriate isomer of 5 in DMSO (0.0105 M). The plate was heated at 70° C. for 36 h. LCMS analysis confirmed that a sampling of acyl hydrazone products were analytically pure (>95%). This stock plate of m- and p-substituted cinnamyl acyl hydrazones was used in screening, as described.

Example 18

(E)-N-hydroxy-3-(4-((E)-2-(2,3,4-trihydroxybenzylidene) hydrazinecarbonyl)phenyl)acrylamide (6a)

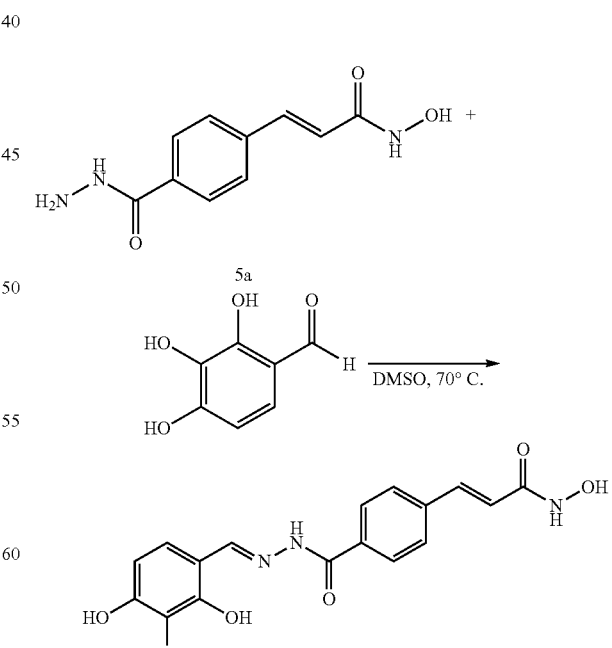

Pandacostat (6a)

Compound 6a was resynthesized and purified to be resubjected to the biochemical assay to confirm the results from the initial library screen. To a 4 dram vial charged with 2,3,4-trihydroxybenzaldehyde (25.9 mg, 0.168 mmol) was added 420 μL of a 200 mM solution of hydrazine 5a (0.084 mmol) in DMSO. The solution was heated on a rotating heating block at 70° C. for 16 h. Reaction progress was monitored via LCMS. Following purification by reverse phase preparatory LCMS (44 mL/min, CH$_3$CN/H$_2$O with 1% formic acid, 5 min gradient), 6a (7 mg) was isolated as a yellow powder (98% pure, by analytical LCMS). $^1$H NMR (300 MHz, DMSO) δ 12.01 (s, 1H), 11.51 (s, 1H), 10.84 (s, 1H), 9.49 (s, 1H), 9.13 (s, 1H), 8.54 (s, 1H), 8.48 (s, 1H), 7.96 (d, J=8.3, 2H), 7.73 (d, J=8.2, 2H), 7.53 (d, J=16.2, 1H), 6.80 (d, J=8.6, 1H), 6.59 (d, J=15.9, 1H), 6.40 (d, J=8.4, 1H); m/z (ES−) 356 ([M-H]).

Example 19

The broad study of histone deacetylases in chemistry, biology and medicine relies on tool compounds to derive mechanistic insights. A phylogenetic analysis of Class I and II HDACs as targets of a comprehensive, structurally diverse panel of inhibitors revealed unexpected isoform selectivity even among compounds widely perceived as non-selective. These data informed the design of a focused library of cinnamic hydroxamates, which allowed the identification of a truly non-selective HDAC inhibitor.

Histone deacetylases (HDACs) regulate diverse cellular processes by modulating protein structure and function. Lysine acetylation is reversibly mediated by HDACs and acetyl transferases, establishing a dynamic post-translational modification state of broad relevance to cell signaling and state. As components of chromatin modifying enzyme complexes, HDACs target the amino-terminal tails of histone proteins affecting chromatin conformation and gene-specific transcription (Minucci, S. et al., *Nat. Rev. Cancer* 2006, 6, 38-51; Lee, K. K. et al., *Nat. Rev. Mol. Cell. Biol.* 2007, 8, 284-295). Recent research has identified a significant number of non-histone protein substrates, extending the mechanistic relevance and research interest in HDACs well beyond the field of chromatin biology.

The common classification of human deacetylases is based on molecular phylogenetic analysis of primary structure, subsequently grouped based on homology to yeast enzymes LIT. This approach yields four distinct classes that vary in size and function. Class I (HDAC1, 2, 3 and 8), Class IIa (HDAC4, 5, 7 and 9), Class IIb (HDAC6 and 10) and Class IV (HDAC 11) HDACs contain predicted zinc-dependent deacetylase domains (de Ruijter, A. J. et al. *Biochem. J.* 2003, 370, 737-749). The Class III proteins form a structurally and mechanistically distinct Class of NAD+dependent hydrolases (Sirtuins; Sirt1-7) (Smith, B. C. et al. *Chem. Biol.* 2008, 15, 1002-1013). Studies of human deacetylases have benefitted from the availability of small-molecule HDAC inhibitors (HDACi), most of which as a group obey a common "cap-linker-chelator" pharmacophore model (Sternson, S. M. et al. *Org. Lett.* 2001, 3, 4239-4242). The remarkable demonstration of pro-differentiation and anti-proliferative effects in cancer model systems prompted the further development of these tool compounds into investigational agents for therapeutic use in humans. One pharmaceutical HDACi has been approved for use in humans (SAHA; Zolinza© (vorinostat) Merck Research Laboratories) and more than ten additional compounds are in advanced clinical testing (Bolden, I. E. et al. *Nat. Rev. Drug. Discov.* 2006, 5, 769-784). As such, there is considerable interest in HDACi as tool compounds for cellular biology and as therapeutic agents for the treatment of cancer, inflammatory conditions and infectious diseases.

Widely maintained is the perception that many of the currently used small-molecule inhibitors are non-selective (Bolden, I. E. et al. *Nat. Rev. Drug. Discov.* 2006, 5, 769-784). Recent research has revealed unique aspects of Class IIa HDAC biochemistry, which calls into question the accuracy of prior homogeneous assays for reporting target potency (Jones, P. et al. *Bioorg. Med. Chem. Lett.* 2008, 18, 1814-1819). This is problematic as the mechanistic understanding of Class IIa HDACs is expanding, enhanced by the availability of genetic probes of protein function such as silencing reagents and knock-out mice (Zhou, X. et al. *Proc. Natl. Acad. Sci. U.S.A.* 2000, 97, 1056-1061; Parra, M. et al. *J. Biol. Chem.* 2005, 280, 13762-13770; Mottet, D. et al. *Circ. Res.* 2007, 101, 1237-1246; Renthal, W. et al. *Neuron* 2007, 56, 517-529; Tsankova, N. M. et al. *Nat. Neurosci.*, 2006, 9, 519-525; Bolger, T. A. et al. *J. Neurosci.* 2005, 25, 9544-9553; Cohen, T. J. et al. *J. Biol. Chem.* 2007, 282, 33752-33759). Key regulatory roles have been suggested in immune tolerance, cardiac remodeling and neuronal death. We therefore endeavored to derive a more complete knowledge of isoform-specific potency and to instruct a more thoughtful use of these compounds as chemical probes of discrete HDAC targets in both the research and clinical setting.

Figure 4:
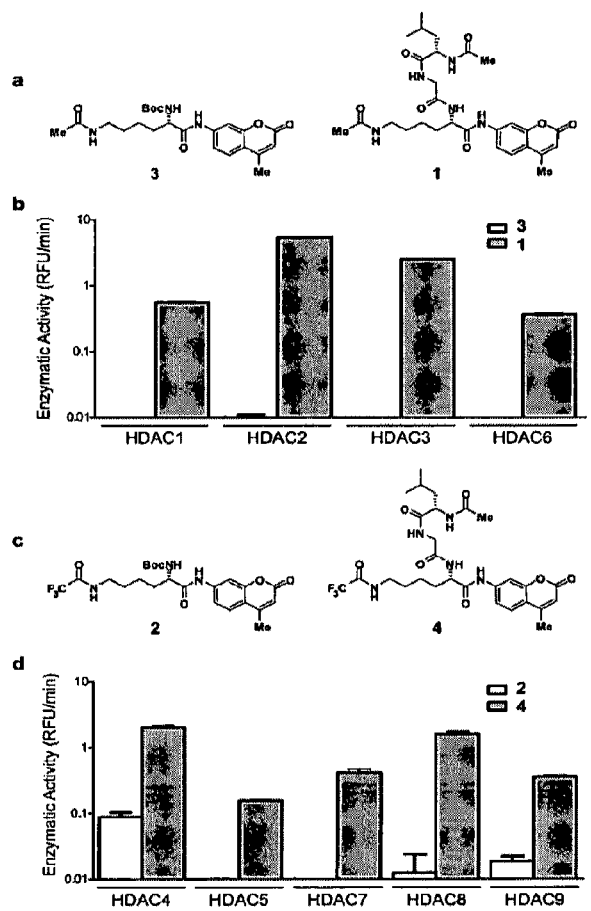
FIG. 4 illustrates comparative profiling of HDAC substrates identifying preferences distinct from molecular phylogenetic class assignments. (a) Chemical structure of substrates 1 and 3. (b) Comparative activity of HDAC1, 2, 3 and 6 for Boc-protected acetyl-lysine substrate 3 and tripeptide acetyl-lysine substrate 1, studied at equivalent substrate concentrations (10 µM). Substrate 1 is the preferred substrate for these Class I and IIb enzymes. (c) Chemical structure of substrates 2 and 4. (d) Comparative activity of HDAC4, 5, 7, 8 and 9 for Boc-protected trifluoro acetyl-lysine substrate 2 and tripeptide trifluoro acetyl-lysine substrate 4, studied at equivalent substrate concentrations (10 µM). Substrate 4 is the preferred substrate for these Class I and IIa enzymes. The robust activity of HDAC8 for trifluoro acetyl lysine-based substrates resonates with published observations from the Schwienhorst laboratory, who have innovated HDAC assay design and substrate preference determination. (Minucci et al. *Nat. Rev. Cancer* 2006, 6, 38-51; Lee et al. *Nat. Rev. Mol. Cell. Biol.* 2007, 8, 284-295.)
Figure 5:
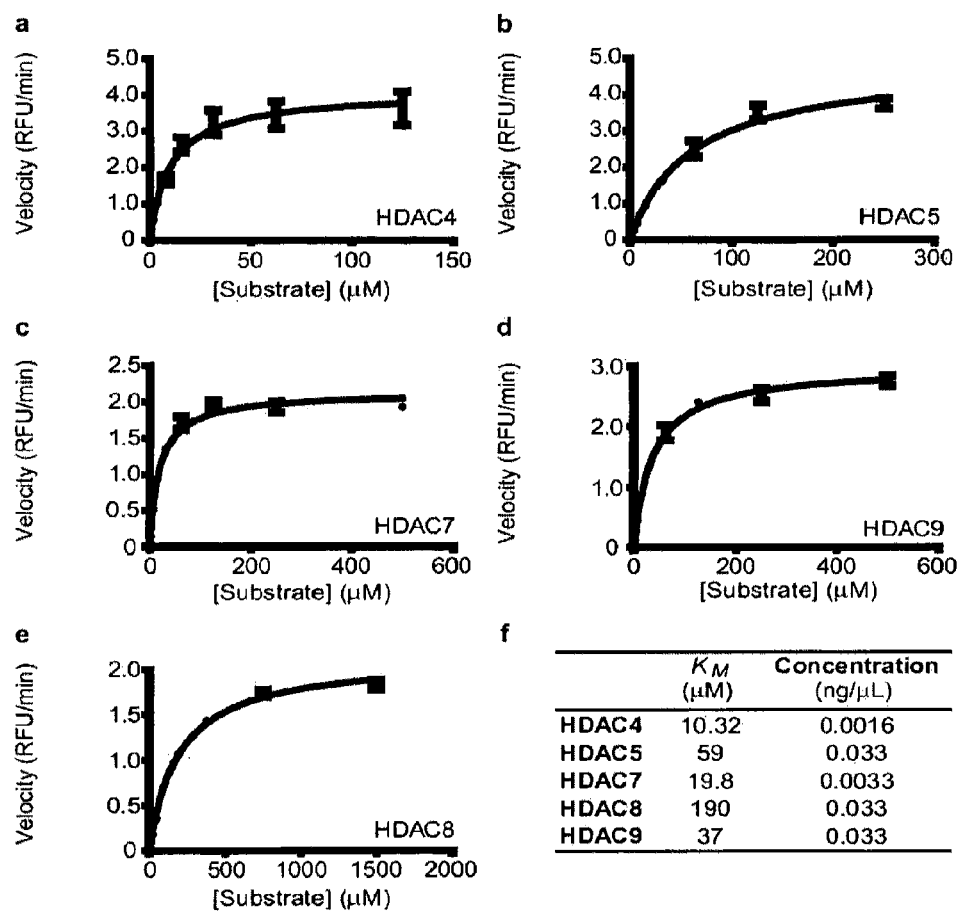
FIG. 5 illustrates the determination of $K_M$ for substrate 4. (a-e) Michaelis-Menten Plots for substrate 4 and human, recombinant HDACs (as labeled) in a miniaturized, kinetic trypsin-coupled assay. (f) Table of $K_M$ values derived. Also provided are concentrations of enzymes required for the miniaturized HDAC assay, afforded by substrate 4. The reduction in enzyme used per well enables reagent-efficient compound annotation as well as high-throughput screening.

We have synthesized and assembled a panel of structurally-diverse small-molecule HDACi that resemble most of the relevant literature reported tool compounds and pharmacologically developed clinical candidates (FIG. 2). Recently, we have optimized a miniaturized kinetic assay for biochemical profiling of HDAC 1, 2, 3, 6 and 8 (Bowers, A. et al. *J. Am. Chem. Soc.* 2008, 130, 11219-11222). However, implementation of this assay for Class IIa HDACs proved challenging due to the low catalytic turnover of the acetylated tripeptide substrate (1) as well as a Class IIa-specific substrate reported by Jones et. al. (2), both of which require a prohibitively significant amount of enzyme (Jones, P. et al. *Bioorg. Med. Chem. Lett.*, 2008, 18, 1814-1819; Riester, D. et al. *Biochem. Biophys. Res. Commun.* 2004, 324, 1116-1123). During assay development, we observed diminished turnover by Class I HDACs of Boc-protected substrate 3 compared to tripeptide substrate 1 (FIG. 4) (Riester, D. et al. *Biochem. Biophys. Res. Commun.* 2004, 324, 1116-1123). We therefore devised a new tripeptide substrate 4, which features as 2 the relatively labile and sterically more demanding trifluoroacetyl group that is readily hydrolyzed by the catalytically less avid Class IIa HDACs (FIG. 1a,b). With substrate 4, Class IIa HDACs exhibit markedly faster kinetics further reducing requisite enzyme concentration (0.002-0.03 ng/μL; FIGS. 4 and 5) and allowing a high-throughput, precise profiling of HDACi against all Class IIa enzymes (FIG. 2).

Using statistical methods validated for assessing evolutionary relatedness, we constructed a chemical genetic phylogeny of deacetylases derived from these kinetic data (FIG. 1c). This approach was selected to prompt inferences into biochemical, pharmacologic and structural relationships. The analysis revealed a number of unexpected findings. First and foremost, the Class IIa enzymes are not targeted by most HDACi at pharmacologically-relevant concentrations. None of the inhibitors tested demonstrated a preference for Class IIa enzymes. In fact, significant inhibitory activity was only observed several orders of magnitude above the Ki for Class I/Hb enzymes. Consequently, none of the inhibitors tested is suitable for use as a tool compound to inhibit Class IIa function in settings where Class I/Hb enzymes are functionally present (i.e. in cells).

Figure 6:
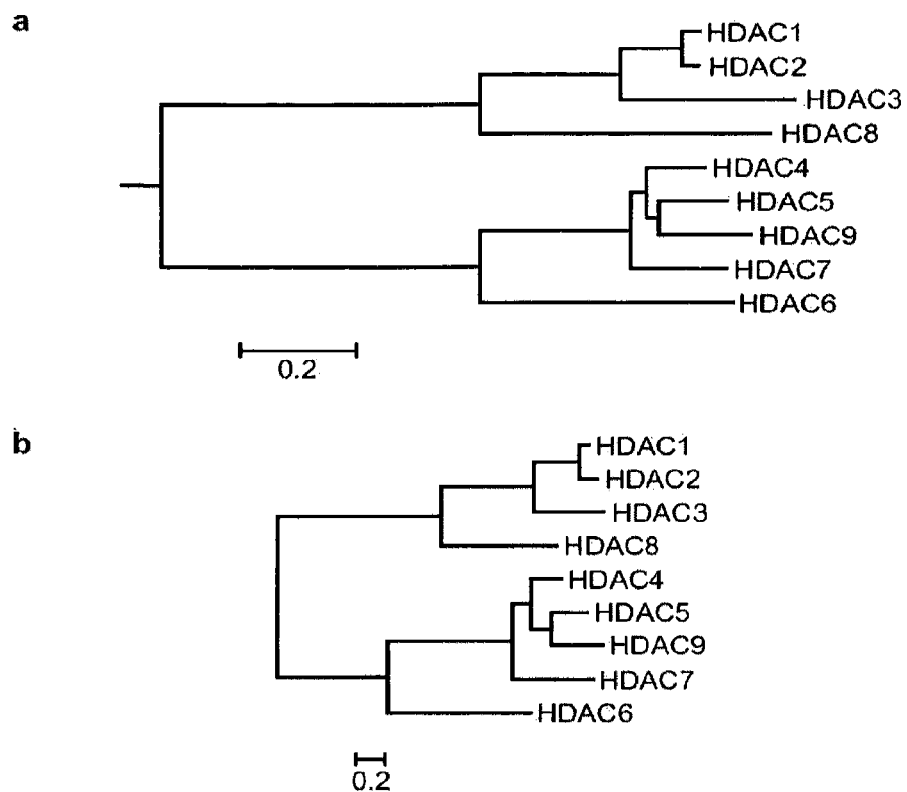
FIG. 6 illustrates the phylogenetic analysis of human HDAC1-9. Amino acid sequences for each human histone deacetylase were retrieved from the National Centers for Biotechnology Information, and aligned using MAFFT as described above. (a) A neighbor-joining method with bootstrap resampling was utilized to compute evolutionary distance data for all conserved sites (Saitou, N. et. al *Mol. Biol. Evol.* 1987, 4, 406-425). Amino acid replacement was performed using the maximum-likelihood approach of Whelan and Goldman (Whelan, S. et. al. *Mol. Biol. Evol.* 2001, 18, 691-699). Analyses were performed using the online research portal of Dr. Katoh (http://align.bmr.kyushu-u.ac.jp/mafft/softwaref). (b) Phylogenetic tree reconstruction was performed on MAFFT aligned sequence using reported rapid bootstrapping and rapid maximum likelihood search algorithms (Randomized Axelerated Maximum Likelihood (RAxML) (Stamatakis, A., Hoover, P. & Rougemont, J. A rapid bootstrap algorithm for the RAxML Web servers. *Syst Biol* 57, 758-71 (2008)); Cyberinfrastructure for Phylogenetic Research online portal (http://www.phylo.org/). (a,b) Phylogenetic trees were generated using Molecular Evolutionary Genetics Analysis software (Kumar, S., Nei, M., Dudley, J. & Tamura, K. MEGA: a biologist-centric software for evolutionary analysis of DNA and protein sequences. *Brief Bioinform.* 9, 299-306 (2008)). Notably, both methods of phylogenetic analysis produced identically branched trees.

Interrogating the bidirectional hierarchical clustering of small molecules and proteins, remarkable chemotype-deacetylase relationships emerge. Driving the striking alignment of HDACi are principally the linker-chelator features, as most clearly observed with the benzamides (ortho-aminoanilides MS-275, CI-994 and MGDC-0103). In the second dimension, a provocative correlation was observed when comparing this chemical phylogeny to the molecular phylogeny of HDACII-9 (FIG. 6). HDACs with known, high sequence and predicted structural identity exhibit relatedness in both analyses. Yet pharmacology defies phylogeny for HDAC6 and HDAC8, between which Class assignments are reversed. Here, the inhibitor sensitivity emulates the substrate preferences, as for all deacetylases studied (FIG. 1b), rendering 4 also the preferred reagent for biochemical studies of HDAC8.

Figure 7:
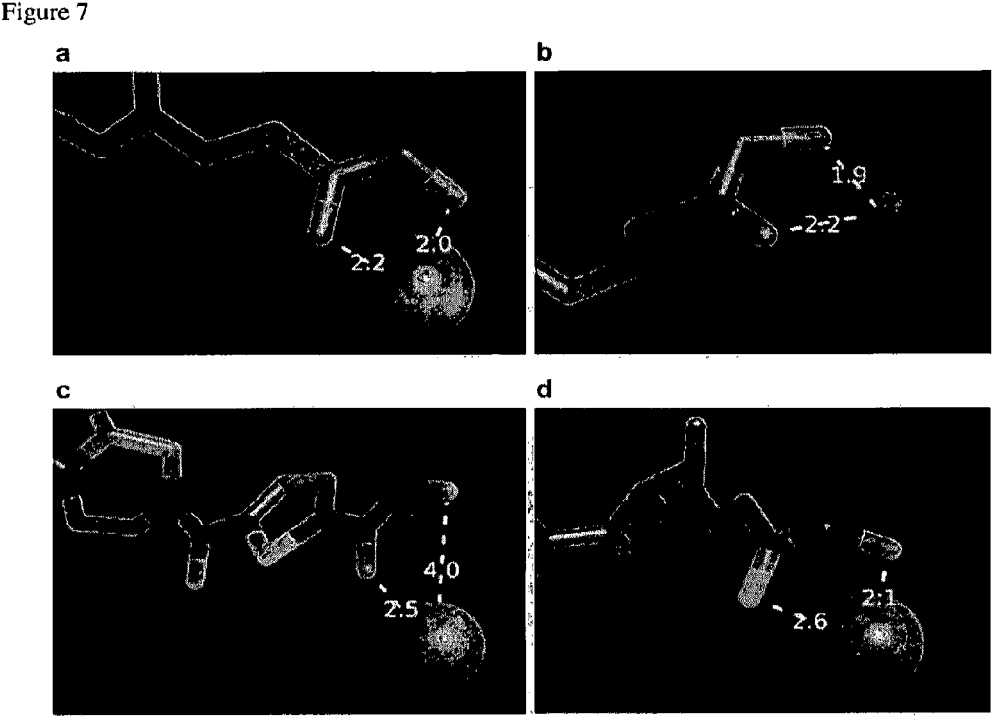
FIG. 7 shows the examination of zinc chelation by HDAC inhibitors in published, crystallographic data. (a) Trichostatin A bound to HDAC8 (1T64) (Somoza, J. R. et. al. *Structure* 2004, 1325-1334). (b) SAHA bound to a bacterial Class II histone deacetylase homologue (1ZZ1) (Nielsen, T. K. et. al. *J. Mol. Biol.* 2005, 354, 107-120). (c) HDAC4 in complex with hydroxamate based inhibitors (2VQM) (Bottomley, M. J. et. al. *J. Biol. Chem.* 2008, 283, 26694-26704). (d) HDAC7 in complex with TSA (3C10) (Schuetz, A. *J. Biol. Chem. et. al.* 2008-283, 11355-11363). All data were obtained from the Protein Data Bank (Research Collaboratory for Structural Bioinformatics) and images were created in PyMOL Molecular Viewer (DeLano, W. L. The PyMOL Molecular Graphics System (2002) DeLano Scientific, Palo Alto, Calif., USA.).

The inability of orthoaminoanilides to inhibit Class IIa HDACs was not surprising based on prior studies of HDAC6 and HDAC8, which suggested extraordinary selectivity for HDAC 1, 2 and 3. However, the overall lack of potency of hydroxamic acid-based inhibitors was highly unexpected. We interpret this observation based on the available crystal structures HDAC4 (2VQM) and HDAC7 (3COZ, 3C10) bound to hydroxamate inhibitors. None of the ligand-protein complexes shows the expected bidentate chelation geometry of the central Zinc cation, as observed in the structures of ligand-bound human HDAC8 (1T64, 1T69) and bacterial homologs (e.g. 1 ZZ7). According to calculations by Wiest and Helquist, the tight bidentate complexation is a result of the deprotonation of the hydroxamic acid upon ligand binding (Wang, D. et al. *J. Org. Chem.* 2007, 72, 5446-5549). The observed geometry in the published structures, however, is more in line with weaker monodentate binding mode of the neutral form of the hydroxamic acid (FIG. 7) (Wang, D. et al. *J. Org. Chem.* 2007, 72, 5446-5549). Common to all Class IIa HDACs is the substitution of a tyrosine residue in the active site, which is conserved in Class I enzymes, as a histidine. Arrowsmith (HDAC7) and Gallinari and Jones (HDAC4) have shown that the mutation of the respective histidine to tyrosine markedly increases the biochemical activity of both enzymes (Schuetz, A. et al. *J. Biol. Chem.* 2008, 283, 11355-11363; Bottomley, M. J. et al. *J. Biol. Chem.* 2008, 283, 26694-26704; Lahm, A. et al. *Proc. Natl. Acad. Sci. U.S.A.* 2007, 104, 17335-17340). Interestingly, in the Class I structures, this tyrosine forms a hydrogen bond to the hydroxamic acid carbonyl, which will increase binding affinity through hydrogen bond formation and as we speculate, sufficiently lower the pKa of the bound chelator facilitating deprotonation and consequently tighter binding. Consistent with this model is the 100-fold increased affinity observed with the hydroxamate LAQ-824 for the H976Y HDAC4 gain of function mutant (Jones, P. et al. *Bioorg. Med. Chem. Lett.* 2008, 18, 1814-1819; Schuetz, A. et al. *J. Biol. Chem.* 2008, 283, 11355-11363; Bottomley, M. J. et al. *J. Biol. Chem.* 2008, 283, 26694-26704). These observations may explain, in part, the differential potency of hydroxamate-based HDAC inhibitors and provide useful guidance for Class IIa-selective inhibitor design.

Figure 3:
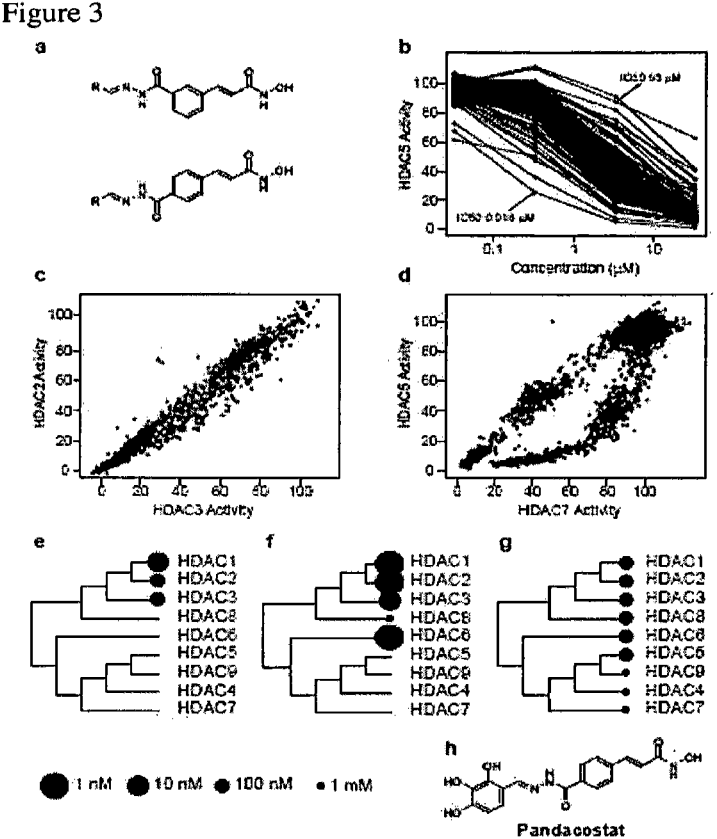
FIG. 3 illustrates the synthesis and testing of an HDAC-biased chemical library and identification of a non-selective HDAC inhibitor. (a) Library design of meta- and para-substituted hydroxamic acid HDAC inhibitors, utilizing parallel condensation of aldehydes, efficiently samples chemical diversity at the capping feature. (b) Biochemical profiling data for the para-substituted sub-library (n=160 compounds), presented in dose-response format for inhibition of HDAC5. Structural variation in the capping feature was observed to confer a broad range of potency, as illustrated with the most ($IC_{50}$=18 nM) and least ($IC_{50}$=55 µM) potent small molecules tested. (c) Comparative biochemical profiling of meta- (red) and para-substituted (blue) sub-libraries for relative inhibition of HDAC2 and HDAC3. The complete library was studied and is displayed at a range of concentrations (0.03, 0.3, 3.0 and 30.0 µM). Compounds of this structural class do not discriminate between HDAC2 and HDAC3. (d) Comparative biochemical profiling of meta- (red) and para-substituted (blue) sub-libraries for relative inhibition of HDAC5 and HDAC7. The complete library was studied and is displayed at a range of concentrations (0.03, 0.3, 3.0 and 30.0 µM). Para-substituted cinnamic hydroxamic acids exhibit increased potency for HDAC5, relative to meta-substituted regioisomers. (e-g) Specificity profiles of (e) MS275, (f) SAHA and (g) pandacostat overlaying molecular phylogeny (Fabian et. al. *Nat. Biotechnol.* 2005, 23, 329-336) HDAC dendrograms are adapted from FIG. 6. Circles are proportionate in size to K on a logarithmic scale, as shown. (h) Chemical structure of pandacostat.

The new knowledge that HDACi are, indeed, much more selective than previously appreciated incited an interest to discover a truly non-selective inhibitor. Such a tool compound would have great utility to the research community. As suggested by the chemical phylogenetics, the central clustering of cinnamic hydroxamates suggests this pharmacophore as most leveraged for non-selectivity. We and others have observed dramatic contributions to ligand potency and selectivity by the structure and conformation of HDACi capping features (Bowers, A. A. et al., *J. Am. Chem. Soc.* 2009; Wong, J. C. et al. *Chem. Biol.* 2004, 11, 1279-1291). Thus, we endeavored to expand a library of capped cinnamic hydroxamic acids, based on a high-throughput, parallel synthesis scheme we have used previously with success in targeting individual HDACs (Vegas, A. J. et al., *Angew. Chem. Int. Ed Engl.* 2007, 46, 7960-7964; Patel, V. et al. *J. Med. Chem.* 2009). This approach involves the clean and efficient condensation of a hydrazide-based linker-chelator feature with a diverse collection of aldehydes to readily explore the chemical space of the capping group. Meta- and para-substituted hydrazide-functionalized cinnamic hydroxamic acids were prepared and condensed with a set of 160 aliphatic and aromatic aldehydes to yield a HDAC-biased library of 320 compounds (FIG. 3a). The entire library was profiled against Class I and IIa HDACs in dose-ranging format to provide a richly annotated data set.

Figure 8:
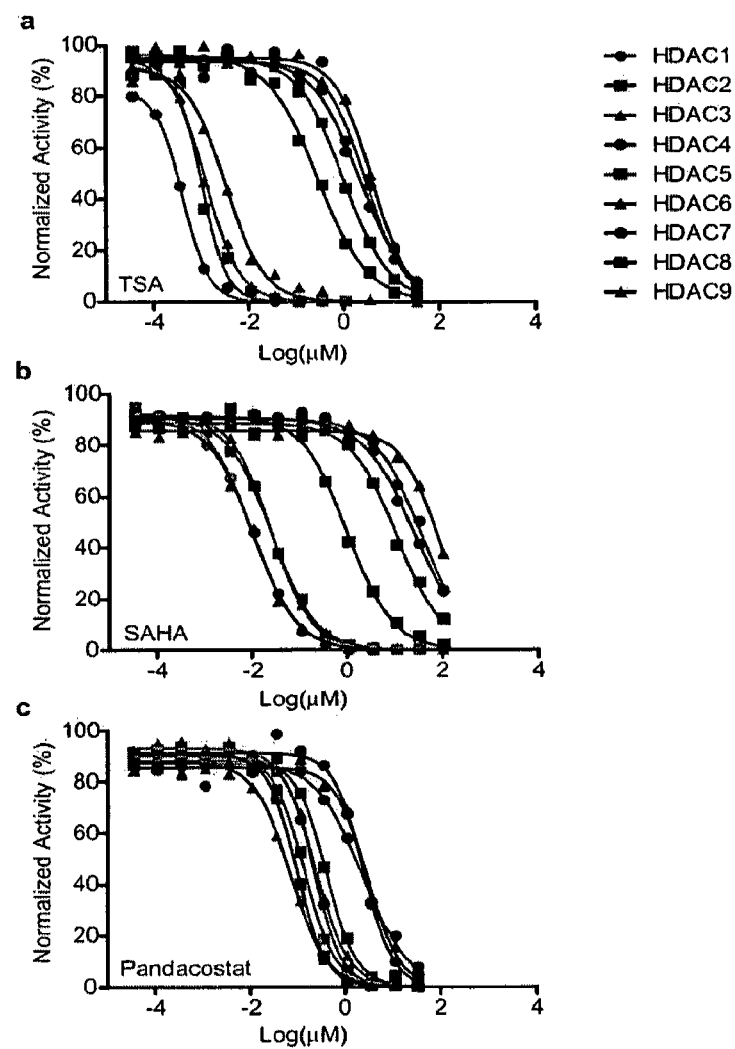
FIG. 8 illustrates the comparative biochemical profiling of (a) trichostatin A (TSA), (b) SAHA, and (c) pandacostat, for inhibition of HDAC1-9. Compounds were arrayed in 384-well plate format as library stock solutions at 10 mM top concentration. Dilution series (3-fold) were created by hand micropipette. Compounds were studied for inhibition of HDACs following robotic pin transfer and a brief pre-incubation period. Dose-response data are presented for each compound. Data comprise the mean of three replicates. Curves were fit by logistic regression using Graph Pad Prism. These data confirm the unexpected selectivity of TSA and SAHA; they also confirm the markedly improved selectivity of pandacostat.
Figure 9:
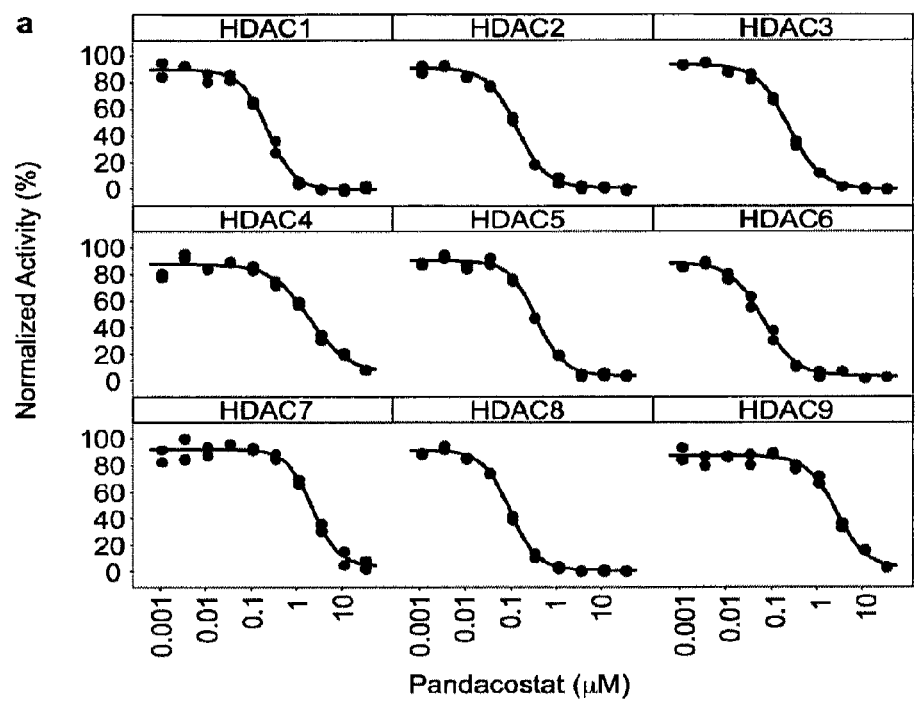
FIG. 9 shows the biochemical inhibition of HDAC1-9 by pandacostat. (a) Visualization of biochemical inhibition of individual HDAC isoforms by pandacostat. (b) Summary of pandacostat $K_i$ values for HDAC1-9 presented with standard deviation (Spotfire DecisionSite).
Figure 14:
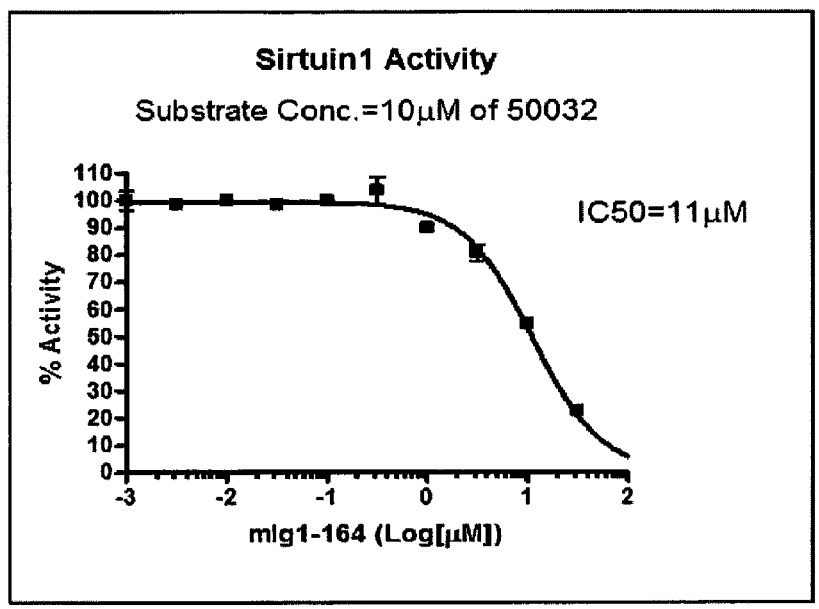
FIG. 14 illustrates the effects of pandacostat (Mlg-1-164) on Sirtuin 1 activity.
Figure 16:
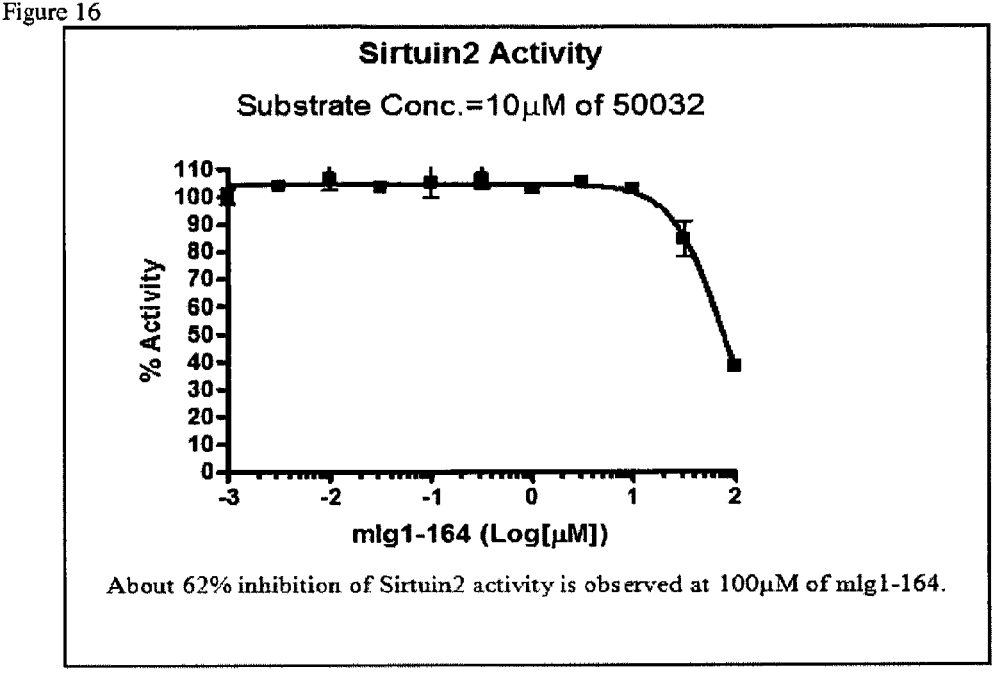
FIG. 16 illustrates the effects of pandacostat (Mlg-1-164) on Sirtuin 2 activity.
Figure 18:
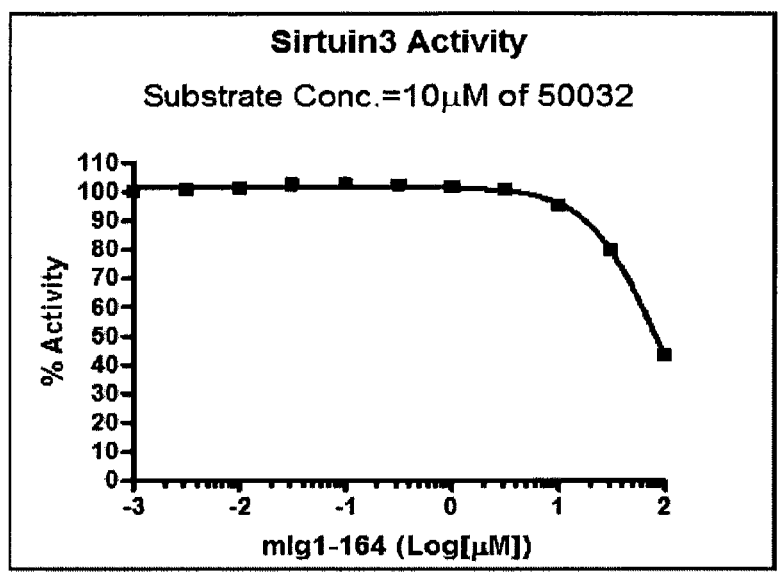
FIG. 18 illustrates the effects of pandacostat (Mlg-1-164) on Sirtuin 3 activity.
Figure 19A:
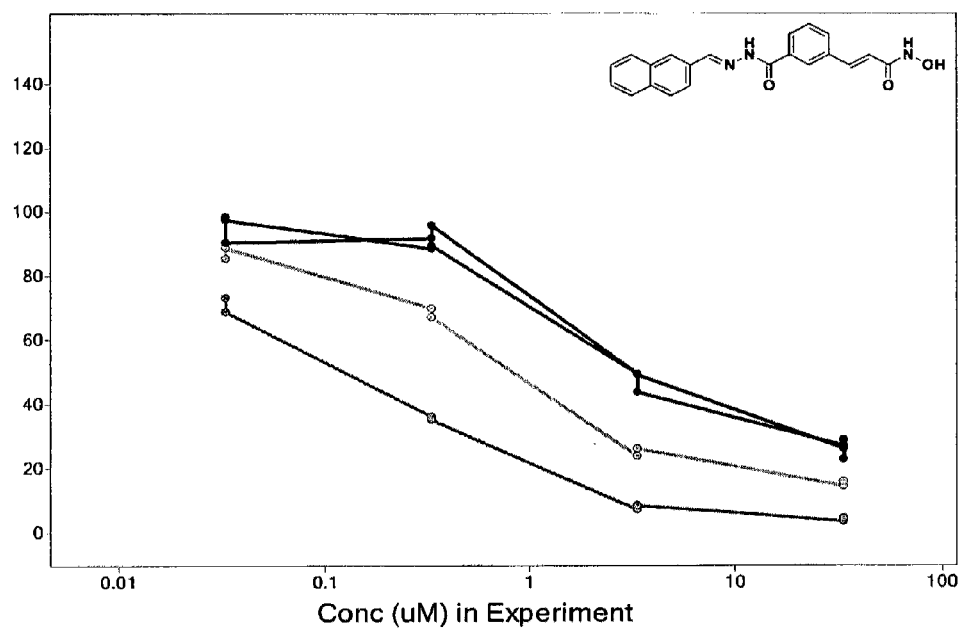
FIG. 19A-D illustrates the inhibitory effects of four exemplary inventive cinnamic hydroxamates at various concentrations on HDAC4 (yellow), HDAC5 (green), HDAC7 (blue), and HDAC9 (purple).
Figure 19B:
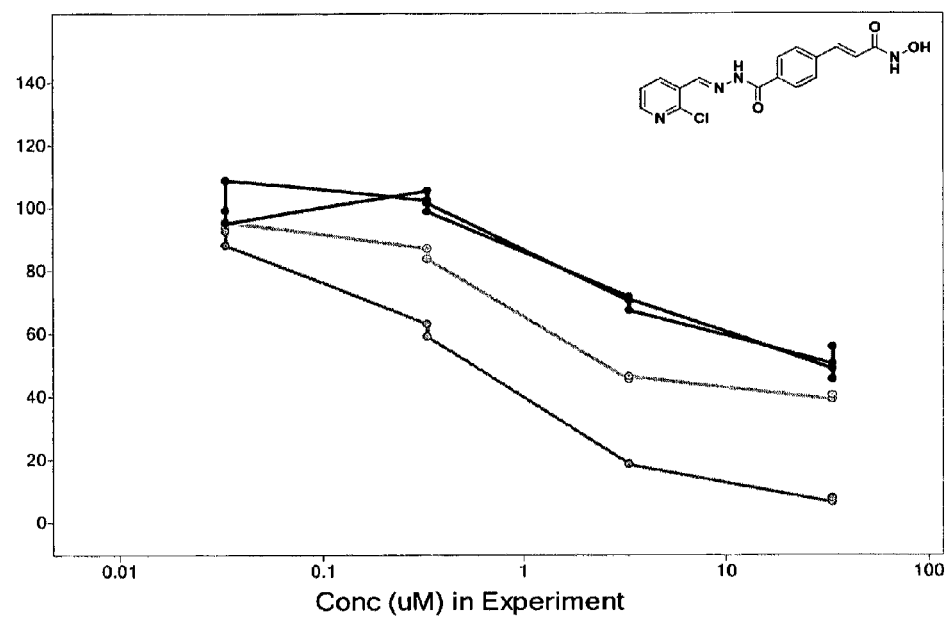
Figure 19C:
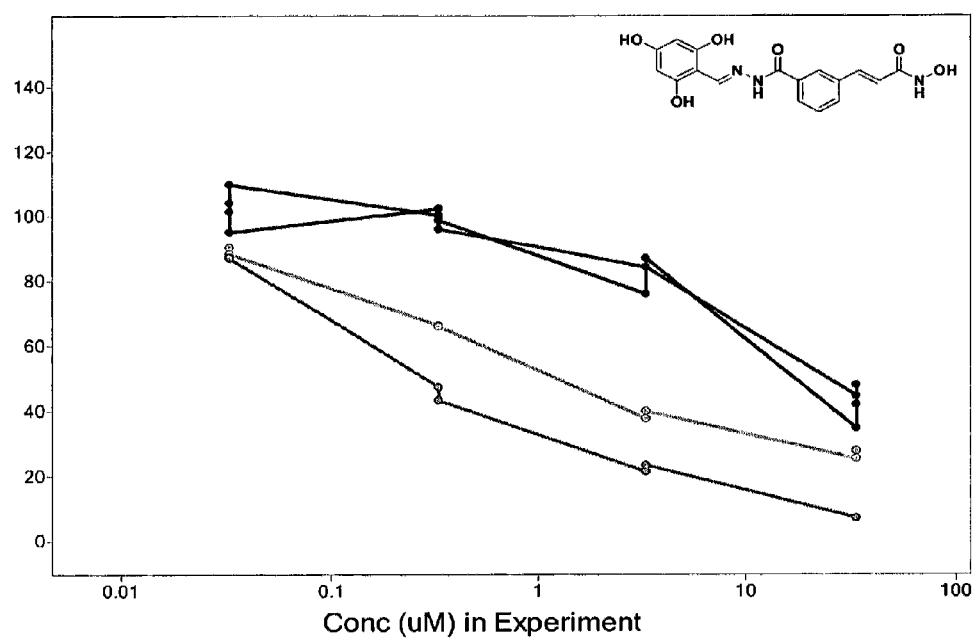
Figure 19D:
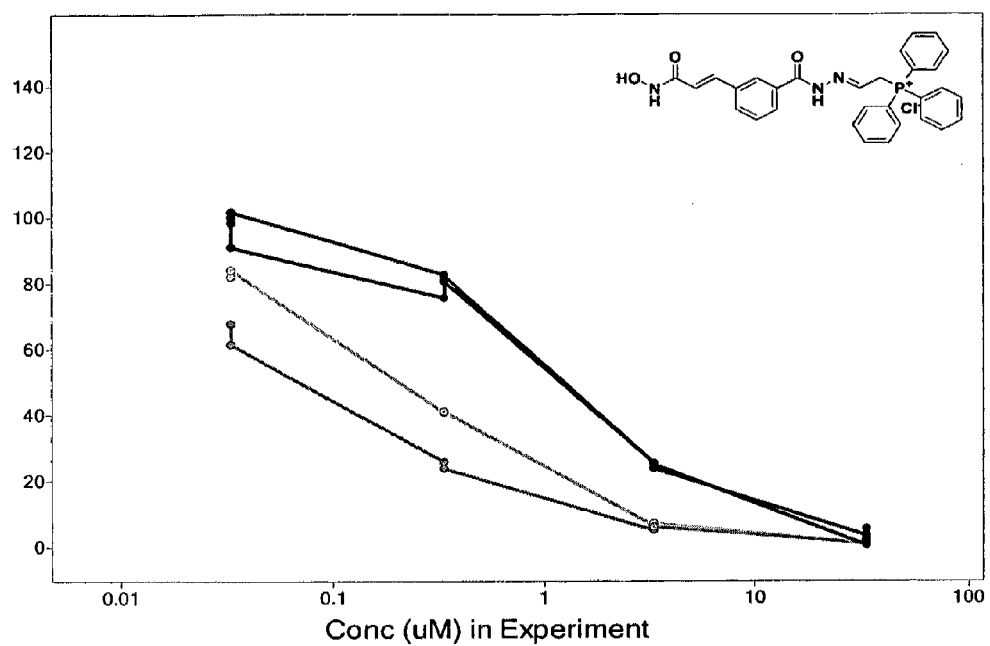

The capping feature was confirmed to confer a dramatic effect on target potency, as shown in FIG. 3b. Pair-wise comparison of potency for individual deacetylases revealed a substantial impact of linker substitution and geometry on target selectivity, particularly evident between HDAC6 and other Class IIa enzymes (FIG. 3c,d). Based on these profiling data, we selected four compounds with high potency against Class IIa HDACs relative to Class I inhibition. These compounds were resynthesized on 30 mg scale, purified by reversed phase HPLC and assayed in dense dose-response format for the accurate determination of potency and selectivity. One compound was identified, which uniformly inhibited all profiled HDAC isoforms, in contrast to control compounds MS-275, SAHA and trichostatin A (FIG. 3e,f,g; FIGS. 8 and 9). We term this compound pandacostat (FIG. 3h).

We present, for the first time, the kinetic study of the biochemically active HDACs and a comprehensive library of tool and pharmaceutical deacetylase inhibitors. These data are derived from robust assays and a novel substrate, which allow for the rapid and efficient study of Class IIa HDACs. Our studies have revealed the unexpected selectivity of previously perceived "non-selective" HDAC inhibitors. From literature-reported crystallographic data and ab initio calculations, we provide a rationale for the diminished potency that will guide future ligand development for Class IIa HDACs. Recognizing the broad, potential utility of a non-selective HDACi, we synthesized a library of Class IIa-biased inhibitors and identified the first pan-HDACi reported, to date. In studying the chemical phylogenetics of HDACs, we demonstrate how a focused, structurally-diverse library of small molecules can be used for the functional classification of a protein family.

Example 20

Biochemical HDAC Assay

The inhibitory effect of compounds on HDAC1-9 function was determined in vitro using an optimized homogenous assay performed in 384-well plate format. In this assay, recombinant, full-length HDAC protein (HDAC1 3.33 ng/µL, HDAC2 1 ng/µL, HDAC3/NCOR2 0.17 ng/µL, HDAC4 0.0016 ng/µL, HDAC5 0.033 ng/µL, HDAC6 1.3 ng/µL, HDAC7 0.0033 ng/µL, HDAC8 0.033 ng/µL, HDAC9 0.033 ng/µL; BPS Biosciences) is incubated with a commercially-available fluorophore conjugated substrate at a concentration equivalent to the substrate $K_m$ (1.6 µM for HDAC1, 3 µM for HDAC2, 6 µM for HDAC3 and 16 mM for HDAC6; concentrations of 4 for HDAC4, 5, 7, 8, 9 are provided FIG. 50. Reactions are performed in assay buffer (50 mM HEPES, 100 mM KCl, 0.001% Tween-20, 0.05% BSA, 200 µM TCEP, pH 7.4) and followed for fluorigenic release of 7-amino-4-methylcoumarin from substrate upon deacetylase and trypsin enzymatic activity. Fluorescence measurements are obtained approximately every five minutes using a multilabel plate reader and plate-stacker (Envision; Perkin-Elmer). Data are analyzed on a plate-by-plate basis for the linear range of fluorescence over time. The first derivative of data obtained from the plate capture corresponding to the mid-linear range is imported into analytical software and annotated with well identity and compound concentration (Spotfire DecisionSite). Replicate experimental data from incubations with inhibitor are normalized to control, solvent-only wells.

Example 21

Statistical Methods

Biochemical inhibition of HDAC enzymes by small-molecule inhibitors is measured as described in Example 20. Data are analyzed by logistic regression with determination of IC50 and standard deviation (Spotfire DecisionSite and GraphPad Prism). Calculation of Ki is determined using a derivation of the standard formula Ki=[Inhibitor]/((VON;)* (1+S/Km))–[Substrate]/Km)–1. Multiple sequence alignment of human HDAC1-9 by Multiple Alignment were performed using Fast Fourier Transform (MAFFT). Amino acid sequences for each human histone deacetylase were retrieved from the National Centers for Biotechnology Information (HDAC1 Accession No. Q13547; HDAC2 Accession No. Q92769; HDAC3 Accession No. 015379; HDAC4 Accession No. P56524; HDAC5 Accession No. Q9UQL6; HDAC6 Accession No. Q9UBN7; HDAC7 Accession No. Q8WUI4; HDAC8 Accession No. Q9BY41; HDAC9 Accession No. Q9BY41). Alignments were generated using MAFFT version 6 (online portal; http://align.bmr.kyushu-u.ac.jp/maff/softwareo, as described). Phylogenetic analysis was performed as described in FIG. 6. In brief, first a neighbor-joining method with bootstrap resampling was utilized to compute evolutionary distance data for all conserved sites (Saitou et al. *Mol. Biol. Evol.* 1987, 4, 406-425). Amino acid replacement was performed using the maximum likelihood approach of Whelan and Goldman (Whelan et al. *Mol. Biol. Evol.* 2001, 18, 691-699). Analyses were performed using the online research portal of Dr. Katch (http://align.bmr.kyushu-u.ac.jp/mafft/software/). Phylogenetic tree reconstruction was performed on MAFFT aligned sequence using reported rapid bootstrapping and rapid maximum likelihood search algorithms (Randomized Axelerated Maximum Likelihood (RAxML) 5; Cyberinfrastructure for Phylogenetic Research online portal; hftp://www.phylo.org/). Phylogenetic trees were generated using Molecular Evolutionary Genetics Analysis software 6. Bidirectional hierarchical clustering was performed on biochemical profiling data (Ki) for each HDAC1-9 by generating a pairwise distance matrix using the unweighted pair group method with arithmetic mean and a Euclidean distance similarity measure (Spotfire DecisionSite).

Example 22

The purpose of the study is to determine the effects of pandacostat on the enzymatic activities of recombinant human Sirtuins using in vitro enzymatic assays.

| Compound | Compound Supplied | Dissolving Solvent | Stock Concentration | Test Range (µM) | Intermediate Dilution |
|---|---|---|---|---|---|
| Pandacostat | Solution | | 10 mM | 0.003-100 | 10% DMSO in HDAC Assay Buffer |

A series of compound dilutions (10 fold higher than final concentrations) are made in 10% DMSO in HDAC assay buffer. 5 µl of each dilution is added to 50 µl of the reaction mixture so that the final concentration of DMSO is 1% in all of reactions.

Enzymes and Substrates

| Assay | Enzyme (ng)/Reaction | Substrate |
|---|---|---|
| Sirtuin1 | 200 | 10 µM HDAC Substrate 1 |
| Sirtuin2 | 1,500 | 10 µM HDAC Substrate 1 |
| Sirtuin3 | 1,000 | 10 µM HDAC Substrate 1 |

All of the enzymatic reactions were conducted in duplicate at room temperature for 3 hours in a 50 µl mixture containing HDAC assay buffer, 5 µg BSA, 100 µM NAD$^+$, 10 µM HDAC substrate 1, a sirtuin enzyme, and the test compound.

After enzymatic reactions, 50 µl of 2×HDAC Developer was added to each well and the plate was incubated at room temperature for an additional 20 minutes. Fluorescence intensity was measured at an excitation of 360 nm and an emission of 460 nm using a BioTek Synergy™ 2 microplate reader.

Sirtuin activity assays were performed in duplicates at each concentration. The fluorescent intensity data were analyzed using the computer software, Graphpad Prism. In the absence of the compound, the fluorescent intensity ($F_t$) in each data set was defined as 100% activity. In the absence of the sirtuin, the fluorescent intensity ($F_b$) in each data set was defined as 0% activity. The percent activity in the presence of each compound was calculated according to the following equation: % activity=$(F-F_b)/(F_t-F_b)$, where F=the fluorescent intensity in the presence of the compound, $F_b$=the fluorescent intensity in the absence of the sirtuin, and $F_t$=the fluorescent intensity in the absence of the compound.

The values of % activity versus a series of compound concentrations were then plotted using non-linear regression analysis of Sigmoidal dose-response curve generated with the equation $Y=B+(T-B)/1+10^{((Log\ EC50-X)\times Hill\ Slope)}$, where Y=percent activity, B=minimum percent activity, T=maximum percent activity, X=logarithm of compound and Hill Slope=slope factor or Hill coefficient. The IC$_{50}$ value was determined by the concentration causing a half-maximal percent activity.

The IC$_{50}$ values of the compound against sirtuins are summarized in FIG. 12. If the IC$_{50}$ value is not available, the % inhibition of the compound at the highest testing concentration was calculated.

The effects of pendacostat on the individual Sirtuin activity are summarized in FIGS. 13-18. Depicted in FIG. 16 about 62% inhibition of Sirtuin2 activity is observed at 100 μM pendactostat, while in FIG. 18 about 57% inhibition of Sirtuin3 activity is observed at 100 μM of pendacostat.

What is claimed is:

1. A compound of formula:

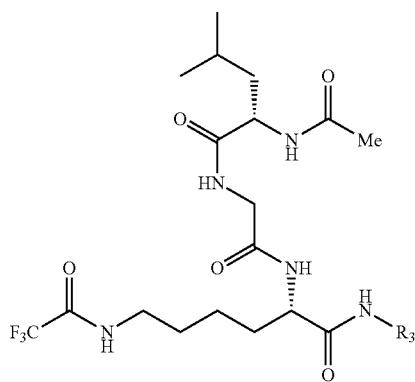

wherein $R_3$ is a fluorescent tag;
or salt thereof.

2. The compound of claim 1, wherein $R_3$ comprises coumarin.

3. The compound of claim 1, wherein the compound is:

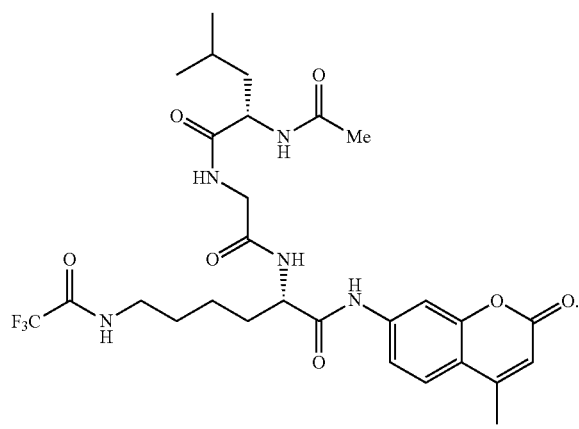 [SMILES: CC(=O)N[C@@H](CC(C)C)C(=O)NCC(=O)N[C@@H](CCCCNC(=O)C(F)(F)F)C(=O)Nc1ccc2c(C)cc(=O)oc2c1]

4. The compound of claim 1, wherein the fluorescent tag of $R_3$ can be cleaved by an enzyme.

5. An assay for determining the inhibitory effect of a test compound on an HDAC protein comprising: incubating the HDAC protein with a substrate of claim 1 in the presence of a test compound; and determining the activity of the HDAC protein.

6. An assay for determining the inhibitory effect of a test compound on an HDAC protein comprising incubating the HDAC protein with a substrate of formula:

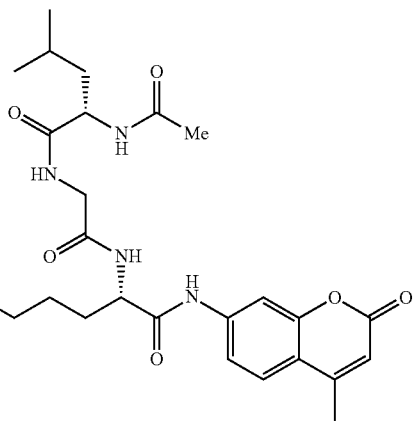

in the presence of a test compound; and determining the activity of the HDAC protein by monitoring the release of 7-amino-4-methylcoumarin after cleavage by trypsin.

7. The compound of claim 1, wherein the fluorescent tag is selected from a group consisting of brodifacoum, bromadiolone, coumafuryl, difenacoum, auraptene, ensaculin, phenprocoumon, warfarin, and derivatives thereof.

8. The compound of claim 4, wherein the enzyme is esterase.

9. The compound of claim 4, wherein the enzyme is protease.

10. The compound of claim 4, wherein the enzyme is serine protease.

11. The compound of claim 4, wherein the enzyme is trypsin.

12. The compound of claim 1, wherein the fluorescent tag of $R_3$ can be removed by a mechanical process.

13. The compound of claim 1, wherein $R_3$ comprises a coumarin derivative thereof.

14. The assay of claim 5, wherein the step of determining the activity of the HDAC protein comprises monitoring the release of the fluorescent tag from the substrate.

15. The assay of claim 5, wherein the fluorescent tag comprises coumarin or a derivative thereof.

16. The assay of claim 5, wherein the assay is carried out at a concentration of the substrate greater than the substrate $K_m$.

17. The assay of claim 5, wherein the assay is carried out at a concentration of the substrate approximately equivalent to the substrate $K_m$.

18. The assay of claim 5, wherein the concentration of the substrate is 1-20 μM.

19. The assay of claim 5, wherein the HDAC protein is a Class II HDAC.

20. The assay of claim 5, wherein the HDAC protein is 0.01-5 ng/μL.

21. The assay of claim 5, wherein the HDAC protein is 0.1-0.5 ng/μL.

* * * * *

UNITED STATES PATENT AND TRADEMARK OFFICE
CERTIFICATE OF CORRECTION

PATENT NO. : 8,716,344 B2
APPLICATION NO. : 13/389814
DATED : May 6, 2014
INVENTOR(S) : Ralph Mazitschek et al.

It is certified that error appears in the above-identified patent and that said Letters Patent is hereby corrected as shown below:

In the Specification

Please replace the paragraph at Column 1, Lines 15-18, with the following paragraph:
--This invention was made with Government support under grant CA078048 awarded by the National Institutes of Health (NIH). The Government has certain rights to this invention.--

Signed and Sealed this
Fifth Day of May, 2020

Andrei Iancu
*Director of the United States Patent and Trademark Office*